US010032319B2

(12) United States Patent
Ricci

(10) Patent No.: US 10,032,319 B2
(45) Date of Patent: Jul. 24, 2018

(54) BIFURCATED COMMUNICATIONS TO A THIRD PARTY THROUGH A VEHICLE

(71) Applicant: NIO USA, Inc., San Jose, CA (US)

(72) Inventor: Christopher P. Ricci, Saratoga, CA (US)

(73) Assignee: NIO USA, Inc., San Jose, CA (US)

( * ) Notice: Subject to any disclaimer, the term of this patent is extended or adjusted under 35 U.S.C. 154(b) by 0 days.

(21) Appl. No.: 15/396,620

(22) Filed: Dec. 31, 2016

(65) Prior Publication Data

US 2018/0012427 A1 Jan. 11, 2018

Related U.S. Application Data

(60) Provisional application No. 62/359,563, filed on Jul. 7, 2016, provisional application No. 62/378,348, filed on Aug. 23, 2016.

(51) Int. Cl.
*G07C 5/00* (2006.01)
*G07B 15/06* (2011.01)
(Continued)

(52) U.S. Cl.
CPC .............. *G07C 5/008* (2013.01); *B60W 40/08* (2013.01); *B60W 50/08* (2013.01);
(Continued)

(58) Field of Classification Search
CPC .. G07C 2/008; G07B 15/063; G01C 21/3617; G08G 1/017; G08G 1/096838;
(Continued)

(56) References Cited

U.S. PATENT DOCUMENTS 4,361,202 A 11/1982 Minovitch
4,476,954 A 10/1984 Johnson et al.
(Continued)

FOREIGN PATENT DOCUMENTS

CN 1417755 5/2003
CN 1847817 10/2006
(Continued)

OTHER PUBLICATIONS

Liu et al., A Survey of Payment Card Industry Data Security Standard, 2010, IEEE, p. 287-303 (Year: 2010).*
(Continued)

*Primary Examiner* — McDieunel Marc
(74) *Attorney, Agent, or Firm* — Sheridan Ross P.C.

(57) ABSTRACT

A vehicle is provided that determines a need for communication with a third party vendor, retrieves a user rule from the memory (the user rule defines to which third party vendor the vehicle can send a first communication to address the need and defines a geographic location of the third party vendor relative to a current location of the vehicle, a monetary amount the vehicle can pay to a third party vendor for a product or service to address the need, and a time limit for the third party vendor to provide the product or service to address the need), based on the user rule, selects a third party vendor from among multiple possible third party vendors, and when determined by the user rule, automatically sends the first communication to the selected third party vendor to address the need. The first communication is associated with an order for the product or service, and the processor provides an authorization to the selected third party vendor to complete the order. The vehicle uses different antennas positioned at different physical locations on an exterior of the vehicle to provide the first communication and authorization to the selected third party vendor.

21 Claims, 59 Drawing Sheets

(51) Int. Cl.

| | | |
|---|---|---|
| *G01C 21/36* | (2006.01) | |
| *B60W 50/08* | (2012.01) | |
| *B60W 40/08* | (2012.01) | |
| *G08G 1/017* | (2006.01) | |
| *G08G 1/0968* | (2006.01) | |
| *G01S 13/93* | (2006.01) | |

(52) U.S. Cl.
CPC ....... *G01C 21/3617* (2013.01); *G07B 15/063* (2013.01); *G08G 1/017* (2013.01); *G08G 1/096838* (2013.01); *B60W 2540/00* (2013.01); *G01S 2013/936* (2013.01)

(58) Field of Classification Search
CPC . G01S 2013/936; B60W 40/08; B60W 50/08; B60W 2540/00
See application file for complete search history.

(56) References Cited

U.S. PATENT DOCUMENTS

| | | |
|---|---|---|
| 4,754,255 A | 6/1988 | Sanders et al. |
| 4,875,391 A | 10/1989 | Leising et al. |
| 5,136,498 A | 8/1992 | McLaughlin et al. |
| 5,204,817 A | 4/1993 | Yoshida |
| 5,363,306 A | 11/1994 | Kuwahara et al. |
| 5,508,689 A | 4/1996 | Rado et al. |
| 5,521,815 A | 5/1996 | Rose |
| 5,529,138 A | 6/1996 | Shaw et al. |
| 5,531,122 A | 7/1996 | Chatham et al. |
| 5,572,201 A | 11/1996 | Graham et al. |
| 5,572,450 A | 11/1996 | Worthy |
| 5,610,821 A | 3/1997 | Gazis et al. |
| 5,648,769 A | 7/1997 | Sato et al. |
| 5,710,702 A | 1/1998 | Hayashi et al. |
| 5,794,164 A | 8/1998 | Heckert et al. |
| 5,797,134 A | 8/1998 | McMillan et al. |
| 5,812,067 A | 9/1998 | Bergholz et al. |
| 5,825,283 A | 10/1998 | Camhi |
| 5,838,251 A | 11/1998 | Brinkmeyer et al. |
| 5,847,661 A | 12/1998 | Ricci |
| 5,890,080 A | 3/1999 | Coverdill et al. |
| 5,928,294 A | 7/1999 | Zelinkovsky |
| 5,949,345 A | 9/1999 | Beckert et al. |
| 5,983,161 A | 11/1999 | Lemelson et al. |
| 5,986,575 A | 11/1999 | Jones et al. |
| 6,038,426 A | 3/2000 | Williams, Jr. |
| 6,081,756 A | 6/2000 | Mio et al. |
| D429,684 S | 8/2000 | Johnson |
| 6,128,003 A | 10/2000 | Smith et al. |
| 6,141,620 A | 10/2000 | Zyburt et al. |
| 6,148,261 A | 11/2000 | Obradovich et al. |
| 6,152,514 A | 11/2000 | McLellen |
| 6,157,321 A | 12/2000 | Ricci |
| 6,198,996 B1 | 3/2001 | Berstis |
| 6,199,001 B1 | 3/2001 | Ohta et al. |
| 6,202,008 B1 | 3/2001 | Beckert et al. |
| 6,252,544 B1 | 6/2001 | Hoffberg |
| 6,267,428 B1 | 7/2001 | Baldas et al. |
| 6,302,438 B1 | 10/2001 | Stopper, Jr. et al. |
| 6,310,542 B1 | 10/2001 | Gehlot |
| 6,317,058 B1 | 11/2001 | Lemelson et al. |
| 6,339,826 B2 | 1/2002 | Hayes, Jr. et al. |
| 6,356,838 B1 | 3/2002 | Paul |
| 6,388,579 B1 | 5/2002 | Adcox et al. |
| 6,480,224 B1 | 11/2002 | Brown |
| 6,502,022 B1 | 12/2002 | Chastain et al. |
| 6,519,519 B1 | 2/2003 | Stopczynski |
| 6,526,335 B1 | 2/2003 | Treyz et al. |
| 6,557,752 B1 | 5/2003 | Yacoob |
| 6,563,910 B2 | 5/2003 | Menard et al. |
| 6,587,739 B1 | 7/2003 | Abrams et al. |
| 6,598,227 B1 | 7/2003 | Berry et al. |
| 6,607,212 B1 | 8/2003 | Reimer et al. |
| 6,617,981 B2 | 9/2003 | Basinger |
| 6,662,077 B2 | 12/2003 | Haag |
| 6,675,081 B2 | 1/2004 | Shuman et al. |
| 6,678,747 B2 | 1/2004 | Goossen et al. |
| 6,681,176 B2 | 1/2004 | Funk et al. |
| 6,690,260 B1 | 2/2004 | Ashihara |
| 6,690,940 B1 | 2/2004 | Brown et al. |
| 6,724,920 B1 | 4/2004 | Berenz et al. |
| 6,754,580 B1 | 6/2004 | Ask et al. |
| 6,757,593 B2 | 6/2004 | Mori et al. |
| 6,762,684 B1 | 7/2004 | Camhi |
| 6,765,495 B1 | 7/2004 | Dunning et al. |
| 6,778,888 B2 | 8/2004 | Cataldo et al. |
| 6,782,240 B1 | 8/2004 | Tabe |
| 6,785,531 B2 | 8/2004 | Lepley et al. |
| 6,816,783 B2 | 11/2004 | Hashima et al. |
| 6,820,259 B1 | 11/2004 | Kawamata et al. |
| 6,944,533 B2 | 9/2005 | Obradovich et al. |
| 6,950,022 B2 | 9/2005 | Breed |
| 6,958,707 B1 | 10/2005 | Siegel |
| 6,992,580 B2 | 1/2006 | Kotzin et al. |
| 7,019,641 B1 | 3/2006 | Lakshmanan et al. |
| 7,020,544 B2 | 3/2006 | Shinada et al. |
| 7,021,691 B1 | 4/2006 | Schmidt et al. |
| 7,042,345 B2 | 5/2006 | Ellis |
| 7,047,129 B2 | 5/2006 | Uotani |
| 7,058,898 B2 | 6/2006 | McWalter et al. |
| 7,096,431 B2 | 8/2006 | Tambata et al. |
| 7,142,696 B1 | 11/2006 | Engelsberg et al. |
| 7,164,117 B2 | 1/2007 | Breed et al. |
| 7,187,947 B1 | 3/2007 | White et al. |
| 7,203,598 B1 | 4/2007 | Whitsell |
| 7,233,861 B2 | 6/2007 | Van Buer et al. |
| 7,239,960 B2 | 7/2007 | Yokota et al. |
| 7,277,454 B2 | 10/2007 | Mocek et al. |
| 7,284,769 B2 | 10/2007 | Breed |
| 7,289,645 B2 | 10/2007 | Yamamoto et al. |
| 7,295,921 B2 | 11/2007 | Spencer et al. |
| 7,313,547 B2 | 12/2007 | Mocek et al. |
| 7,333,012 B1 | 2/2008 | Nguyen |
| 7,343,148 B1 | 3/2008 | O'Neil |
| 7,386,376 B2 | 6/2008 | Basir et al. |
| 7,386,799 B1 | 6/2008 | Clanton et al. |
| 7,432,829 B2 | 10/2008 | Poltorak |
| 7,474,264 B2 | 1/2009 | Bolduc et al. |
| 7,493,140 B2 | 2/2009 | Michmerhuizen et al. |
| 7,526,539 B1 | 4/2009 | Hsu |
| 7,548,815 B2 | 6/2009 | Watkins et al. |
| 7,566,083 B2 | 7/2009 | Vitito |
| 7,606,660 B2 | 10/2009 | Diaz et al. |
| 7,606,867 B1 | 10/2009 | Singhal et al. |
| 7,643,913 B2 | 1/2010 | Taki et al. |
| 7,650,234 B2 | 1/2010 | Obradovich et al. |
| 7,671,764 B2 | 3/2010 | Uyeki et al. |
| 7,680,596 B2 | 3/2010 | Uyeki et al. |
| 7,683,771 B1 | 3/2010 | Loeb |
| 7,711,468 B1 | 5/2010 | Levy |
| 7,734,315 B2 | 6/2010 | Rathus et al. |
| 7,748,021 B2 | 6/2010 | Obradovich et al. |
| RE41,449 E | 7/2010 | Krahnstoever et al. |
| 7,791,499 B2 | 9/2010 | Mohan et al. |
| 7,796,190 B2 | 9/2010 | Basso et al. |
| 7,802,832 B2 | 9/2010 | Carnevali |
| 7,821,421 B2 | 10/2010 | Tamir et al. |
| 7,832,762 B2 | 11/2010 | Breed |
| 7,864,073 B2 | 1/2011 | Lee et al. |
| 7,872,591 B2 | 1/2011 | Kane et al. |
| 7,873,471 B2 | 1/2011 | Gieseke |
| 7,881,703 B2 | 2/2011 | Roundtree et al. |
| 7,891,004 B1 | 2/2011 | Gelvin et al. |
| 7,891,719 B2 | 2/2011 | Carnevali |
| 7,899,610 B2 | 3/2011 | McClellan |
| 7,966,678 B2 | 6/2011 | Ten Eyck et al. |
| 7,969,290 B2 | 6/2011 | Waeller et al. |
| 7,969,324 B2 | 6/2011 | Chevion et al. |
| 8,060,631 B2 | 11/2011 | Collart et al. |
| 8,064,925 B1 | 11/2011 | Sun et al. |
| 8,066,313 B2 | 11/2011 | Carnevali |
| 8,098,170 B1 | 1/2012 | Szczerba et al. |
| 8,113,564 B2 | 2/2012 | Carnevali |

(56) References Cited

U.S. PATENT DOCUMENTS

| | | |
|---|---|---|
| 8,131,419 B2 | 3/2012 | Ampunan et al. |
| 8,157,310 B2 | 4/2012 | Carnevali |
| 8,162,368 B2 | 4/2012 | Carnevali |
| 8,175,802 B2 | 5/2012 | Forstall et al. |
| 8,233,919 B2 | 7/2012 | Haag et al. |
| 8,245,609 B1 | 8/2012 | Greenwald et al. |
| 8,306,514 B1 | 11/2012 | Nunally |
| 8,334,847 B2 | 12/2012 | Tomkins |
| 8,346,233 B2 | 1/2013 | Aaron et al. |
| 8,346,432 B2 | 1/2013 | Van Wiemeersch et al. |
| 8,350,721 B2 | 1/2013 | Can |
| 8,352,282 B2 | 1/2013 | Jensen et al. |
| 8,369,263 B2 | 2/2013 | Dowling et al. |
| 8,417,449 B1 | 4/2013 | Denise |
| 8,432,260 B2 | 4/2013 | Talty et al. |
| 8,442,389 B2 | 5/2013 | Kashima et al. |
| 8,442,758 B1 | 5/2013 | Rovik et al. |
| 8,467,965 B2 | 6/2013 | Chang |
| 8,497,842 B2 | 7/2013 | Tomkins et al. |
| 8,498,809 B2 | 7/2013 | Bill |
| 8,509,982 B2 | 8/2013 | Montemerlo et al. |
| 8,521,410 B2 | 8/2013 | Mizuno et al. |
| 8,527,143 B2 | 9/2013 | Tan |
| 8,527,146 B1 | 9/2013 | Jackson et al. |
| 8,532,574 B2 | 9/2013 | Kirsch |
| 8,543,330 B2 | 9/2013 | Taylor et al. |
| 8,547,340 B2 | 10/2013 | Sizelove et al. |
| 8,548,669 B2 | 10/2013 | Naylor |
| 8,559,183 B1 | 10/2013 | Davis |
| 8,577,600 B1 | 11/2013 | Pierfelice |
| 8,578,279 B2 | 11/2013 | Chen et al. |
| 8,583,292 B2 | 11/2013 | Preston et al. |
| 8,589,073 B2 | 11/2013 | Guha et al. |
| 8,600,611 B2 | 12/2013 | Seize |
| 8,613,385 B1 | 12/2013 | Hulet et al. |
| 8,621,645 B1 | 12/2013 | Spackman |
| 8,624,727 B2 | 1/2014 | Saigh et al. |
| 8,634,984 B2 | 1/2014 | Sumizawa |
| 8,644,165 B2 | 2/2014 | Saarimaki et al. |
| 8,660,735 B2 | 2/2014 | Tengler et al. |
| 8,671,068 B2 | 3/2014 | Harber et al. |
| 8,688,372 B2 | 4/2014 | Bhogal et al. |
| 8,705,527 B1 | 4/2014 | Addepalli et al. |
| 8,706,143 B1 | 4/2014 | Elias |
| 8,718,797 B1 | 5/2014 | Addepalli et al. |
| 8,725,311 B1 | 5/2014 | Breed |
| 8,730,033 B2 | 5/2014 | Yarnold et al. |
| 8,737,986 B2 | 5/2014 | Rhoads et al. |
| 8,761,673 B2 | 6/2014 | Sakata |
| 8,774,842 B2 | 7/2014 | Jones et al. |
| 8,779,947 B2 | 7/2014 | Tengler et al. |
| 8,782,262 B2 | 7/2014 | Collart et al. |
| 8,793,065 B2 | 7/2014 | Seltzer et al. |
| 8,798,918 B2 | 8/2014 | Onishi et al. |
| 8,805,110 B2 | 8/2014 | Rhoads et al. |
| 8,812,171 B2 | 8/2014 | Fillev et al. |
| 8,817,761 B2 | 8/2014 | Gruberman et al. |
| 8,825,031 B2 | 9/2014 | Aaron et al. |
| 8,825,277 B2 | 9/2014 | McClellan et al. |
| 8,825,382 B2 | 9/2014 | Liu |
| 8,826,261 B1 | 9/2014 | Anand Ag et al. |
| 8,838,088 B1 | 9/2014 | Henn et al. |
| 8,862,317 B2 | 10/2014 | Shin et al. |
| 8,977,408 B1 | 3/2015 | Cazanas et al. |
| 9,043,016 B2 | 5/2015 | Filippov et al. |
| 9,229,905 B1 | 1/2016 | Penilla et al. |
| 9,694,685 B2 * | 7/2017 | Ricci ............... B60L 3/0015 |
| 2001/0010516 A1 | 8/2001 | Roh et al. |
| 2001/0015888 A1 | 8/2001 | Shaler et al. |
| 2002/0009978 A1 | 1/2002 | Dukach et al. |
| 2002/0023010 A1 | 2/2002 | Rittmaster et al. |
| 2002/0026278 A1 | 2/2002 | Feldman et al. |
| 2002/0045484 A1 | 4/2002 | Eck et al. |
| 2002/0065046 A1 | 5/2002 | Mankins et al. |
| 2002/0077985 A1 | 6/2002 | Kobata et al. |
| 2002/0095249 A1 | 7/2002 | Lang |
| 2002/0097145 A1 | 7/2002 | Tumey et al. |
| 2002/0103622 A1 | 8/2002 | Burge |
| 2002/0105968 A1 | 8/2002 | Pruzan et al. |
| 2002/0110146 A1 | 8/2002 | Thayer et al. |
| 2002/0126876 A1 | 9/2002 | Paul et al. |
| 2002/0128774 A1 | 9/2002 | Takezaki et al. |
| 2002/0143461 A1 | 10/2002 | Burns et al. |
| 2002/0143643 A1 | 10/2002 | Catan |
| 2002/0152010 A1 | 10/2002 | Colmenarez et al. |
| 2002/0154217 A1 | 10/2002 | Ikeda |
| 2002/0169551 A1 | 11/2002 | Inoue et al. |
| 2002/0174021 A1 | 11/2002 | Chu et al. |
| 2003/0004624 A1 | 1/2003 | Wilson et al. |
| 2003/0007227 A1 | 1/2003 | Ogino |
| 2003/0055557 A1 | 3/2003 | Dutta et al. |
| 2003/0060937 A1 | 3/2003 | Shinada et al. |
| 2003/0065432 A1 | 4/2003 | Shuman et al. |
| 2003/0101451 A1 | 5/2003 | Bentolila et al. |
| 2003/0109972 A1 | 6/2003 | Tak |
| 2003/0125846 A1 | 7/2003 | Yu et al. |
| 2003/0132666 A1 | 7/2003 | Bond et al. |
| 2003/0149530 A1 | 8/2003 | Stopczynski |
| 2003/0158638 A1 | 8/2003 | Yakes et al. |
| 2003/0182435 A1 | 9/2003 | Redlich et al. |
| 2003/0202683 A1 | 10/2003 | Ma et al. |
| 2003/0204290 A1 | 10/2003 | Sadler et al. |
| 2003/0230443 A1 | 12/2003 | Cramer et al. |
| 2004/0017292 A1 | 1/2004 | Reese et al. |
| 2004/0024502 A1 | 2/2004 | Squires et al. |
| 2004/0036622 A1 | 2/2004 | Dukach et al. |
| 2004/0039500 A1 | 2/2004 | Amendola et al. |
| 2004/0039504 A1 | 2/2004 | Coffee et al. |
| 2004/0068364 A1 | 4/2004 | Zhao et al. |
| 2004/0070920 A1 | 4/2004 | Flueli |
| 2004/0093155 A1 | 5/2004 | Simonds et al. |
| 2004/0117494 A1 | 6/2004 | Mitchell et al. |
| 2004/0128062 A1 | 7/2004 | Ogino et al. |
| 2004/0153356 A1 | 8/2004 | Lockwood et al. |
| 2004/0162019 A1 | 8/2004 | Horita et al. |
| 2004/0180653 A1 | 9/2004 | Royalty |
| 2004/0182574 A1 | 9/2004 | Adnan et al. |
| 2004/0193347 A1 | 9/2004 | Harumoto et al. |
| 2004/0203974 A1 | 10/2004 | Seibel |
| 2004/0204837 A1 | 10/2004 | Singleton |
| 2004/0209594 A1 | 10/2004 | Naboulsi |
| 2004/0217850 A1 | 11/2004 | Perttunen et al. |
| 2004/0225557 A1 | 11/2004 | Phelan et al. |
| 2004/0255123 A1 | 12/2004 | Noyama et al. |
| 2004/0257208 A1 | 12/2004 | Huang et al. |
| 2004/0260470 A1 | 12/2004 | Rast |
| 2005/0012599 A1 | 1/2005 | DeMatteo |
| 2005/0031100 A1 | 2/2005 | Iggulden et al. |
| 2005/0038598 A1 | 2/2005 | Oesterling et al. |
| 2005/0042999 A1 | 2/2005 | Rappaport |
| 2005/0065678 A1 | 3/2005 | Smith et al. |
| 2005/0065711 A1 | 3/2005 | Dahlgren et al. |
| 2005/0086051 A1 | 4/2005 | Brulle-Drews |
| 2005/0093717 A1 | 5/2005 | Lilja |
| 2005/0097541 A1 | 5/2005 | Holland |
| 2005/0114864 A1 | 5/2005 | Surace |
| 2005/0122235 A1 | 6/2005 | Teffer et al. |
| 2005/0124211 A1 | 6/2005 | Diessner et al. |
| 2005/0130744 A1 | 6/2005 | Eck et al. |
| 2005/0144156 A1 | 6/2005 | Barber |
| 2005/0149752 A1 | 7/2005 | Johnson et al. |
| 2005/0153760 A1 | 7/2005 | Varley |
| 2005/0159853 A1 | 7/2005 | Takahashi et al. |
| 2005/0159892 A1 | 7/2005 | Chung |
| 2005/0192727 A1 | 9/2005 | Shostak et al. |
| 2005/0197748 A1 | 9/2005 | Holst et al. |
| 2005/0197767 A1 | 9/2005 | Nortrup |
| 2005/0251324 A1 | 11/2005 | Wiener et al. |
| 2005/0261815 A1 | 11/2005 | Cowelchuk et al. |
| 2005/0278093 A1 | 12/2005 | Kameyama |
| 2005/0283284 A1 | 12/2005 | Grenier et al. |
| 2006/0015819 A1 | 1/2006 | Hawkins et al. |
| 2006/0036358 A1 | 2/2006 | Hale et al. |
| 2006/0044119 A1 | 3/2006 | Egelhaaf |

(56) References Cited

U.S. PATENT DOCUMENTS

| | | |
|---|---|---|
| 2006/0047386 A1 | 3/2006 | Kanevsky et al. |
| 2006/0058948 A1 | 3/2006 | Blass et al. |
| 2006/0059229 A1 | 3/2006 | Bain et al. |
| 2006/0125631 A1 | 6/2006 | Sharony |
| 2006/0130033 A1 | 6/2006 | Stoffels et al. |
| 2006/0142933 A1 | 6/2006 | Feng |
| 2006/0173841 A1 | 8/2006 | Bill |
| 2006/0175403 A1 | 8/2006 | McConnell et al. |
| 2006/0184319 A1 | 8/2006 | Seick et al. |
| 2006/0212909 A1 | 9/2006 | Girard et al. |
| 2006/0241836 A1 | 10/2006 | Kachouh et al. |
| 2006/0243056 A1 | 11/2006 | Sundermeyer et al. |
| 2006/0250272 A1 | 11/2006 | Puamau |
| 2006/0253307 A1 | 11/2006 | Warren et al. |
| 2006/0259210 A1 | 11/2006 | Tanaka et al. |
| 2006/0274829 A1 | 12/2006 | Siemens et al. |
| 2006/0282204 A1 | 12/2006 | Breed |
| 2006/0287807 A1 | 12/2006 | Teffer |
| 2006/0287865 A1 | 12/2006 | Cross et al. |
| 2006/0288382 A1 | 12/2006 | Vitito |
| 2006/0290516 A1 | 12/2006 | Muehlsteff et al. |
| 2007/0001831 A1 | 1/2007 | Raz et al. |
| 2007/0002032 A1 | 1/2007 | Powers et al. |
| 2007/0010942 A1 | 1/2007 | Bill |
| 2007/0015485 A1 | 1/2007 | DeBiasio et al. |
| 2007/0028370 A1 | 2/2007 | Seng |
| 2007/0032225 A1 | 2/2007 | Konicek et al. |
| 2007/0057781 A1 | 3/2007 | Breed |
| 2007/0061057 A1 | 3/2007 | Huang et al. |
| 2007/0067614 A1 | 3/2007 | Berry et al. |
| 2007/0069880 A1 | 3/2007 | Best et al. |
| 2007/0083298 A1 | 4/2007 | Pierce et al. |
| 2007/0088488 A1 | 4/2007 | Reeves et al. |
| 2007/0103328 A1 | 5/2007 | Lakshmanan et al. |
| 2007/0115101 A1 | 5/2007 | Creekbaum et al. |
| 2007/0118301 A1 | 5/2007 | Andarawis et al. |
| 2007/0120697 A1 | 5/2007 | Ayoub et al. |
| 2007/0135995 A1 | 6/2007 | Kikuchi et al. |
| 2007/0156317 A1 | 7/2007 | Breed |
| 2007/0182625 A1 | 8/2007 | Kerai et al. |
| 2007/0182816 A1 | 8/2007 | Fox |
| 2007/0185969 A1 | 8/2007 | Davis |
| 2007/0192486 A1 | 8/2007 | Wilson et al. |
| 2007/0194902 A1 | 8/2007 | Blanco et al. |
| 2007/0194944 A1 | 8/2007 | Galera et al. |
| 2007/0195997 A1 | 8/2007 | Paul et al. |
| 2007/0200663 A1 | 8/2007 | White et al. |
| 2007/0208860 A1 | 9/2007 | Zellner et al. |
| 2007/0213090 A1 | 9/2007 | Holmberg |
| 2007/0228826 A1 | 10/2007 | Jordan et al. |
| 2007/0233341 A1 | 10/2007 | Logsdon |
| 2007/0250228 A1 | 10/2007 | Reddy et al. |
| 2007/0257815 A1 | 11/2007 | Gunderson et al. |
| 2007/0276596 A1 | 11/2007 | Solomon et al. |
| 2007/0280505 A1 | 12/2007 | Breed |
| 2008/0005974 A1 | 1/2008 | Delgado Vazquez et al. |
| 2008/0023253 A1 | 1/2008 | Prost-Fin et al. |
| 2008/0027337 A1 | 1/2008 | Dugan et al. |
| 2008/0033635 A1 | 2/2008 | Obradovich et al. |
| 2008/0042824 A1 | 2/2008 | Kates |
| 2008/0051957 A1 | 2/2008 | Breed et al. |
| 2008/0052627 A1 | 2/2008 | Oguchi |
| 2008/0071465 A1 | 3/2008 | Chapman et al. |
| 2008/0082237 A1 | 4/2008 | Breed |
| 2008/0086455 A1 | 4/2008 | Meisels et al. |
| 2008/0090522 A1 | 4/2008 | Oyama |
| 2008/0104227 A1 | 5/2008 | Birnie et al. |
| 2008/0119994 A1 | 5/2008 | Kameyama |
| 2008/0129475 A1 | 6/2008 | Breed et al. |
| 2008/0143085 A1 | 6/2008 | Breed et al. |
| 2008/0147280 A1 | 6/2008 | Breed |
| 2008/0148374 A1 | 6/2008 | Spaur et al. |
| 2008/0154712 A1 | 6/2008 | Wellman |
| 2008/0154957 A1 | 6/2008 | Taylor et al. |
| 2008/0161986 A1 | 7/2008 | Breed |
| 2008/0164985 A1 | 7/2008 | Iketani et al. |
| 2008/0169940 A1 | 7/2008 | Lee et al. |
| 2008/0174451 A1 | 7/2008 | Harrington et al. |
| 2008/0212215 A1 | 9/2008 | Schofield et al. |
| 2008/0216067 A1 | 9/2008 | Villing |
| 2008/0228358 A1 | 9/2008 | Wang et al. |
| 2008/0234919 A1 | 9/2008 | Ritter et al. |
| 2008/0252487 A1 | 10/2008 | McClellan et al. |
| 2008/0253613 A1 | 10/2008 | Jones et al. |
| 2008/0255721 A1 | 10/2008 | Yamada |
| 2008/0255722 A1 | 10/2008 | McClellan et al. |
| 2008/0269958 A1 | 10/2008 | Filev et al. |
| 2008/0281508 A1 | 11/2008 | Fu |
| 2008/0300778 A1 | 12/2008 | Kuznetsov |
| 2008/0305780 A1 | 12/2008 | Williams et al. |
| 2008/0319602 A1 | 12/2008 | McClellan et al. |
| 2009/0006525 A1 | 1/2009 | Moore |
| 2009/0024419 A1 | 1/2009 | McClellan et al. |
| 2009/0037719 A1 | 2/2009 | Sakthikumar et al. |
| 2009/0040026 A1 | 2/2009 | Tanaka |
| 2009/0055178 A1 | 2/2009 | Coon |
| 2009/0082951 A1 | 3/2009 | Graessley |
| 2009/0099720 A1 | 4/2009 | Elgali |
| 2009/0112393 A1 | 4/2009 | Maten et al. |
| 2009/0112452 A1 | 4/2009 | Buck et al. |
| 2009/0119657 A1 | 5/2009 | Link, II |
| 2009/0125174 A1 | 5/2009 | Delean |
| 2009/0132294 A1 | 5/2009 | Haines |
| 2009/0138336 A1 | 5/2009 | Ashley et al. |
| 2009/0144622 A1 | 6/2009 | Evans et al. |
| 2009/0157312 A1 | 6/2009 | Black et al. |
| 2009/0158200 A1 | 6/2009 | Palahnuk et al. |
| 2009/0180668 A1 | 7/2009 | Jones et al. |
| 2009/0189373 A1 | 7/2009 | Schramm et al. |
| 2009/0189979 A1 | 7/2009 | Smyth |
| 2009/0195370 A1 | 8/2009 | Huffman et al. |
| 2009/0210257 A1 | 8/2009 | Chalfant et al. |
| 2009/0216935 A1 | 8/2009 | Flick |
| 2009/0222200 A1 | 9/2009 | Link et al. |
| 2009/0224931 A1 | 9/2009 | Dietz et al. |
| 2009/0224942 A1 | 9/2009 | Goudy et al. |
| 2009/0234578 A1 | 9/2009 | Newby et al. |
| 2009/0241883 A1 | 10/2009 | Nagoshi et al. |
| 2009/0254446 A1 | 10/2009 | Chernyak |
| 2009/0264849 A1 | 10/2009 | La Croix |
| 2009/0275321 A1 | 11/2009 | Crowe |
| 2009/0278750 A1 | 11/2009 | Man et al. |
| 2009/0278915 A1 | 11/2009 | Kramer et al. |
| 2009/0279839 A1 | 11/2009 | Nakamura et al. |
| 2009/0284359 A1 | 11/2009 | Huang et al. |
| 2009/0287405 A1 | 11/2009 | Liu et al. |
| 2009/0299572 A1 | 12/2009 | Fujikawa et al. |
| 2009/0312998 A1 | 12/2009 | Berckmans et al. |
| 2009/0319181 A1 | 12/2009 | Khosravy et al. |
| 2010/0008053 A1 | 1/2010 | Osternack et al. |
| 2010/0023204 A1 | 1/2010 | Basir et al. |
| 2010/0035620 A1 | 2/2010 | Naden et al. |
| 2010/0036560 A1 | 2/2010 | Wright et al. |
| 2010/0042498 A1 | 2/2010 | Schalk |
| 2010/0052945 A1 | 3/2010 | Breed |
| 2010/0057337 A1 | 3/2010 | Fuchs |
| 2010/0066498 A1 | 3/2010 | Fenton |
| 2010/0069115 A1 | 3/2010 | Liu |
| 2010/0070338 A1 | 3/2010 | Siotia et al. |
| 2010/0077094 A1 | 3/2010 | Howarter et al. |
| 2010/0085213 A1 | 4/2010 | Turnock et al. |
| 2010/0087987 A1 | 4/2010 | Huang et al. |
| 2010/0090817 A1 | 4/2010 | Yamaguchi et al. |
| 2010/0097178 A1 | 4/2010 | Pisz et al. |
| 2010/0097239 A1 | 4/2010 | Campbell et al. |
| 2010/0097458 A1 | 4/2010 | Zhang et al. |
| 2010/0106344 A1 | 4/2010 | Edwards et al. |
| 2010/0106418 A1 | 4/2010 | Kindo et al. |
| 2010/0118025 A1 | 5/2010 | Smith et al. |
| 2010/0121570 A1 | 5/2010 | Tokue et al. |
| 2010/0121645 A1 | 5/2010 | Seitz et al. |
| 2010/0125387 A1 | 5/2010 | Sehyun et al. |
| 2010/0125405 A1 | 5/2010 | Chae et al. |
| 2010/0125811 A1 | 5/2010 | Moore et al. |

(56) References Cited

U.S. PATENT DOCUMENTS

| | | |
|---|---|---|
| 2010/0127847 A1 | 5/2010 | Evans et al. |
| 2010/0131300 A1 | 5/2010 | Collopy et al. |
| 2010/0134958 A1 | 6/2010 | Disaverio et al. |
| 2010/0136944 A1 | 6/2010 | Taylor et al. |
| 2010/0137037 A1 | 6/2010 | Basir |
| 2010/0144284 A1 | 6/2010 | Chutorash et al. |
| 2010/0145700 A1 | 6/2010 | Kennewick et al. |
| 2010/0145987 A1 | 6/2010 | Harper et al. |
| 2010/0152976 A1 | 6/2010 | White et al. |
| 2010/0169432 A1 | 7/2010 | Santori et al. |
| 2010/0174474 A1 | 7/2010 | Nagase |
| 2010/0179712 A1 | 7/2010 | Pepitone et al. |
| 2010/0185341 A1 | 7/2010 | Wilson et al. |
| 2010/0188831 A1 | 7/2010 | Ortel |
| 2010/0197359 A1 | 8/2010 | Harris |
| 2010/0202346 A1 | 8/2010 | Sitzes et al. |
| 2010/0211259 A1 | 8/2010 | McClellan |
| 2010/0211282 A1 | 8/2010 | Nakata et al. |
| 2010/0211300 A1 | 8/2010 | Jaffe et al. |
| 2010/0211304 A1 | 8/2010 | Hwang et al. |
| 2010/0211441 A1 | 8/2010 | Sprigg et al. |
| 2010/0217458 A1 | 8/2010 | Schweiger et al. |
| 2010/0222939 A1 | 9/2010 | Namburu et al. |
| 2010/0228404 A1 | 9/2010 | Link et al. |
| 2010/0234071 A1 | 9/2010 | Shabtay et al. |
| 2010/0235042 A1 | 9/2010 | Ying |
| 2010/0235744 A1 | 9/2010 | Schultz |
| 2010/0235891 A1 | 9/2010 | Oglesbee et al. |
| 2010/0250071 A1 | 9/2010 | Pala et al. |
| 2010/0253493 A1 | 10/2010 | Szczerba et al. |
| 2010/0256836 A1 | 10/2010 | Mudalige |
| 2010/0265104 A1 | 10/2010 | Zlojutro |
| 2010/0268426 A1 | 10/2010 | Pathak et al. |
| 2010/0274410 A1 | 10/2010 | Tsien et al. |
| 2010/0280751 A1 | 11/2010 | Breed |
| 2010/0287303 A1 | 11/2010 | Smith et al. |
| 2010/0289632 A1 | 11/2010 | Seder et al. |
| 2010/0289643 A1 | 11/2010 | Trundle et al. |
| 2010/0291427 A1 | 11/2010 | Zhou |
| 2010/0295676 A1 | 11/2010 | Khachaturov et al. |
| 2010/0304640 A1 | 12/2010 | Sofman et al. |
| 2010/0305807 A1 | 12/2010 | Basir et al. |
| 2010/0306080 A1 | 12/2010 | Trandal et al. |
| 2010/0306309 A1 | 12/2010 | Santori et al. |
| 2010/0306435 A1 | 12/2010 | Nigoghosian et al. |
| 2010/0315218 A1 | 12/2010 | Cades et al. |
| 2010/0321151 A1 | 12/2010 | Matsuura et al. |
| 2010/0325626 A1 | 12/2010 | Greschler et al. |
| 2010/0332130 A1 | 12/2010 | Shimizu et al. |
| 2011/0015853 A1 | 1/2011 | DeKock et al. |
| 2011/0018736 A1 | 1/2011 | Carr |
| 2011/0021213 A1 | 1/2011 | Carr |
| 2011/0021234 A1 | 1/2011 | Tibbits et al. |
| 2011/0028138 A1 | 2/2011 | Davies-Moore et al. |
| 2011/0035098 A1 | 2/2011 | Goto et al. |
| 2011/0035141 A1 | 2/2011 | Barker et al. |
| 2011/0040438 A1 | 2/2011 | Kluge et al. |
| 2011/0050589 A1 | 3/2011 | Yan et al. |
| 2011/0053506 A1 | 3/2011 | Lemke et al. |
| 2011/0077808 A1 | 3/2011 | Hyde et al. |
| 2011/0078024 A1 | 3/2011 | Messier et al. |
| 2011/0080282 A1 | 4/2011 | Kleve et al. |
| 2011/0082615 A1 | 4/2011 | Small et al. |
| 2011/0084824 A1 | 4/2011 | Tewari et al. |
| 2011/0090078 A1 | 4/2011 | Kim et al. |
| 2011/0092159 A1 | 4/2011 | Park et al. |
| 2011/0093154 A1 | 4/2011 | Moinzadeh et al. |
| 2011/0093158 A1 | 4/2011 | Theisen et al. |
| 2011/0093438 A1 | 4/2011 | Poulsen |
| 2011/0093846 A1 | 4/2011 | Moinzadeh et al. |
| 2011/0105097 A1 | 5/2011 | Tadayon et al. |
| 2011/0106375 A1 | 5/2011 | Sundaram et al. |
| 2011/0112717 A1 | 5/2011 | Resner |
| 2011/0112969 A1 | 5/2011 | Zaid et al. |
| 2011/0117933 A1 | 5/2011 | Andersson |
| 2011/0119344 A1 | 5/2011 | Eustis |
| 2011/0130915 A1 | 6/2011 | Wright et al. |
| 2011/0134749 A1 | 6/2011 | Speks et al. |
| 2011/0137520 A1 | 6/2011 | Rector et al. |
| 2011/0145331 A1 | 6/2011 | Christie et al. |
| 2011/0172873 A1 | 7/2011 | Szwabowski et al. |
| 2011/0175754 A1 | 7/2011 | Karpinsky |
| 2011/0183658 A1 | 7/2011 | Zellner |
| 2011/0187520 A1 | 8/2011 | Filev et al. |
| 2011/0193707 A1 | 8/2011 | Ngo |
| 2011/0193726 A1 | 8/2011 | Szwabowski et al. |
| 2011/0195699 A1 | 8/2011 | Tadayon et al. |
| 2011/0197187 A1 | 8/2011 | Roh |
| 2011/0205047 A1 | 8/2011 | Patel et al. |
| 2011/0209079 A1 | 8/2011 | Tarte et al. |
| 2011/0210867 A1 | 9/2011 | Benedikt |
| 2011/0212717 A1 | 9/2011 | Rhoads et al. |
| 2011/0221656 A1 | 9/2011 | Haddick et al. |
| 2011/0224865 A1 | 9/2011 | Gordon et al. |
| 2011/0224898 A1 | 9/2011 | Scofield et al. |
| 2011/0225527 A1 | 9/2011 | Law et al. |
| 2011/0227757 A1 | 9/2011 | Chen et al. |
| 2011/0231091 A1 | 9/2011 | Gourlay et al. |
| 2011/0234369 A1 | 9/2011 | Cai et al. |
| 2011/0245999 A1 | 10/2011 | Kordonowy |
| 2011/0246210 A1 | 10/2011 | Matsur |
| 2011/0247013 A1 | 10/2011 | Feller et al. |
| 2011/0251734 A1 | 10/2011 | Schepp et al. |
| 2011/0257973 A1 | 10/2011 | Chutorash et al. |
| 2011/0267204 A1 | 11/2011 | Chuang et al. |
| 2011/0267205 A1 | 11/2011 | McClellan et al. |
| 2011/0286676 A1 | 11/2011 | El Dokor |
| 2011/0291886 A1 | 12/2011 | Krieter |
| 2011/0291926 A1 | 12/2011 | Gokturk et al. |
| 2011/0298808 A1 | 12/2011 | Rovik |
| 2011/0301844 A1 | 12/2011 | Aono |
| 2011/0307354 A1 | 12/2011 | Erman et al. |
| 2011/0307570 A1 | 12/2011 | Speks |
| 2011/0309926 A1 | 12/2011 | Eikelenberg et al. |
| 2011/0309953 A1 | 12/2011 | Petite et al. |
| 2011/0313653 A1 | 12/2011 | Lindner |
| 2011/0320089 A1 | 12/2011 | Lewis |
| 2012/0006610 A1 | 1/2012 | Wallace et al. |
| 2012/0010807 A1 | 1/2012 | Zhou |
| 2012/0016581 A1 | 1/2012 | Mochizuki et al. |
| 2012/0029852 A1 | 2/2012 | Goff et al. |
| 2012/0030002 A1 | 2/2012 | Bous et al. |
| 2012/0030512 A1 | 2/2012 | Wadhwa et al. |
| 2012/0038489 A1 | 2/2012 | Goldshmidt |
| 2012/0046822 A1 | 2/2012 | Anderson |
| 2012/0047530 A1 | 2/2012 | Shkedi |
| 2012/0053793 A1 | 3/2012 | Sala et al. |
| 2012/0053888 A1 | 3/2012 | Stahlin et al. |
| 2012/0059789 A1 | 3/2012 | Sakai et al. |
| 2012/0065815 A1 | 3/2012 | Hess |
| 2012/0065834 A1 | 3/2012 | Senart |
| 2012/0068956 A1 | 3/2012 | Jira et al. |
| 2012/0071097 A1 | 3/2012 | Matsushita et al. |
| 2012/0072244 A1 | 3/2012 | Collins et al. |
| 2012/0074770 A1 | 3/2012 | Lee |
| 2012/0083960 A1 | 4/2012 | Zhu et al. |
| 2012/0083971 A1 | 4/2012 | Preston |
| 2012/0084773 A1 | 4/2012 | Lee et al. |
| 2012/0089299 A1 | 4/2012 | Breed |
| 2012/0092251 A1 | 4/2012 | Hashimoto et al. |
| 2012/0101876 A1 | 4/2012 | Turvey et al. |
| 2012/0101914 A1 | 4/2012 | Kumar et al. |
| 2012/0105613 A1 | 5/2012 | Weng et al. |
| 2012/0106114 A1 | 5/2012 | Caron et al. |
| 2012/0109446 A1 | 5/2012 | Yousefi et al. |
| 2012/0109451 A1 | 5/2012 | Tan |
| 2012/0110356 A1 | 5/2012 | Yousefi et al. |
| 2012/0113822 A1 | 5/2012 | Letner |
| 2012/0115446 A1 | 5/2012 | Guatama et al. |
| 2012/0116609 A1 | 5/2012 | Jung et al. |
| 2012/0116678 A1 | 5/2012 | Witmer |
| 2012/0116696 A1 | 5/2012 | Wank |
| 2012/0146766 A1 | 6/2012 | Geisler et al. |
| 2012/0146809 A1 | 6/2012 | Oh et al. |

(56) References Cited

U.S. PATENT DOCUMENTS

| | | |
|---|---|---|
| 2012/0149341 A1 | 6/2012 | Tadayon et al. |
| 2012/0150651 A1 | 6/2012 | Hoffberg et al. |
| 2012/0155636 A1 | 6/2012 | Muthaiah |
| 2012/0158436 A1 | 6/2012 | Bauer et al. |
| 2012/0173900 A1 | 7/2012 | Diab et al. |
| 2012/0173905 A1 | 7/2012 | Diab et al. |
| 2012/0179325 A1 | 7/2012 | Faenger |
| 2012/0179547 A1 | 7/2012 | Besore et al. |
| 2012/0188876 A1 | 7/2012 | Chow et al. |
| 2012/0197523 A1 | 8/2012 | Kirsch |
| 2012/0197669 A1 | 8/2012 | Kote et al. |
| 2012/0204166 A1 | 8/2012 | Ichihara |
| 2012/0210160 A1 | 8/2012 | Fuhrman |
| 2012/0215375 A1 | 8/2012 | Chang |
| 2012/0217928 A1 | 8/2012 | Kulidjian |
| 2012/0218125 A1 | 8/2012 | Demirdjian et al. |
| 2012/0226413 A1 | 9/2012 | Chen et al. |
| 2012/0238286 A1 | 9/2012 | Mallavarapu et al. |
| 2012/0239242 A1 | 9/2012 | Uehara |
| 2012/0242510 A1 | 9/2012 | Choi et al. |
| 2012/0254763 A1 | 10/2012 | Protopapas et al. |
| 2012/0254804 A1 | 10/2012 | Shema et al. |
| 2012/0259951 A1 | 10/2012 | Schalk et al. |
| 2012/0265359 A1 | 10/2012 | Das |
| 2012/0274459 A1 | 11/2012 | Jaisimha et al. |
| 2012/0274481 A1 | 11/2012 | Ginsberg et al. |
| 2012/0284292 A1 | 11/2012 | Rechsteiner et al. |
| 2012/0289217 A1 | 11/2012 | Reimer et al. |
| 2012/0289253 A1 | 11/2012 | Haag et al. |
| 2012/0296567 A1 | 11/2012 | Breed |
| 2012/0313771 A1 | 12/2012 | Wottlifff, III |
| 2012/0316720 A1 | 12/2012 | Hyde et al. |
| 2012/0317561 A1 | 12/2012 | Aslam et al. |
| 2012/0323413 A1 | 12/2012 | Kedar-Dongarkar et al. |
| 2012/0327231 A1 | 12/2012 | Cochran et al. |
| 2013/0005263 A1 | 1/2013 | Sakata |
| 2013/0005414 A1 | 1/2013 | Bindra et al. |
| 2013/0013157 A1 | 1/2013 | Kim et al. |
| 2013/0019252 A1 | 1/2013 | Haase et al. |
| 2013/0024060 A1 | 1/2013 | Sukkarie et al. |
| 2013/0030645 A1 | 1/2013 | Divine et al. |
| 2013/0030811 A1 | 1/2013 | Olleon et al. |
| 2013/0031540 A1 | 1/2013 | Throop et al. |
| 2013/0031541 A1 | 1/2013 | Wilks et al. |
| 2013/0035063 A1 | 2/2013 | Fisk et al. |
| 2013/0046624 A1 | 2/2013 | Calman |
| 2013/0050069 A1 | 2/2013 | Ota |
| 2013/0055096 A1 | 2/2013 | Kim et al. |
| 2013/0059607 A1 | 3/2013 | Herz et al. |
| 2013/0063336 A1 | 3/2013 | Sugimoto et al. |
| 2013/0066512 A1 | 3/2013 | Willard et al. |
| 2013/0067599 A1 | 3/2013 | Raje et al. |
| 2013/0075530 A1 | 3/2013 | Shander et al. |
| 2013/0079964 A1 | 3/2013 | Sukkarie et al. |
| 2013/0083805 A1 | 4/2013 | Lu et al. |
| 2013/0085787 A1 | 4/2013 | Gore et al. |
| 2013/0086164 A1 | 4/2013 | Wheeler et al. |
| 2013/0099915 A1 | 4/2013 | Prasad et al. |
| 2013/0103196 A1 | 4/2013 | Monceaux et al. |
| 2013/0105264 A1 | 5/2013 | Ruth et al. |
| 2013/0116882 A1 | 5/2013 | Link et al. |
| 2013/0116915 A1 | 5/2013 | Ferreira et al. |
| 2013/0134730 A1 | 5/2013 | Ricci |
| 2013/0135118 A1 | 5/2013 | Ricci |
| 2013/0138591 A1 | 5/2013 | Ricci |
| 2013/0138714 A1 | 5/2013 | Ricci |
| 2013/0139140 A1 | 5/2013 | Rao et al. |
| 2013/0141247 A1 | 6/2013 | Ricci |
| 2013/0141252 A1 | 6/2013 | Ricci |
| 2013/0143495 A1 | 6/2013 | Ricci |
| 2013/0143546 A1 | 6/2013 | Ricci |
| 2013/0143601 A1 | 6/2013 | Ricci |
| 2013/0144459 A1 | 6/2013 | Ricci |
| 2013/0144460 A1 | 6/2013 | Ricci |
| 2013/0144461 A1 | 6/2013 | Ricci |
| 2013/0144462 A1 | 6/2013 | Ricci |
| 2013/0144463 A1 | 6/2013 | Ricci et al. |
| 2013/0144469 A1 | 6/2013 | Ricci |
| 2013/0144470 A1 | 6/2013 | Ricci |
| 2013/0144474 A1 | 6/2013 | Ricci |
| 2013/0144486 A1 | 6/2013 | Ricci |
| 2013/0144520 A1 | 6/2013 | Ricci |
| 2013/0144657 A1 | 6/2013 | Ricci |
| 2013/0145065 A1 | 6/2013 | Ricci |
| 2013/0145279 A1 | 6/2013 | Ricci |
| 2013/0145297 A1 | 6/2013 | Ricci et al. |
| 2013/0145360 A1 | 6/2013 | Ricci |
| 2013/0145401 A1 | 6/2013 | Ricci |
| 2013/0145482 A1 | 6/2013 | Ricci et al. |
| 2013/0147638 A1 | 6/2013 | Ricci |
| 2013/0151031 A1 | 6/2013 | Ricci |
| 2013/0151065 A1 | 6/2013 | Ricci |
| 2013/0151088 A1 | 6/2013 | Ricci |
| 2013/0151288 A1 | 6/2013 | Bowne et al. |
| 2013/0152003 A1 | 6/2013 | Ricci et al. |
| 2013/0154298 A1 | 6/2013 | Ricci |
| 2013/0157640 A1 | 6/2013 | Aycock |
| 2013/0157647 A1 | 6/2013 | Kolodziej |
| 2013/0158778 A1 | 6/2013 | Tengler et al. |
| 2013/0158821 A1 | 6/2013 | Ricci |
| 2013/0166096 A1 | 6/2013 | Jotanovic |
| 2013/0166097 A1 | 6/2013 | Ricci |
| 2013/0166098 A1 | 6/2013 | Lavie et al. |
| 2013/0166152 A1 | 6/2013 | Butterworth |
| 2013/0166208 A1 | 6/2013 | Forstall et al. |
| 2013/0167159 A1 | 6/2013 | Ricci et al. |
| 2013/0173531 A1 | 7/2013 | Rinearson et al. |
| 2013/0179689 A1 | 7/2013 | Matsumoto et al. |
| 2013/0181847 A1 | 7/2013 | Willig et al. |
| 2013/0190978 A1 | 7/2013 | Kato et al. |
| 2013/0194108 A1 | 8/2013 | Lapiotis et al. |
| 2013/0197796 A1 | 8/2013 | Obradovich et al. |
| 2013/0198031 A1 | 8/2013 | Mitchell et al. |
| 2013/0198737 A1 | 8/2013 | Ricci |
| 2013/0198802 A1 | 8/2013 | Ricci |
| 2013/0200991 A1 | 8/2013 | Ricci et al. |
| 2013/0203400 A1 | 8/2013 | Ricci |
| 2013/0204455 A1 | 8/2013 | Chia et al. |
| 2013/0204457 A1 | 8/2013 | King |
| 2013/0204466 A1 | 8/2013 | Ricci |
| 2013/0204484 A1 | 8/2013 | Ricci |
| 2013/0204493 A1 | 8/2013 | Ricci et al. |
| 2013/0204943 A1 | 8/2013 | Ricci |
| 2013/0205026 A1 | 8/2013 | Ricci |
| 2013/0205412 A1 | 8/2013 | Ricci |
| 2013/0207794 A1 | 8/2013 | Patel et al. |
| 2013/0212065 A1 | 8/2013 | Rahnama |
| 2013/0212659 A1 | 8/2013 | Maher et al. |
| 2013/0215116 A1 | 8/2013 | Siddique et al. |
| 2013/0218412 A1 | 8/2013 | Ricci |
| 2013/0218445 A1 | 8/2013 | Basir |
| 2013/0219039 A1 | 8/2013 | Ricci |
| 2013/0226365 A1 | 8/2013 | Brozovich |
| 2013/0226371 A1 | 8/2013 | Rovik et al. |
| 2013/0226392 A1 | 8/2013 | Schneider et al. |
| 2013/0226449 A1 | 8/2013 | Rovik et al. |
| 2013/0226622 A1 | 8/2013 | Adamson et al. |
| 2013/0227648 A1 | 8/2013 | Ricci |
| 2013/0231784 A1 | 9/2013 | Rovik et al. |
| 2013/0231800 A1 | 9/2013 | Ricci |
| 2013/0232142 A1 | 9/2013 | Nielsen et al. |
| 2013/0238165 A1 | 9/2013 | Garrett et al. |
| 2013/0241720 A1 | 9/2013 | Ricci et al. |
| 2013/0245882 A1 | 9/2013 | Ricci |
| 2013/0250933 A1 | 9/2013 | Yousefi et al. |
| 2013/0261871 A1 | 10/2013 | Hobbs et al. |
| 2013/0261966 A1 | 10/2013 | Wang et al. |
| 2013/0265178 A1 | 10/2013 | Tengler et al. |
| 2013/0274997 A1 | 10/2013 | Chien |
| 2013/0279111 A1 | 10/2013 | Lee |
| 2013/0279491 A1 | 10/2013 | Rubin et al. |
| 2013/0282238 A1 | 10/2013 | Ricci et al. |
| 2013/0282357 A1 | 10/2013 | Rubin et al. |
| 2013/0282946 A1 | 10/2013 | Ricci |

(56) References Cited

U.S. PATENT DOCUMENTS

| | | |
|---|---|---|
| 2013/0288606 A1 | 10/2013 | Kirsch |
| 2013/0293364 A1 | 11/2013 | Ricci et al. |
| 2013/0293452 A1 | 11/2013 | Ricci et al. |
| 2013/0293480 A1 | 11/2013 | Kritt et al. |
| 2013/0295901 A1 | 11/2013 | Abramson et al. |
| 2013/0295908 A1 | 11/2013 | Zeinstra et al. |
| 2013/0295913 A1 | 11/2013 | Matthews et al. |
| 2013/0300554 A1 | 11/2013 | Braden |
| 2013/0301584 A1 | 11/2013 | Addepalli et al. |
| 2013/0304371 A1 | 11/2013 | Kitatani et al. |
| 2013/0308265 A1 | 11/2013 | Arnouse |
| 2013/0309977 A1 | 11/2013 | Heines et al. |
| 2013/0311038 A1 | 11/2013 | Kim et al. |
| 2013/0325453 A1 | 12/2013 | Levien et al. |
| 2013/0325568 A1 | 12/2013 | Mangalvedkar et al. |
| 2013/0329372 A1 | 12/2013 | Wilkins |
| 2013/0332023 A1 | 12/2013 | Bertosa et al. |
| 2013/0338914 A1 | 12/2013 | Weiss |
| 2013/0339027 A1 | 12/2013 | Dokor et al. |
| 2013/0344856 A1 | 12/2013 | Silver et al. |
| 2013/0345929 A1 | 12/2013 | Bowden et al. |
| 2014/0028542 A1 | 1/2014 | Lovitt et al. |
| 2014/0032014 A1 | 1/2014 | DeBiasio et al. |
| 2014/0054957 A1 | 2/2014 | Bellis |
| 2014/0058672 A1 | 2/2014 | Wansley et al. |
| 2014/0066014 A1 | 3/2014 | Nicholson et al. |
| 2014/0067201 A1 | 3/2014 | Visintainer et al. |
| 2014/0067564 A1 | 3/2014 | Yuan |
| 2014/0070917 A1 | 3/2014 | Protopapas |
| 2014/0081544 A1 | 3/2014 | Fry |
| 2014/0088798 A1 | 3/2014 | Himmelstein |
| 2014/0096068 A1 | 4/2014 | Dewan et al. |
| 2014/0097955 A1 | 4/2014 | Lovitt et al. |
| 2014/0109075 A1 | 4/2014 | Hoffman et al. |
| 2014/0109080 A1 | 4/2014 | Ricci |
| 2014/0120829 A1 | 5/2014 | Bhamidipati et al. |
| 2014/0121862 A1 | 5/2014 | Zarrella et al. |
| 2014/0125802 A1 | 5/2014 | Beckert et al. |
| 2014/0143839 A1 | 5/2014 | Ricci |
| 2014/0164611 A1 | 6/2014 | Molettiere et al. |
| 2014/0168062 A1 | 6/2014 | Katz et al. |
| 2014/0168436 A1 | 6/2014 | Pedicino |
| 2014/0169621 A1 | 6/2014 | Burr |
| 2014/0171752 A1 | 6/2014 | Park et al. |
| 2014/0172727 A1 | 6/2014 | Abhyanker et al. |
| 2014/0188533 A1 | 7/2014 | Davidson |
| 2014/0195272 A1 | 7/2014 | Sadiq et al. |
| 2014/0198216 A1 | 7/2014 | Zhai et al. |
| 2014/0200737 A1 | 7/2014 | Lortz et al. |
| 2014/0207328 A1 | 7/2014 | Wolf et al. |
| 2014/0220966 A1 | 8/2014 | Muetzel et al. |
| 2014/0222298 A1 | 8/2014 | Gurin |
| 2014/0223384 A1 | 8/2014 | Graumann |
| 2014/0240089 A1 | 8/2014 | Chang |
| 2014/0244078 A1 | 8/2014 | Downey et al. |
| 2014/0244111 A1 | 8/2014 | Gross et al. |
| 2014/0244156 A1 | 8/2014 | Magnusson et al. |
| 2014/0245277 A1 | 8/2014 | Petro et al. |
| 2014/0245278 A1 | 8/2014 | Zellen |
| 2014/0245284 A1 | 8/2014 | Alrabady et al. |
| 2014/0252091 A1 | 9/2014 | Morse et al. |
| 2014/0257627 A1 | 9/2014 | Hagan, Jr. |
| 2014/0267035 A1 | 9/2014 | Schalk et al. |
| 2014/0277936 A1 | 9/2014 | El Dokor et al. |
| 2014/0278070 A1 | 9/2014 | McGavran et al. |
| 2014/0278071 A1 | 9/2014 | San Filippo et al. |
| 2014/0281971 A1 | 9/2014 | Isbell, III et al. |
| 2014/0282161 A1 | 9/2014 | Cash |
| 2014/0282278 A1 | 9/2014 | Anderson et al. |
| 2014/0282470 A1 | 9/2014 | Buga et al. |
| 2014/0282931 A1 | 9/2014 | Protopapas |
| 2014/0292545 A1 | 10/2014 | Nemoto |
| 2014/0292665 A1 | 10/2014 | Lathrop et al. |
| 2014/0303899 A1 | 10/2014 | Fung |
| 2014/0306799 A1 | 10/2014 | Ricci |
| 2014/0306814 A1 | 10/2014 | Ricci |
| 2014/0306817 A1 | 10/2014 | Ricci |
| 2014/0306826 A1 | 10/2014 | Ricci |
| 2014/0306833 A1 | 10/2014 | Ricci |
| 2014/0306834 A1 | 10/2014 | Ricci |
| 2014/0306835 A1 | 10/2014 | Ricci |
| 2014/0307655 A1 | 10/2014 | Ricci |
| 2014/0307724 A1 | 10/2014 | Ricci |
| 2014/0308902 A1 | 10/2014 | Ricci |
| 2014/0309789 A1 | 10/2014 | Ricci |
| 2014/0309790 A1 | 10/2014 | Ricci |
| 2014/0309804 A1 | 10/2014 | Ricci |
| 2014/0309805 A1 | 10/2014 | Ricci |
| 2014/0309806 A1 | 10/2014 | Ricci |
| 2014/0309813 A1 | 10/2014 | Ricci |
| 2014/0309814 A1 | 10/2014 | Ricci et al. |
| 2014/0309815 A1 | 10/2014 | Ricci et al. |
| 2014/0309838 A1 | 10/2014 | Ricci |
| 2014/0309839 A1 | 10/2014 | Ricci et al. |
| 2014/0309842 A1 | 10/2014 | Jefferies et al. |
| 2014/0309847 A1 | 10/2014 | Ricci |
| 2014/0309849 A1 | 10/2014 | Ricci |
| 2014/0309852 A1 | 10/2014 | Ricci |
| 2014/0309853 A1 | 10/2014 | Ricci |
| 2014/0309862 A1 | 10/2014 | Ricci |
| 2014/0309863 A1 | 10/2014 | Ricci |
| 2014/0309864 A1 | 10/2014 | Ricci |
| 2014/0309865 A1 | 10/2014 | Ricci |
| 2014/0309866 A1 | 10/2014 | Ricci |
| 2014/0309867 A1 | 10/2014 | Ricci |
| 2014/0309868 A1 | 10/2014 | Ricci |
| 2014/0309869 A1 | 10/2014 | Ricci |
| 2014/0309870 A1 | 10/2014 | Ricci et al. |
| 2014/0309871 A1 | 10/2014 | Ricci |
| 2014/0309872 A1 | 10/2014 | Ricci |
| 2014/0309873 A1 | 10/2014 | Ricci |
| 2014/0309874 A1 | 10/2014 | Ricci |
| 2014/0309875 A1 | 10/2014 | Ricci |
| 2014/0309876 A1 | 10/2014 | Ricci |
| 2014/0309877 A1 | 10/2014 | Ricci |
| 2014/0309878 A1 | 10/2014 | Ricci |
| 2014/0309879 A1 | 10/2014 | Ricci |
| 2014/0309880 A1 | 10/2014 | Ricci |
| 2014/0309885 A1 | 10/2014 | Ricci |
| 2014/0309886 A1 | 10/2014 | Ricci |
| 2014/0309891 A1 | 10/2014 | Ricci |
| 2014/0309892 A1 | 10/2014 | Ricci |
| 2014/0309893 A1 | 10/2014 | Ricci |
| 2014/0309913 A1 | 10/2014 | Ricci et al. |
| 2014/0309919 A1 | 10/2014 | Ricci |
| 2014/0309920 A1 | 10/2014 | Ricci |
| 2014/0309921 A1 | 10/2014 | Ricci et al. |
| 2014/0309922 A1 | 10/2014 | Ricci |
| 2014/0309923 A1 | 10/2014 | Ricci |
| 2014/0309927 A1 | 10/2014 | Ricci |
| 2014/0309929 A1 | 10/2014 | Ricci |
| 2014/0309930 A1 | 10/2014 | Ricci |
| 2014/0309934 A1 | 10/2014 | Ricci |
| 2014/0309935 A1 | 10/2014 | Ricci |
| 2014/0309982 A1 | 10/2014 | Ricci |
| 2014/0310031 A1 | 10/2014 | Ricci |
| 2014/0310075 A1 | 10/2014 | Ricci |
| 2014/0310103 A1 | 10/2014 | Ricci |
| 2014/0310186 A1 | 10/2014 | Ricci |
| 2014/0310277 A1 | 10/2014 | Ricci |
| 2014/0310379 A1 | 10/2014 | Ricci et al. |
| 2014/0310594 A1 | 10/2014 | Ricci et al. |
| 2014/0310610 A1 | 10/2014 | Ricci |
| 2014/0310702 A1 | 10/2014 | Ricci et al. |
| 2014/0310739 A1 | 10/2014 | Ricci et al. |
| 2014/0310788 A1 | 10/2014 | Ricci |
| 2014/0322676 A1 | 10/2014 | Raman |
| 2014/0347207 A1 | 11/2014 | Zeng et al. |
| 2014/0347265 A1 | 11/2014 | Allen et al. |
| 2015/0007155 A1 | 1/2015 | Hoffman et al. |
| 2015/0012186 A1 | 1/2015 | Horseman |
| 2015/0032366 A1 | 1/2015 | Man et al. |
| 2015/0032670 A1 | 1/2015 | Brazell |
| 2015/0057839 A1 | 2/2015 | Chang et al. |

(56) References Cited

U.S. PATENT DOCUMENTS

| | | |
|---|---|---|
| 2015/0061895 A1 | 3/2015 | Ricci |
| 2015/0081133 A1 | 3/2015 | Schulz |
| 2015/0081167 A1 | 3/2015 | Pisz et al. |
| 2015/0088423 A1 | 3/2015 | Tuukkanen |
| 2015/0088515 A1 | 3/2015 | Beaumont et al. |
| 2015/0116200 A1 | 4/2015 | Kurosawa et al. |
| 2015/0146605 A1 | 5/2015 | Rubin et al. |
| 2015/0158499 A1 | 6/2015 | Koravadi |
| 2015/0178034 A1 | 6/2015 | Penilla et al. |
| 2015/0363986 A1 | 12/2015 | Hoyos et al. |
| 2016/0008985 A1 | 1/2016 | Kim et al. |
| 2016/0070527 A1 | 3/2016 | Ricci |
| 2016/0086391 A1 | 3/2016 | Ricci |
| 2016/0269456 A1 | 9/2016 | Ricci |
| 2016/0269469 A1 | 9/2016 | Ricci |
| 2017/0136880 A1* | 5/2017 | Ricci ............... B60L 3/0015 |
| 2017/0136887 A1* | 5/2017 | Ricci ............... B60L 11/182 |
| 2017/0136902 A1* | 5/2017 | Ricci ............... B60L 11/1825 |
| 2017/0136903 A1* | 5/2017 | Ricci ............... B60L 11/1827 |
| 2017/0136904 A1* | 5/2017 | Ricci ............... B60L 11/1827 |
| 2017/0136905 A1* | 5/2017 | Ricci ............... B60L 11/1829 |
| 2017/0136907 A1* | 5/2017 | Ricci ............... B60L 3/0015 |
| 2017/0136910 A1* | 5/2017 | Ricci ............... B60L 11/1844 |
| 2018/0012279 A1* | 1/2018 | Ricci ............... G06Q 30/0625 |

FOREIGN PATENT DOCUMENTS

| | | |
|---|---|---|
| CN | 101303878 | 11/2008 |
| CN | 102467827 | 5/2012 |
| EP | 1223567 | 7/2002 |
| EP | 1484729 | 12/2004 |
| EP | 2192015 | 6/2010 |
| JP | 2004-284450 | 10/2004 |
| KR | 2006-0128484 | 12/2006 |
| WO | WO 2007/126204 | 11/2007 |
| WO | WO 2012/102879 | 8/2012 |
| WO | WO 2013/074866 | 5/2013 |
| WO | WO 2013/074867 | 5/2013 |
| WO | WO 2013/074868 | 5/2013 |
| WO | WO 2013/074897 | 5/2013 |
| WO | WO 2013/074899 | 5/2013 |
| WO | WO 2013/074901 | 5/2013 |
| WO | WO 2013/074919 | 5/2013 |
| WO | WO 2013/074981 | 5/2013 |
| WO | WO 2013/074983 | 5/2013 |
| WO | WO 2013/075005 | 5/2013 |
| WO | WO 2013/181310 | 12/2013 |
| WO | WO 2014/014862 | 1/2014 |
| WO | WO 2014/143563 | 9/2014 |
| WO | WO 2014/158667 | 10/2014 |
| WO | WO 2014/158672 | 10/2014 |
| WO | WO 2014/158766 | 10/2014 |
| WO | WO 2014/172312 | 10/2014 |
| WO | WO 2014/172313 | 10/2014 |
| WO | WO 2014/172316 | 10/2014 |
| WO | WO 2014/172320 | 10/2014 |
| WO | WO 2014/172322 | 10/2014 |
| WO | WO 2014/172323 | 10/2014 |
| WO | WO 2014/172327 | 10/2014 |
| WO | WO 2016/145073 | 9/2016 |
| WO | WO 2016/145100 | 9/2016 |

OTHER PUBLICATIONS

U.S. Appl. No. 15/396,591, filed Dec. 31, 2016, Ricci.
U.S. Appl. No. 15/396,592, filed Dec. 31, 2016, Ricci.
U.S. Appl. No. 15/396,595, filed Dec. 31, 2016, Ricci.
U.S. Appl. No. 15/396,597, filed Dec. 31, 2016, Ricci.
U.S. Appl. No. 15/396,601, filed Dec. 31, 2016, Ricci.
U.S. Appl. No. 15/396,604, filed Dec. 31, 2016, Ricci.
U.S. Appl. No. 15/396,607, filed Dec. 31, 2016, Ricci.
U.S. Appl. No. 15/396,610, filed Dec. 31, 2016, Ricci.
U.S. Appl. No. 15/396,613, filed Dec. 31, 2016, Ricci.
U.S. Appl. No. 15/396,616, filed Dec. 31, 2016, Ricci.
"How NFC Works," Near Field Communication, retrieved from http://nearfieldcommunication.org/how-it-works.html, retrieved on Sep. 27, 2016, 1 page.
"Near Field Communication Technology Standards," Near Field Communication, retrieved from http://nearfieldcommunication.org/technology.html, retrieved on Sep. 27, 2016, 1 page.
"Near Field Communication versus Bluetooth," Near Field Communication, retrieved from http://nearfieldcommunication.org/bluetooth.html, retrieved on Sep. 27, 2016, 1 page.
"Near Field versus Far Field," Near Field Communication, retrieved from http://nearfieldcommunication.org/far-field.html, retrieved on Sep. 27, 2016, 1 page.
"NFC SD and SIM Cards," Near Field Communication, retrieved from http://nearfieldcommunication.org/sd-sim-cards.html, retrieved on Sep. 27, 2016, 1 page.
Profis, "Everything you need to know about NFC and mobile payments," CNET, 2014, retrieved from https://www.cnet.com/how-to/how-nfc-works-and-mobile-payments/, 8 pages.
Strickland, "How Near Field Communication Works," Near Field Communication, retrieved from http://electronics.howstuffworks.com/near-field-communication.htm, retrieved on Sep. 27, 2016, 11 pages.
U.S. Appl. No. 61/567,962, filed Dec. 7, 2011, Baarman et al.
"Nexus 10 Guidebook for Android," Google Inc., © 2012, Edition 1.2, 166 pages.
"Self-Driving: Self-Driving Autonomous Cars," available at http://www.automotivetechnologies.com/autonomous-self-driving-cars, accessed Dec. 2016, 9 pages.
Amor-Segan et al., "Towards the Self Healing Vehicle," Automotive Electronics, Jun. 2007, 2007 3rd Institution of Engineering and Technology Conference, 7 pages.
Bennett, "Meet Samsung's Version of Apple AirPlay," CNET.com, Oct. 10, 2012, 11 pages.
Cairnie et al., "Using Finger-Pointing to Operate Secondary Controls in Automobiles," Proceedings of the IEEE Intelligent Vehicles Symposium 2000, Oct. 3-5, 2000, 6 pages.
Clark, "How Self-Driving Cars Work: The Nuts and Bolts Behind Google's Autonomous Car Program," Feb. 21, 2015, available at http://www.makeuseof.com/tag/how-self-driving-cars-work-the-nuts-and-bolts-behind-googles-autonomous-car-program/, 9 pages.
Deaton et al., "How Driverless Cars Will Work," Jul. 1, 2008, HowStuffWorks.com. <http://auto.howstuffworks.com/under-the-hood/trends-innovations/driverless-car.htm> Sep. 18, 2017, 10 pages.
Dumbaugh, "Safe Streets, Livable Streets: A Positive Approach to urban Roadside Design," Ph.D. dissertation for School of Civil & Environ. Engr., Georgia Inst. of Technology, Dec. 2005, 235 pages.
Fei et al., "A QoS-aware Dynamic Bandwidth Allocation Algorithm for Relay Stations in IEEE 802.16j-based Vehicular Networks," Proceedings of the 2010 IEEE Global Telecommunications Conference, Dec. 10, 2010, 10 pages.
Ge et al., "Optimal Relay Selection in IEEE 802.16j Multihop Relay Vehicular Networks," IEEE Transactions on Vehicular Technology, 2010, vol. 59(5), pp. 2198-2206.
Guizzo, Erico, "How Google's Self-Driving Car Works," Oct. 18, 2011, available at https://spectrum.ieee.org/automaton/robotics/artificial-intelligence/how-google-self-driving-car-works, 5 pages.
Heer et al., "ALPHA: An Adaptive and Lightweight Protocol for Hop-by-hop Authentication," Proceedings of CoNEXT 2008, Dec. 2008, pp. 1-12.
Jaiinich et al., "Towards a Middleware Approach for a Self-Configurable Automotive Embedded System," International Federation for Information Processing, 2008, pp. 55-65.
Persson "Adaptive Middleware for Self-Configurable Embedded Real-Time Systems," KTH Industrial Engineering and Management, 2009, pp. iii-71 and references.
Raychaudhuri et al., "Emerging Wireless Technologies and the Future Mobile Internet," p. 48, Cambridge Press, 2011, 3 pages.
Stephens, Leah, "How Driverless Cars Work," Interesting Engineering, Apr. 28, 2016, available at https://interestingengineering.com/driverless-cars-work/, 7 pages.

(56) References Cited

OTHER PUBLICATIONS

Stoller, "Leader Election in Distributed Systems with Crash Failures," Indiana University, 1997, pp. 1-15.
Strunk et al., "The Elements of Style," 3d ed., Macmillan Publishing Co., 1979, 3 pages.
Suwatthikul, "Fault detection and diagnosis for in-vehicle networks," Intech, 2010, pp. 283-286 [retrieved from: www.intechopen.com/books/fault-detection-and-diagnosis-for-in-vehicle-networks].
Walter et al., "The smart car seat: personalized monitoring of vital signs in automotive applications." Personal and Ubiquitous Computing, Oct. 2011, vol. 15, No. 7, pp. 707-715.
Wolf et al., "Design, Implementation, and Evaluation of a Vehicular Hardware Security Module," ICISC'11 Proceedings of the 14th Int'l Conf. Information Security & Cryptology, Springer-Verlag Berlin, Heidelberg, 2011, pp. 302-318.
International Search Report and Written Opinion for PCT Application No. PCT/US2017/041061, dated Sep. 14, 2017, 8 pages.
Official Action for U.S. Appl. No. 15/396,616, dated Aug. 24, 2017, 8 pages.
Notice of Allowance for U.S. Appl. No. 15/396,616, dated Jan. 24, 2018, 9 pages.

\* cited by examiner

| | Charging Type | Compatible Vehicle Charging Panel Types | Compatible Vehicle Storage Units | Available Automation Level | Charging Service Status | Charge Rate | Cost | Other | Shielding |
|---|---|---|---|---|---|---|---|---|---|
| 310J | Station: manual | Roof, Side | x, z | Low | Up | Low | $100 | A, B, C | On |
| | Station: manual | Roof, Side | x, z | Low | Up | Medium | $150 | A, C | On |
| | Station: manual | Roof, Side | x, z | Low | Up | High | $400 | A, B, C | On |
| 310K | Station: robotic | Roof, Side | x, z | Medium | Down | Medium | $150 | A, B, D | On |
| | Station: robotic | Roof, Side | x, z | High | Down | High | $500 | B, D | On |
| | Station: robotic | Roof, Side | x, z | High | Down | High | $500 | B, C | On |
| 310L | Roadway | Side, Lower | x, z | Low | Up | Low | $50 | A, C, E | Off |
| | Roadway | Side, Lower | x, z | Medium | Up | Low | $100 | A, C, E | Off |
| | Roadway | Side, Lower | x, z | Medium | Up | Low | $100 | A, C, E | Off |
| 310M | Emergency: truck | Roof, Side, Lower | x, y | Low | Up | Low | $150 | A, B | Off |
| | Emergency: truck | Roof, Side, Lower | x, y | Medium | Up | Medium | $200 | A, B | Off |
| | Emergency: truck | Roof, Side, Lower | x, y | Medium | Up | High | $500 | A, D | Off |
| 310N | Emergency: UAV | Roof | x | High | Down | Medium | $500 | A, B, C | Off |
| | Emergency: UAV | Roof | x | High | Down | High | $800 | B | Off |
| | Emergency: UAV | Roof | x | Low | Down | High | $800 | B | Off |
| 310O | Overhead | Roof | x, y | Low | Up | Low | $150 | B, D | Off |
| | Overhead | Roof | x, y | Medium | Up | Low | $200 | B, C | Off |
| | Overhead | Roof | x, y | Medium | Up | Low | $200 | B, C | Off |

*Fig. 3*

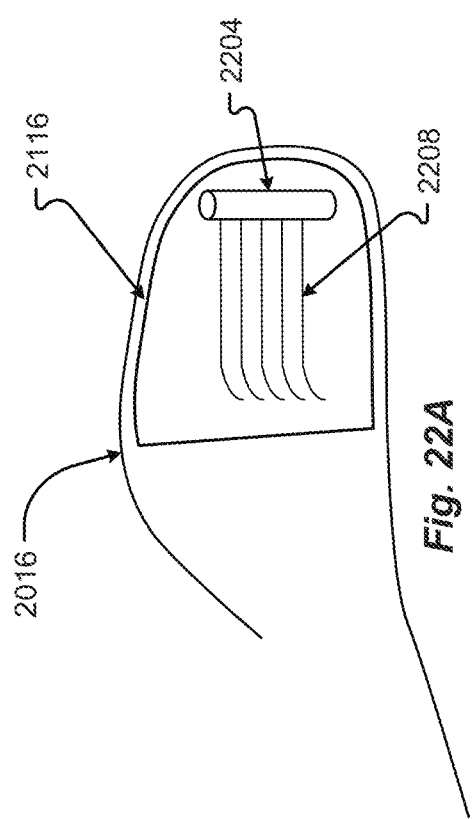
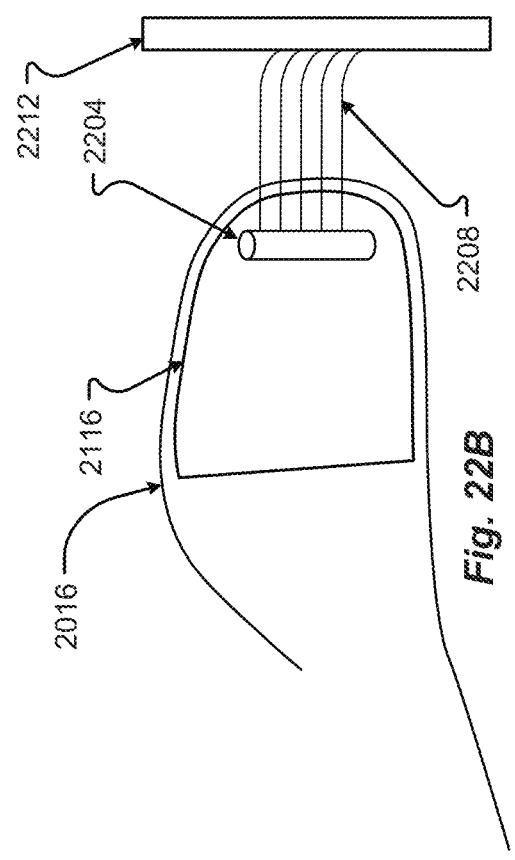
Fig. 22A
Fig. 22B

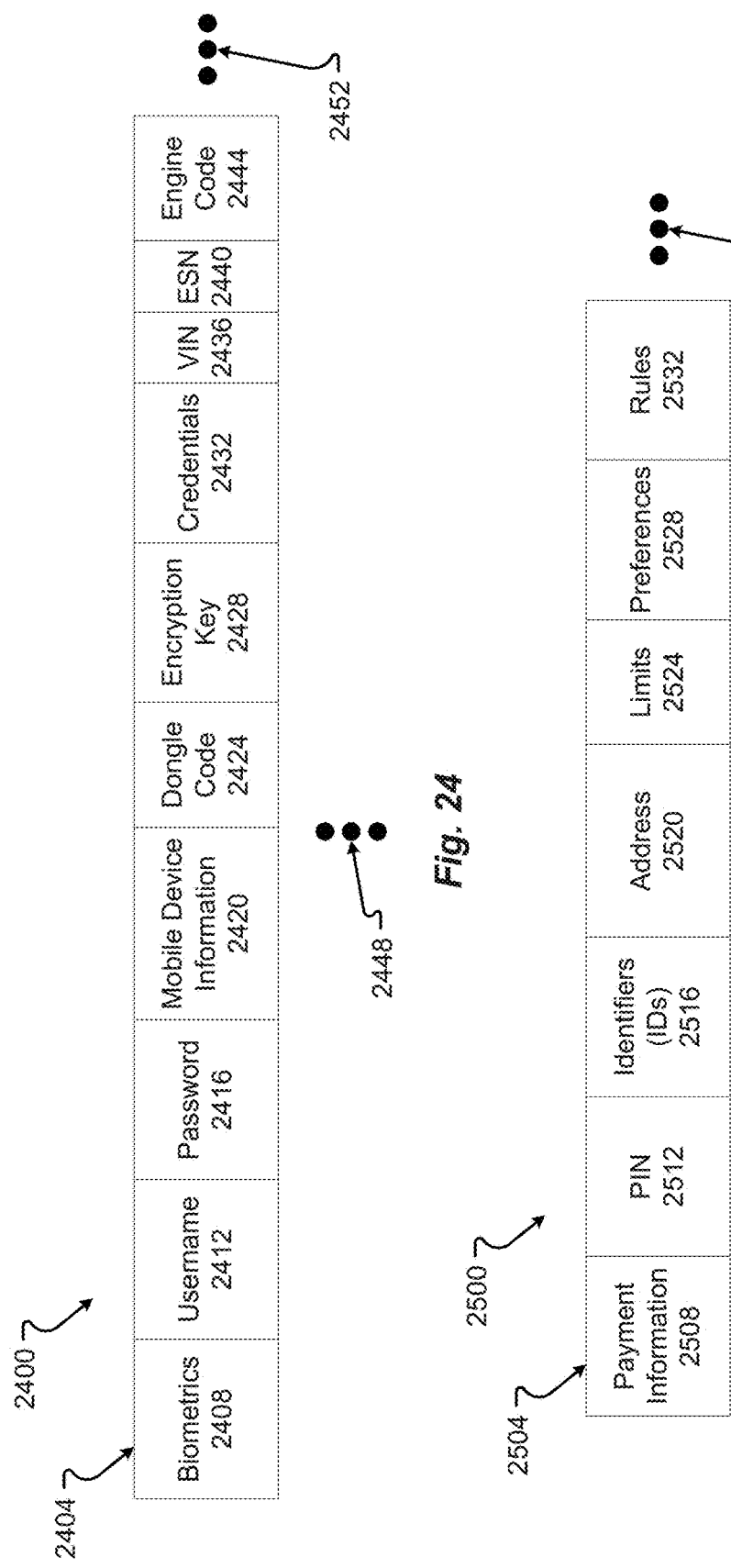

# BIFURCATED COMMUNICATIONS TO A THIRD PARTY THROUGH A VEHICLE

CROSS REFERENCE TO RELATED APPLICATIONS

The present application claims the benefits of and priority, under 35 U.S.C. § 119(e), to U.S. Provisional Application Ser. No. 62/359,563, filed on Jul. 7, 2016 and U.S. Provisional Application Ser. No. 62/378,348, filed on Aug. 23, 2016, both entitled "Next Generation Vehicle." The entire disclosures of the applications listed above are hereby incorporated by reference, in their entirety, for all that they teach and for all purposes.

FIELD

The present disclosure is generally directed to vehicle systems, in particular, toward semi-autonomous or fully autonomous vehicles.

BACKGROUND

In recent years, transportation methods have changed substantially. This change is due in part to a concern over the limited availability of natural resources, a proliferation in personal technology, and a societal shift to adopt more environmentally and user-friendly transportation solutions. These considerations have encouraged the development of a number of new features on vehicles that allow the user to concentrate on other tasks or on driving.

While these vehicles appear to be new they are generally implemented as a number of traditional subsystems that are executed with a communication system. In fact, the design and construction of the vehicles is limited to operations that can be completed by drivers. Among other things, these limitations fail to take advantage of the autonomous nature of vehicles.

BRIEF DESCRIPTION OF THE DRAWINGS

FIG. 3 is a diagram of an embodiment of a data structure for storing information about a vehicle in an environment;

FIG. 22A is a two-dimensional diagram of a physical interconnection between the vehicle and a receiving port;

FIG. 22B is another two-dimensional diagram of a physical interconnection between the vehicle and a receiving port;

FIG. 24 is a block diagram of data that may be stored in the vehicle;

FIG. 25 is a block diagram of data that may be communicated between the vehicle and a third party;

DETAILED DESCRIPTION

Embodiments of the present disclosure will be described in connection with a vehicle, and in accordance with one exemplary embodiment an electric vehicle and/or hybrid-electric vehicle and associated systems.

With attention to FIGS. 1-11, embodiments of the electric vehicle system 10 and method of use are depicted.

Figure 1:
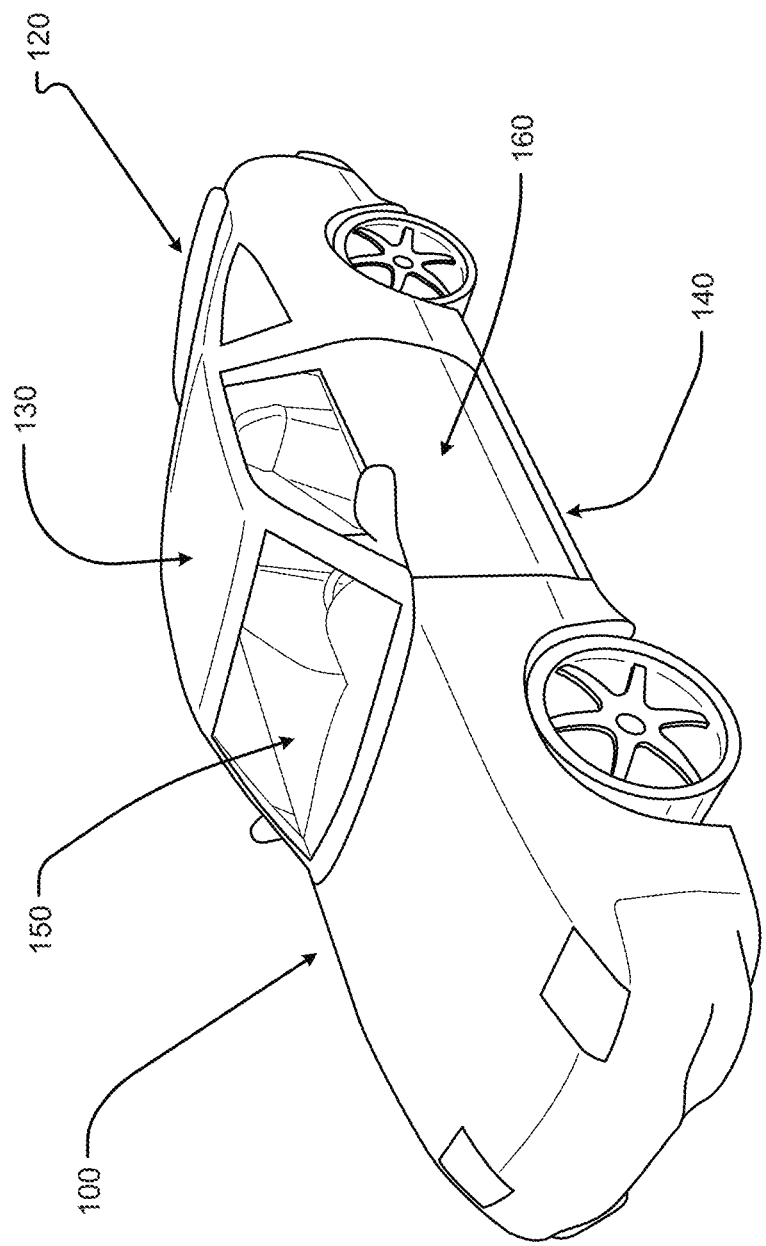
FIG. 1 shows a vehicle in accordance with embodiments of the present disclosure.

Referring to FIG. 1, the electric vehicle system comprises electric vehicle 100. The electric vehicle 100 comprises vehicle front 110, vehicle aft 120, vehicle roof 130, vehicle side 160, vehicle undercarriage 140 and vehicle interior 150.

Figure 2:
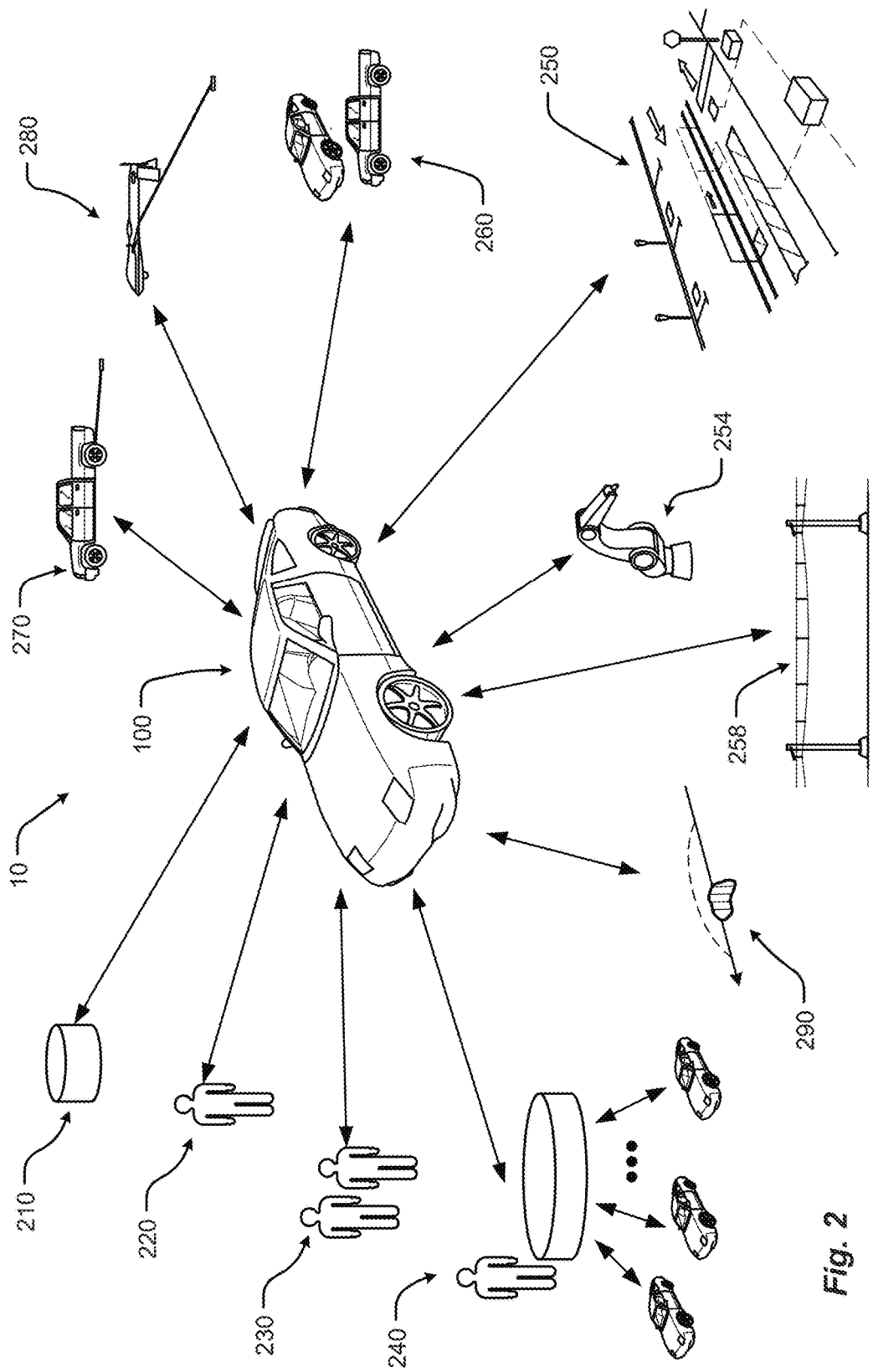
FIG. 2 shows a vehicle in an environment in accordance with embodiments of the present disclosure.

Referring to FIG. 2, the vehicle 100 is depicted in a plurality of exemplary environments. The vehicle 100 may operate in any one or more of the depicted environments in any combination. Other embodiments are possible but are not depicted in FIG. 2. Generally, the vehicle 100 may operate in environments which enable charging of the vehicle 100 and/or operation of the vehicle 100. More specifically, the vehicle 100 may receive a charge via one or more means comprising emergency charging vehicle system 270, aerial vehicle charging system 280, roadway system 250, robotic charging system 254 and overhead charging system 258. The vehicle 100 may interact and/or operate in an environment comprising one or more other roadway vehicles 260. The vehicle 100 may engage with elements within the vehicle 100 comprising vehicle driver 220, vehicle passengers 220 and vehicle database 210. In one embodiment, vehicle database 210 does not physically reside in the vehicle 100 but is instead accessed remotely, e.g. by wireless communication, and resides in another location such as a residence or business location. Vehicle 100 may operate autonomously and/or semi-autonomously in an autonomous environment 290 (here, depicted as a roadway environment presenting a roadway obstacle of which the vehicle 100 autonomously identifies and steers the vehicle 100 clear of the obstacle). Furthermore, the vehicle 100 may engage with a remote operator system 240, which may provide fleet management instructions or control.

FIG. 3 is a diagram of an embodiment of a data structure 300 for storing information about a vehicle 100 in an environment. The data structure may be stored in vehicle database 210. Generally, data structure 300 identifies operational data associated with charging types 310A. The data structures 300 may be accessible by a vehicle controller. The data contained in data structure 300 enables, among other things, for the vehicle 100 to receive a charge from a given charging type.

Exemplar data comprises charging type 310A comprising a manual charging station 310J, robotic charging station 310K such as robotic charging system 254, a roadway charging system 310L such as those of roadway system 250, an emergency charging system 310M such as that of emergency charging vehicle system 270, an emergency charging system 310N such as that of aerial vehicle charging system 280, and overhead charging type 310O such as that of overhead charging system 258.

Compatible vehicle charging panel types 310B comprise locations on vehicle 100 wherein charging may be received, such as vehicle roof 130, vehicle side 160 and vehicle lower or undercarriage 140. Compatible vehicle storage units 310C data indicates storage units types that may receive power from a given charging type 310A. Available automation level 310D data indicates the degree of automation available for a given charging type; a high level may indicate full automation, allowing the vehicle driver 220 and/or vehicle passengers 230 to not involve themselves in charging operations, while a low level of automation may require the driver 220 and/or occupant 230 to manipulate/position a vehicle charging device to engage with a particular charging type 310A to receive charging. Charging status 310E indicates whether a charging type 310A is available for charging (i.e. is "up") or is unavailable for charging (i.e. is "down"). Charge rate 310F provides a relative value for time to charge, while Cost 310G indicates the cost to vehicle 100 to receive a given charge. The Other data element 310H may provide additional data relevant to a given charging type 310A, such as a recommended separation distance between a vehicle charging plate and the charging source. The Shielding data element 310I indicates if electromagnetic shielding is recommended for a given charging type 310A and/or charging configuration. Further data fields 310P, 310Q are possible.

Figure 4A:
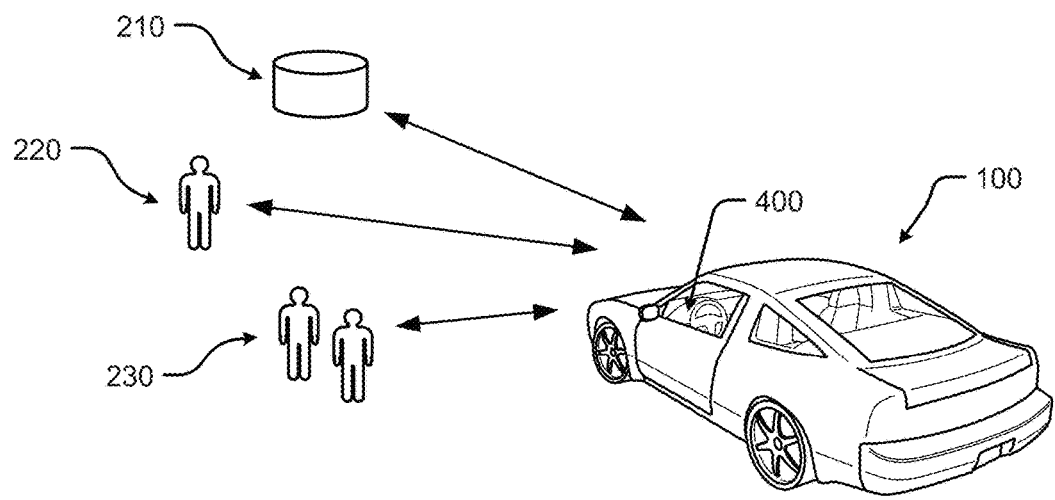
FIG. 4A shows a vehicle in a user environment in accordance with embodiments of the present disclosure.

FIG. 4A depicts the vehicle 100 in a user environment comprising vehicle database 210, vehicle driver 220 and vehicle passengers 230. Vehicle 100 further comprises vehicle instrument panel 400 to facilitate or enable interactions with one or more of vehicle database 210, vehicle driver 220 and vehicle passengers 230. In one embodiment, driver 210 interacts with instrument panel 400 to query database 210 so as to locate available charging options and to consider or weigh associated terms and conditions of the charging options. Once a charging option is selected, driver 210 may engage or operate a manual control device (e.g., a joystick) to position a vehicle charging receiver panel so as to receive a charge.

Figure 4B:
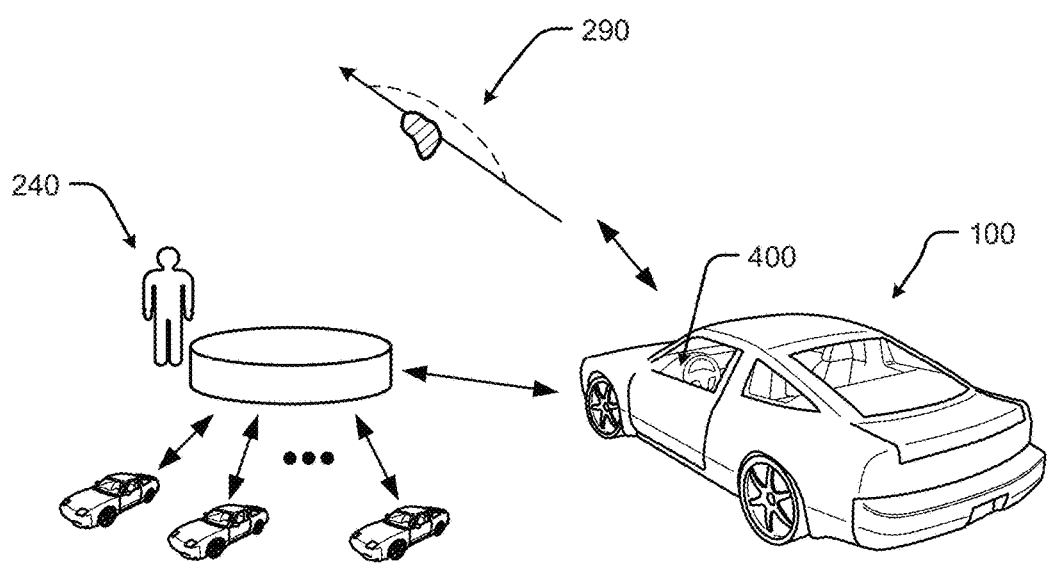
FIG. 4B shows a vehicle in a fleet management and automated operation environment in accordance with embodiments of the present disclosure.

FIG. 4B depicts the vehicle 100 in a user environment comprising a remote operator system 240 and an autonomous driving environment 290. In the remote operator system 240 environment, a fleet of electric vehicles 100 (or mixture of electric and non-electric vehicles) is managed and/or controlled remotely. For example, a human operator may dictate that only certain types of charging types are to be used, or only those charging types below a certain price point are to be used. The remote operator system 240 may comprise a database comprising operational data, such as fleet-wide operational data. In another example, the vehicle 100 may operate in an autonomous driving environment 290 wherein the vehicle 100 is operated with some degree of autonomy, ranging from complete autonomous operation to semi-automation wherein only specific driving parameters (e.g., speed control or obstacle avoidance) are maintained or controlled autonomously. In FIG. 4B, autonomous driving environment 290 depicts an oil slick roadway hazard that triggers that triggers the vehicle 100, while in an automated obstacle avoidance mode, to automatically steer around the roadway hazard.

Figure 4C:
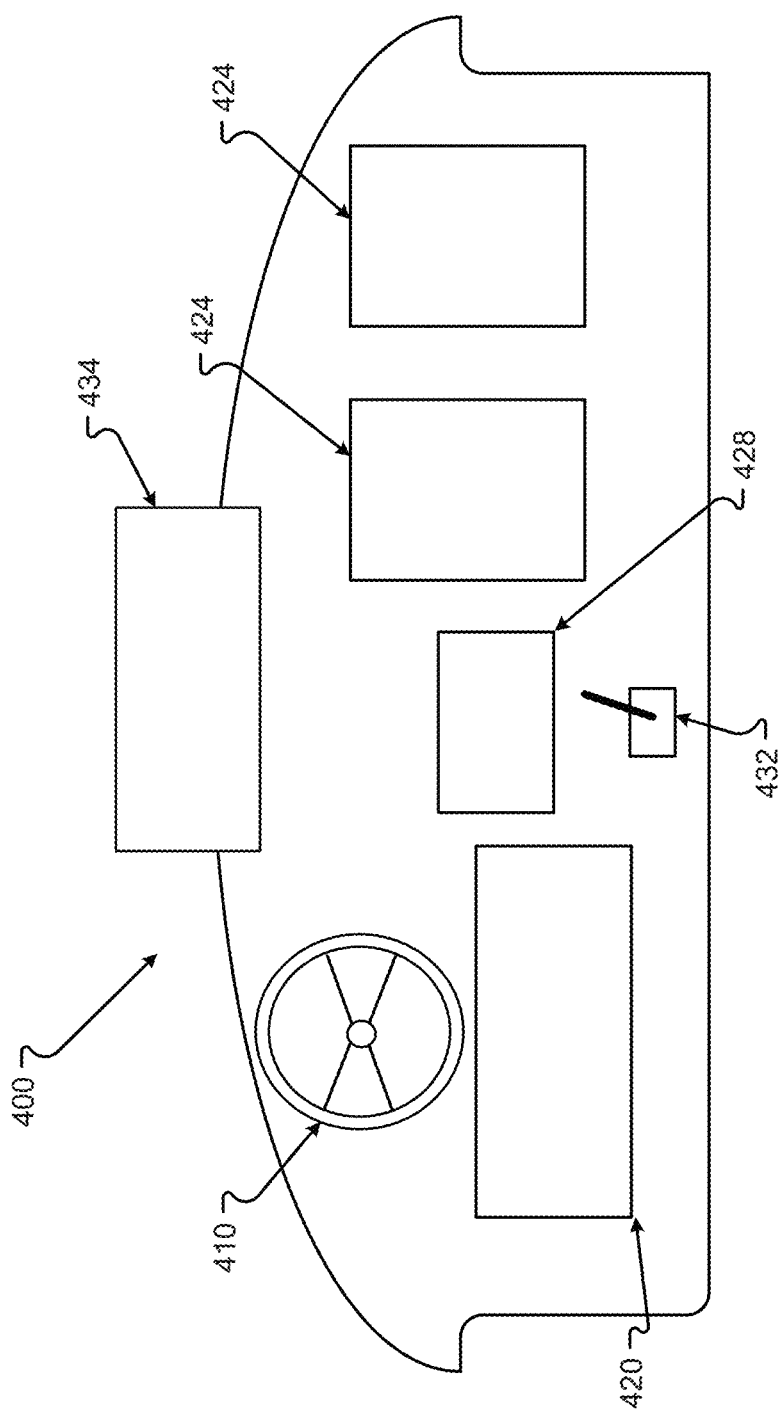
FIG. 4C shows an embodiment of the instrument panel of the vehicle according to one embodiment of the present disclosure.

FIG. 4C shows one embodiment of the vehicle instrument panel 400 of vehicle 100. Instrument panel 400 of vehicle 100 comprises steering wheel 410, vehicle operational display 420 (which would provide basic driving data such as speed), one or more auxiliary displays 424 (which may display, e.g., entertainment applications such as music or radio selections), heads-up display 434 (which may provide, e.g., guidance information such as route to destination, or obstacle warning information to warn of a potential collision, or some or all primary vehicle operational data such as speed), power management display 428 (which may provide, e.g., data as to electric power levels of vehicle 100), and charging manual controller 432 (which provides a physical input, e.g. a joystick, to manual maneuver, e.g., a vehicle charging plate to a desired separation distance). One or more of displays of instrument panel 400 may be touch-screen displays. One or more displays of instrument panel 400 may be mobile devices and/or applications residing on a mobile device such as a smart phone.

Figure 5:
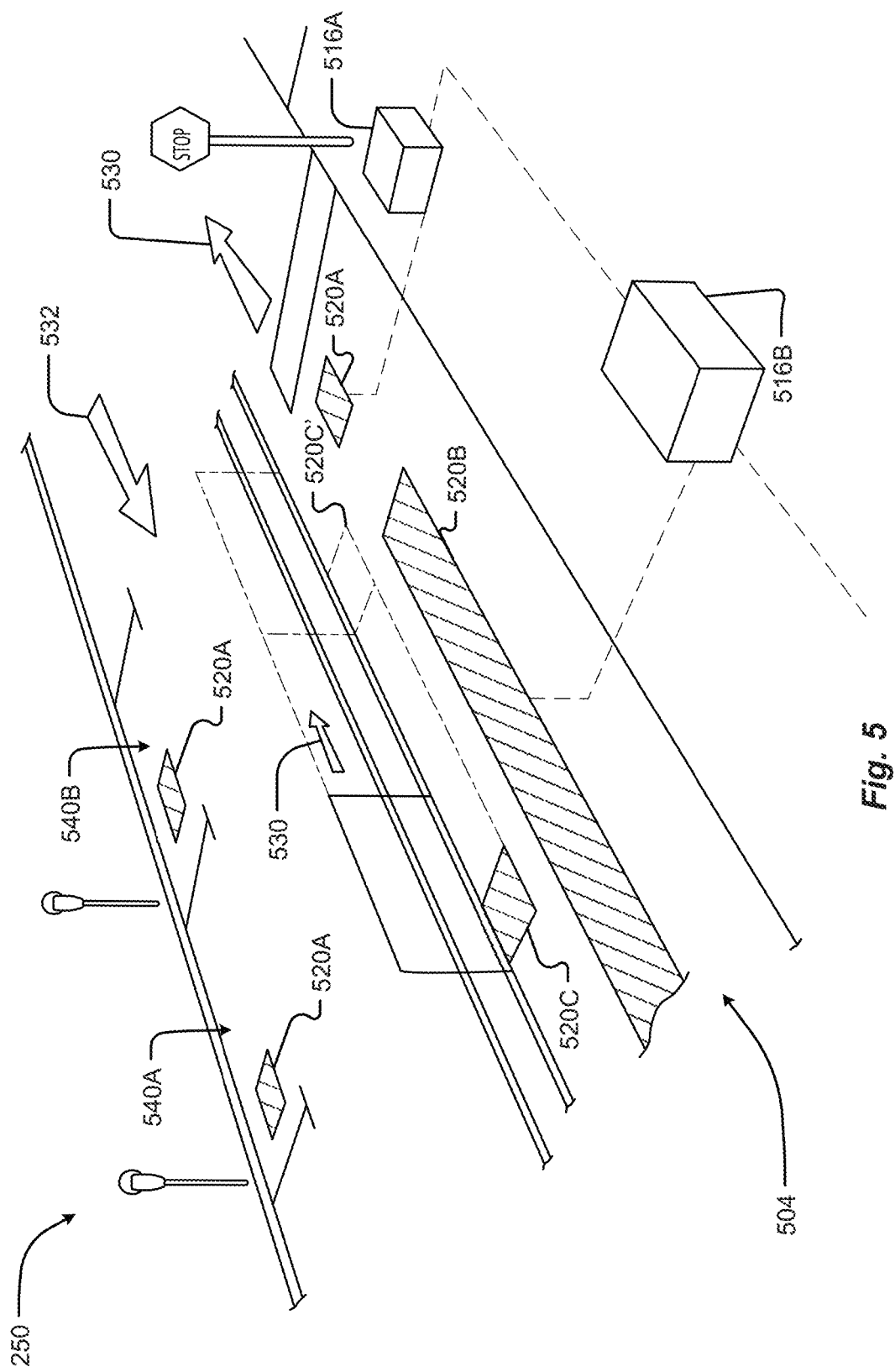
FIG. 5 shows charging areas associated with an environment in accordance with embodiments of the present disclosure.

FIG. 5 depicts a charging environment of a roadway charging system 250. The charging area may be in the roadway 504, on the roadway 504, or otherwise adjacent to the roadway 504, and/or combinations thereof. This static charging area 520B may allow a charge to be transferred even while the electrical vehicle 100 is moving. For example, the static charging area 520B may include a charging transmitter (e.g., conductor, etc.) that provides a transfer of energy when in a suitable range of a receiving unit (e.g., an inductor pick up, etc.). In this example, the receiving unit may be a part of the charging panel associated with the electrical vehicle 100.

The static charging areas 520A, 520B may be positioned a static area such as a designated spot, pad, parking space 540A, 540B, traffic controlled space (e.g., an area adjacent to a stop sign, traffic light, gate, etc.), portion of a building, portion of a structure, etc., and/or combinations thereof. Some static charging areas may require that the electric vehicle 100 is stationary before a charge, or electrical energy transfer, is initiated. The charging of vehicle 100 may occur by any of several means comprising a plug or other protruding feature. The power source 516A, 516B may include a receptacle or other receiving feature, and/or vice versa.

The charging area may be a moving charging area 520C. Moving charging areas 520C may include charging areas associated with one or more portions of a vehicle, a robotic charging device, a tracked charging device, a rail charging device, etc., and/or combinations thereof. In a moving charging area 520C, the electrical vehicle 100 may be configured to receive a charge, via a charging panel, while the vehicle 100 is moving and/or while the vehicle 100 is stationary. In some embodiments, the electrical vehicle 100 may synchronize to move at the same speed, acceleration, and/or path as the moving charging area 520C. In one embodiment, the moving charging area 520C may synchronize to move at the same speed, acceleration, and/or path as the electrical vehicle 100. In any event, the synchronization may be based on an exchange of information communicated across a communications channel between the electric vehicle 100 and the charging area 520C. Additionally or alternatively, the synchronization may be based on information associated with a movement of the electric vehicle 100 and/or the moving charging area 520C. In some embodiments, the moving charging area 520C may be configured to move along a direction or path 532 from an origin position to a destination position 520C'.

In some embodiments, a transformer may be included to convert a power setting associated with a main power supply to a power supply used by the charging areas 520A-C. For example, the transformer may increase or decrease a voltage associated with power supplied via one or more power transmission lines.

Figure 6:
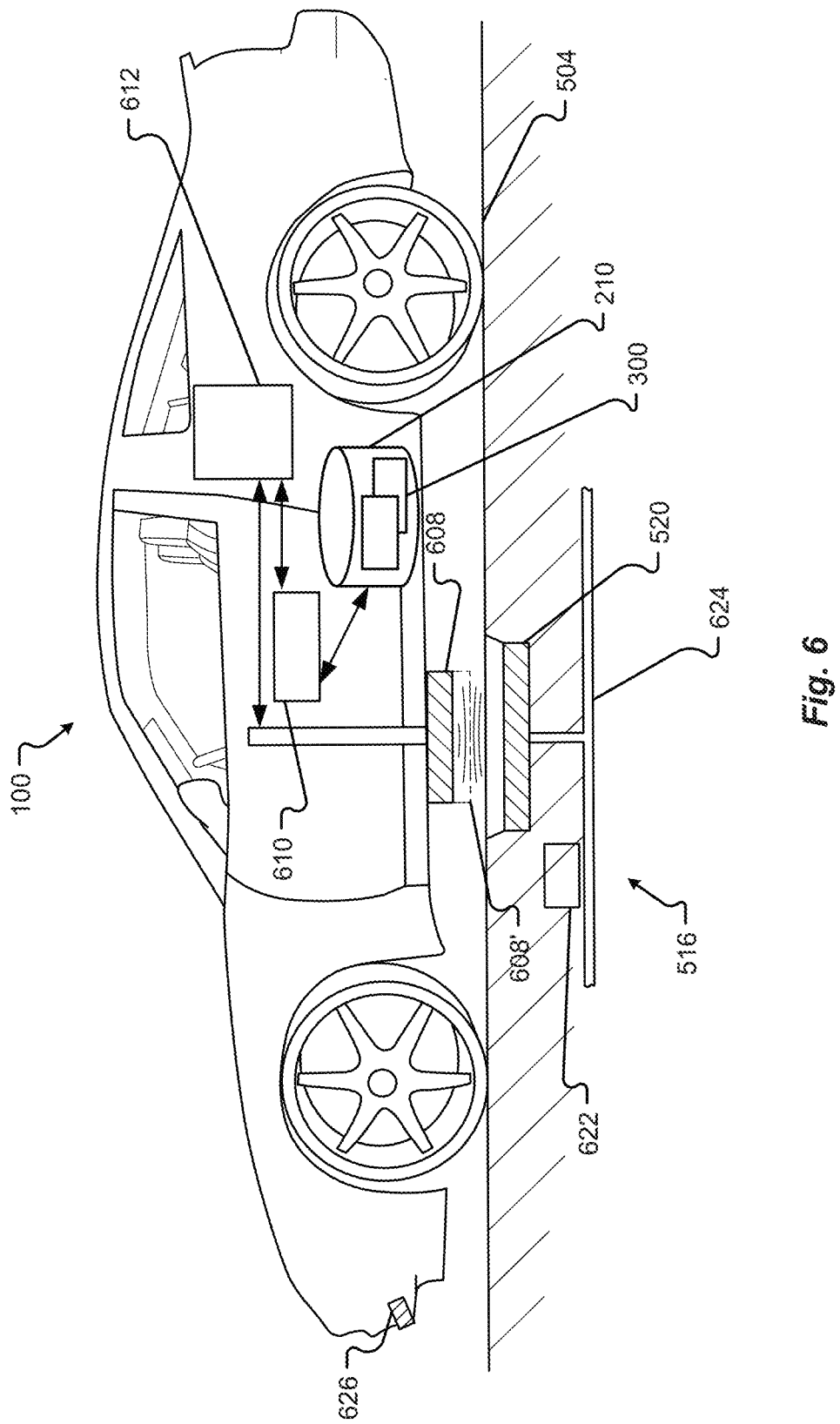
FIG. 6 shows a vehicle in a roadway charging environment in accordance with embodiments of the present disclosure.

Referring to FIG. 6, a vehicle 100 is shown in a charging environment in accordance with embodiments of the present disclosure. The system 10 comprises a vehicle 100, an electrical storage unit 612, an external power source 516 able to provide a charge to the vehicle 100, a charging panel 608 mounted on the vehicle 100 and in electrical communication with the electrical storage unit 612, and a vehicle charging panel controller 610. The charging panel controller 610 may determine if the electrical storage unit requires charging and if conditions allow for deployment of a charging panel. The vehicle charging panel 608 may operate in at least a retracted state and a deployed state (608 and 608' as shown is FIG. 6), and is movable by way of an armature.

The charging panel controller 610 may receive signals from vehicle sensors 626 to determine, for example, if a hazard is present in the path of the vehicle 100 such that deployment of the vehicle charging panel 608 is inadvisable. The charging panel controller 610 may also query vehicle database 210 comprising data structures 300 to establish other required conditions for deployment. For example, the database may provide that a particular roadway does not provide a charging service or the charging service is inactive, wherein the charging panel 108 would not be deployed.

The power source 516 may include at least one electrical transmission line 624 and at least one power transmitter or charging area 520. During a charge, the charging panel 608 may serve to transfer energy from the power source 516 to at least one energy storage unit 612 (e.g., battery, capacitor, power cell, etc.) of the electric vehicle 100.

Figure 7:
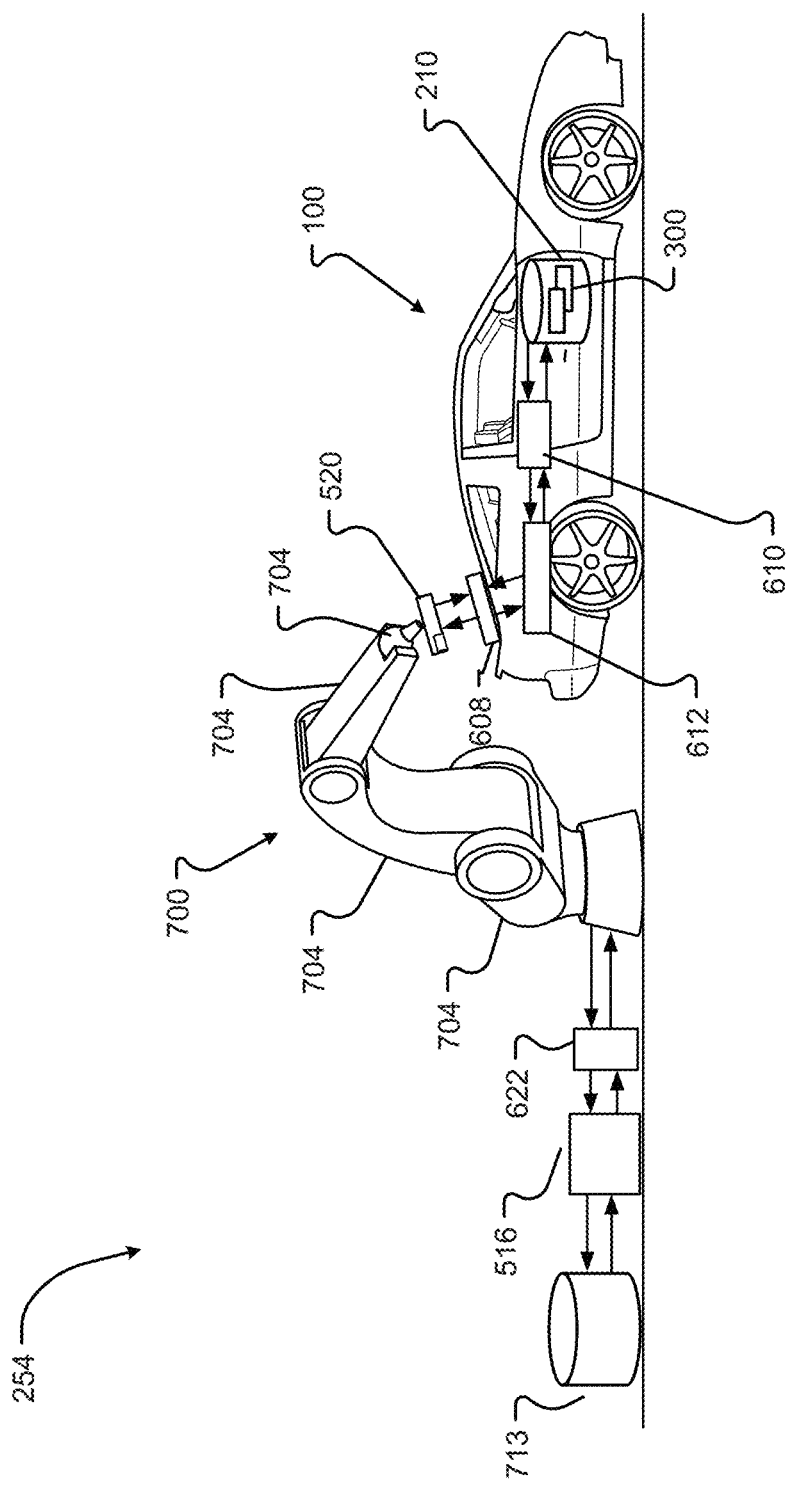
FIG. 7 shows a vehicle in a robotic charging station environment in accordance with another embodiment of the present disclosure.

FIG. 7 shows a vehicle 100 in a charging station environment 254 in accordance with another embodiment of the present disclosure. Generally, in this embodiment of the invention, charging occurs from a robotic unit 700.

Robotic charging unit 700 comprises one or more robotic unit arms 704, at least one robotic unit arm 704 interconnected with charging plate 520. The one or more robotic unit arms 704 maneuver charging plate 520 relative to charging panel 608 of vehicle 100. Charging plate 520 is positioned to a desired or selectable separation distance, as assisted by a separation distance sensor disposed on charging plate 520. Charging plate 520 may remain at a finite separation distance from charging panel 608, or may directly contact charging panel (i.e. such that separation distance is zero). Charging may be by induction. In alternative embodiments, separation distance sensor is alternatively or additionally disposed on robotic arm 704. Vehicle 100 receives charging via charging panel 608 which in turn charges energy storage unit 612. Charging panel controller 610 is in communication with energy storage unit 612, charging panel 608, vehicle database 300, charge provider controller 622, and/or any one of elements of instrument panel 400.

Robotic unit further comprises, is in communication with and/or is interconnected with charge provider controller 622, power source 516 and a robotic unit database. Power source 516 supplies power, such as electrical power, to charge plate 520 to enable charging of vehicle 100 via charging panel 608. Controller 622 maneuvers or operates robotic unit 704, either directly and/or completely or with assistance from a remote user, such as a driver or passenger in vehicle 100 by way of, in one embodiment, charging manual controller 432.

Figure 8:
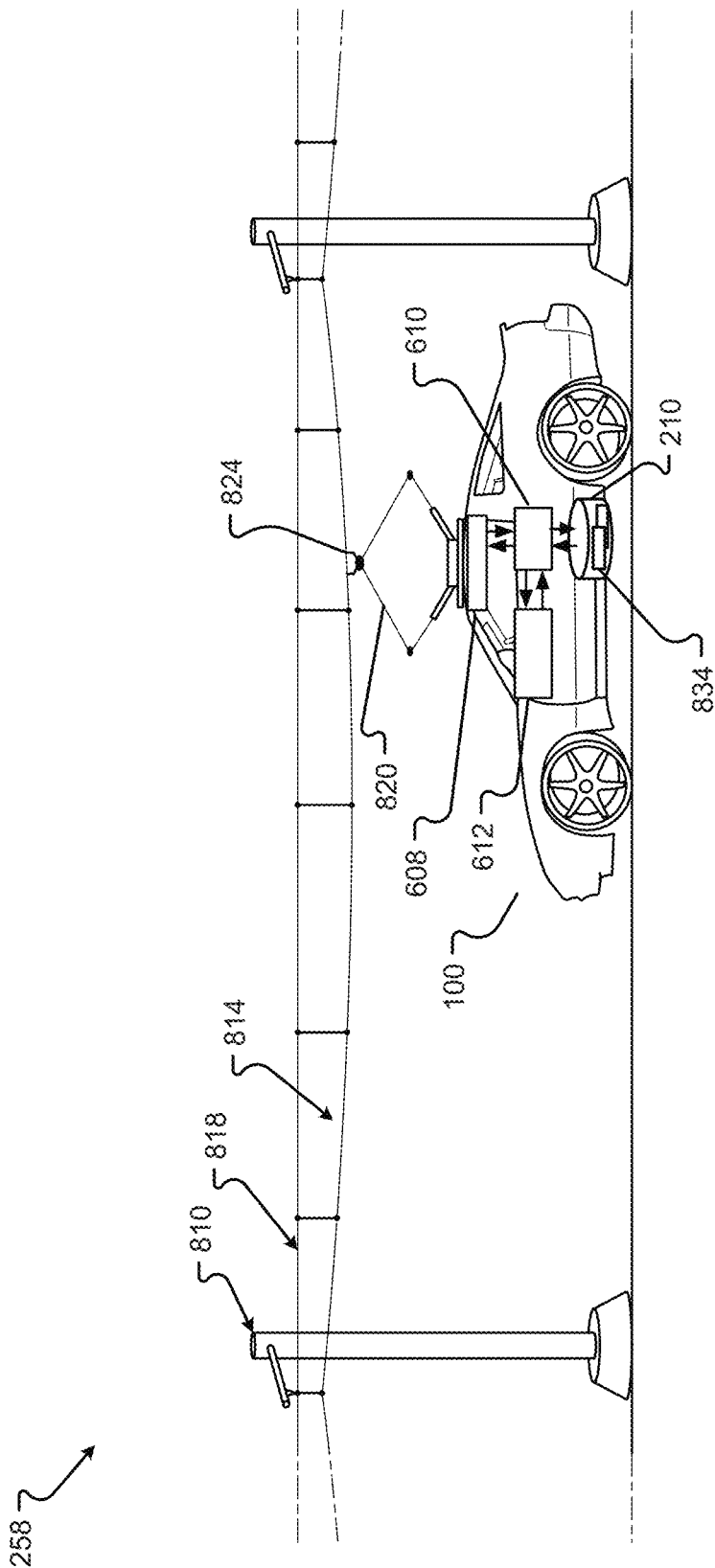
FIG. 8 shows a vehicle in an overhead charging environment in accordance with another embodiment of the present disclosure.

FIG. 8 shows a vehicle 100 in an overhead charging environment in accordance with another embodiment of the present disclosure. Generally, in this embodiment of the invention, charging occurs from an overhead towered charging system 258, similar to existing commuter rail systems. Such an overhead towered system 258 may be easier to build and repair compared to in-roadway systems. Generally, the invention includes a specially-designed overhead roadway charging system comprising an overhead charging cable or first wire 814 that is configured to engage an overhead contact 824 which provides charge to charging panel 608 which provides charge to vehicle energy storage unit 612. The overhead towered charging system 258 may further comprise second wire 818 to provide stability and structural strength to the roadway charging system 800. The first wire 814 and second wire 818 are strung between towers 810.

The overhead charging cable or first wire 814 is analogous to a contact wire used to provide charging to electric trains or other vehicles. An external source provides or supplies electrical power to the first wire 814. The charge provider comprises an energy source i.e. a provider battery and a provider charge circuit or controller in communication with the provider battery. The overhead charging cable or first wire 814 engages the overhead contact 824 which is in electrical communication with charge receiver panel 108. The overhead contact 824 may comprise any known means to connect to overhead electrical power cables, such as a pantograph 820, a bow collector, a trolley pole or any means known to those skilled in the art. Further disclosure regarding electrical power or energy transfer via overhead systems is found in US Pat. Publ. No. 2013/0105264 to Ruth entitled "Pantograph Assembly," the entire contents of which are incorporated by reference for all purposes. In one embodiment, the charging of vehicle 100 by overhead charging system 800 via overhead contact 824 is by any means know to those skilled in the art, to include those described in the above-referenced US Pat. Publ. No. 2013/0105264 to Ruth.

The overhead contact 824 presses against the underside of the lowest overhead wire of the overhead charging system, i.e. the overhead charging cable or first wire 814, aka the contact wire. The overhead contact 824 may be electrically conductive. Alternatively or additionally, the overhead contact 824 may be adapted to receive electrical power from overhead charging cable or first wire 814 by inductive charging.

In one embodiment, the receipt and/or control of the energy provided via overhead contact 824 (as connected to the energy storage unit 612) is provided by receiver charge circuit or charging panel controller 110.

Overhead contact 824 and/or charging panel 608 may be located anywhere on vehicle 100, to include, for example, the roof, side panel, trunk, hood, front or rear bumper of the charge receiver 100 vehicle, as long as the overhead contact 824 may engage the overhead charging cable or first wire 814. Charging panel 108 may be stationary (e.g. disposed on the roof of vehicle 100) or may be moveable, e.g. moveable with the pantograph 820. Pantograph 820 may be positioned in at least two states comprising retracted and extended. In the extended state pantograph 820 engages first wire 814 by way of the overhead contact 824. In the retracted state, pantograph 820 may typically reside flush with the roof of vehicle 100 and extend only when required for charging. Control of the charging and/or positioning of the charging plate 608, pantograph 820 and/or overhead contact 824 may be manual, automatic or semi-automatic (such as via controller 610); said control may be performed through a GUI engaged by driver or occupant of receiving vehicle 100 and/or driver or occupant of charging vehicle.

Figure 9:
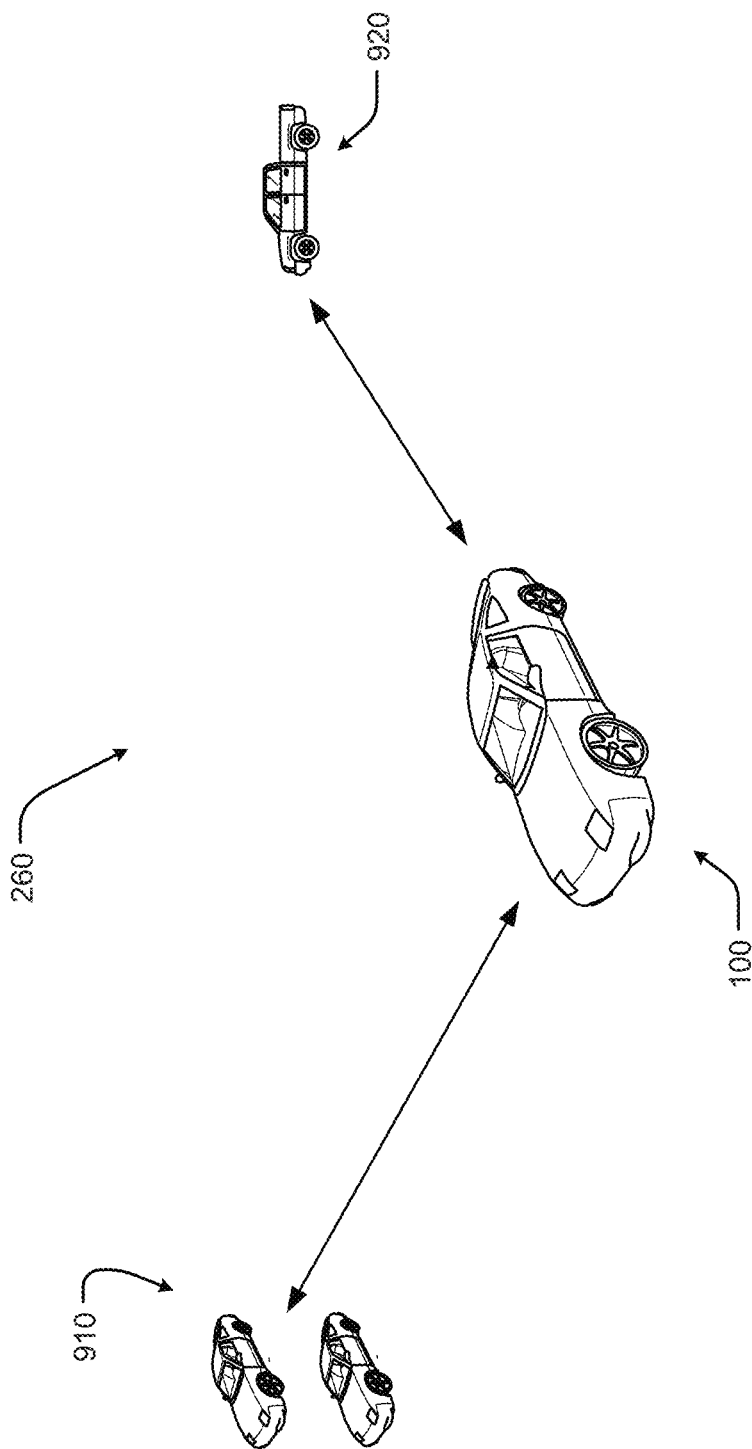
FIG. 9 shows a vehicle in a roadway environment comprising roadway vehicles in accordance with another embodiment of the present disclosure.

FIG. 9 shows a vehicle in a roadway environment comprising roadway vehicles 260 in accordance with another embodiment of the present disclosure. Roadway vehicles 260 comprise roadway passive vehicles 910 and roadway active vehicles 920. Roadway passive vehicles 910 comprise vehicles that are operating on the roadway of vehicle 100 but do no cooperatively or actively engage with vehicle 100. Stated another way, roadway passive vehicles 910 are simply other vehicles operating on the roadway with the vehicle 100 and must be, among other things, avoided (e.g., to include when vehicle 100 is operating in an autonomous or semi-autonomous manner). In contrast, roadway active vehicles 920 comprise vehicles that are operating on the roadway of vehicle 100 and have the capability to, or actually are, actively engaging with vehicle 100. For example, the emergency charging vehicle system 270 is a roadway active vehicle 920 in that it may cooperate or engage with vehicle 100 to provide charging. In some embodiments, vehicle 100 may exchange data with a roadway active vehicle 920 such as, for example, data regarding charging types available to the roadway active vehicle 920.

Figure 10:
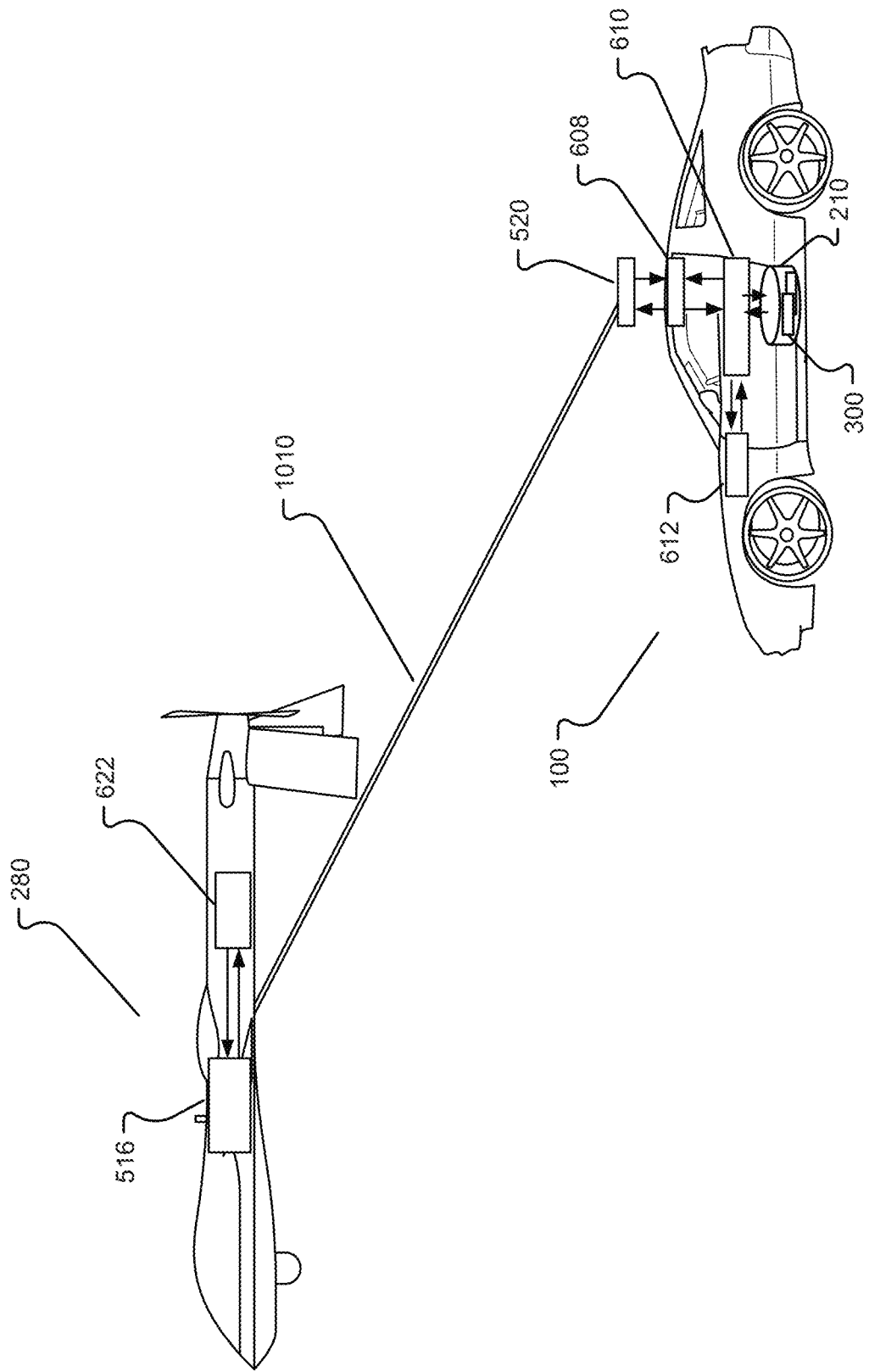
FIG. 10 shows a vehicle in an aerial vehicle charging environment in accordance with another embodiment of the present disclosure.

FIG. 10 shows a vehicle in an aerial vehicle charging environment in accordance with another embodiment of the present disclosure. Generally, this embodiment involves an aerial vehicle ("AV"), such as an Unmanned Aerial Vehicle (UAV), flying over or near a vehicle to provide a charge. The UAV may also land on the car to provide an emergency (or routine) charge. Such a charging scheme may be particularly suited for operations in remote areas, in high traffic situations, and/or when the car is moving. The AV may be a specially-designed UAV, aka RPV or drone, with a charging panel that can extend from the AV to provide a charge. The AV may include a battery pack and a charging circuit to deliver a charge to the vehicle. The AV may be a manned aerial vehicle, such as a piloted general aviation aircraft, such as a Cessna 172.

With reference to FIG. 10, an exemplar embodiment of a vehicle charging system 100 comprising a charge provider configured as an aerial vehicle 280, the aerial vehicle 280 comprising a power source 516 and charge provider controller 622. The AV may be semi-autonomous or fully autonomous. The AV may have a remote pilot/operator providing control inputs. The power source 516 is configured to provide a charge to a charging panel 608 of vehicle 100. The power source 516 is in communication with the charge provider controller 622. The aerial vehicle 280 provides a tether 1010 to deploy or extend charging plate 520 near to charging panel 608. The tether 1010 may comprise a chain, rope, rigid or semi-rigid tow bar or any means to position charging plate 520 near charging panel 608. For example, tether 1010 may be similar to a refueling probe used by airborne tanker aircraft when refueling another aircraft.

In one embodiment, the charging plate 520 is not in physical interconnection to AV 280, that is, there is no tether 1010. In this embodiment, the charging plate 520 is positioned and controlled by AV 280 by way of a controller on AV 280 or in communication with AV 280.

In one embodiment, the charging plate 520 position and/or characteristics (e.g. charging power level, flying separation distance, physical engagement on/off) are controlled by vehicle 100 and/or a user in or driver of vehicle 100.

Charge or power output of power source 516 is provided or transmitted to charger plate 620 by way of a charging cable or wire, which may be integral to tether 1010. In one embodiment, the charging cable is non-structural, that is, it provides zero or little structural support to the connection between AV 280 and charger plate 520.

Charging panel 608 of vehicle 100 receives power from charger plate 520. Charging panel 608 and charger plate 520 may be in direct physical contact (termed a "contact" charger configuration) or not in direct physical contact (termed a "flyer" charger configuration), but must be at or below a threshold (separation) distance to enable charging, such as by induction. Energy transfer or charging from the charger plate 520 to the charging panel 608 is inductive charging (i.e. use of an EM field to transfer energy between two objects). The charging panel 608 provides received power to energy storage unit 612 by way of charging panel controller 610. Charging panel controller 610 is in communication with vehicle database 210, vehicle database 210 comprising an AV charging data structure.

Charging panel 508 may be located anywhere on vehicle 100, to include, for example, the roof, side panel, trunk, hood, front or rear bumper and wheel hub of vehicle 100. Charging panel 608 is mounted on the roof of vehicle 100 in the embodiment of FIG. 10. In some embodiments, charging panel 608 may be deployable, i.e. may extend or deploy only when charging is needed. For example, charging panel 608 may typically reside flush with the roof of vehicle 100 and extend when required for charging. Similarly, charger plate 520 may, in one embodiment, not be connected to AV 280 by way of tether 1010 and may instead be mounted directly on the AV 280, to include, for example, the wing, empennage, undercarriage to include landing gear, and may be deployable or extendable when required. Tether 1010 may be configured to maneuver charging plate 520 to any position on vehicle 100 so as to enable charging. In one embodiment, the AV 280 may land on the vehicle 100 so as to enable charging through direct contact (i.e. the aforementioned contact charging configuration) between the charging plate 520 and the charging panel 608 of vehicle 100. Charging may occur while both AV 280 and vehicle 100 are moving, while both vehicle 100 and AV 280 are not moving (i.e., vehicle 100 is parked and AV 280 lands on top of vehicle 100), or while vehicle 100 is parked and AV 280 is hovering or circling above. Control of the charging and/or positioning of the charging plate 520 may be manual, automatic or semi-automatic; said control may be performed through a GUI engaged by driver or occupant of receiving vehicle 100 and/or driver or occupant of charging AV 280.

Figure 11:
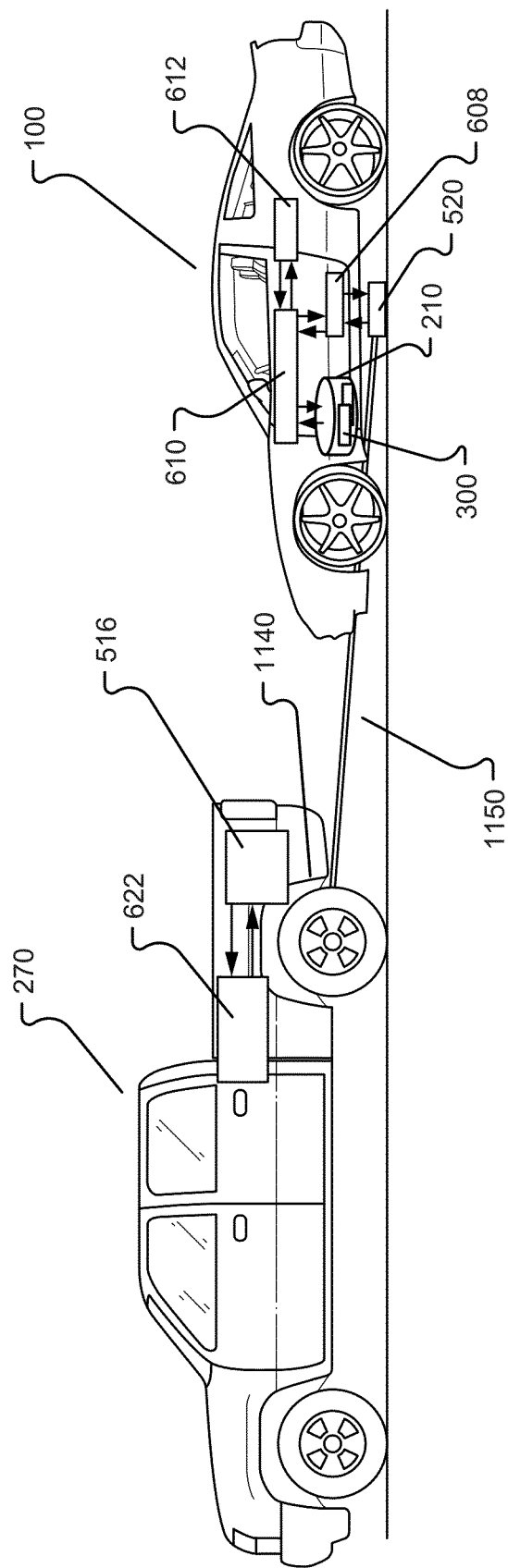
FIG. 11 shows a vehicle in an emergency charging environment in accordance with embodiments of the present disclosure.

FIG. 11 is an exemplar embodiment of a vehicle emergency charging system comprising an emergency charging vehicle 270 and charge receiver vehicle 100 is disclosed. The emergency charging vehicle 270 is a road vehicle, such as a pick-up truck, as shown in FIG. 11. The emergency charging vehicle 270 is configured to provide a charge to a charge receiver vehicle 100, such as an automobile. The emergency charging vehicle 270 comprises an energy source i.e. a charging power source 516 and a charge provider controller 622 in communication with the charging power source 516. The emergency charging vehicle 270 provides a towed and/or articulated charger plate 520, as connected to the emergency charging vehicle 270 by connector 1150. The connector 1150 may comprise a chain, rope, rigid or semi-rigid tow bar or any means to position charger plate 520 near the charging panel 608 of vehicle 100. Charge or power output of charging power source 516 is provided or transmitted to charger plate 520 by way of charging cable or wire 1140. In one embodiment, the charging cable 1140 is non-structural, that is, it provides little or no structural support to the connection between emergency charging vehicle 270 and charging panel 608. Charging panel 608 (of vehicle 100) receives power from charger plate 520. Charger plate 520 and charging panel 608 may be in direct physical contact or not in direct physical contact, but must be at or below a threshold separation distance to enable charging, such as by induction. Charger plate 520 may comprise wheels or rollers so as to roll along roadway surface. Charger plate 520 may also not contact the ground surface and instead be suspended above the ground; such a configuration may be termed a "flying" configuration. In the flying configuration, charger plate may form an aerodynamic surface to, for example, facilitate stability and control of the positioning of the charging plate 520. Energy transfer or charging from the charger plate 520 to the charge receiver panel 608 is through inductive charging (i.e. use of an EM field to transfer energy between two objects). The charging panel 608 provides received power to energy storage unit 612 directly or by way of charging panel controller 610. In one embodiment, the receipt and/or control of the energy provided via the charging panel 608 is provided by charging panel controller 610.

Charging panel controller 610 may be located anywhere on charge receiver vehicle 100, to include, for example, the roof, side panel, trunk, hood, front or rear bumper and wheel hub of charge receiver 100 vehicle. In some embodiments, charging panel 608 may be deployable, i.e. may extend or deploy only when charging is needed. For example, charging panel 608 may typically stow flush with the lower plane of vehicle 100 and extend when required for charging. Similarly, charger plate 520 may, in one embodiment, not be connected to the lower rear of the emergency charging vehicle 270 by way of connector 1150 and may instead be mounted on the emergency charging vehicle 270, to include, for example, the roof, side panel, trunk, hood, front or rear bumper and wheel hub of emergency charging vehicle 270. Connector 1150 may be configured to maneuver connector plate 520 to any position on emergency charging vehicle 270 so as to enable charging. Control of the charging and/or positioning of the charging plate may be manual, automatic or semi-automatic; said control may be performed through a GUI engaged by driver or occupant of receiving vehicle and/or driver or occupant of charging vehicle.

Figure 12:
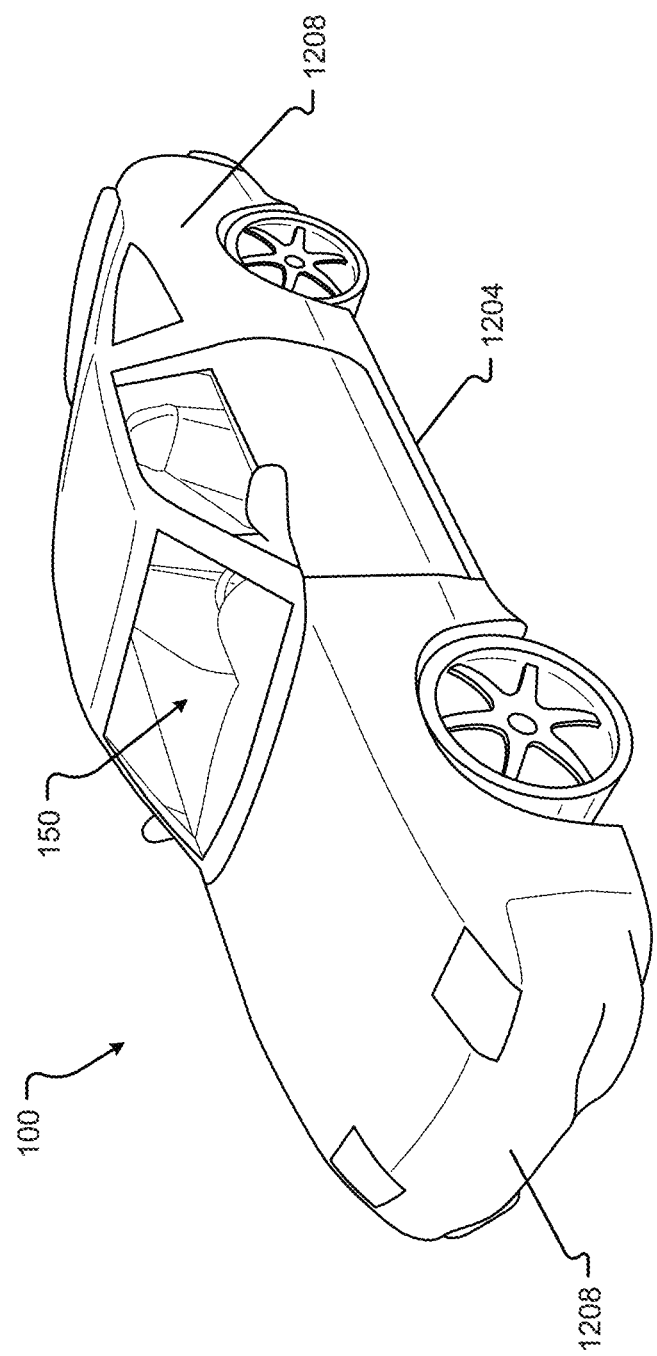
FIG. 12 is a perspective view of a vehicle in accordance with embodiments of the present disclosure.

FIG. 12 shows a perspective view of a vehicle 100 in accordance with embodiments of the present disclosure. Although shown in the form of a car, it should be appreciated that the vehicle 100 described herein may include any conveyance or model of a conveyance, where the conveyance was designed for the purpose of moving one or more tangible objects, such as people, animals, cargo, and the like. The term "vehicle" does not require that a conveyance moves or is capable of movement. Typical vehicles may include but are in no way limited to cars, trucks, motorcycles, busses, automobiles, trains, railed conveyances, boats, ships, marine conveyances, submarine conveyances, airplanes, space craft, flying machines, human-powered conveyances, and the like. In any event, the vehicle 100 may include a frame 1204 and one or more body panels 1208 mounted or affixed thereto. The vehicle 100 may include one or more interior components (e.g., components inside an interior space 150, or user space, of a vehicle 100, etc.), exterior components (e.g., components outside of the interior space 150, or user space, of a vehicle 100, etc.), drive systems, controls systems, structural components.

Figure 13:
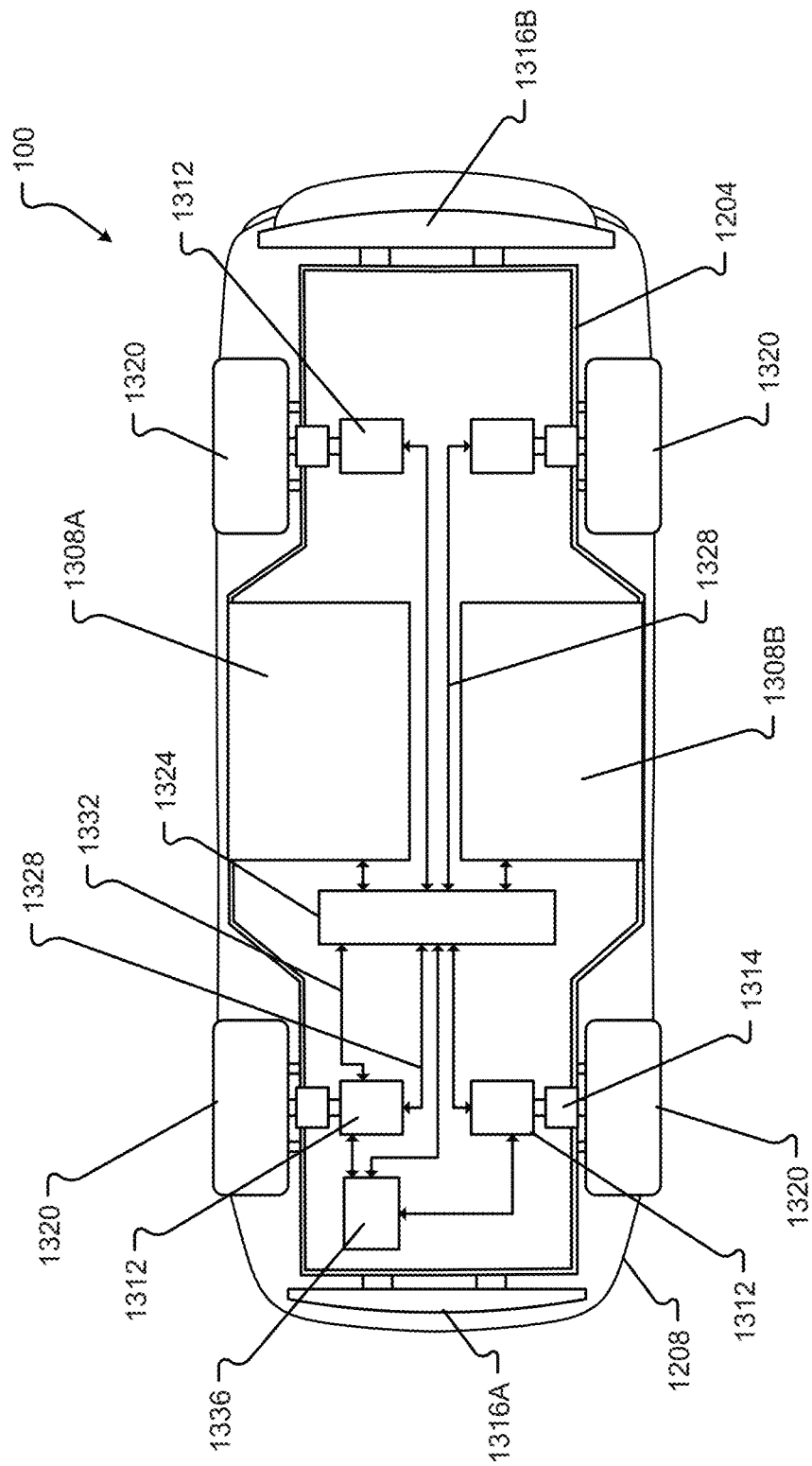
FIG. 13 is a plan view of a vehicle in accordance with at least some embodiments of the present disclosure.

Referring now to FIG. 13, a plan view of a vehicle 100 will be described in accordance with embodiments of the present disclosure. As provided above, the vehicle 100 may comprise a number of electrical and/or mechanical systems, subsystems, etc. The mechanical systems of the vehicle 100 can include structural, power, safety, and communications subsystems, to name a few. While each subsystem may be described separately, it should be appreciated that the components of a particular subsystem may be shared between one or more other subsystems of the vehicle 100.

The structural subsystem includes the frame 1204 of the vehicle 100. The frame 1204 may comprise a separate frame and body construction (i.e., body-on-frame construction), a unitary frame and body construction (i.e., a unibody construction), or any other construction defining the structure of the vehicle 100. The frame 1204 may be made from one or more materials including, but in no way limited to steel, titanium, aluminum, carbon fiber, plastic, polymers, etc., and/or combinations thereof. In some embodiments, the frame 1204 may be formed, welded, fused, fastened, pressed, etc., combinations thereof, or otherwise shaped to define a physical structure and strength of the vehicle 100. In any event, the frame 1204 may comprise one or more surfaces, connections, protrusions, cavities, mounting points, tabs, slots, or other features that are configured to receive other components that make up the vehicle 100. For example, the body panels, powertrain subsystem, controls systems, interior components, communications subsystem, and safety subsystem may interconnect with, or attach to, the frame 1204 of the vehicle 100.

The frame 1204 may include one or more modular system and/or subsystem connection mechanisms. These mechanisms may include features that are configured to provide a selectively interchangeable interface for one or more of the systems and/or subsystems described herein. The mechanisms may provide for a quick exchange, or swapping, of components while providing enhanced security and adaptability over conventional manufacturing or attachment. For instance, the ability to selectively interchange systems and/or subsystems in the vehicle 100 allow the vehicle 100 to adapt to the ever-changing technological demands of society and advances in safety. Among other things, the mechanisms may provide for the quick exchange of batteries, capacitors, power sources 1308A, 1308B, motors 1312, engines, safety equipment, controllers, user interfaces, interiors exterior components, body panels 1208, bumpers 1316, sensors, etc., and/or combinations thereof. Additionally or alternatively, the mechanisms may provide unique security hardware and/or software embedded therein that, among other things, can prevent fraudulent or low quality construction replacements from being used in the vehicle 100. Similarly, the mechanisms, subsystems, and/or receiving features in the vehicle 100 may employ poka-yoke, or mistake-proofing, features that ensure a particular mechanism is always interconnected with the vehicle 100 in a correct position, function, etc.

By way of example, complete systems or subsystems may be removed and/or replaced from a vehicle 100 utilizing a single minute exchange principle. In some embodiments, the frame 1204 may include slides, receptacles, cavities, protrusions, and/or a number of other features that allow for quick exchange of system components. In one embodiment, the frame 1204 may include tray or ledge features, mechanical interconnection features, locking mechanisms, retaining mechanisms, etc., and/or combinations thereof. In some embodiments, it may be beneficial to quickly remove a used power source 1308A, 1308B (e.g., battery unit, capacitor unit, etc.) from the vehicle 100 and replace the used power source 1308A, 1308B with a charged power source. Continuing this example, the power source 1308A, 1308B may include selectively interchangeable features that interconnect with the frame 1204 or other portion of the vehicle 100. For instance, in a power source 1308A, 1308B replacement, the quick release features may be configured to release the power source 1308A, 1308B from an engaged position and slide or move away from the frame 1204 of a vehicle 100. Once removed, the power source 1308A, 1308B may be replaced (e.g., with a new power source, a charged power source, etc.) by engaging the replacement power source into a system receiving position adjacent to the vehicle 100. In some embodiments, the vehicle 100 may include one or more actuators configured to position, lift, slide, or otherwise engage the replacement power source with the vehicle 100. In one embodiment, the replacement power source may be inserted into the vehicle 100 or vehicle frame 1204 with mechanisms and/or machines that are external or separate from the vehicle 100.

In some embodiments, the frame 1204 may include one or more features configured to selectively interconnect with other vehicles and/or portions of vehicles. These selectively interconnecting features can allow for one or more vehicles to selectively couple together and decouple for a variety of purposes. For example, it is an aspect of the present disclosure that a number of vehicles may be selectively coupled together to share energy, increase power output, provide security, decrease power consumption, provide towing services, and/or provide a range of other benefits. Continuing this example, the vehicles may be coupled together based on travel route, destination, preferences, settings, sensor information, and/or some other data. The coupling may be initiated by at least one controller of the vehicle and/or traffic control system upon determining that a coupling is beneficial to one or more vehicles in a group of vehicles or a traffic system. As can be appreciated, the power consumption for a group of vehicles traveling in a same direction may be reduced or decreased by removing any aerodynamic separation between vehicles. In this case, the vehicles may be coupled together to subject only the foremost vehicle in the coupling to air and/or wind resistance during travel. In one embodiment, the power output by the group of vehicles may be proportionally or selectively controlled to provide a specific output from each of the one or more of the vehicles in the group.

The interconnecting, or coupling, features may be configured as electromagnetic mechanisms, mechanical couplings, electromechanical coupling mechanisms, etc., and/or combinations thereof. The features may be selectively deployed from a portion of the frame 1204 and/or body of the vehicle 100. In some cases, the features may be built into the frame 1204 and/or body of the vehicle 100. In any event, the features may deploy from an unexposed position to an exposed position or may be configured to selectively engage/disengage without requiring an exposure or deployment of the mechanism from the frame 1204 and/or body. In some embodiments, the interconnecting features may be configured to interconnect one or more of power, communications, electrical energy, fuel, and/or the like. One or more of the power, mechanical, and/or communications connections between vehicles may be part of a single interconnection mechanism. In some embodiments, the interconnection mechanism may include multiple connection mechanisms. In any event, the single interconnection mechanism or the interconnection mechanism may employ the poka-yoke features as described above.

The power system of the vehicle 100 may include the powertrain, power distribution system, accessory power system, and/or any other components that store power, provide power, convert power, and/or distribute power to one or more portions of the vehicle 100. The powertrain may include the one or more electric motors 1312 of the vehicle 100. The electric motors 1312 are configured to convert electrical energy provided by a power source into mechanical energy. This mechanical energy may be in the form of a rotational or other output force that is configured to propel or otherwise provide a motive force for the vehicle 100.

In some embodiments, the vehicle 100 may include one or more drive wheels 1320 that are driven by the one or more electric motors 1312 and motor controllers 1314. In some cases, the vehicle 100 may include an electric motor 1312 configured to provide a driving force for each drive wheel 1320. In other cases, a single electric motor 1312 may be configured to share an output force between two or more drive wheels 1320 via one or more power transmission components. It is an aspect of the present disclosure that the powertrain include one or more power transmission components, motor controllers 1314, and/or power controllers that can provide a controlled output of power to one or more of the drive wheels 1320 of the vehicle 100. The power transmission components, power controllers, or motor controllers 1314 may be controlled by at least one other vehicle controller described herein.

As provided above, the powertrain of the vehicle 100 may include one or more power sources 1308A, 1308B. These one or more power sources 1308A, 1308B may be configured to provide drive power, system and/or subsystem power, accessory power, etc. While described herein as a single power source 1308 for sake of clarity, embodiments of the present disclosure are not so limited. For example, it should be appreciated that independent, different, or separate power sources 1308A, 1308B may provide power to various systems of the vehicle 100. For instance, a drive power source may be configured to provide the power for the one or more electric motors 1312 of the vehicle 100, while a system power source may be configured to provide the power for one or more other systems and/or subsystems of the vehicle 100. Other power sources may include an accessory power source, a backup power source, a critical system power source, and/or other separate power sources. Separating the power sources 1308A, 1308B in this manner may provide a number of benefits over conventional vehicle systems. For example, separating the power sources 1308A, 1308B allow one power source 1308 to be removed and/or replaced independently without requiring that power be removed from all systems and/or subsystems of the vehicle 100 during a power source 1308 removal/replacement. For instance, one or more of the accessories, communications, safety equipment, and/or backup power systems, etc., may be maintained even when a particular power source 1308A, 1308B is depleted, removed, or becomes otherwise inoperable.

In some embodiments, the drive power source may be separated into two or more cells, units, sources, and/or systems. By way of example, a vehicle 100 may include a first drive power source 1308A and a second drive power source 1308B. The first drive power source 1308A may be operated independently from or in conjunction with the second drive power source 1308B and vice versa. Continuing this example, the first drive power source 1308A may be removed from a vehicle while a second drive power source 1308B can be maintained in the vehicle 100 to provide drive power. This approach allows the vehicle 100 to significantly reduce weight (e.g., of the first drive power source 1308A, etc.) and improve power consumption, even if only for a temporary period of time. In some cases, a vehicle 100 running low on power may automatically determine that pulling over to a rest area, emergency lane, and removing, or "dropping off," at least one power source 1308A, 1308B may reduce enough weight of the vehicle 100 to allow the vehicle 100 to navigate to the closest power source replacement and/or charging area. In some embodiments, the removed, or "dropped off," power source 1308A may be collected by a collection service, vehicle mechanic, tow truck, or even another vehicle or individual.

The power source 1308 may include a GPS or other geographical location system that may be configured to emit a location signal to one or more receiving entities. For instance, the signal may be broadcast or targeted to a specific receiving party. Additionally or alternatively, the power source 1308 may include a unique identifier that may be used to associate the power source 1308 with a particular vehicle 100 or vehicle user. This unique identifier may allow an efficient recovery of the power source 1308 dropped off. In some embodiments, the unique identifier may provide information for the particular vehicle 100 or vehicle user to be billed or charged with a cost of recovery for the power source 1308.

The power source 1308 may include a charge controller 1324 that may be configured to determine charge levels of the power source 1308, control a rate at which charge is drawn from the power source 1308, control a rate at which charge is added to the power source 1308, and/or monitor a health of the power source 1308 (e.g., one or more cells, portions, etc.). In some embodiments, the charge controller 1324 or the power source 1308 may include a communication interface. The communication interface can allow the charge controller 1324 to report a state of the power source 1308 to one or more other controllers of the vehicle 100 or even communicate with a communication device separate and/or apart from the vehicle 100. Additionally or alternatively, the communication interface may be configured to receive instructions (e.g., control instructions, charge instructions, communication instructions, etc.) from one or more other controllers of the vehicle 100 or a communication device that is separate and/or apart from the vehicle 100.

The powertrain includes one or more power distribution systems configured to transmit power from the power source 1308 to one or more electric motors 1312 in the vehicle 100. The power distribution system may include electrical interconnections 1328 in the form of cables, wires, traces, wireless power transmission systems, etc., and/or combinations thereof. It is an aspect of the present disclosure that the vehicle 100 include one or more redundant electrical interconnections 1332 of the power distribution system. The redundant electrical interconnections 1332 can allow power to be distributed to one or more systems and/or subsystems of the vehicle 100 even in the event of a failure of an electrical interconnection portion of the vehicle 100 (e.g., due to an accident, mishap, tampering, or other harm to a particular electrical interconnection, etc.). In some embodiments, a user of a vehicle 100 may be alerted via a user interface associated with the vehicle 100 that a redundant electrical interconnection 1332 is being used and/or damage has occurred to a particular area of the vehicle electrical system. In any event, the one or more redundant electrical interconnections 1332 may be configured along completely different routes than the electrical interconnections 1328 and/or include different modes of failure than the electrical interconnections 1328 to, among other things, prevent a total interruption power distribution in the event of a failure.

In some embodiments, the power distribution system may include an energy recovery system 1336. This energy recovery system 1336, or kinetic energy recovery system, may be configured to recover energy produced by the movement of a vehicle 100. The recovered energy may be stored as electrical and/or mechanical energy. For instance, as a vehicle 100 travels or moves, a certain amount of energy is required to accelerate, maintain a speed, stop, or slow the vehicle 100. In any event, a moving vehicle has a certain amount of kinetic energy. When brakes are applied in a typical moving vehicle, most of the kinetic energy of the vehicle is lost as the generation of heat in the braking mechanism. In an energy recovery system 1336, when a vehicle 100 brakes, at least a portion of the kinetic energy is converted into electrical and/or mechanical energy for storage. Mechanical energy may be stored as mechanical movement (e.g., in a flywheel, etc.) and electrical energy may be stored in batteries, capacitors, and/or some other electrical storage system. In some embodiments, electrical energy recovered may be stored in the power source 1308. For example, the recovered electrical energy may be used to charge the power source 1308 of the vehicle 100.

The vehicle 100 may include one or more safety systems. Vehicle safety systems can include a variety of mechanical and/or electrical components including, but in no way limited to, low impact or energy-absorbing bumpers 1316A, 1316B, crumple zones, reinforced body panels, reinforced frame components, impact bars, power source containment zones, safety glass, seatbelts, supplemental restraint systems, air bags, escape hatches, removable access panels, impact sensors, accelerometers, vision systems, radar systems, etc., and/or the like. In some embodiments, the one or more of the safety components may include a safety sensor or group of safety sensors associated with the one or more of the safety components. For example, a crumple zone may include one or more strain gages, impact sensors, pressure transducers, etc. These sensors may be configured to detect or determine whether a portion of the vehicle 100 has been subjected to a particular force, deformation, or other impact. Once detected, the information collected by the sensors may be transmitted or sent to one or more of a controller of the vehicle 100 (e.g., a safety controller, vehicle controller, etc.) or a communication device associated with the vehicle 100 (e.g., across a communication network, etc.).

Figure 14:
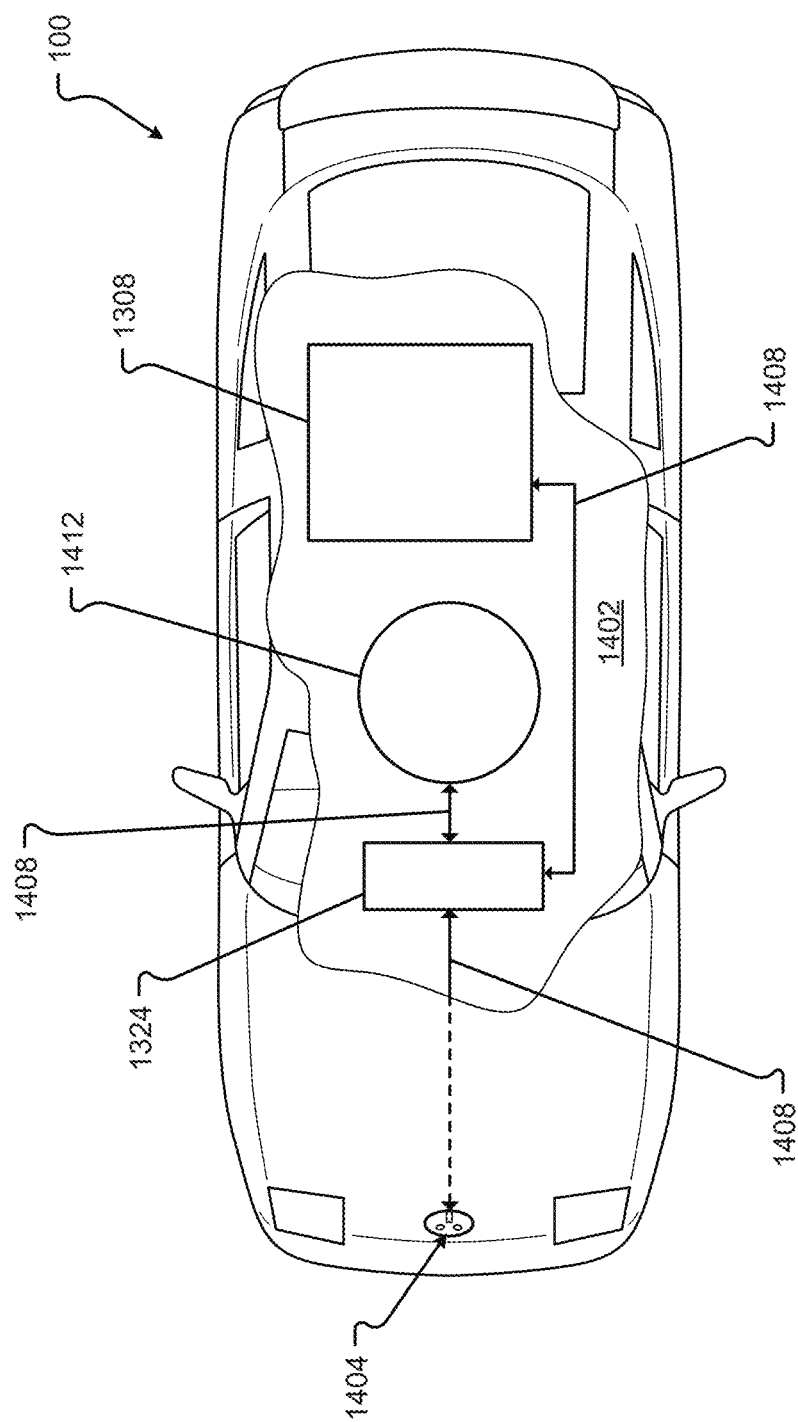
FIG. 14 is a plan view of a vehicle in accordance with embodiments of the present disclosure.

FIG. 14 shows a plan view of the vehicle 100 in accordance with embodiments of the present disclosure. In particular, FIG. 14 shows a broken section 1402 of a charging system for the vehicle 100. The charging system may include a plug or receptacle 1404 configured to receive power from an external power source (e.g., a source of power that is external to and/or separate from the vehicle 100, etc.). An example of an external power source may include the standard industrial, commercial, or residential power that is provided across power lines. Another example of an external power source may include a proprietary power system configured to provide power to the vehicle 100. In any event, power received at the plug/receptacle 1404 may be transferred via at least one power transmission interconnection 1408. Similar, if not identical, to the electrical interconnections 1328 described above, the at least one power transmission interconnection 1408 may be one or more cables, wires, traces, wireless power transmission systems, etc., and/or combinations thereof. Electrical energy in the form of charge can be transferred from the external power source to the charge controller 1324. As provided above, the charge controller 1324 may regulate the addition of charge to the power source 1308 of the vehicle 100 (e.g., until the power source 1308 is full or at a capacity, etc.).

In some embodiments, the vehicle 100 may include an inductive charging system and inductive charger 1412. The inductive charger 1412 may be configured to receive electrical energy from an inductive power source external to the vehicle 100. In one embodiment, when the vehicle 100 and/or the inductive charger 1412 is positioned over an inductive power source external to the vehicle 100, electrical energy can be transferred from the inductive power source to the vehicle 100. For example, the inductive charger 1412 may receive the charge and transfer the charge via at least one power transmission interconnection 1408 to the charge controller 1324 and/or the power source 1308 of the vehicle 100. The inductive charger 1412 may be concealed in a portion of the vehicle 100 (e.g., at least partially protected by the frame 1204, one or more body panels 1208, a shroud, a shield, a protective cover, etc., and/or combinations thereof) and/or may be deployed from the vehicle 100. In some embodiments, the inductive charger 1412 may be configured to receive charge only when the inductive charger 1412 is deployed from the vehicle 100. In other embodiments, the inductive charger 1412 may be configured to receive charge while concealed in the portion of the vehicle 100.

In addition to the mechanical components described herein, the vehicle 100 may include a number of user interface devices. The user interface devices receive and translate human input into a mechanical movement or electrical signal or stimulus. The human input may be one or more of motion (e.g., body movement, body part movement, in two-dimensional or three-dimensional space, etc.), voice, touch, and/or physical interaction with the components of the vehicle 100. In some embodiments, the human input may be configured to control one or more functions of the vehicle 100 and/or systems of the vehicle 100 described herein. User interfaces may include, but are in no way limited to, at least one graphical user interface of a display device, steering wheel or mechanism, transmission lever or button (e.g., including park, neutral, reverse, and/or drive positions, etc.), throttle control pedal or mechanism, brake control pedal or mechanism, power control switch, communications equipment, etc.

Figure 15:
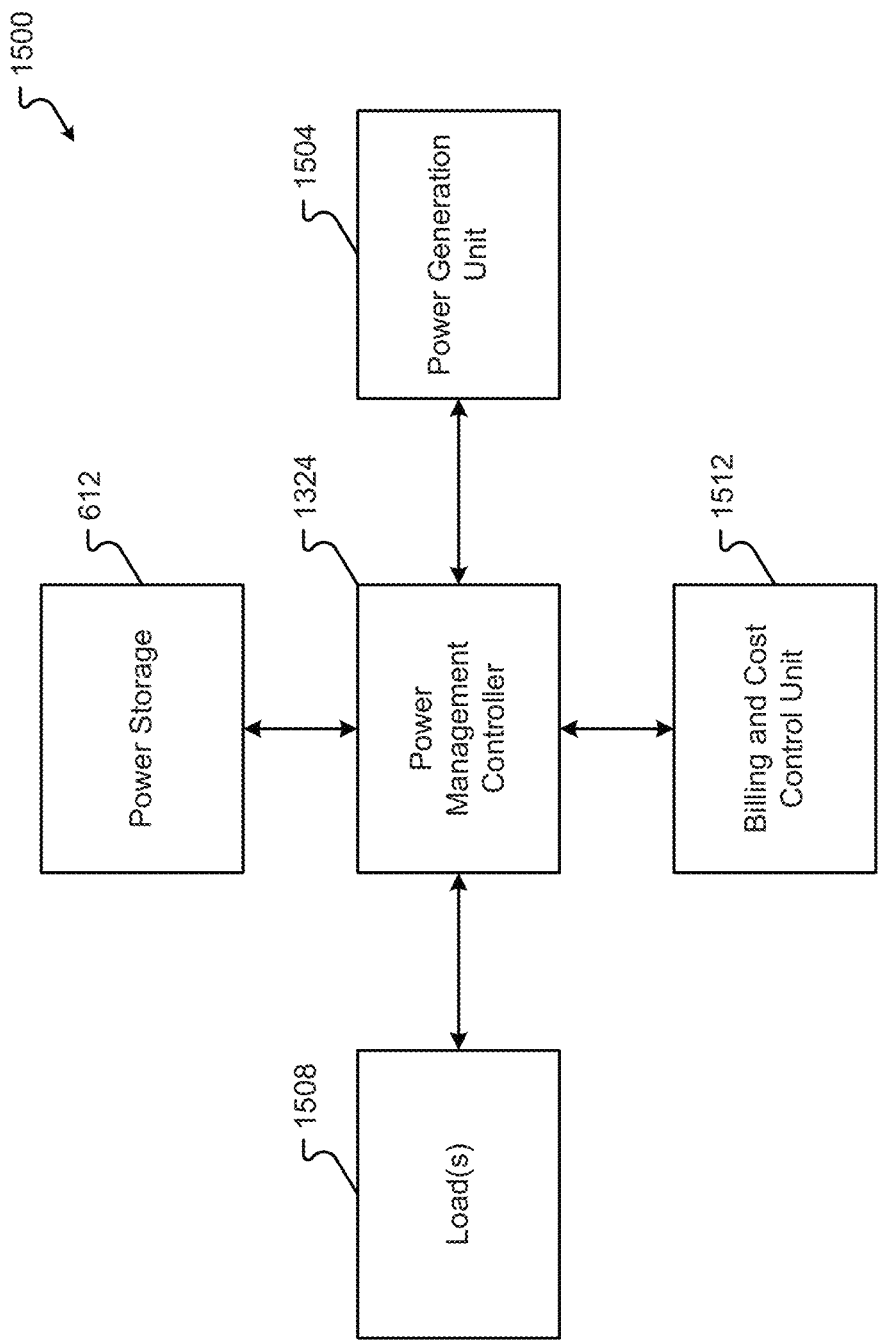
FIG. 15 is a block diagram of an embodiment of an electrical system of the vehicle.

An embodiment of the electrical system 1500 associated with the vehicle 100 may be as shown in FIG. 15. The electrical system 1500 can include power source(s) that generate power, power storage that stores power, and/or load(s) that consume power. Power sources may be associated with a power generation unit 1504. Power storage may be associated with a power storage system 612. Loads may be associated with loads 1508. The electrical system 1500 may be managed by a power management controller 1324. Further, the electrical system 1500 can include one or more other interfaces or controllers, which can include the billing and cost control unit 1512.

Figure 16:
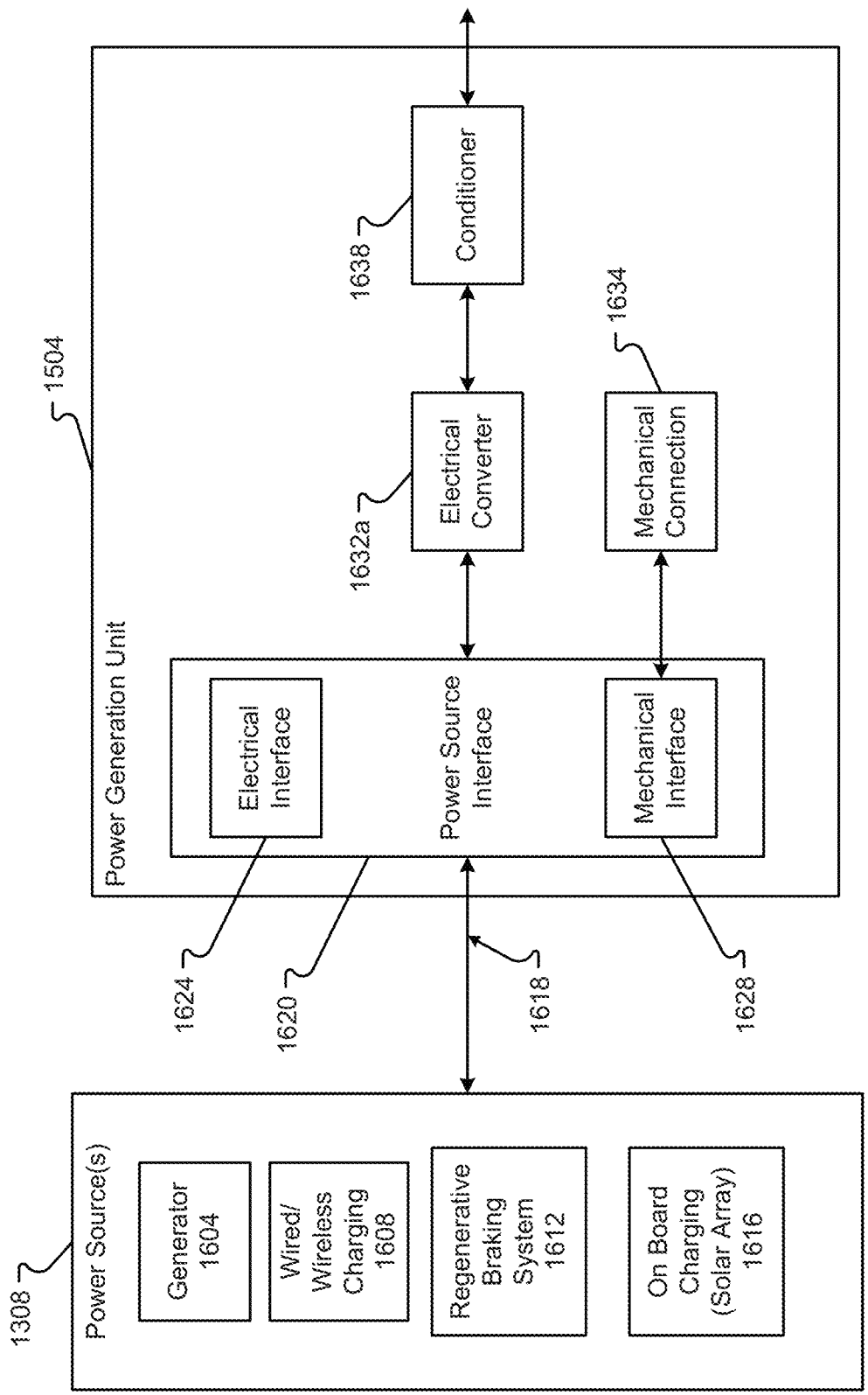
FIG. 16 is a block diagram of an embodiment of a power generation unit associated with the electrical system of the vehicle.

The power generation unit 1504 may be as described in conjunction with FIG. 16. The power storage component 612 may be as described in conjunction with FIG. 17. The loads 1508 may be as described in conjunction with FIG. 18.

The billing and cost control unit 1512 may interface with the power management controller 1324 to determine the amount of charge or power provided to the power storage 612 through the power generation unit 1504. The billing and cost control unit 1512 can then provide information for billing the vehicle owner. Thus, the billing and cost control unit 1512 can receive and/or send power information to third party system(s) regarding the received charge from an external source. The information provided can help determine an amount of money required, from the owner of the vehicle, as payment for the provided power. Alternatively, or in addition, if the owner of the vehicle provided power to another vehicle (or another device/system), that owner may be owed compensation for the provided power or energy, e.g., a credit.

The power management controller 1324 can be a computer or computing system(s) and/or electrical system with associated components, as described herein, capable of managing the power generation unit 1504 to receive power, routing the power to the power storage 612, and then providing the power from either the power generation unit 1504 and/or the power storage 612 to the loads 1508. Thus, the power management controller 1324 may execute programming that controls switches, devices, components, etc. involved in the reception, storage, and provision of the power in the electrical system 1500.

An embodiment of the power generation unit 1504 may be as shown in FIG. 16. Generally, the power generation unit 1504 may be electrically coupled to one or more power sources 1308. The power sources 1308 can include power sources internal and/or associated with the vehicle 100 and/or power sources external to the vehicle 100 to which the vehicle 100 electrically connects. One of the internal power sources can include an on board generator 1604. The generator 1604 may be an alternating current (AC) generator, a direct current (DC) generator or a self-excited generator. The AC generators can include induction generators, linear electric generators, and/or other types of generators. The DC generators can include homopolar generators and/or other types of generators. The generator 1604 can be brushless or include brush contacts and generate the electric field with permanent magnets or through induction. The generator 1604 may be mechanically coupled to a source of kinetic energy, such as an axle or some other power take-off. The generator 1604 may also have another mechanical coupling to an exterior source of kinetic energy, for example, a wind turbine.

Another power source 1308 may include wired or wireless charging 1608. The wireless charging system 1608 may include inductive and/or resonant frequency inductive charging systems that can include coils, frequency generators, controllers, etc. Wired charging may be any kind of grid-connected charging that has a physical connection, although, the wireless charging may be grid connected through a wireless interface. The wired charging system can include connectors, wired interconnections, the controllers, etc. The wired and wireless charging systems 1608 can provide power to the power generation unit 1504 from external power sources 1308.

Internal power sources for power may include a regenerative braking system 1612. The regenerative braking system 1612 can convert the kinetic energy of the moving car into electrical energy through a generation system mounted within the wheels, axle, and/or braking system of the vehicle 100. The regenerative braking system 1612 can include any coils, magnets, electrical interconnections, converters, controllers, etc. required to convert the kinetic energy into electrical energy.

Another source of power 1308, internal to or associated with the vehicle 100, may be a solar array 1616. The solar array 1616 may include any system or device of one or more solar cells mounted on the exterior of the vehicle 100 or integrated within the body panels of the vehicle 100 that provides or converts solar energy into electrical energy to provide to the power generation unit 1504.

The power sources 1308 may be connected to the power generation unit 1504 through an electrical interconnection 1618. The electrical interconnection 1618 can include any wire, interface, bus, etc. between the one or more power sources 1308 and the power generation unit 1504.

The power generation unit 1504 can also include a power source interface 1620. The power source interface 1620 can be any type of physical and/or electrical interface used to receive the electrical energy from the one or more power sources 1308; thus, the power source interface 1620 can include an electrical interface 1624 that receives the electrical energy and a mechanical interface 1628 which may include wires, connectors, or other types of devices or physical connections. The mechanical interface 1608 can also include a physical/electrical connection 1634 to the power generation unit 1504.

The electrical energy from the power source 1308 can be processed through the power source interface 1624 to an electric converter 1632. The electric converter 1632 may convert the characteristics of the power from one of the power sources into a useable form that may be used either by the power storage 612 or one or more loads 1508 within the vehicle 100. The electrical converter 1624 may include any electronics or electrical devices and/or component that can change electrical characteristics, e.g., AC frequency, amplitude, phase, etc. associated with the electrical energy provided by the power source 1308. The converted electrical energy may then be provided to an optional conditioner 1638. The conditioner 1638 may include any electronics or electrical devices and/or component that may further condition the converted electrical energy by removing harmonics, noise, etc. from the electrical energy to provide a more stable and effective form of power to the vehicle 100.

Figure 17:
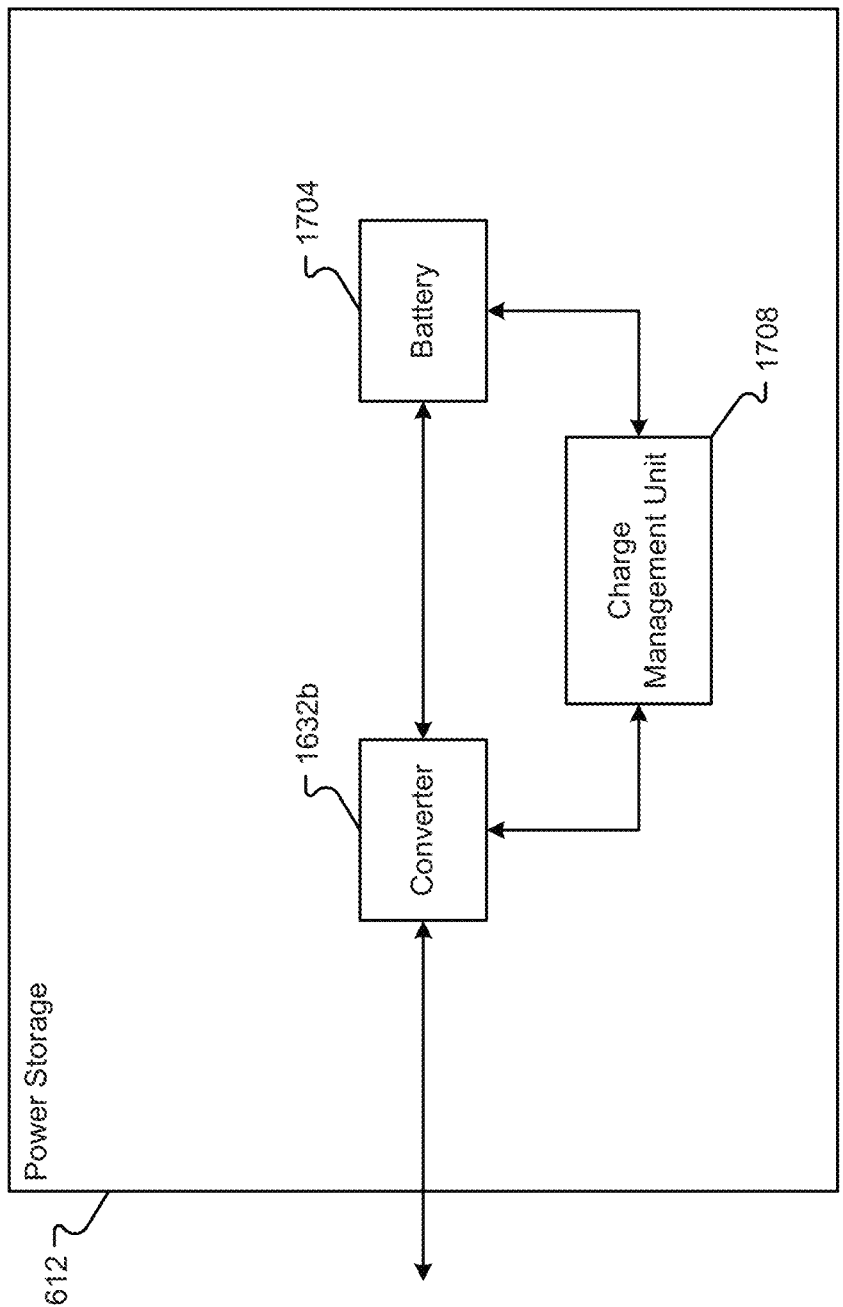
FIG. 17 is a block diagram of an embodiment of power storage associated with the electrical system of the vehicle.

An embodiment of the power storage 1612 may be as shown in FIG. 17. The power storage unit can include an electrical converter 1632b, one or more batteries, one or more rechargeable batteries, one or more capacitors, one or more accumulators, one or more supercapacitors, one or more ultrabatteries, and/or superconducting magnetics 1704, and/or a charge management unit 1708. The converter 1632b may be the same or similar to the electrical converter 1632a shown in FIG. 16. The converter 1632b may be a replacement for the electric converter 1632a shown in FIG. 16 and thus eliminate the need for the electrical converter 1632a as shown in FIG. 16. However, if the electrical converter 1632a is provided in the power generation unit 1504, the converter 1632b, as shown in the power storage unit 612, may be eliminated. The converter 1632b can also be redundant or different from the electrical converter 1632*a* shown in FIG. 16 and may provide a different form of energy to the battery and/or capacitors 1704. Thus, the converter 1632*b* can change the energy characteristics specifically for the battery/capacitor 1704.

The battery 1704 can be any type of battery for storing electrical energy, for example, a lithium ion battery, a lead acid battery, a nickel cadmium battery, etc. Further, the battery 1704 may include different types of power storage systems, such as, ionic fluids or other types of fuel cell systems. The energy storage 1704 may also include one or more high-capacity capacitors 1704. The capacitors 1704 may be used for long-term or short-term storage of electrical energy. The input into the battery or capacitor 1704 may be different from the output, and thus, the capacitor 1704 may be charged quickly but drain slowly. The functioning of the converter 1632 and battery capacitor 1704 may be monitored or managed by a charge management unit 1708.

The charge management unit 1708 can include any hardware (e.g., any electronics or electrical devices and/or components), software, or firmware operable to adjust the operations of the converter 1632 or batteries/capacitors 1704. The charge management unit 1708 can receive inputs or periodically monitor the converter 1632 and/or battery/capacitor 1704 from this information; the charge management unit 1708 may then adjust settings or inputs into the converter 1632 or battery/capacitor 1704 to control the operation of the power storage system 612.

Figure 18:
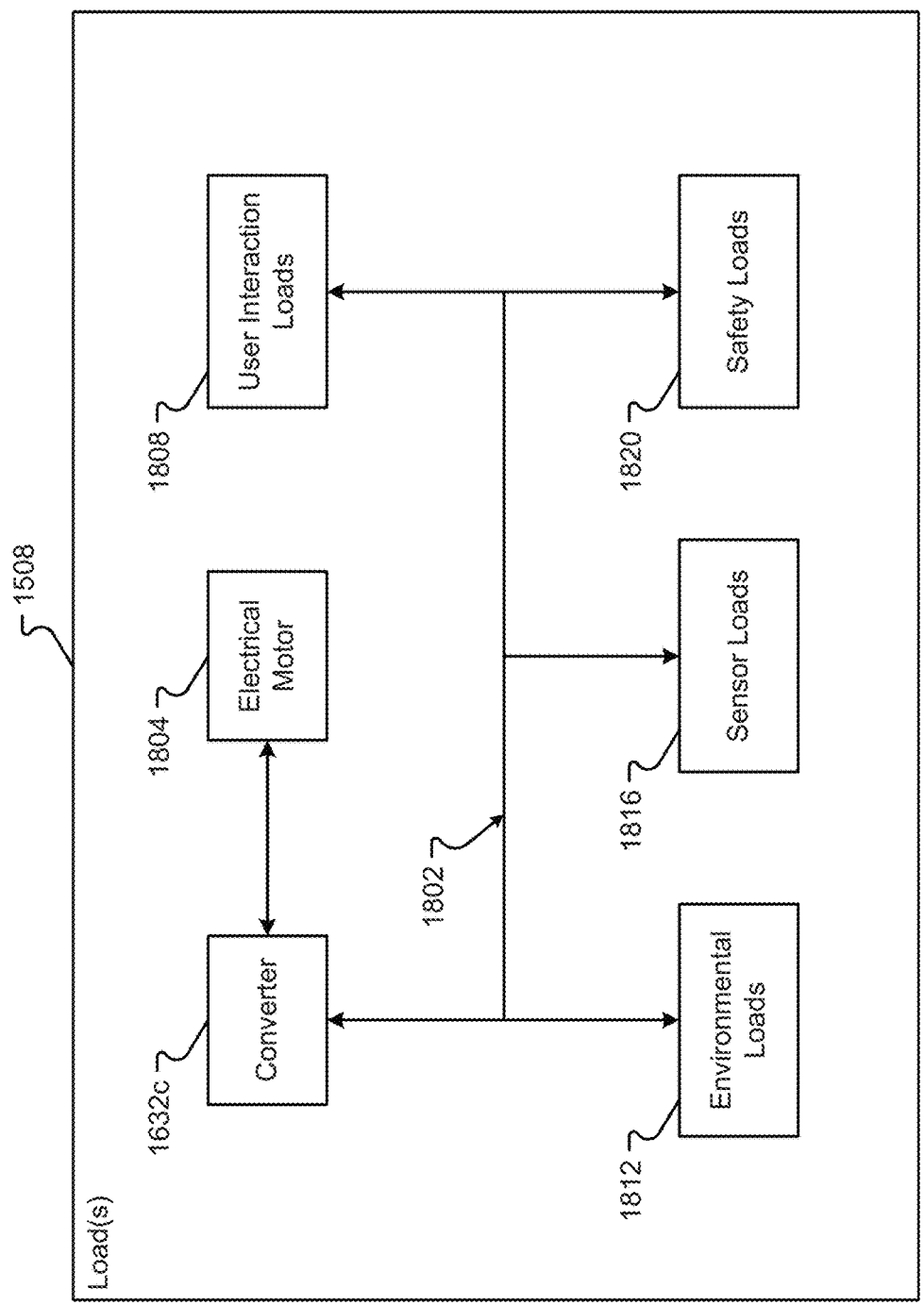
FIG. 18 is a block diagram of an embodiment of loads associated with the electrical system of the vehicle.

An embodiment of one or more loads 1508 associated with the vehicle 100 may be as shown in FIG. 18. The loads 1508 may include a bus or electrical interconnection system 1802, which provides electrical energy to one or more different loads within the vehicle 100. The bus 1802 can be any number of wires or interfaces used to connect the power generation unit 1504 and/or power storage 1612 to the one or more loads 1508. The converter 1632*c* may be an interface from the power generation unit 1504 or the power storage 612 into the loads 1508. The converter 1632*c* may be the same or similar to electric converter 1632*a* as shown in FIG. 16. Similar to the discussion of the converter 1632*b* in FIG. 17, the converter 1632*c* may be eliminated, if the electric converter 1632*a*, shown in FIG. 16, is present. However, the converter 1632*c* may further condition or change the energy characteristics for the bus 1802 for use by the loads 1508. The converter 1632*c* may also provide electrical energy to electric motor 1804, which may power the vehicle 100.

The electric motor 1804 can be any type of DC or AC electric motor. The electric motor may be a direct drive or induction motor using permanent magnets and/or winding either on the stator or rotor. The electric motor 1804 may also be wireless or include brush contacts. The electric motor 1804 may be capable of providing a torque and enough kinetic energy to move the vehicle 100 in traffic.

The different loads 1508 may also include environmental loads 1812, sensor loads 1816, safety loads 1820, user interaction loads 1808, etc. User interaction loads 1808 can be any energy used by user interfaces or systems that interact with the driver and/or passenger(s). These loads 1808 may include, for example, the heads up display, the dash display, the radio, user interfaces on the head unit, lights, radio, and/or other types of loads that provide or receive information from the occupants of the vehicle 100. The environmental loads 1812 can be any loads used to control the environment within the vehicle 100. For example, the air conditioning or heating unit of the vehicle 100 can be environmental loads 1812. Other environmental loads can include lights, fans, and/or defrosting units, etc. that may control the environment within the vehicle 100. The sensor loads 1816 can be any loads used by sensors, for example, air bag sensors, GPS, and other such sensors used to either manage or control the vehicle 100 and/or provide information or feedback to the vehicle occupants. The safety loads 1820 can include any safety equipment, for example, seat belt alarms, airbags, headlights, blinkers, etc. that may be used to manage the safety of the occupants. There may be more or fewer loads than those described herein, although they may not be shown in FIG. 18.

Figure 19:
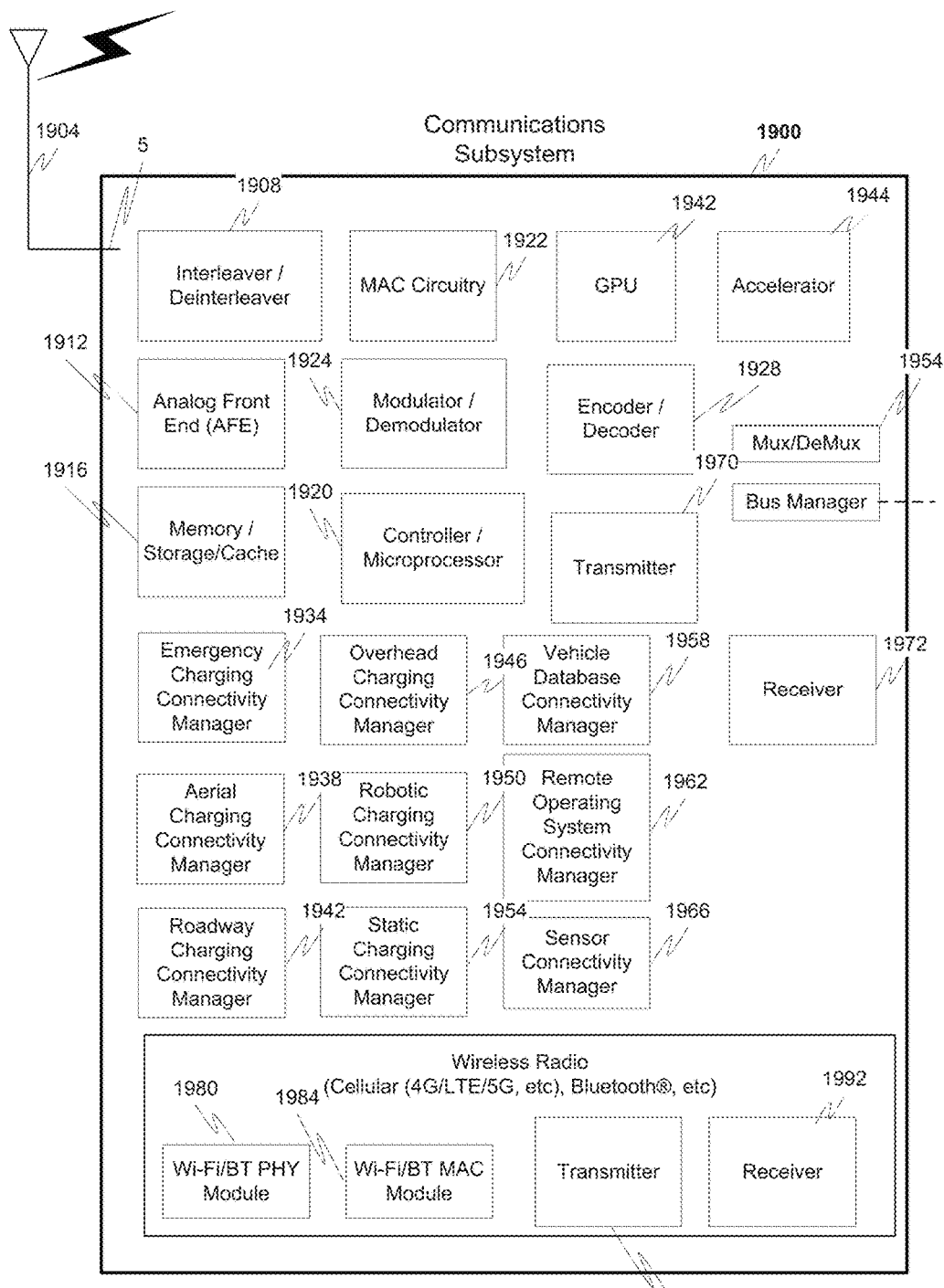
FIG. 19 is a block diagram of an exemplary embodiment of a communications subsystem of the vehicle.

FIG. 19 illustrates an exemplary hardware diagram of communications componentry that can be optionally associated with the vehicle.

The communications componentry can include one or more wired or wireless devices such as a transceiver(s) and/or modem that allows communications not only between the various systems disclosed herein but also with other devices, such as devices on a network, and/or on a distributed network such as the Internet and/or in the cloud.

The communications subsystem can also include inter- and intra-vehicle communications capabilities such as hotspot and/or access point connectivity for any one or more of the vehicle occupants and/or vehicle-to-vehicle communications.

Additionally, and while not specifically illustrated, the communications subsystem can include one or more communications links (that can be wired or wireless) and/or communications busses (managed by the bus manager), including one or more of CANbus, OBD-II, ARCINC 429, Byteflight, CAN (Controller Area Network), D2B (Domestic Digital Bus), FlexRay, DC-BUS, IDB-1394, IEBus, I²C, ISO 9141-1/-2, J1708, J1587, J1850, J1939, ISO 11783, Keyword Protocol 2000, LIN (Local Interconnect Network), MOST (Media Oriended Systems Transport), Multifunction Vehicle Bus, SMARTwireX, SPI, VAN (Vehicle Area Network), and the like or in general any communications protocol and/or standard.

The various protocols and communications can be communicated one or more of wirelessly and/or over transmission media such as single wire, twisted pair, fibre optic, IEEE 1394, MIL-STD-1553, MIL-STD-1773, power-line communication, or the like. (All of the above standards and protocols are incorporated herein by reference in their entirety)

As discussed, the communications subsystem enables communications between any if the inter-vehicle systems and subsystems as well as communications with non-collocated resources, such as those reachable over a network such as the Internet.

The communications subsystem, in addition to well-known componentry (which has been omitted for clarity), the device communications subsystem 1900 includes interconnected elements including one or more of: one or more antennas 1904, an interleaver/deinterleaver 1908, an analog front end (AFE) 1912, memory/storage/cache 1916, controller/microprocessor 1920, MAC circuitry 1922, modulator/demodulator 1924, encoder/decoder 1928, a plurality of connectivity managers 1934-1966, GPU 1942, accelerator 1944, a multiplexer/demultiplexer 1954, transmitter 1970, receiver 1972 and wireless radio 310 components such as a Wi-Fi PHY/Bluetooth® module 1980, a Wi-Fi/BT MAC module 1984, transmitter 1988 and receiver 1992. The various elements in the device 1900 are connected by one or more links/busses 5 (not shown, again for sake of clarity).

The device 400 can have one more antennas 1904, for use in wireless communications such as multi-input multi-output (MIMO) communications, multi-user multi-input multi-output (MU-MIMO) communications Bluetooth®, LTE, 4G, 5G, Near-Field Communication (NFC), etc. The antenna(s) 1904 can include, but are not limited to one or more of directional antennas, omnidirectional antennas, monopoles, patch antennas, loop antennas, microstrip antennas, dipoles, and any other antenna(s) suitable for communication transmission/reception. In an exemplary embodiment, transmission/reception using MIMO may require particular antenna spacing. In another exemplary embodiment, MIMO transmission/reception can enable spatial diversity allowing for different channel characteristics at each of the antennas. In yet another embodiment, MIMO transmission/reception can be used to distribute resources to multiple users for example within the vehicle and/or in another vehicle.

Antenna(s) 1904 generally interact with the Analog Front End (AFE) 1912, which is needed to enable the correct processing of the received modulated signal and signal conditioning for a transmitted signal. The AFE 1912 can be functionally located between the antenna and a digital baseband system in order to convert the analog signal into a digital signal for processing and vice-versa.

The subsystem 1900 can also include a controller/microprocessor 1920 and a memory/storage/cache 1916. The subsystem 1900 can interact with the memory/storage/cache 1916 which may store information and operations necessary for configuring and transmitting or receiving the information described herein. The memory/storage/cache 1916 may also be used in connection with the execution of application programming or instructions by the controller/microprocessor 1920, and for temporary or long term storage of program instructions and/or data. As examples, the memory/storage/cache 1920 may comprise a computer-readable device, RAM, ROM, DRAM, SDRAM, and/or other storage device(s) and media.

The controller/microprocessor 1920 may comprise a general purpose programmable processor or controller for executing application programming or instructions related to the subsystem 1900. Furthermore, the controller/microprocessor 1920 can perform operations for configuring and transmitting/receiving information as described herein. The controller/microprocessor 1920 may include multiple processor cores, and/or implement multiple virtual processors. Optionally, the controller/microprocessor 1920 may include multiple physical processors. By way of example, the controller/microprocessor 1920 may comprise a specially configured Application Specific Integrated Circuit (ASIC) or other integrated circuit, a digital signal processor(s), a controller, a hardwired electronic or logic circuit, a programmable logic device or gate array, a special purpose computer, or the like.

The subsystem 1900 can further include a transmitter 1970 and receiver 1972 which can transmit and receive signals, respectively, to and from other devices, subsystems and/or other destinations using the one or more antennas 1904 and/or links/busses. Included in the subsystem 1900 circuitry is the medium access control or MAC Circuitry 1922. MAC circuitry 1922 provides for controlling access to the wireless medium. In an exemplary embodiment, the MAC circuitry 1922 may be arranged to contend for the wireless medium and configure frames or packets for communicating over the wireless medium.

The subsystem 1900 can also optionally contain a security module (not shown). This security module can contain information regarding but not limited to, security parameters required to connect the device to one or more other devices or other available network(s), and can include WEP or WPA/WPA-2 (optionally+AES and/or TKIP) security access keys, network keys, etc. The WEP security access key is a security password used by Wi-Fi networks. Knowledge of this code can enable a wireless device to exchange information with an access point and/or another device. The information exchange can occur through encoded messages with the WEP access code often being chosen by the network administrator. WPA is an added security standard that is also used in conjunction with network connectivity with stronger encryption than WEP.

The exemplary subsystem 1900 also includes a GPU 1942, an accelerator 1944, a Wi-Fi/BT/BLE PHY module 1980 and a Wi-Fi/BT/BLE MAC module 1984 and wireless transmitter 1988 and receiver 1992.

The various connectivity managers 1934-1966 manage and/or coordinate communications between the subsystem 1900 and one or more of the systems disclosed herein and one or more other devices/systems. The connectivity managers include an emergency charging connectivity manager 1934, an aerial charging connectivity manager 1938, a roadway charging connectivity manager 1942, an overhead charging connectivity manager 1946, a robotic charging connectivity manager 1950, a static charging connectivity manager 1954, a vehicle database connectivity manager 1958, a remote operating system connectivity manager 1962 and a sensor connectivity manager 1966.

The emergency charging connectivity manager 1934 can coordinate not only the physical connectivity between the vehicle and the emergency charging device/vehicle, but can also communicate with one or more of the power management controller, one or more third parties and optionally a billing system(s). As an example, the vehicle can establish communications with the emergency charging device/vehicle to one or more of coordinate interconnectivity between the two (e.g., by spatially aligning the charging receptacle on the vehicle with the charger on the emergency charging vehicle) and optionally share navigation information. Once charging is complete, the amount of charge provided can be tracked and optionally forwarded to, for example, a third party for billing. In addition to being able to manage connectivity for the exchange of power, the emergency charging connectivity manager 1934 can also communicate information, such as billing information to the emergency charging vehicle and/or a third party. This billing information could be, for example, the owner of the vehicle, the driver of the vehicle, company information, or in general any information usable to charge the appropriate entity for the power received.

The aerial charging connectivity manager 1938 can coordinate not only the physical connectivity between the vehicle and the aerial charging device/vehicle, but can also communicate with one or more of the power management controller, one or more third parties and optionally a billing system(s). As an example, the vehicle can establish communications with the aerial charging device/vehicle to one or more of coordinate interconnectivity between the two (e.g., by spatially aligning the charging receptacle on the vehicle with the charger on the emergency charging vehicle) and optionally share navigation information. Once charging is complete, the amount of charge provided can be tracked and optionally forwarded to, for example, a third party for billing. In addition to being able to manage connectivity for the exchange of power, the aerial charging connectivity manager 1938 can similarly communicate information, such as billing information to the aerial charging vehicle and/or a third party. This billing information could be, for example, the owner of the vehicle, the driver of the vehicle, company information, or in general any information usable to charge the appropriate entity for the power received etc., as discussed.

The roadway charging connectivity manager 1942 and overhead charging connectivity manager 1946 can coordinate not only the physical connectivity between the vehicle and the charging device/system, but can also communicate with one or more of the power management controller, one or more third parties and optionally a billing system(s). As one example, the vehicle can request a charge from the charging system when, for example, the vehicle needs or is predicted to need power. As an example, the vehicle can establish communications with the charging device/vehicle to one or more of coordinate interconnectivity between the two for charging and share information for billing. Once charging is complete, the amount of charge provided can be tracked and optionally forwarded to, for example, a third party for billing. This billing information could be, for example, the owner of the vehicle, the driver of the vehicle, company information, or in general any information usable to charge the appropriate entity for the power received etc., as discussed. The person responsible for paying for the charge could also receive a copy of the billing information as is customary. The robotic charging connectivity manager 1950 and static charging connectivity manager 1954 can operate in a similar manner to that described herein.

The vehicle database connectivity manager 1958 allows the subsystem to receive and/or share information stored in the vehicle database. This information can be shared with other vehicle components/subsystems and/or other entities, such as third parties and/or charging systems. The information can also be shared with one or more vehicle occupant devices, such as an app on a mobile device the driver uses to track information about the vehicle and/or a dealer or service/maintenance provider. In general, any information stored in the vehicle database can optionally be shared with any one or more other devices optionally subject to any privacy or confidentially restrictions.

The remote operating system connectivity manager 1962 facilitates communications between the vehicle 100 and any one or more autonomous vehicle systems. These communications can include one or more of navigation information, vehicle information, occupant information, or in general any information related to the remote operation of the vehicle.

The sensor connectivity manager 1966 facilitates communications between any one or more of the vehicle sensors and any one or more of the other vehicle systems. The sensor connectivity manager 1966 can also facilitate communications between any one or more of the sensors and/or vehicle systems and any other destination, such as a service company, app, or in general to any destination where sensor data is needed.

In accordance with one exemplary embodiment, any of the communications discussed herein can be communicated via the conductor(s) used for charging. One exemplary protocol usable for these communications is Power-line communication (PLC). PLC is a communication protocol that uses electrical wiring to simultaneously carry both data, and Alternating Current (AC) electric power transmission or electric power distribution. It is also known as power-line carrier, power-line digital subscriber line (PDSL), mains communication, power-line telecommunications, or power-line networking (PLN). For DC environments in vehicles PLC can be used in conjunction with CAN-bus, LIN-bus over power line (DC-LIN) and DC-BUS.

The communications subsystem can also optionally manage one or more identifiers, such as an IP (internet protocol) address(es), associated with the vehicle and one or other system or subsystems or components therein. These identifiers can be used in conjunction with any one or more of the connectivity managers as discussed herein.

Figure 20:
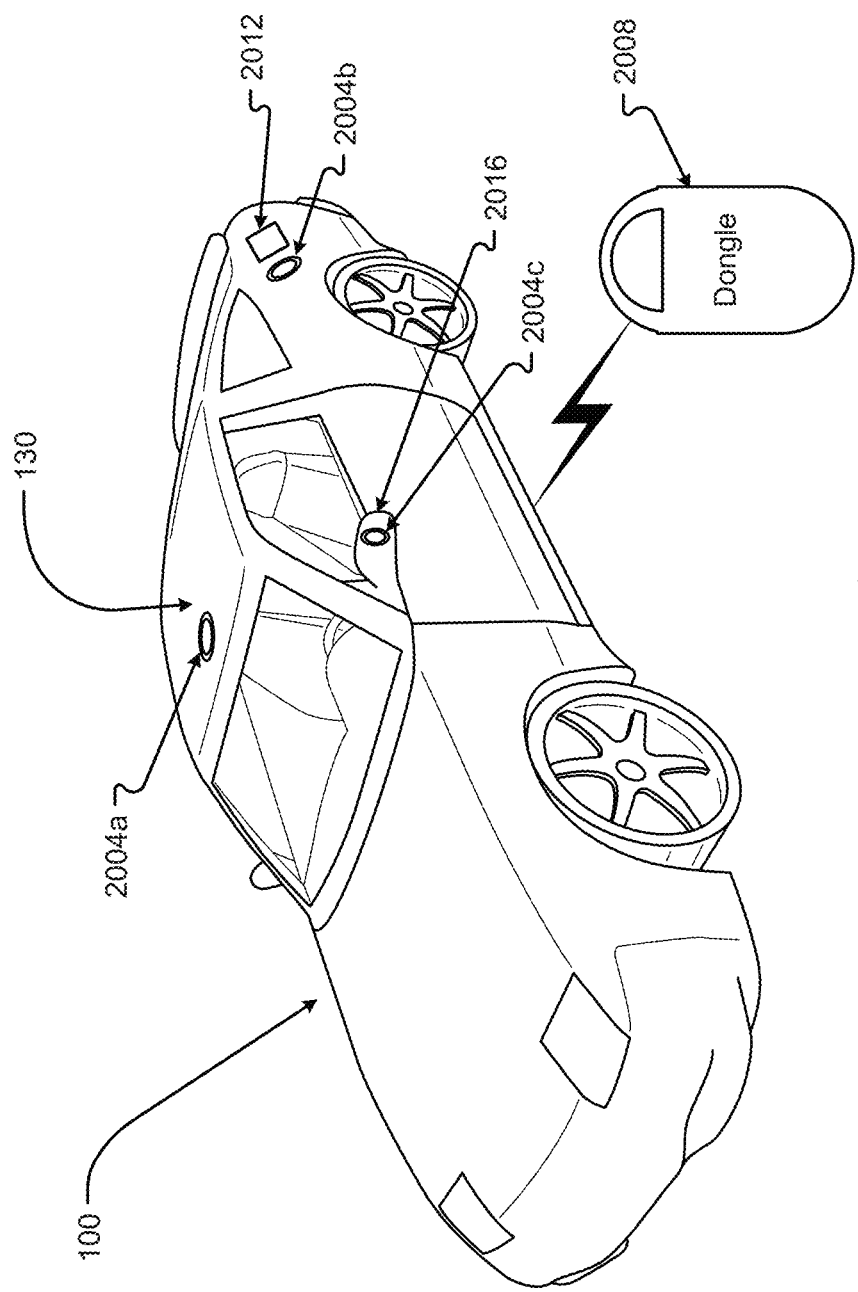
FIG. 20 is another view of a vehicle including communication interfaces positioned on the vehicle.

An alternative or additional embodiment of vehicle 100 may be as shown in FIG. 20. The vehicle 100 may have one or more areas for communicating with the near field communication interface. The areas may include antennas 2004*a*, 2004*b*, and 2004*c*. Antennas can include any type of near field communication (NFC) antenna including loop antennas and other antennas that may be embedded in the panels of the vehicle 100. NFC may employ electromagnetic induction between two loop antennae when NFC devices, antennas 2004*a*, 2004*b*, and 2004*c* exchange information, operating within the globally available unlicensed radio frequency ISM band of 13.56 MHz on ISO/IEC 18000-3 air interface at rates ranging from 106 to 424 Kbit/s. As such, the antennas 2004*a*, 2004*b*, and 2004*c* can also include any transceiver circuitry that completes the electromagnetic induction connection. In some configurations, the antennas 2004 may only include the loop antenna and the antennas 2004 may share a common circuitry to enable NFC communications.

The antennas 2004*a*, 2004*b*, and 2004*c* can communicate using one or more NFC standards. NFC standards cover communications protocols and data exchange formats and are based on existing radio-frequency identification (RFID) standards including ISO/IEC 14443 and Felicity Card (FeliCa). The standards include ISO/IEC 18092 and those defined by the NFC Forum. In addition to the NFC Forum, the GSM Association (GSMA) group defined a platform for the deployment of GSMA NFC Standards within mobile handsets. GSMA's efforts include Trusted Services Manager, Single Wire Protocol, testing/certification and secure element. NFC components incorporated into the antennas 2004*a*, 2004*b*, and 2004*c* can include, for example, the iClass®, veriClass®, and other NFC devices developed by HID®.

The antennas 2004*a*, 2004*b*, and 2004*c* can be placed in locations on the vehicle 100 to allow easier connection with other devices. For example, antenna 2004*a* may be placed on the roof 130 of the vehicle 100 to allow for connection with overhead NFC devices, such as may be found in parking garages. Antenna 2004*c* may be positioned outboard on a mirror 2016 or side panel of the vehicle 100 to better connect with devices on walls or other vertical structures, such as may be found at drive through restaurants and establishments. Another antenna 2004*c* may be within physical proximity to a charging port 2012 or gas tank door to facilitate communications with a charging device or a gas pump. Other antennas 2004 may be positioned in other parts of the vehicle 100 to facilitate other communications with other entities or facilities.

The vehicle 100 may also communicate with a dongle 2008. A dongle 2008 may be another hardware/software component that can communicate wirelessly with the vehicle 100. The dongle 2008 may communicate using an NFC connection or may employ another wireless technology, such as BlueTooth or WLAN technology. A common example of the dongle 2008 is the keyless entry system of many vehicles. Unlike the simple keyless entry system, the dongle 2008 may provide biometric data associated with the user of the dongle 2008. For example, the dongle 2008 may be associated with a single user, which may need to provide a biometric characteristic (e.g., a fingerprint, a voice signature, etc.) to employ the dongle 2008. This biometric signature may be exchanged between the dongle 2008 and the vehicle 100. Further, the presence of the dongle 2008, determined by a continuous connection between the dongle 2008 and the vehicle 100, can indicate the presence of the associated user holding the dongle 2008.

Figure 21:
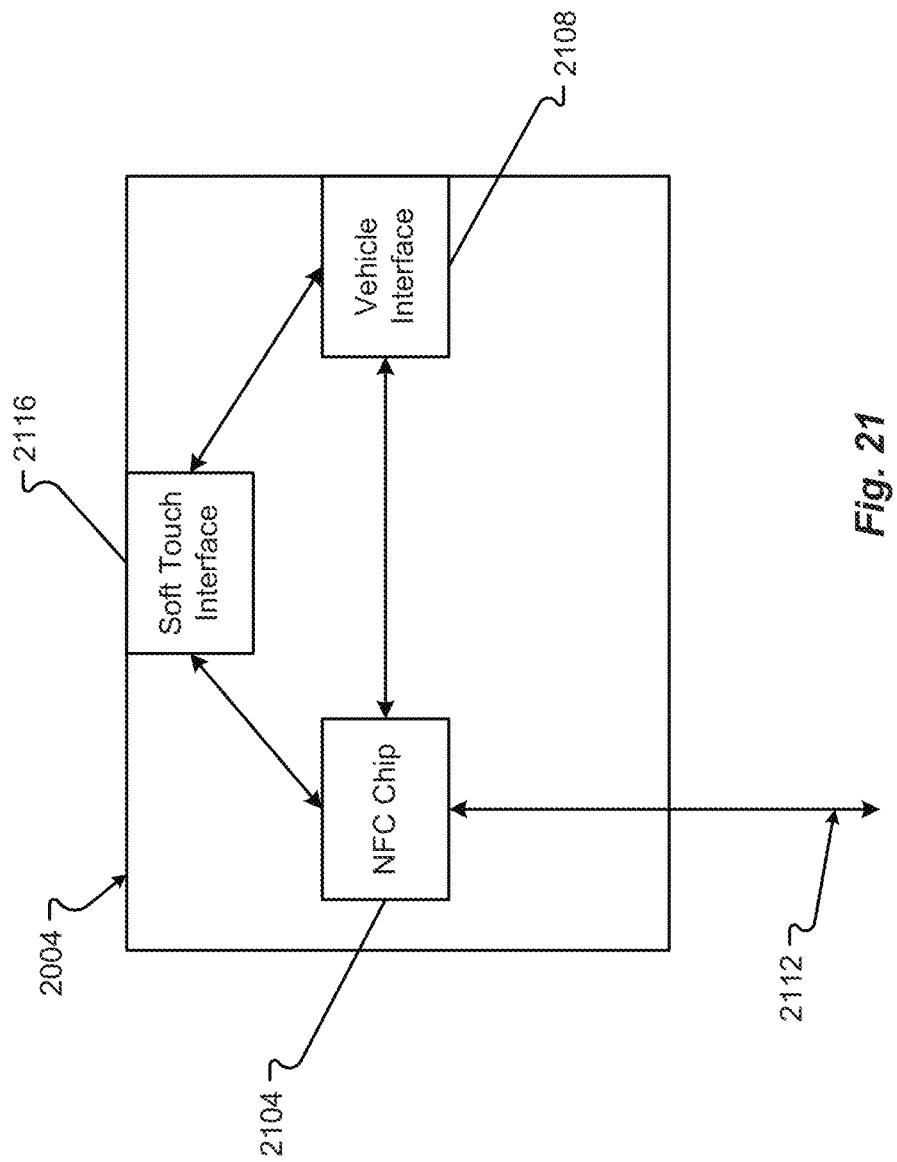
FIG. 21 is a block diagram of a communication interface for conducting secure communications with the vehicle.

An embodiment of the hardware/software configuration associated with the antennas 2004 may be as shown in FIG. 21. The hardware software configuration of the antennas 2004 can include a near field communication chipset 2104 a vehicle interface 2108 and/or a soft touch interface 2116. Each of these different components 2104 through 2116 can include hardware software operable to receive and/or transmit near field communication or other types of communications to and from the vehicle 100.

The near field communication chipset 2104 can include any hardware and software associated with the execution of near field communication communications. As explained previously, loop antenna 2004 of the NFC device can be embedded within the vehicle. However, the other circuitry and components of the near field communication devices may be incorporated into a single NFC chipset 2104. Thus, the NFC chipset 2104 can include the components that receive data from the loop antenna, decode and/or encode information from or onto the transmission, or conduct other functions that allow for communications over the NFC connection. For example, the NFC chipset can include, for example, the iClass®, veriClass®, and other NFC devices developed by HID® or similar hardware and/or software.

The soft touch interface 2116 may include a physical interconnection abilities described in conjunction with FIGS. 22A and 22B. Vehicle interface 2108 can include any hardware and/or software to exchange communications between the NSC chipset 2104 and or the soft touch interface 2116 and the vehicle processor as described in conjunction with FIG. 19. As such, the vehicle interface 2108 can include the application programming interface (API) or other communications capability that can translate, reconfigure, or manage the data from the NFC antenna 2004 to the vehicle communication system described FIG. 19.

An embodiment of a soft touch interface navies described in FIGS. 22A and 22B. The soft touch interface may be mounted on an exterior mirror 2016. Soft touch interface can include an area 2116. The area 2116 may be a cavity or other mounting structure for the soft touch interface. The soft touch interface can include a rotating cylinder 2204. The rotating Senate cylinder may be connected to the mounting structure 2116 such that the rotating cylinder 2204 can rotate through a range of movement. Physically attached to the rotating cylinder 2204 may be armature 2208. Two or more armatures 2208 cab extend from the rotating cylinder 2204. The two or more armatures 2208 may be stored inboard of the area 2116 in a first position. In a second position, as shown in FIG. 22B, the armatures 2208 may extend outboard of the mirror 2016. Amateurs 2208 may connect to or contact a pad 2212. Both the armatures 2208 the pad 2212 may provide for an electric connection. Signals may be passed between the armatures 2208 and the pad 2212 in the configuration shown in FIG. 22B. Other configurations for the soft touch interface are possible. These other configurations may include any type of physical electrical connection that may be optionally made by moving an electrical conduit in contact with another electrically conductive surface.

Figure 23:
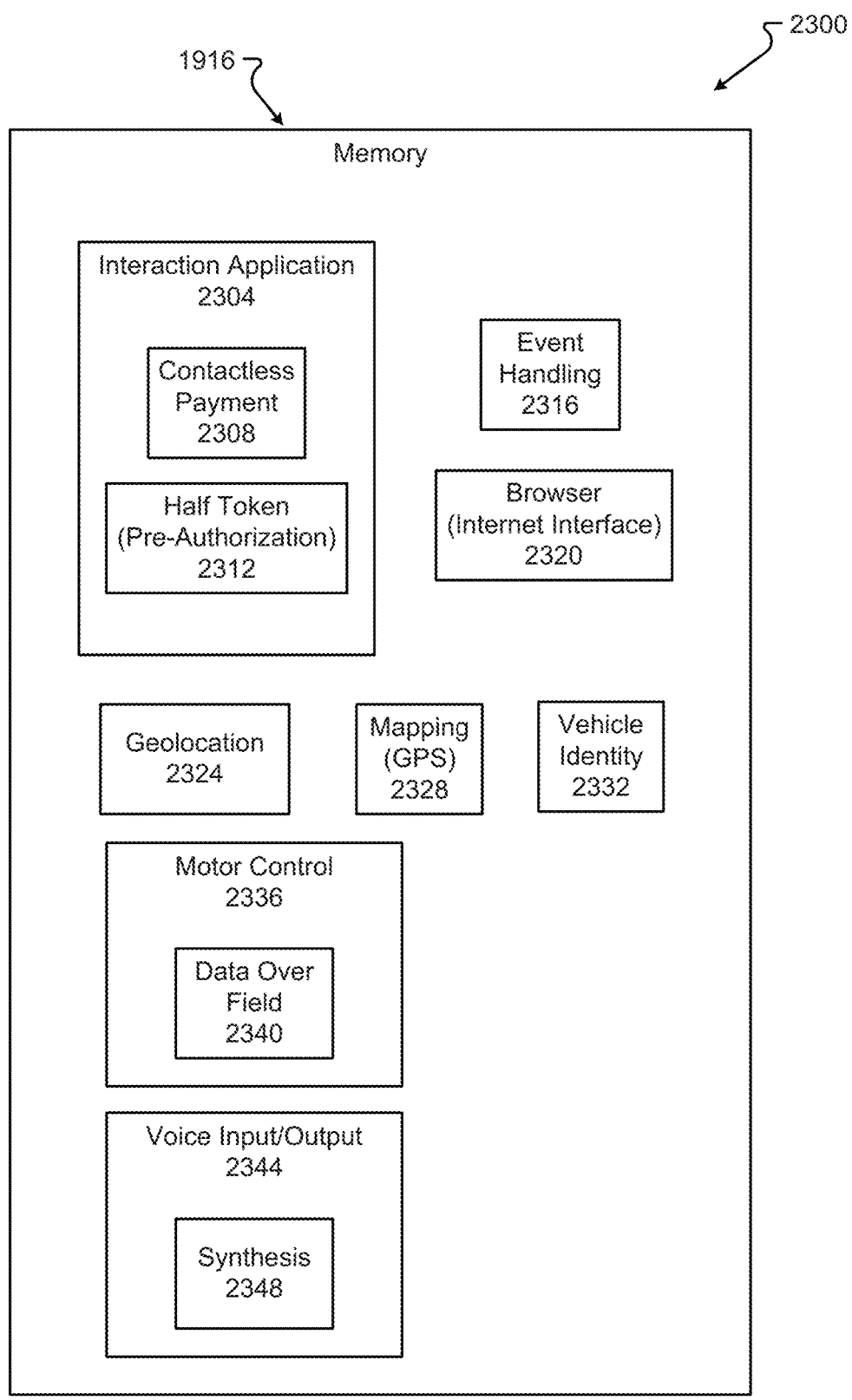
FIG. 23 is a block diagram of hardware and/or software components that may interface a restored in memory for conducting secure communications with the vehicle.

An embodiment of software 2300 that may be stored within the memory 1916 may be as shown in FIG. 23. Software 2300 can include one or more of an interaction application 2304, an event handling application 2316, a browser 2320, a geolocation application 2224, a mapping application 2328, a vehicle identity application 2332, a motor control application 2336, and/or a voice input/output application 2344. The interaction application 2304 can include a contactless payment component 2308 and/or half token application 2312.

The contactless payment application 2308 can conducts financial transactions using the vehicle. Contactless payment application 2308 may conduct the financial transactions with or without user input with third parties. The half token application 2312 can provide half tokens or pre-authorizations to third parties when interacting with those third parties. As such, the half token application 2312 is capable of authenticating or verifying the identity and veracity of the third party or providing that information for the user to the third party. In some configurations, the half token application 2312 is capable of sending authorizations for secure information in two or more packet communications that may be conducted over different communication media such that a higher-level security is achieved for the vehicle 100.

Event handling application 2316 is capable of receiving events associated with the vehicle 100 or the user. Events can include such items as need for charging of the electric vehicle, purchase requests by the user, service needs of the vehicle 100, communication requests by the user, or other types of events. Event handler 2316 can receive the event notifications and instruct other parts or components of the vehicle 100 to respond to the events as received. A browser 2320 can the Internet interface for the vehicle 100 and/or user. Thus, the browser can be any type of Internet interface, for example, Internet Explorer, Safari, Mozilla, etc. The browser 2320 may also provide Internet access to the vehicle 100.

Geolocation application 2324 can provide location information to the vehicle 100. The geolocation information may be provided from a GPS antenna, through triangulation of cellular towers or other known landmarks, or by some other type of location information. Geolocation information may be provided to the mapping application 2228. The mapping application 2228 can provide a coordinated location for the vehicle 100 based on the geolocation information provided by the geolocation application 2324 and one or more maps stored within the vehicle 100. Thus, the mapping application 2328 can resolve the physical locations of vehicle 100 based on the geolocation information.

The vehicle identity application 2332 can determine the identity of one or more occupants of the vehicle 100. Thus, the vehicle identity application 2332 can use one or more characteristics of biometric information to identify users within the vehicle 100. The identity of the users may then be used by other components of the vehicle 100.

The motor control application can control the motor function of the electric vehicle 100. Thus, the motor control application 2336 can accelerate or decelerate the electric motor based on user input or input from an automated driving function. The motor control function 2236 may also include the ability to send information using the motor. As such, the motor control application 2336 can include a data over field application 2340 which can encode data onto the electric field generated by the motor. In another configuration, the motor control application 2336 can cycle the motor in a pattern to convey information to a device that can receive or interpret the electric field of the motor.

The voice input output application 2344 can receive voice input from a user within the vehicle 100. Further, the voice input output can provide sound output to the speakers of the vehicle 100. Sound output can be synthesized voice to convey information to the user. In other configurations, the voice input output application 2344 can provide for the exchange of audio and/or video in a communication between a user of the vehicle 100 and another party. If synthesized voice output is provided, the voice input output application 2344 can include a synthesis module 2348. The synthesis module 2248 can translate written or other signals into voice output that can be sent to the speakers of the vehicle 100. As such, the driver of the vehicle 100 may not read the information but can listen to the information conveyed by the voice input/output application 2344.

An embodiment of data system 2400 that may be stored, retrieved, sent, managed etc. with the vehicle 100 and associated with a user may be as shown in FIG. 24. The data structure 2400 can be stored, received, managed, sent by one or more of the systems in one or more of the processes described herein. The data structure 2404 can represent secure information associated with a user and/or the vehicle 100. This information data structure 2404 can have one or more data fields including, but not limited to: biometrics 2408, username 2412, password 2416, mobile device information 2420, dongle code 2424, encryption key 2428, credentials 2432, vehicle identification number (VIN) 2436, and electronic serial number (ESN) 2440, and/or an engine code 2444. There may be more or fewer fields than those shown in data structure 2404, as represented by ellipses 2452. Further, each user of the vehicle 100 may have their own data structure, as represented by ellipses 2448.

The biometrics field 2408 can include biometric information for the user. This information 2408 can include one of more of, but is not limited to: facial structure, facial recognition information, voiceprint, voice recognition information, eye color, DNA information, fingerprint information, or other types of biometric information that could be used to identify the user. This information 2408 may be gathered by sensors and stored in data structure 2408.

A username 2412 and password 2416 can be identifying information created by a user. The username 2412 can be any type of identifying information that the user can enter to access vehicle systems, and the password 2416 can be another form of data known to the user, used with the username 2414, to authenticate the user. The username 2412 and password 2416 may be created by the user in another computer and downloaded into the vehicle 100 or may be created in the vehicle 100.

The mobile device information 2420 can include any information about one or more mobile devices or other types of devices that may be associated with the user and linked with the vehicle 100. Mobile device information 2420 can include the mobile device number, the media access control (MAC) address, a uniform resource locator (URL), or other types of information that might be associated with a mobile device. Further, mobile device information 2420 can include any kind of Bluetooth link, passcode, or information about a wearable that might provide information about a user.

The dongle code 2420 can be the code or frequency of the dongle 2008. Thus, this information may be associated with the user rather than with the vehicle 100 because the dongle 2008 is more user-specific than vehicle-specific because the user carries the dongle 2008. Information from that dongle 2008 can be associated with any kind of specific information about the user. The encryption key 2428 can be any type of known secret that is common between the vehicle 100 and the user. This encryption key 2428 can include some type of pretty good privacy (PGP) key or other types of encryption information used to encrypt the information in the data structure 2404 or other information described herein.

The credentials 2432 can include any type of other credentials or information that might be used to access the encryption key 2428 or other information described herein. These credentials can be other types of information that may be different than that described previously, such as a barcode or other type of information that might be provided from another device or memory or may have been provided by the user through a user interface.

The VIN 2436 and ESN 2440 can be information about the vehicle 100. This information 2436, 2440 may be provided automatically when the data structure 2404 is created by the processor 5608 of the vehicle 100. The VIN may be stored not only as plates or information physically connected to the vehicle but may also be electronic information stored securely within the vehicle 100. The ESN 2440 may be an identification number for the communication system 1900 of the vehicle 100.

The engine code 2448 can be any type of code related to the electric or gasoline engine. This code 2444 can be provided by the engine through some type of communication with the magnetic or electric field of the engine. This engine code 2448 can be an alphanumeric code, a numeric code, a globally-unique identifier (GUID), or some other type of code. Thus, similar to the VIN 2436 or the ESN 2440, the engine code 2444 can provide an identification of the engine.

Another data system 2500 may be as shown in FIG. 25. Here, the data system 2500 can include one or more other types of secure information associated with the user. The data system 2500 can include one or more data structures 2504, each related to a user, as represented by ellipses 2536. The data structure 2504 can include information that is stored, managed, sent, received, retrieved by the systems described herein. The data structure 2504 can include one or more of, but is not limited to: payment information 2508, a personal identification number (PIN) 2512, identifiers 2516, addresses 2520, limits 2524, preferences 2528, and/or rules 2532. There may be more or fewer fields, associated with data structure 2504, than those shown in FIG. 25, as represented by the ellipses 2540.

Payment information 2508 can be any type of credit card, bank account, or other financial information that might be used in a secure communication payment through or with the vehicle 100. Similarly, the PIN 2512 can be any type of PIN associated with one or more of the financial instruments provided in the payment information 2508. These PINs may be created by the third-party financial institutions and given to the user. The user may enter the PIN 2512 into the vehicle 100 through a user interface, and the vehicle can store the PIN 2512 in data structure 2504.

The IDs 2516 may be any type of information used with the payment information 2508. Thus, the IDs 2516 can include the name on a credit card, an alias, or some other information associated with the payment information 2508. The address 2520, similar to the IDs 2516, can be the address for the user of the payment information 2508. As such, the address 2520 can be the home address, business address, or some other type of address associated with the user having payment information stored in field 2508.

Limits 2524, preferences 2528, and rules 2532 can be user-created fields, may be automatically set, or learned, by machine-learning, based on repetitive processes of the user while in the vehicle 100. Limits 2524 can be any limit on any type of secure communication or secure transaction used with the vehicle 100. These limits 2524 can be in dollars, in a number of transactions, or some other type of limit. Limits 2524 can be associated with the vehicle 100 or may be associated with two or more vehicles and thus may limit transactions across all types of vehicles the user may be associated therewith. Preferences 2528 can be any type of financial or behavior preference of the user. Behavior preference 2528 can be a determination of the desires or wants of a user based on their behavior. For example, if a user buys coffee every morning at a certain Starbucks, that coffee-buying event at the Starbucks can be a preference of the user stored in field 2528. The rules 2532 can be any type of information dictated by the user to control secure communications or transactions with the vehicle 100. For example, the user may preauthorize certain types of transactions or communications with the vehicle 100, or others may not be preauthorized. As such, this preauthorization may be included in the rules field 2532.

Figure 26:
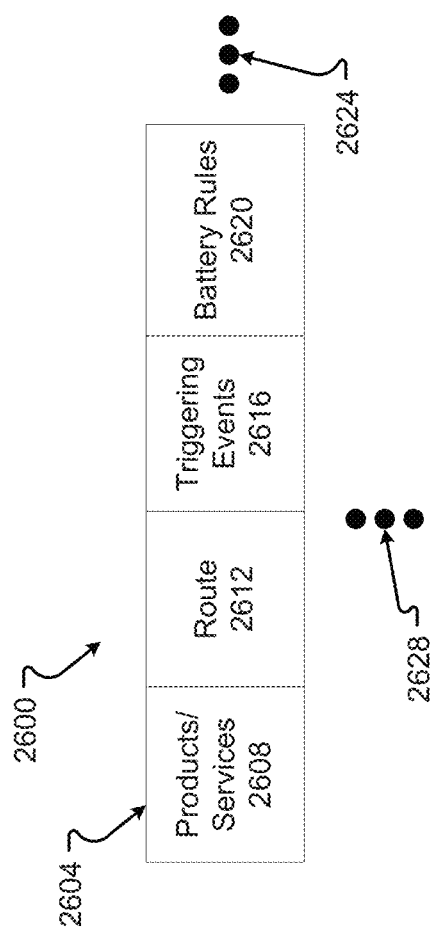
FIG. 26 is a block diagram of data used to do automatic communications between the vehicle and a third party.

Data system 2600 can include one or more types of information regarding a user's behavior or information about the vehicle 100 associated with the user may be as shown in FIG. 26. Each user may have their own type of information stored in the data system 2600, as represented by ellipses 2628. The information may be stored in the data structure 2604 that includes one or more of, but is not limited to: a product services field 2608, a route field 2612, a triggering events field 2616, and/or battery rules field 2620. There may be more or fewer fields than those shown in data structure 2604, as represented by ellipses 2624.

The product services field 2608 can include any type of product or service bought by the user while operating the vehicle 100. For example, the products or services 2608 can represent such things as food purchases, gasoline purchases, car wash purchases, toll purchases, parking purchases, or other types of events that occur with and/or are associated with the vehicle 100. The lists of products and services 2608 may also include a context about when or where things were bought, what time the user bought them, how often they bought them, and other types of information. As such, this information of products and/service purchases 2608 can be generated and developed into preferences 2528, as explained previously with FIG. 25.

An embodiment of one or more routes taken by the user may be stored in route field 2612. These routes 2612 may be the consistent or common routes taken by the user and may also include information about what types of products or services may be offered along those routes. This information 2612 can allow the vehicle 100 to present options to the user or conduct automatic communications or transactions along such routes 2612.

Triggering events 2616 may be predetermined events that may cause certain purchases or communications to be conducted automatically by the vehicle 100. For example, a triggering event 2616 of inclement weather may cause the user to automatically purchase heightened map and weather data for the vehicle display. In other events, triggering events 2616 may be set once the user enters the vehicle 100 before conducting a drive. For example, a user can establish what communications or transactions are preauthorized for that drive when the triggering event 2616 of starting the vehicle occurs.

Battery rules 2620 can be what type of actions may be allowed for charging, discharging, changing, or managing the battery charge. These battery rules 2620 can include one or more of, but are not limited to: where batteries may be charged or replaced, where a vehicle 100 is allowed to get a charge without authorization, and other types of information. As such, the battery rules 2620 can manage the financial transactions conducted and associated with the battery.

Figure 27:
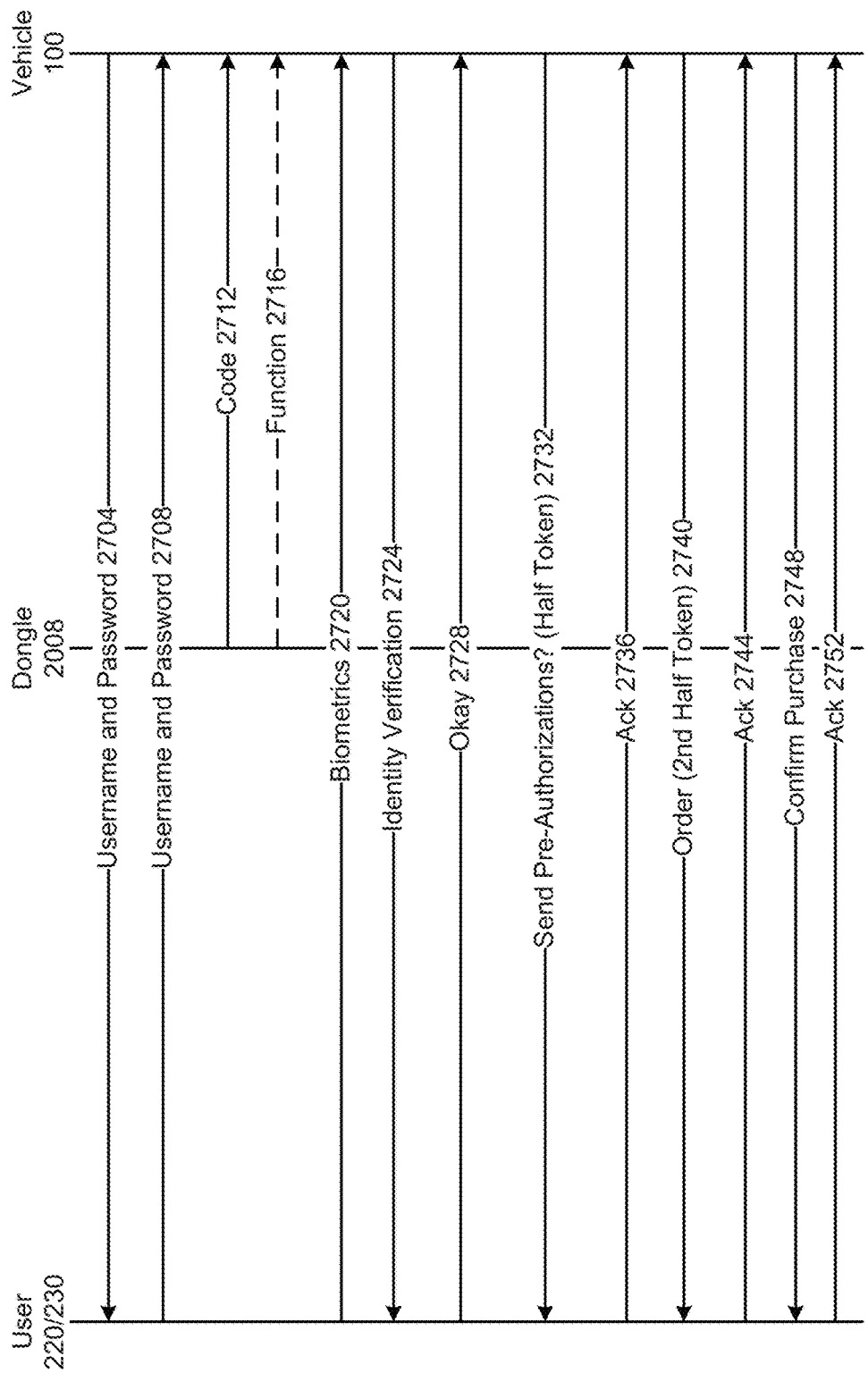
FIG. 27 is a communication diagram between a user in a vehicle including a dongle.

An embodiment of a signaling diagram between the vehicle 100 and a user 220 may be as shown in FIG. 27. This signaling arrangement shown in FIG. 27 may occur when the user enters the vehicle 100 and then begins to drive the vehicle 100. Upon entering the vehicle 100, the user 220 may start the vehicle 100 or generate an event with the vehicle 100 that indicates a drive is about to begin.

The vehicle 100 may then request the user's username 2412 and password 2416, in signal 2704. The username and password request may be sent to a user interface displayed on a display associated with the vehicle 100. In other configurations, the username 2412 and/or password 2416 may be requested and provided to the vehicle 100 with a user interface event and an audio or other type of response or gesture, in signal 2708. The response from the user 220 can provide the credentials for the vehicle 100 to authenticate the user. In some configurations, the dongle 2008 may send a code 2712 to the vehicle 100. As the dongle 2008 is associated with the user 220, this code 2712 can identify the user to the vehicle 100. Along with the code 2712, the dongle 2008 may send a function or a request for an operation, optionally in step 2716. A function can be some type of request for the vehicle to perform an operation such as starting the vehicle 100, opening doors, opening windows, or doing some other kind of task. This function 2716 can also be a request to conduct a secure communication or transaction that may be authorized only with the dongle 2008. As such, even if the user's vehicle 100 is stolen, without the dongle 2008, financial transactions may not be conducted.

Biometrics may also be collected by vehicle 100, in signal 2720. Sensors 5437, within the vehicle 100, may obtain biometric information from the user 220. This biometric information can be a visual recordings of the user's face, may be a voice recording, may be some other physical characteristics recorded by the sensors 5437 within the vehicle 100. This biometric information can be compared to biometrics information 2408. If there is a positive comparison with the biometric information 2408 and the user is identified, the vehicle 100 may send an identity verification signal 2724 back to the user 220. The vehicle 100 may present some identity verification to the user interface to allow the user to understand that they have been identified. The user 220 may respond by providing an okay signal 2728 back to the vehicle 100. The okay signal 2728 may be given in a user interface or may be a voice or a hand gesture within the vehicle 100 and recorded by the vehicle sensors 5437.

In some configurations, the vehicle 100 may ask for a preauthorization or a half-token provided by the user, in signal 2732. Here, the vehicle 100 may present a user interface or an audio request to the user 220 requesting whether the user wishes to authorize certain automatic communications or automatic transactions before the drive begins. If the user does desire such type of automation, the user 220 may send an ack or acknowledge signal 2736 back to the vehicle 100. The ack signal 2736 can again be a user interface input, may be a voice command, some type of gesture or other type of response between the user 220 and the vehicle 100.

The vehicle 100 may then send a second token, e.g., an order, 2740 to a user 220. The order 2740 may be an automated request to a third party for some type of product or service. This order 2740 may be presented to the user interface to allow the user to acknowledge whether the order should be made in signal 2744. If acknowledged, the vehicle 100 can confirm the purchase to the user, in signal 2748, after making the proper purchase, transaction and/or communication with the third party. This confirmed purchase then may be acknowledged by the user 220, in signal 2752.

Figure 28:
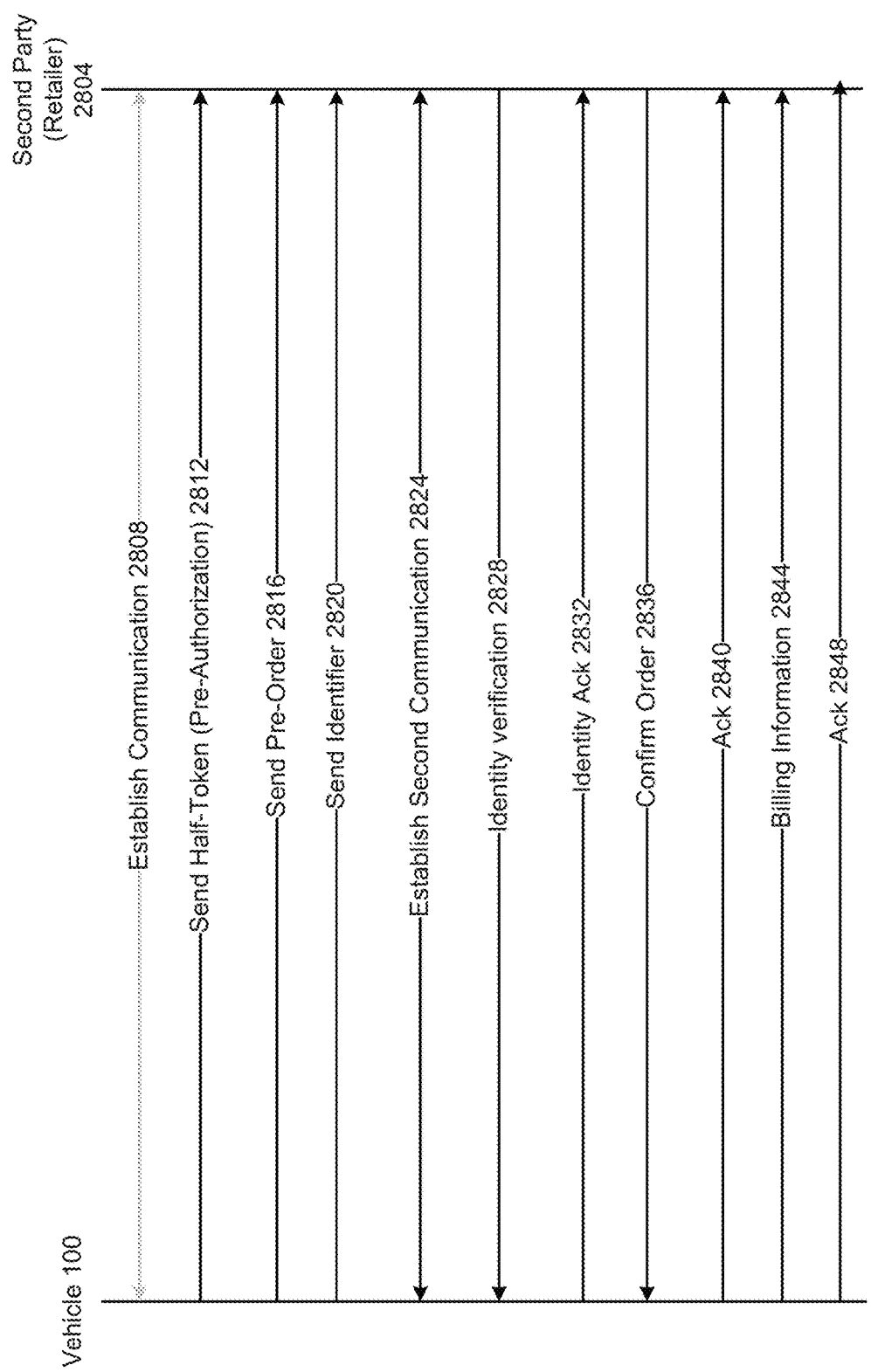
FIG. 28 is a communication diagram between a vehicle and a second party.

Another embodiment of a signaling process between a vehicle 100 and a second party, such as a retailer 2804, may be as shown in FIG. 28. An initial signaling 2808 for establishing communications between the vehicle 100 and the second party 2804 may involve nearfield communications, such as through an RFID device, wireless communications either through a cellular or 802.11 link. Regardless of the format, the vehicle 100 and the second party 2804 can establish some communication connection through signal(s) 2808.

The vehicle 100 may then send a half-token or preauthorization for some type of good or service or other type of secure communication to the second party, in signal 2812. The half-token signal 2812 may include some secure communication data, but may not be a complete set of data for the second party to conduct an activity without a second set or portion of information. Thereinafter, the vehicle 100 may send a preorder or other type of secure communication 2816 to the second party 2804; the half-token 2812 may authenticate or authorize a transaction, the order may be the next step in identifying what is desired by the user of the vehicle 100. The vehicle 100 may then send an identifier 2820 for identifying the user and/or vehicle. This information 2820 can be sent in a long-distance communication without the vehicle/user in the physical proximity of the second party 2804. As such, the identifying information 2820 can later be used to identify that vehicle/user when the vehicle 100 does arrive within physical proximity of the second party 2804.

Sometime thereinafter, after vehicle 100 drives to second party 2804 and a second communication establishment may be conducted with signals 2824. The vehicle 100 can establish communications that require physical proximity, for example, nearfield communications or some other type of communication connection. Thereinafter, the second party 2804 may send a request to identify or verify the identity of the vehicle 100 and/or user 220, in signal 2828. This signal 2828 may be a request for more information to complete the token. The vehicle 100 can send an acknowledgement signal 2832 to the second party 2804.

The second party may then send a confirm order signal 2836, which may be acknowledged by the vehicle 100 in signal 2840. The confirm order 2836 may cause the vehicle 100 to present information to the user interface for the user 220 to confirm the order and/or information previously sent by the vehicle 100. Upon acknowledging the order, the user 220 can authorize the vehicle 100 to send billing information, in signal 2844. Billing information 2844 may be the second, matching half-token sent to the second party 2804. Billing information thus may complete the information needed by the second party 2804 to conduct or provide the service or good ordered in signal 2816. The second party 2804 may acknowledge the billing information in signal 2848.

FIGS. 28 through 41 provide user interfaces that may be presented on the display 5472 within the vehicle 100. These user interfaces may be provided in a heads-up display, in a display in the head unit, or some other type of display. The user interfaces can include both dynamic and static components. The dynamic components can receive user input and be user-selectable devices. The dynamic components can include tabs at the top of the user interface 2912, which, when selected, provide for different types of user interfaces. Further, they may include menus, dropdown menus, text-boxes, radio buttons, or other types of selectable devices that provide user input into the vehicle's processing system 5608.

Figure 29:
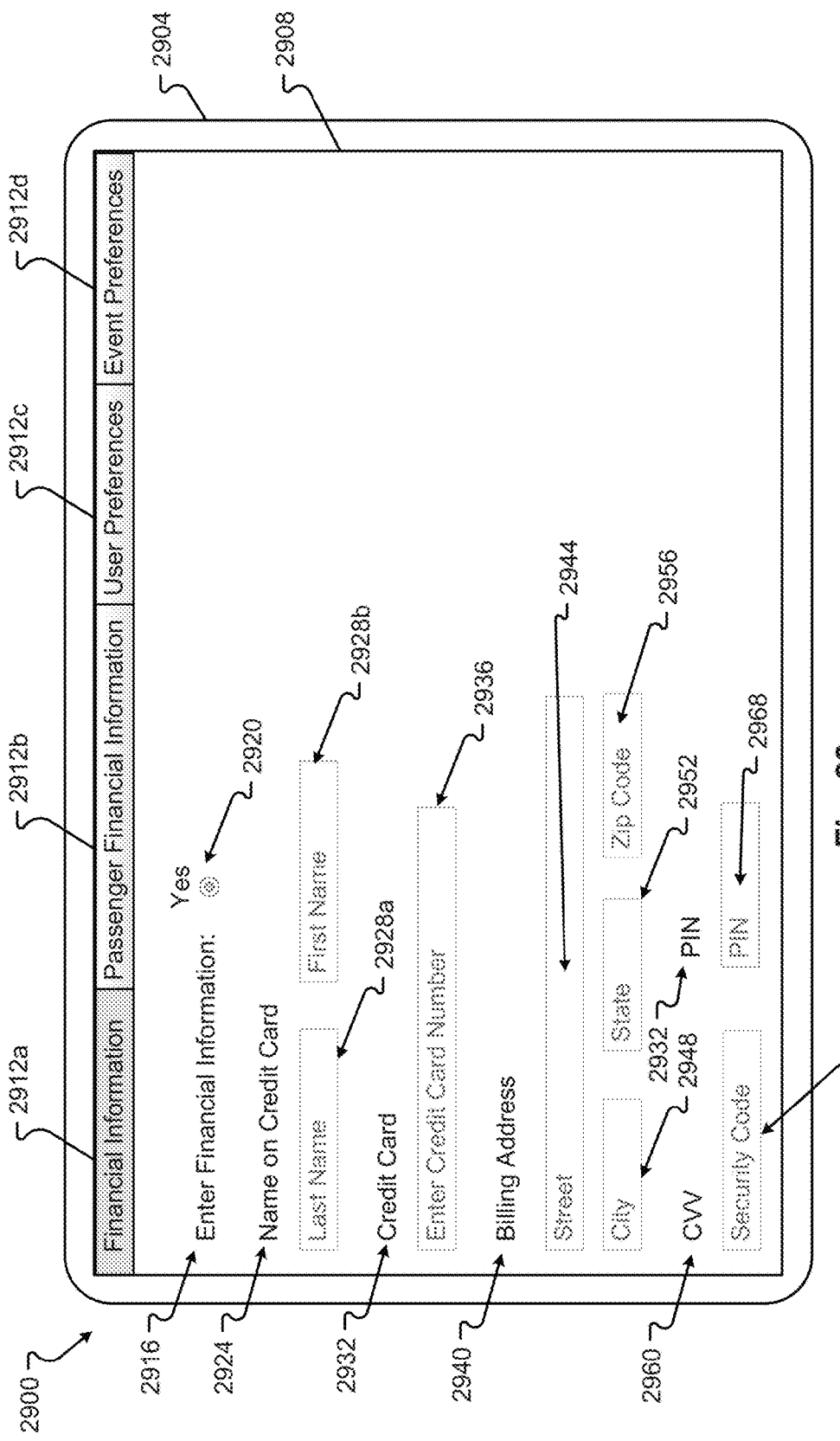
FIG. 29 is a user interface provided within the vehicle.

FIG. 29 provides a first user interface 2900 to allow the user to enter financial information into the vehicle 100 to be securely stored therein. The display 2904 can include a frame and a display portion 2908 to a window or other type of user interface (while a window is generally use in a desktop environment, the term "window" here can describe a portion of content displayed together where the content is generally interrelated). The window or user interface may be associated with one of two or more tabs 2912. In FIG. 29, window 2908 can be associated with financial information tab 2912a, which has different visual indicia, for example a shading or different color for tab 2912a compared to the other tabs 2912b through 2912d.

To enter financial information, the user may be provided with an indication 2916 that the user can select a radio button 2920 to enter financial information. If selected, the user can then enter information under different categories indicated by static information displays. For example, the name on the credit card may be presented in indication 2924 where the user could enter their name in fields 2928a and 2928b. A credit card number indication 2932 provides for a text box 2936 that allows the user to enter their credit card number into text box 2936. The billing address field 2940 allows for the user to enter their street, city, state, and ZIP code in fields 2944, 2948, 2952, and 2956, respectively. A security code field 2960 allows the user to enter their security code (CVV) from the back of their credit card in field 2964, or their PIN for the credit card in field 2968. Through the user interface 2908, the user can enter all their financial information which then may be used automatically by the vehicle 100 in secure communications.

Figure 30A:
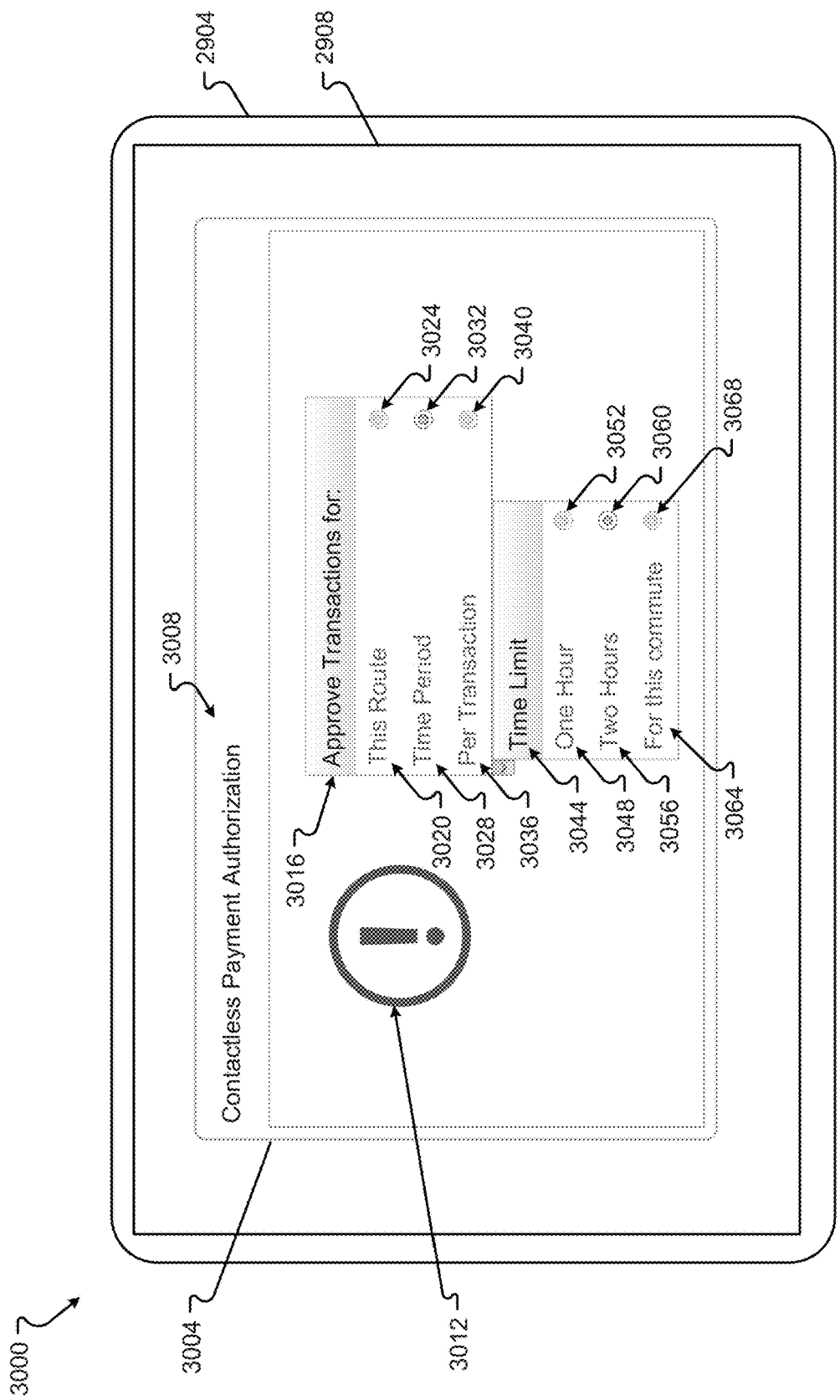
FIG. 30A is another user interface provided within the vehicle.

Another user interface 3000 is shown in FIG. 30A. This user interface embodiment 3000 includes an information box 3004. The box or window 3004 includes a banner 3008 indicating that the user can use this interface to approve contactless payments or authorize those contactless payments. An icon 3012 indicates that the user interface 3004 provides for information or input and requires user attention.

A dropdown menu or selection menu, having banner 3016, allows a user to approve transactions for different types of events. For example, the user may, according to the banners 3020, 3028, and 3036, approve transactions for a particular route, time period, or per transaction by selecting one of the radio buttons 3024, 3032, or 3040, respectively. For any one of the items—for instance, the time period selection 3028, 3032—a dropdown menu 3044, with the banner 3044 for time limit, may be presented. Thus, for the time period selection 3028, the user may have different types of time periods from which to select. For example, the selections 3048, 3056, and 3064 indicate that the user can select approval of transactions or payment authorizations for a one-hour time period, a two-hour time period, or for a particular commute, by selecting radio buttons 3052, 3060, 3068, respectively.

Figure 30B:
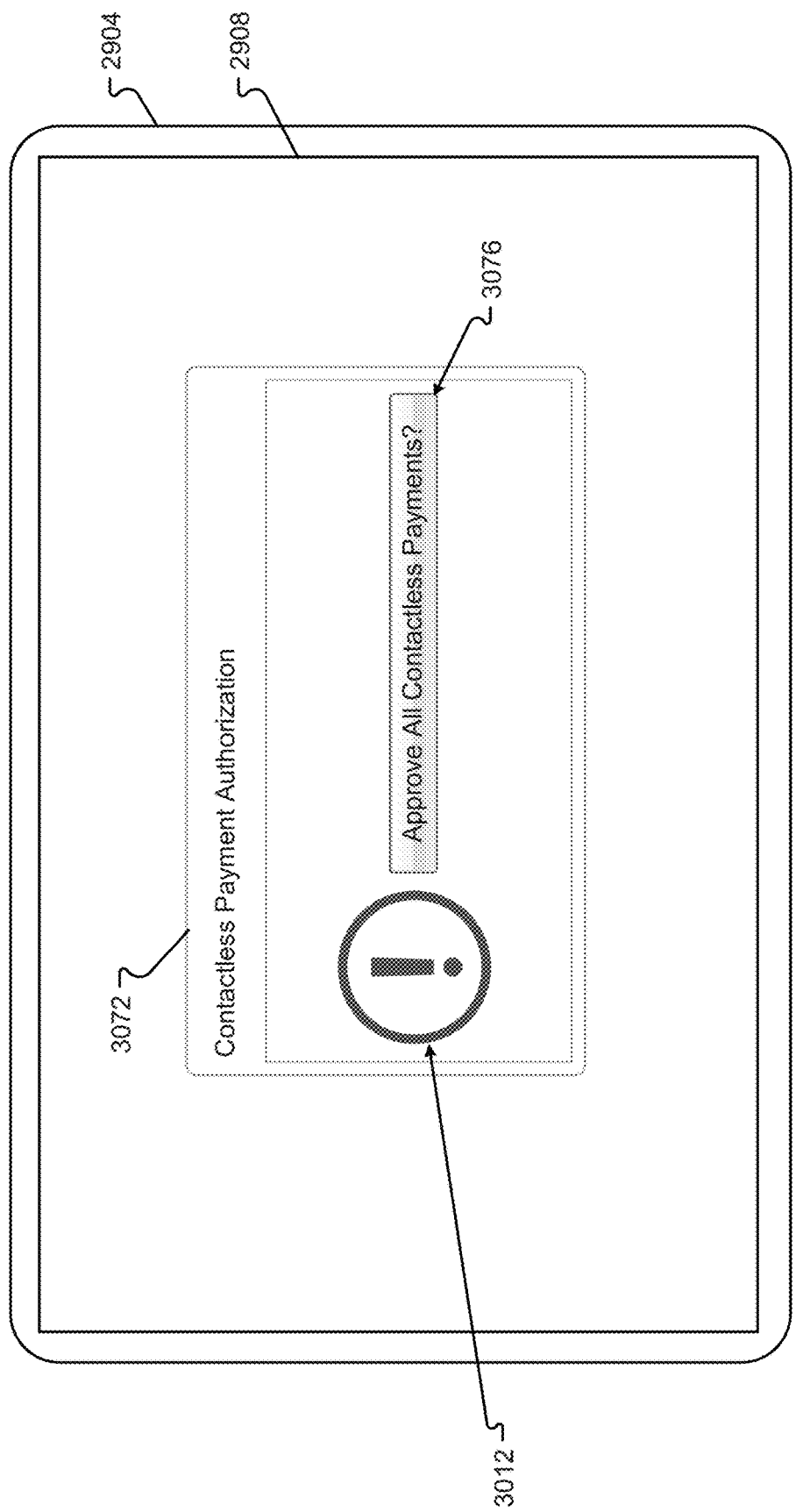
FIG. 30B is another user interface provided within the vehicle.

Another embodiment of a window user interface 3072 may be as shown in FIG. 30B. Another popup window 3072 for contactless payment authorization having icon 3012 may also be presented. Here, the user may have a user-selectable device, for example, a button 3076, that allows the user to approve all contactless payments rather than enter in the information shown in FIG. 30A.

Figure 31:
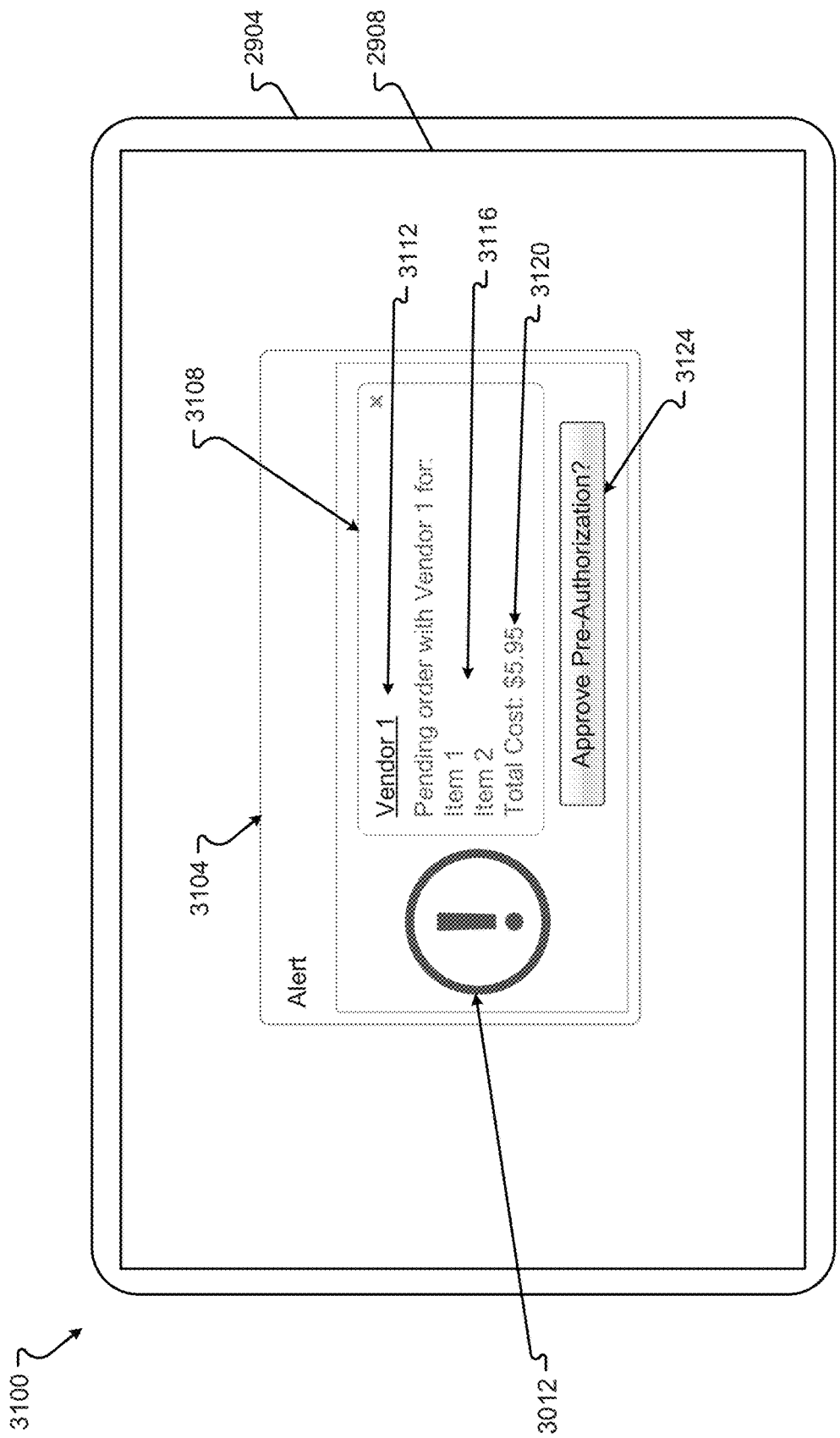
FIG. 31 is another user interface provided within the vehicle.

Another user interface 3100 for authorizing a particular transaction may be as shown in FIG. 31. A window 3104 that provides an alert may be shown in the user interface 2908.

The alert 3104 can include an information box 3108 that describes some transaction or pre-order. This pre-order may be for a vendor provided in banner 3112. The pre-order items may be listed in section 3116 with a cost or price for the order in portion 3120. This information may be indicative of a pre-order or an order made automatically by the vehicle 100. The user may then approve this preauthorization or pre-order by selecting a user-selectable device, for example, the button 3124.

Figure 32:
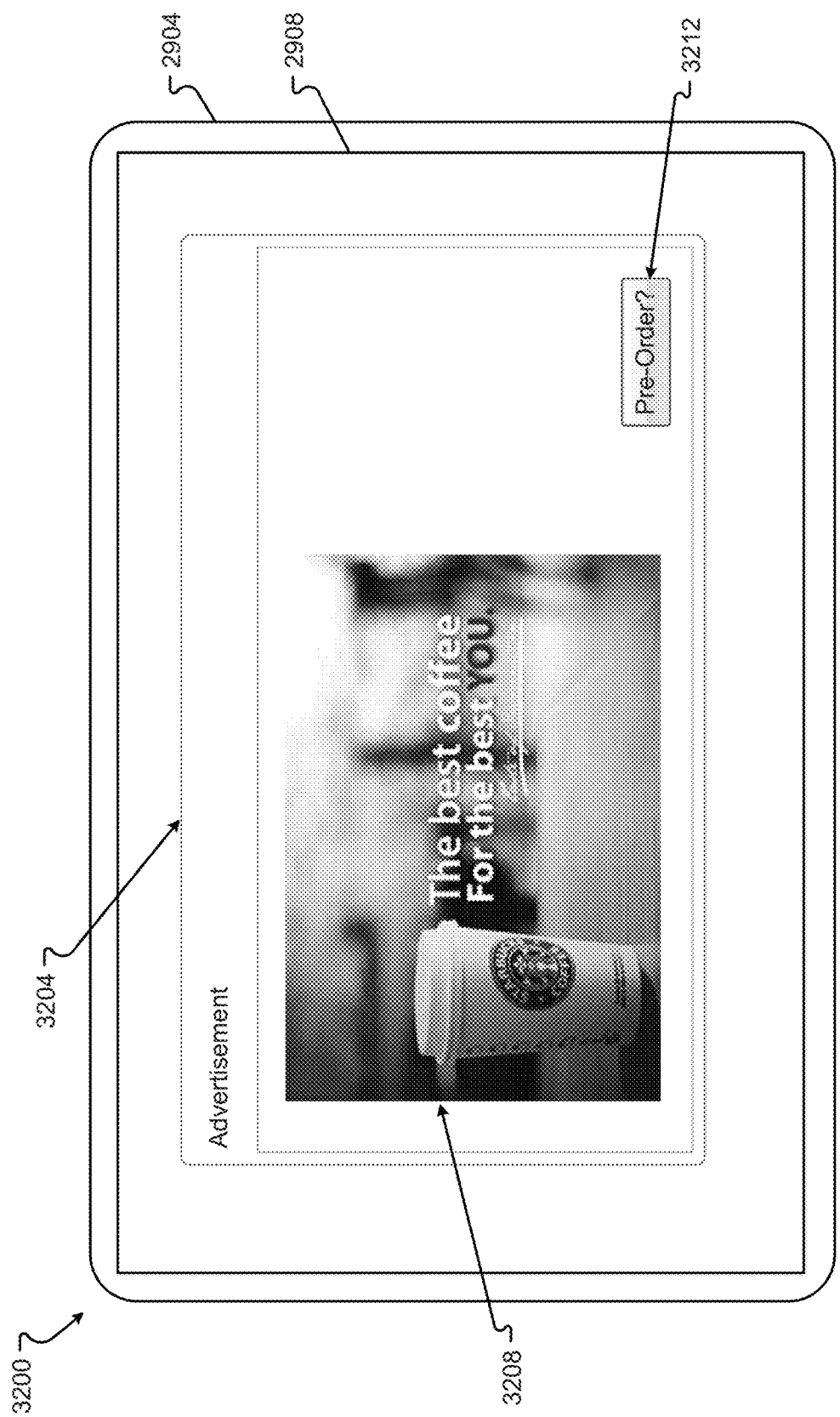
FIG. 32 is another user interface provided within the vehicle.

Another embodiment of a user interface 3200 that provides for placing ads within the user interface 2908 of the vehicle 100 may be as shown in FIG. 32. In this configuration, a popup window 3204 containing an advertisement 3208 may be shown in the user interface 2908. This advertisement 3208 may be associated with a specific product commonly used by the user or may be a product available on the route currently being taken. The user may pre-order that item by selecting user-selectable device 3212 to order the product or service provided in the advertisement 3208.

Figure 33:
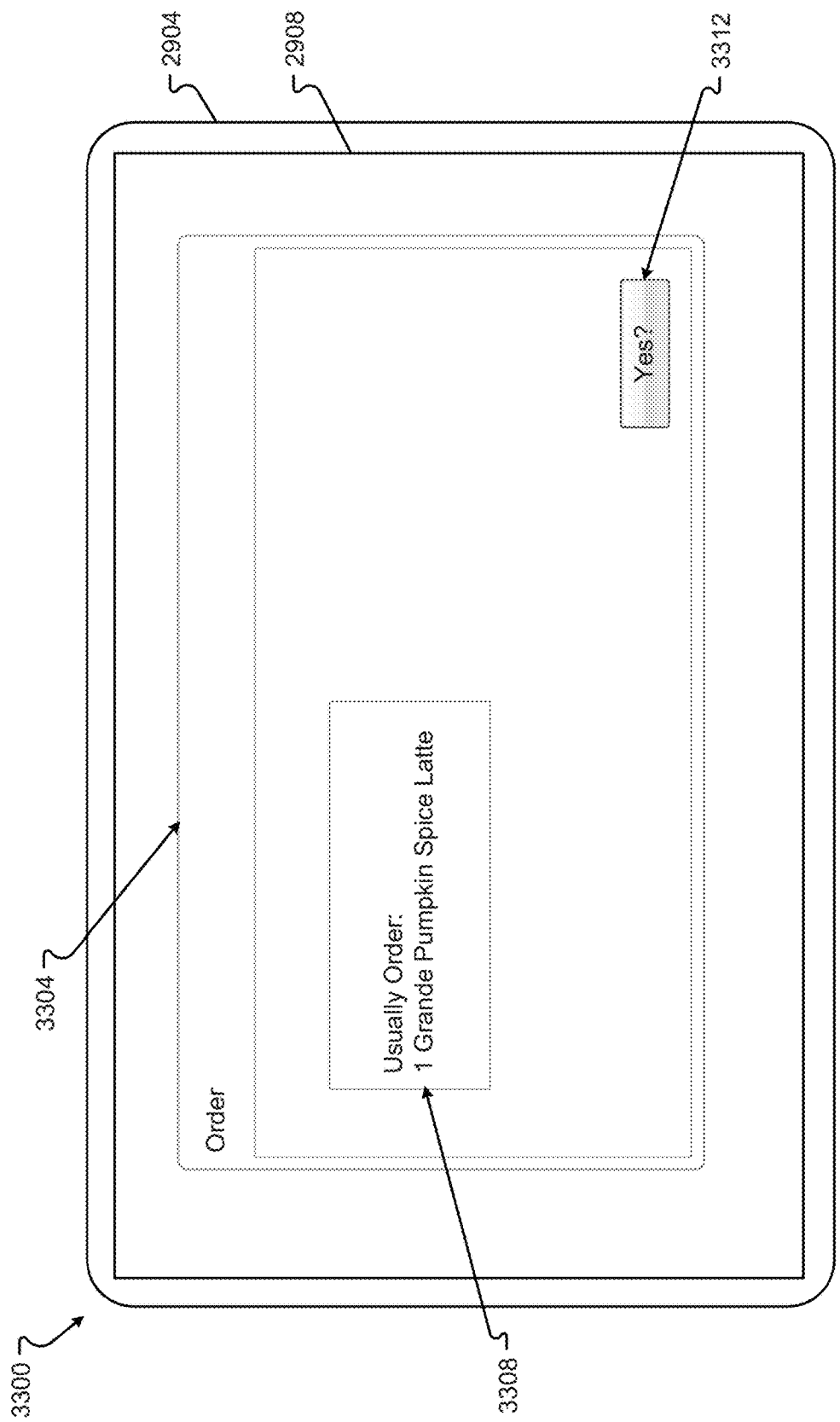
FIG. 33 is another user interface provided within the vehicle.

Another approval or authorization user interface 3300 to conduct a transaction u may be shown in FIG. 33. The user interface 2908 includes another window 3304 to conduct an order. A typical or usual order may be listed in section 3308. For example, the current order is for a coffee from a particular vendor. This order may be a preference gleaned from the preferences information 2528. By presenting this order and selecting user-selectable device 3312 through user input, the user can authorize the vehicle 100 to automatically purchase such item.

Figure 34:
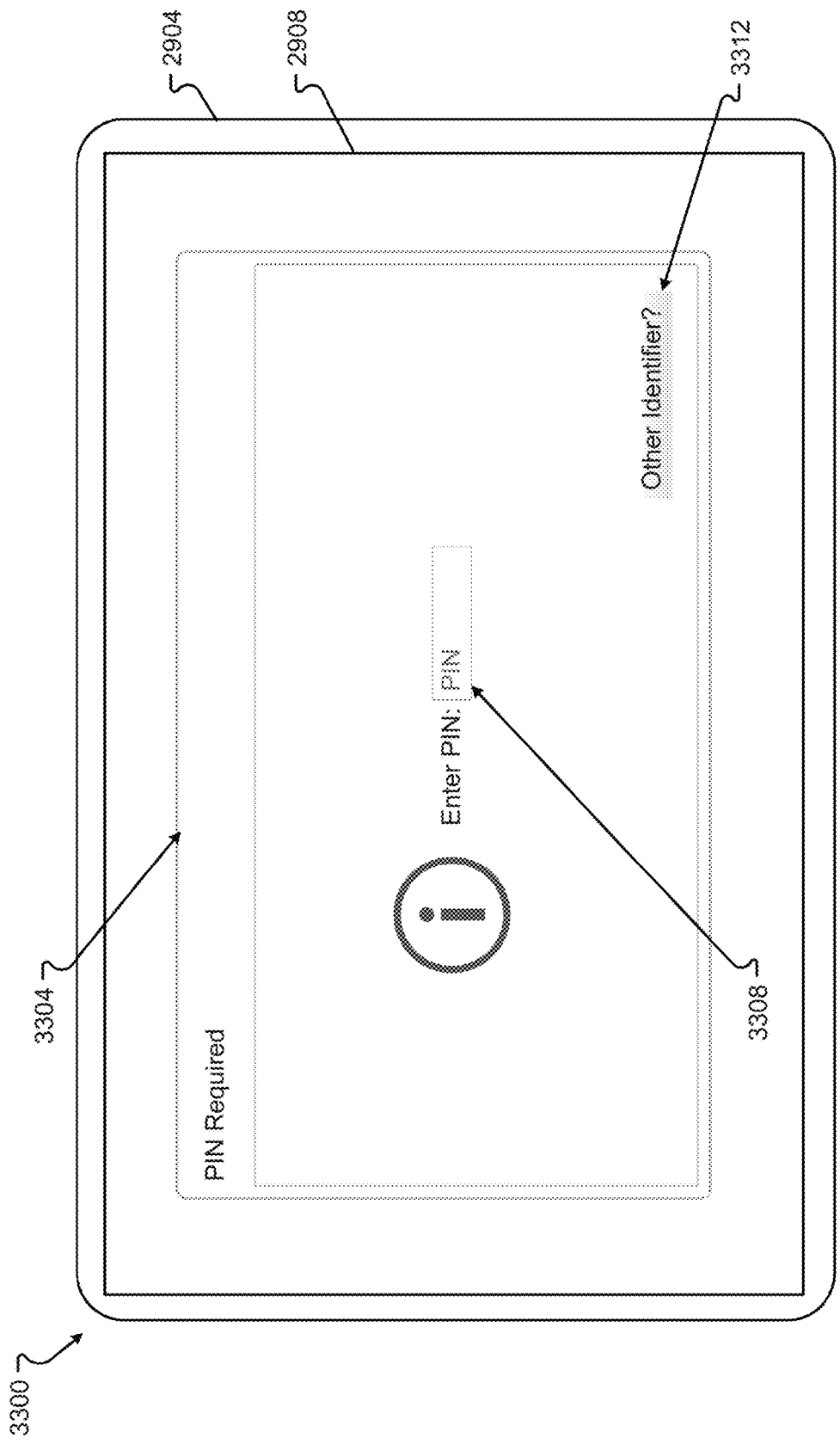
FIG. 34 is another user interface provided within the vehicle.

Further authorization information that may be used for conducting transactions through the vehicle 100 may be as shown in FIG. 34. The user interface 3300 can include another window 3304 in interface 2908. The user interface window 3304 can include further information required by a user to complete a transaction. In this case, PIN information that may be the same or similar to PIN 2512 may be provided by the user. The field 3308 allows the user to enter the PIN through input through a keyboard presented on the user interface or through a phone or other device. This PIN 2512 may then be used to present the second half-token to the vendor for completing a transaction. It may also be possible for the user to select some other type of identifier by selecting user interface device 3312. Other identifiers can include such things as a biometric identifier, username and password, or some other type of identifier explained previously.

Figure 35:
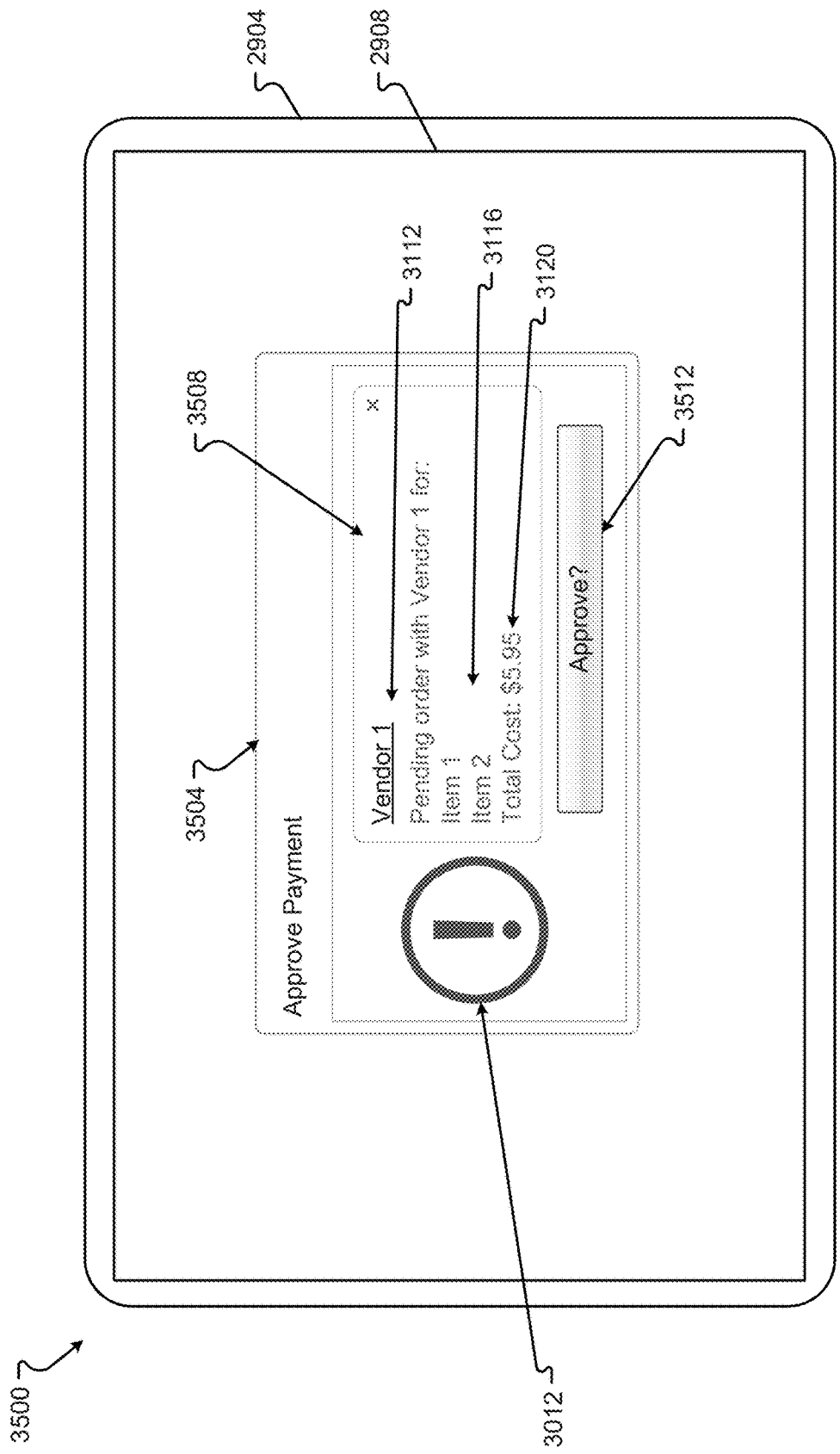
FIG. 35 is another user interface provided within the vehicle.

Another user interface 3500 for approving an order that was already preordered may be as shown in FIG. 35. Here, user interface 2908 includes the window 3504 for allowing approval of payment. The window 3504 includes a box 3508 that provides the information about the order that is to be completed. This box 3508 may include a banner 3112 and a portion 3116 for including the items ordered and a portion 3120 including the cost or price of the order. This order may be finally approved by the user by selecting the user interface device 3512 through touch input or some other type of input.

Figure 36A:
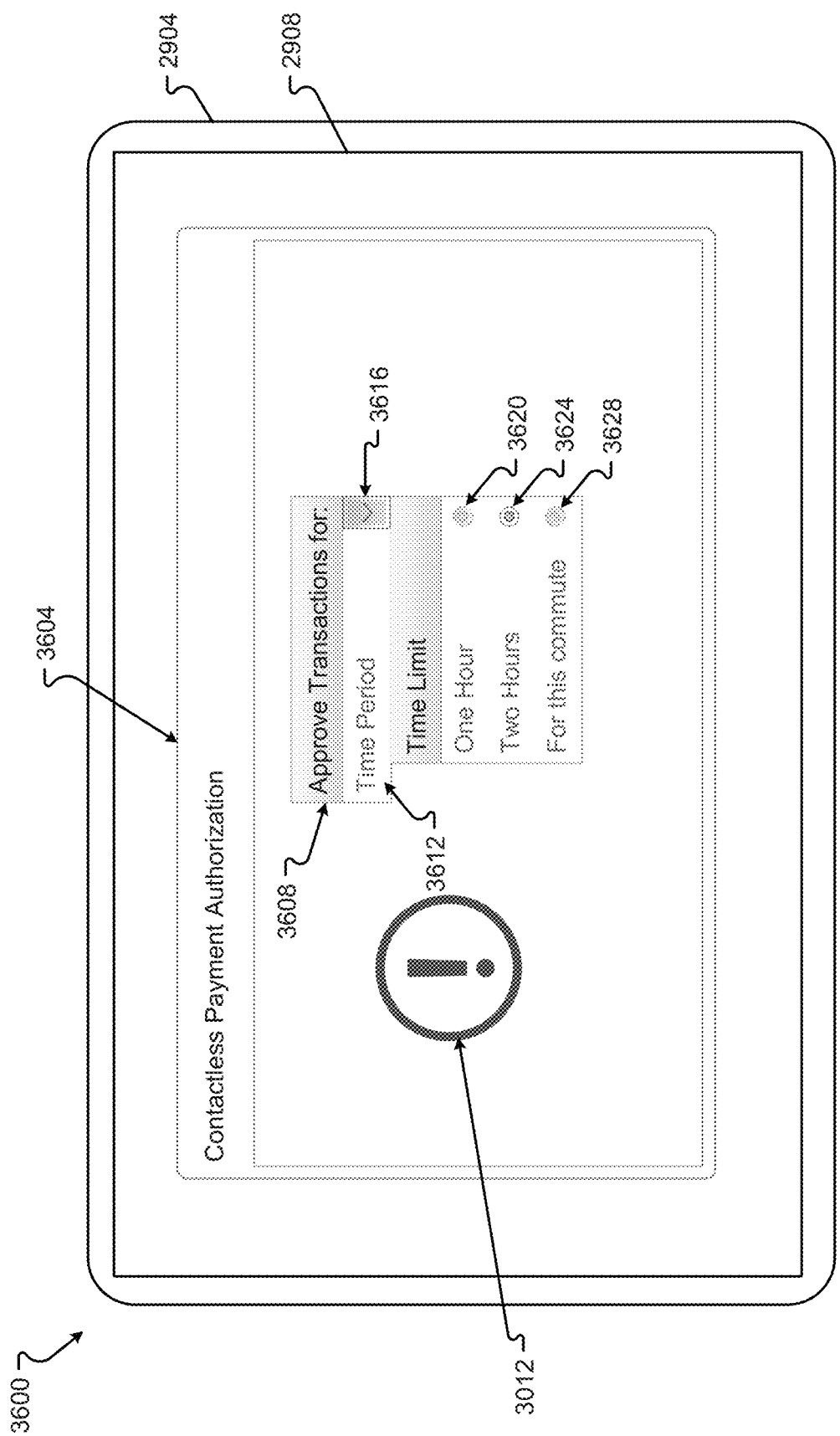
FIG. 36A is another user interface provided within the vehicle.

Another user interface 3600 for approving transactions for a particular type of event may be as shown in FIG. 36A. A window 3604 may be presented in user interface 2908. The window 3604 can include a dropdown menu 3608 with user-selectable device 3616 to select the type of event for which to approve transactions. The banner 3612 can list what type of approval is being given. Selecting the user-selectable device 3616 can cause a dropdown menu to provide further granularity in the selection. For example, a time limit may be selected by selecting radio buttons 3620, 3624, and/or radio button 3628. As such, the user can provide for authorization of secure communications and payments for a particular time period using user interface 3604.

Figure 36B:
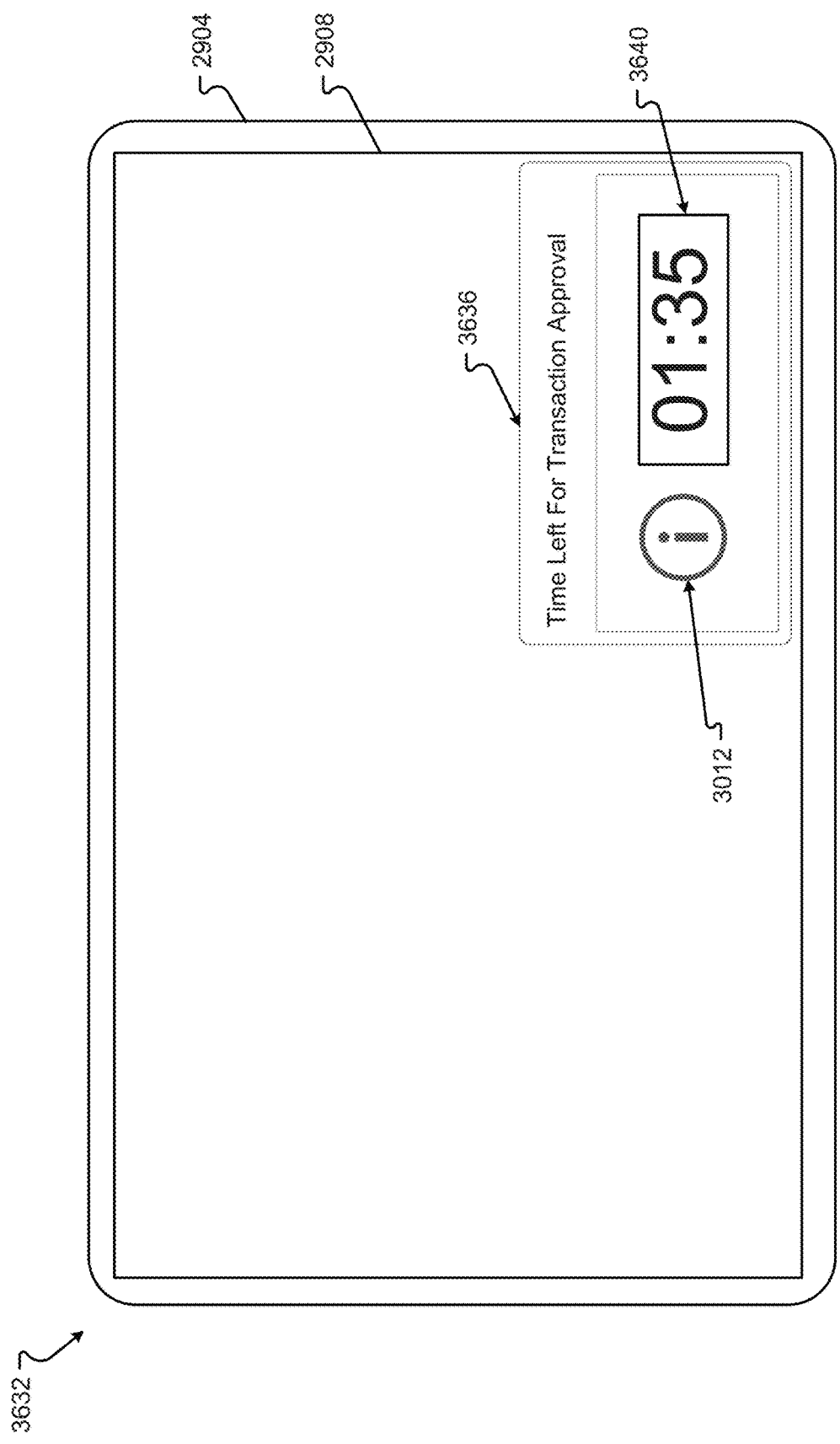
FIG. 36B is another user interface provided within the vehicle.

Another embodiment of a user interface 3632 that includes a popup information box 3636 may be as shown in FIG. 36B. Here, the user may have already-completed or automatic orders completed. Box 3636 provide the user information about how much time is left for transaction approval in countdown clock 3640. This clock 3640 counts down from some certain amount of time (e.g., five (5) minutes) until the pre-order is canceled, and the transaction is left unapproved.

Figure 37:
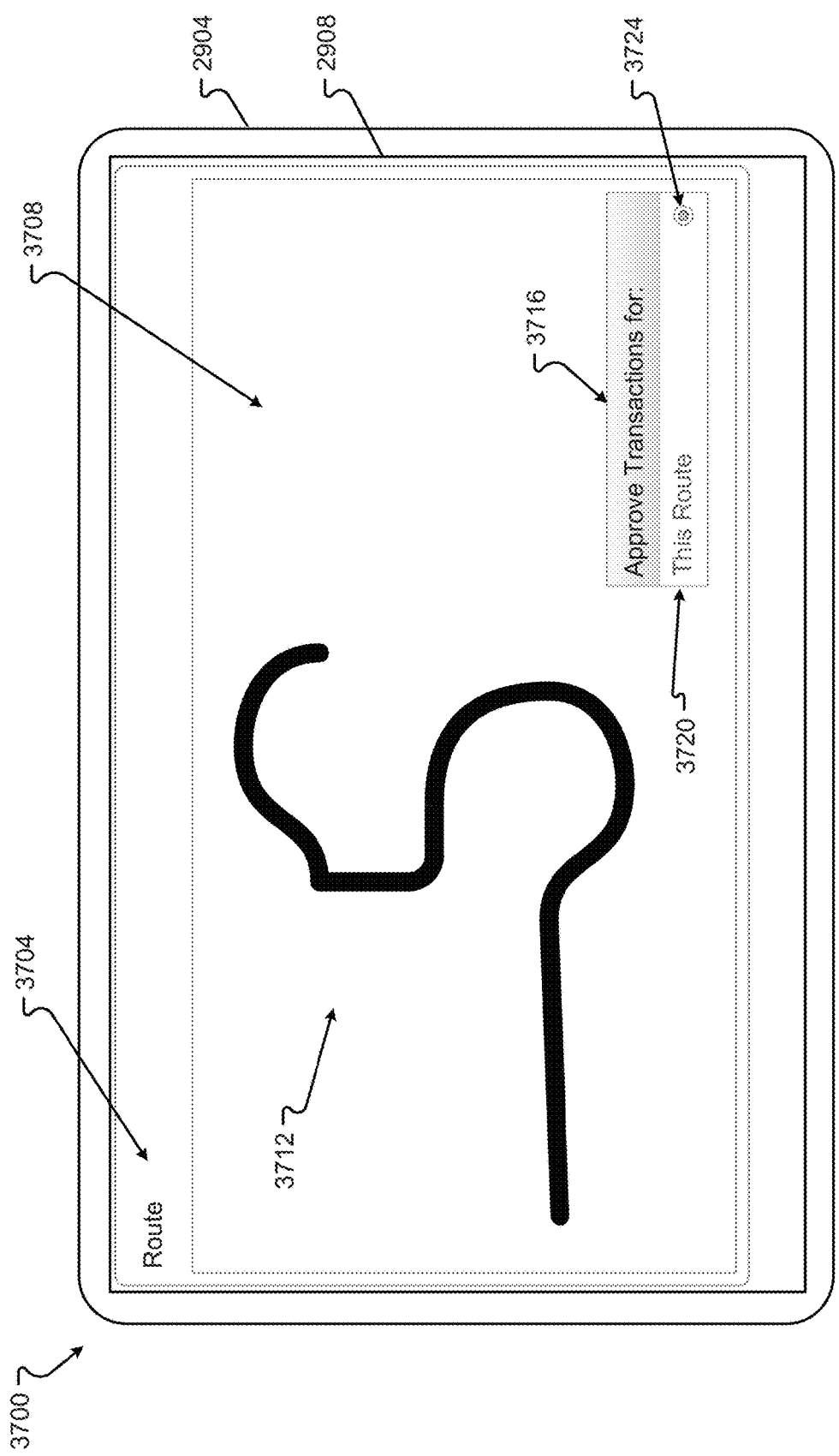
FIG. 37 is another user interface provided within the vehicle.

A user interface 3700 for allowing a user to approve transactions or communications along a particular route may be as shown in FIG. 37. Here, the user interface 2908 may include a window 3704 that is associated with a map 3708. This map 3708 may include a projected route 3712. The window 3704 may also include a popup box 3716 with banner 3720 that indicates that by selecting button 3724, the user can approve any transaction along the route 3712. In this way, the user is allowed to complete secure communications or transactions along route 3712 through the vehicle 100 without requiring further user input during this travel.

Figure 38:
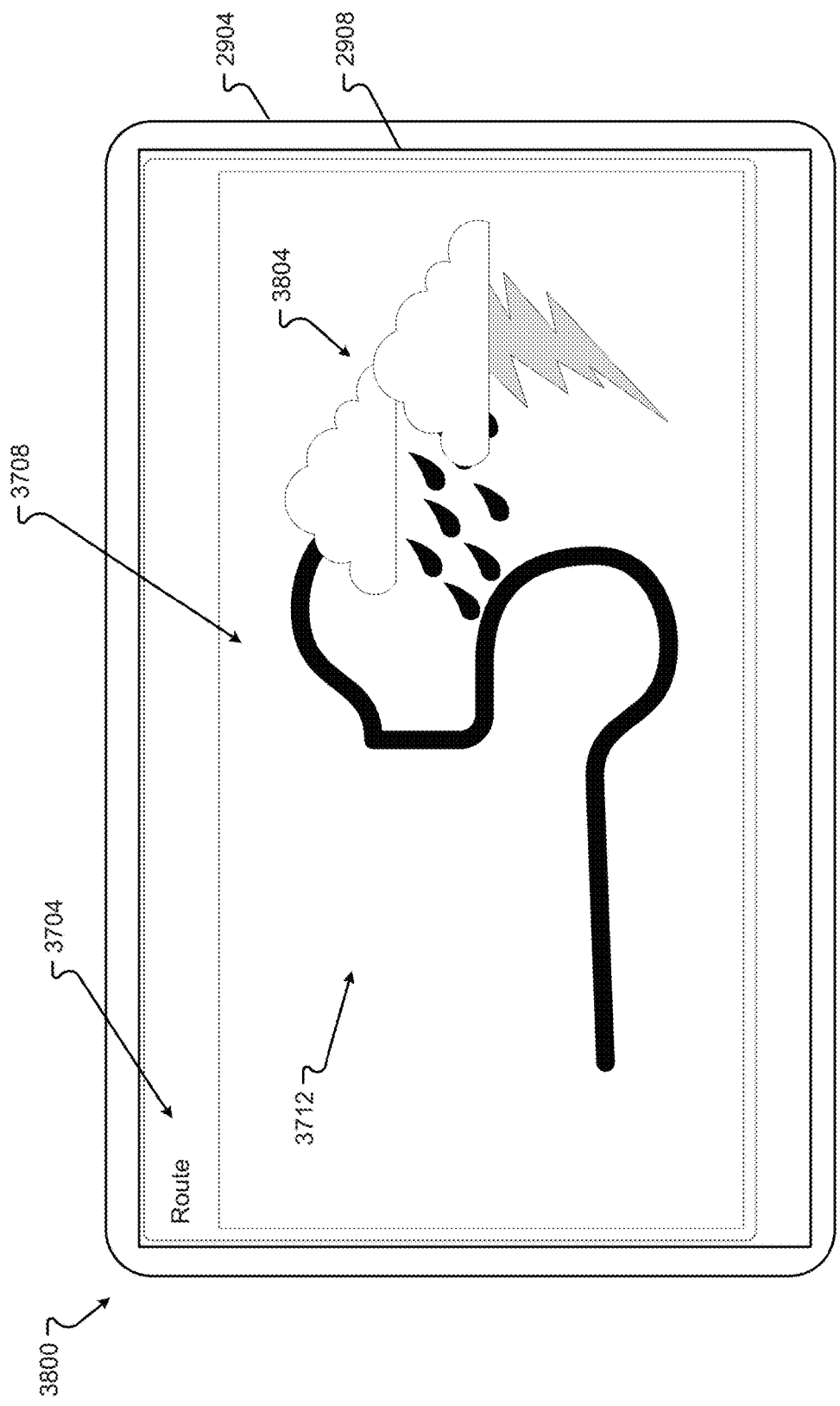
FIG. 38 is another user interface provided within the vehicle.

Another user interface 3800 similar to user interface 3704 shown in FIG. 37 is provided in FIG. 38. Here, further information is provided about the route 3712, such as weather data 3804. A user may preapprove for enhanced navigation or enhanced data. This approval allows the user interface 3704 to provide weather information 3804 or other types of data for which the user must pay. Thus, if inclement weather is imminent, the vehicle 100 may make an automatic transaction to provide this further information and pay for that information. These types of transactions may be pre-authorized by the user.

Figure 39:
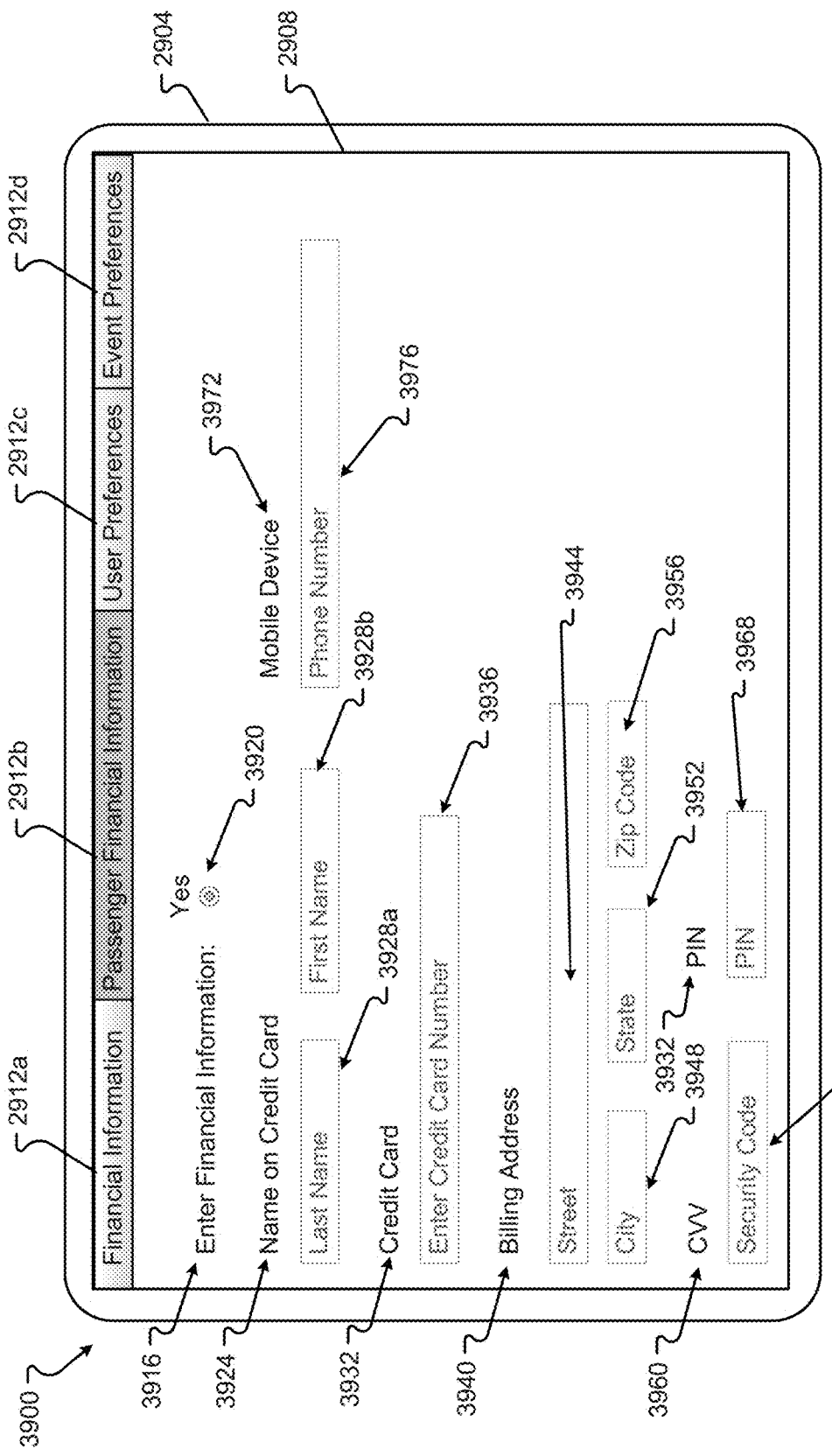
FIG. 39 is another user interface provided within the vehicle.

An embodiment of a user interface 3900 for receiving and/or providing financial information about a passenger in the vehicle 100 may be as shown in FIG. 39. The fields 2916-2968 are the same or similar to those fields 2916 through 2968 as shown in FIG. 29. As such, these fields 2916-2968 will not be explained further except that the fields 2916-2968 are used to enter information for a passenger rather than a driver, as represented by tab 2912b having different visual indicia than tabs 2912a, 2912c, or 2912d.

Two additional fields 3972, 3976, in user interface 3900, allow the passenger to enter their mobile device information. This mobile device information 3972 and 3976 allows the vehicle 100 to identify the user and communicate the passenger's financial information when being identified within the vehicle 100. Also, having the mobile device information 3972, 3976 allows the vehicle 100 to conduct transactions through the mobile device rather than through the vehicle 100, if desired.

Figure 40:
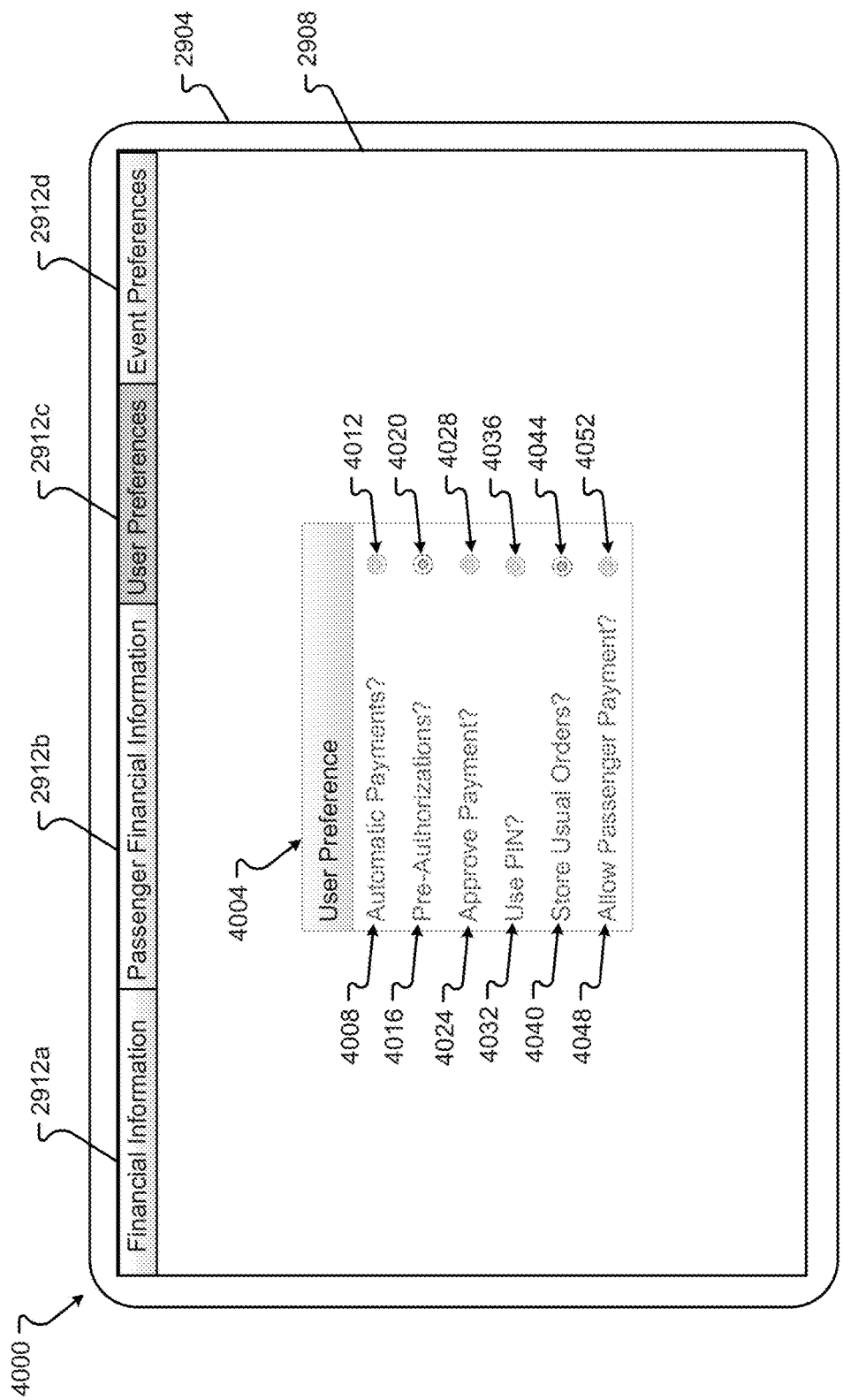
FIG. 40 is another user interface provided within the vehicle.

Another user interface 4000, within display 2908, related to user preferences, as represented by different visual indicia on tab 2912c, may be as shown in FIG. 40. User preferences may include a window 4004 that includes various fields 4008 through 4052 for specifying different preferences for how secure communications or financial transactions may be conducted by the user. Each field 4008, 4016, 4024, 4032, 4040, and 4048 may have an associated radio button 4012, 4020, 4028, 4036, 4044, and 4052 to receive user input that indicates preferences for secure communications.

The fields 4008-4052 may include selections for automatic payments (allows the vehicle 100 conduct payments without user input), pre-authorizations (requires the vehicle 100 to get authorization for orders), approve payment (requires the vehicle 100 to get approval for payments), use of PIN (requires the vehicle 100 to obtain a PIN for payments), store usual orders (requires the vehicle 100 to store common or recurring orders), allow passenger payment (allows a passenger to associated payment information with the vehicle 100 and make payments). Any one of these preferences may be provided or selected by selecting radio buttons 4012, 4020, 4028, 4036, 4044, and 4052.

Figure 41:
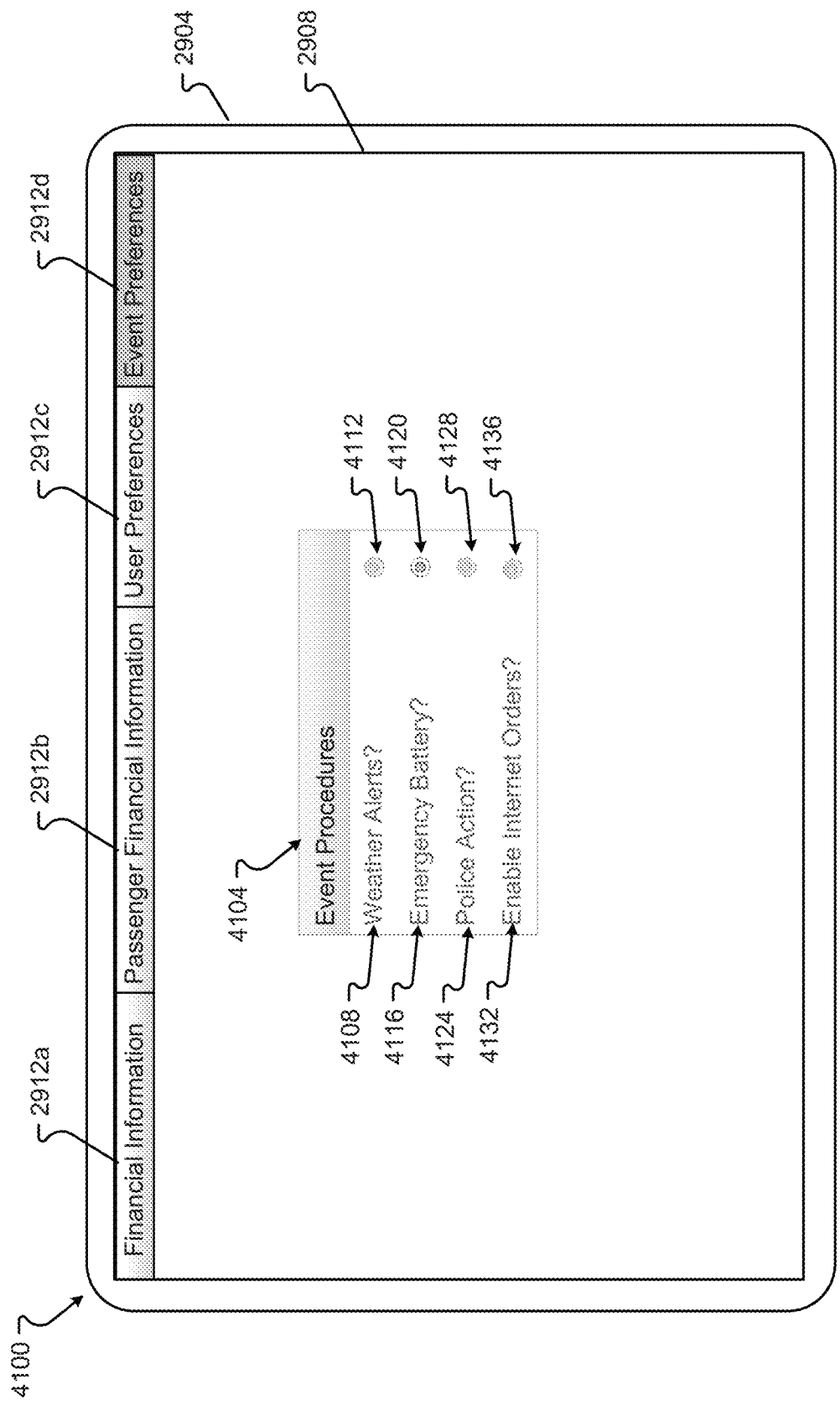
FIG. 41 is another user interface provided within the vehicle.

An embodiment of a user interface 4100 associated with event preferences, as represented by tab 2912d having different visual indicia, may be as shown in FIG. 41. Window 4104 may be provided that provides for the vehicle 100 to conduct particular procedures if certain, future events occur. These events may include weather alerts 4108, emergency battery alerts 4116, police action alerts 4124, or enable internet orders 4132. Any of these different selections 4108, 4116, 4124 may be completed by selecting one or more of the radio buttons 4112, 4120, 4128, 4136. Weather alerts 4108 allow the user to automatically purchase further information about weather if necessary. Emergency battery events 4116 can allow for purchasing or pre-purchasing battery charging if necessary. Police action event 4124 can allow for communications of routes or information on the route display when there is a police action. Finally, internet orders 4132 may allow the vehicle 100 to purchase services or goods through the Internet if radio button 3146 is selected.

Figure 42:
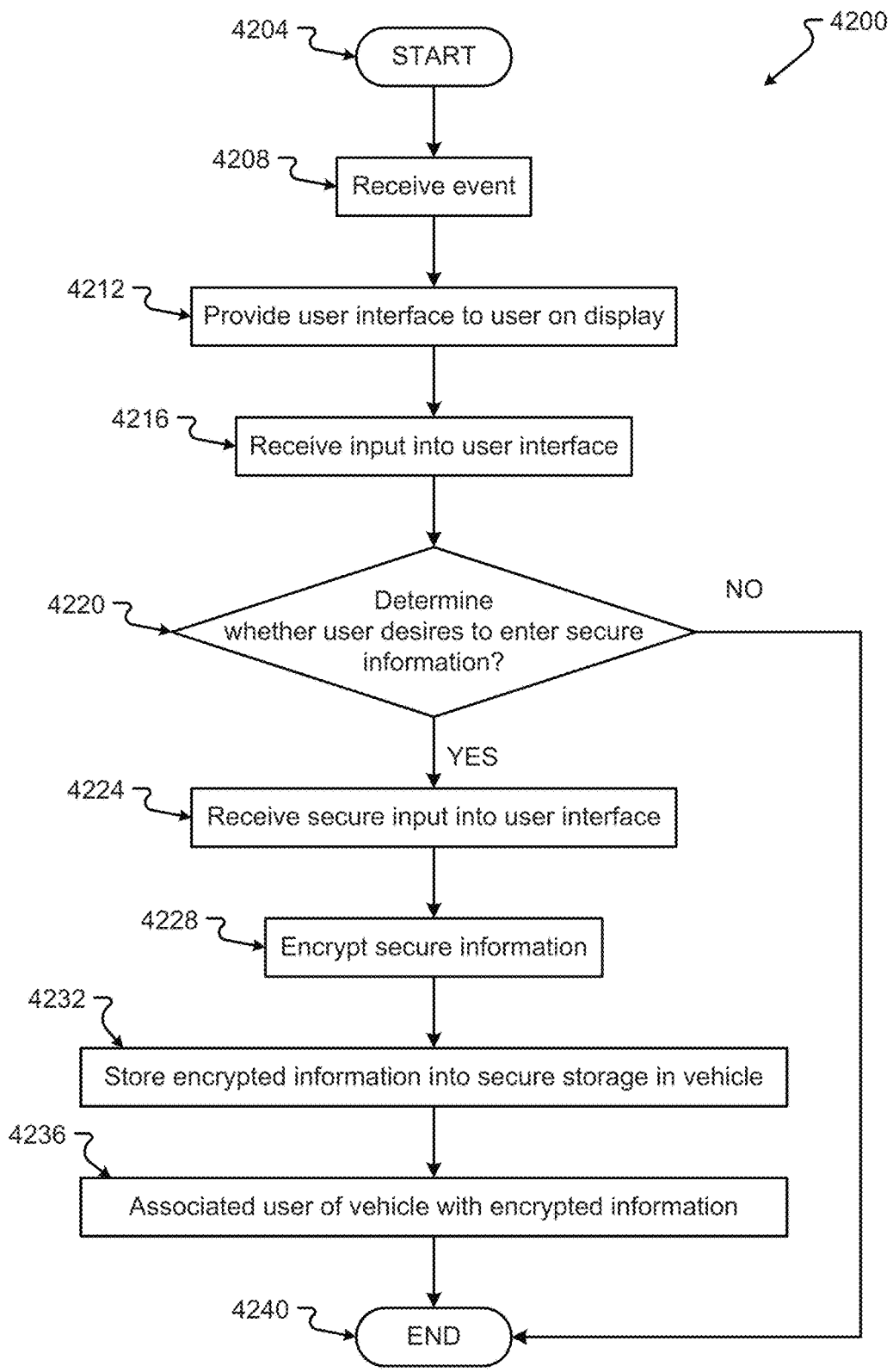
FIG. 42 is another user interface provided within the vehicle.

An embodiment of a method 4200 for receiving and storing user secure information may be as shown in FIG. 42. Generally, the method 4200 starts with a start operation 4204 and ends with operation 4240. The method 4200 can include more or fewer steps or can arrange the order of the steps differently than those shown in FIG. 42. The method 4200 can be executed as a set of computer-executable instructions executed by a computer system or processor and encoded or stored on a computer readable medium. In other configurations, the method 4200 may be executed by a series of components, circuits, gates, etc. created in a hardware device, such as a System of Chip (SOC), Application Specific Integrated Circuit (ASIC), and/r a Field Programmable Gate Array (FPGA). Hereinafter, the method 4200 shall be explained with reference to the systems, components, circuits, modules, software, data structures, signaling processes, models, environments, vehicles, etc. described in conjunction with FIGS. 1-41 and 54A-56.

A processor or CPU 5608 can receive an event, in step 4208. The event can be the starting of the vehicle 100, a connection made by a user with the dongle 2008, or another event. This event can cause the CPU 5608 to present a user interface 2900 on a display 5616.

In step 4212, the CPU 5608 renders the user interface 2900 for displaying on the output device 5616. The output device 5616 can include the screen 2904 provided in the head unit, a heads-up display, or some other type of display within the vehicle 100. From the user interface 2900, the CPU 5608 can receive input into the user interface 2908, in step 4216. The input can be the entry or determination of whether or not the user desires to enter financial information to be associated with the vehicle 100.

In step 4220, the CPU 5608 determines whether the user desires to enter secure information. For example, the user may select radio button 2920 to alert the CPU 5608 that the user desires to enter secure information. If secure information is desired to be entered, the method 4200 proceeds "YES" to step 4224. However, if no information is desired to be entered, method 4200 proceeds "NO" to step 4240.

In step 4224, the CPU 5608 receives secure input through the user interface 2900. Here, the user may enter information about their finances or financial information in fields 2924 through 2968. This information may be provided to the CPU 5608, or the information may then be buffered in memory 5636. In step 4228, the CPU 5608 can encrypt the information and store it within memory 5636. The encryption key may be some secret shared between the user and the vehicle 100. This encryption information may be provided in another user interface, through voice input, or through some other input. Further, there may be other types of encryption keys that may be associated with biometrics or other information.

In step 4232, the CPU 5608 stores the encrypted information in secure storage within the vehicle 100. Secure storage can be a separate secure area of storage 5636. In some configurations, this secure storage may be accessed differently and may be physically separated from working memory 5636. In other configurations, the secure storage may be a separate part of the working memory 5636 that may be accessed with different protocols. Upon storing this information, the CPU 5608 associates the user of the vehicle 100 with the encrypted information, in step 4236. Here, the user's biometrics 2408, username 2412, password 2416 etc. may be stored with data structure 2504 or other information to associate the user with the information.

Figure 43:
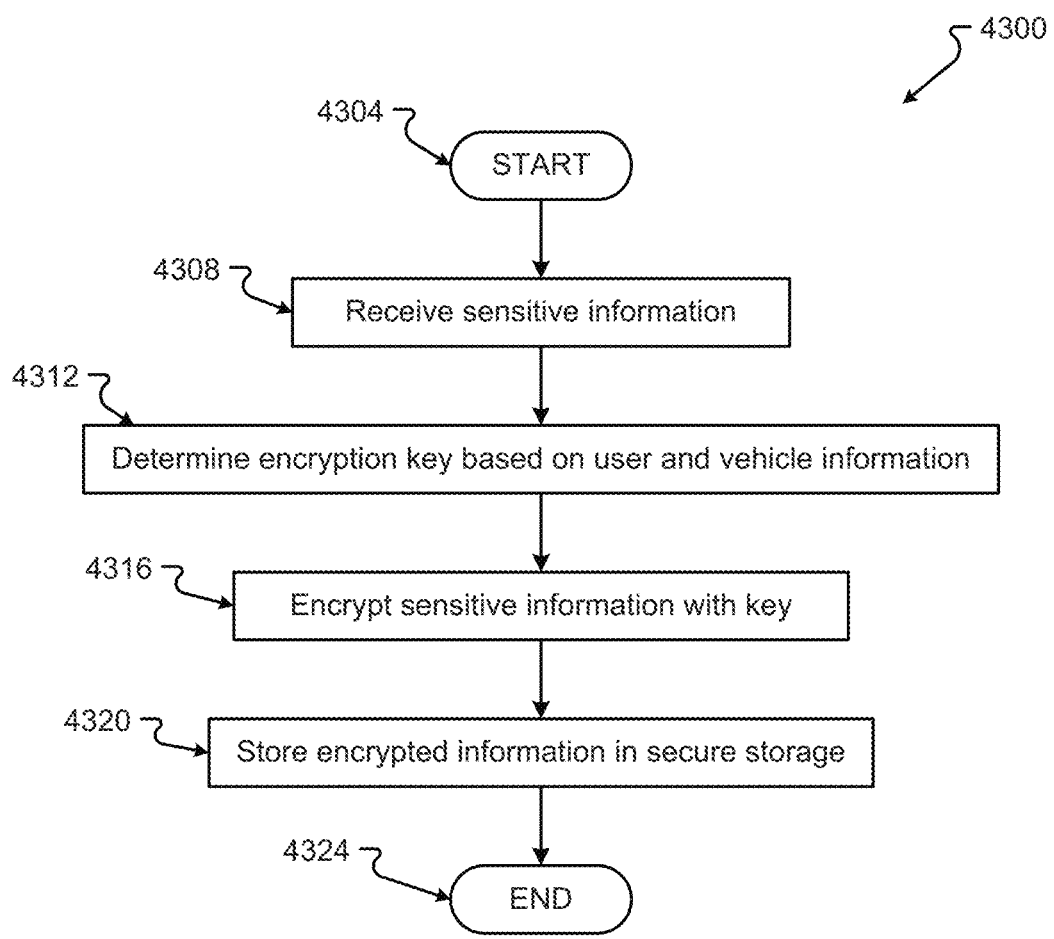
FIG. 43 is a flow diagram of an embodiment of a method for providing secure communications with a vehicle.

A method 4300 for encrypting the sensitive information, as described in conjunction with FIG. 42, may be as shown in FIG. 43. The method 4300 can be conducted by the CPU 5608 for encrypting the sensitive information in the memory 5636 of the vehicle 100. Generally, the method 4300 starts with a start operation 4304 and ends with operation 4324. The method 4300 can include more or fewer steps or can arrange the order of the steps differently than those shown in FIG. 43. The method 4300 can be executed as a set of computer-executable instructions executed by a computer system or processor and encoded or stored on a computer readable medium. In other configurations, the method 4300 may be executed by a series of components, circuits, gates, etc. created in a hardware device, such as a System of Chip (SOC), Application Specific Integrated Circuit (ASIC), and/r a Field Programmable Gate Array (FPGA). Hereinafter, the method 4300 shall be explained with reference to the systems, components, circuits, modules, software, data structures, signaling processes, models, environments, vehicles, etc. described in conjunction with FIGS. 1-42 and 54A-56.

In step 4308, the CPU 5608 can receive sensitive information, as described in conjunction with FIG. 42. In step 4312, the CPU 5608 can determine an encryption key based on the user and/or vehicle information. As such, the CPU 5608 can associate the VIN 2436, the ESN 2440, the engine code 2444, or other information associated with the vehicle 100 with the user and the user information, for example, biometrics 2408, username 2412, password 2416, mobile device information 2420, dongle code 2424, etc. This user and vehicle information may be associated together to create the encryption key.

In step 4316, the CPU 5608 can encrypt the sensitive information received in step 4308 with the key. This key would be associated with both the vehicle and the user and may not be accessed without the presence of the user within the vehicle 100 or if the user is not associated with the vehicle 100. As such, if the vehicle 100 is stolen, the information cannot be accessed. Further, another user cannot enter the vehicle 100 and use the information, and the user may not use some other vehicle for secure communications with the information. The encrypted information may then be stored in working memory 5636 or in storage 5620, 5624, in step 4320. As such, the CPU 5608 can permanently store the information in secure storage as encrypted information that becomes difficult to use except when the user is associated with the vehicle 100.

Thus, operator or owner financial information and user biometric data can be stored in an encrypted memory 5624, 5636 on the vehicle 100, such as in encrypted RAM or other storage medium. If RAM were to be encrypted, it must be decrypted automatically for usage by the CPU 5608. In some configurations, the CPU 5608 does not operate on the RAM directly. The CPU 5608 loads code and data from the RAM into the CPU's internal caches. The loading/unloading process is transparent for both the applications 5644 and the operating system 5640.

An automatic RAM encryption system can be embodied in hardware, for example, in the CPU 5608. If encryption were to be done in the RAM, an attacker may be able to freeze the RAM and then plug the RAM into a different machine to extract the information. In a similar manner, decryption in an external RAM controller may not prevent active attacks. The automatic RAM encryption system could also defeat a cold boot attack or a platform reset attack in which an attacker, with physical access to a computer, is able to retrieve encryption keys from a running operating system after using a cold reboot to restart the machine. This type of attack relies on the data remanence property of DRAM and SRAM to retrieve memory contents that remain readable in the seconds to minutes after power has been removed.

In additional or alternative configurations, disk encryption techniques can also be employed. When a user first powers on the vehicle and before the operating system 5640 can boot up, the user must unlock his or her disk by supplying the correct encryption key. The files that make up the operating system are on the encrypted disk, so there is no way for the computer 5608 to work with the operating system 5640 until the disk is unlocked.

In some configurations, inputting a security credential, like a passphrase or biometric identifier, does not unlock the whole disk but unlocks an encryption key, which in turn unlocks everything on the disk. This indirection allows a user to change his or her passphrase (if a passphrase is used) without having to re-encrypt the disk with a new key and also makes it possible to have multiple passphrases, other security credentials, or combinations thereof that can unlock the disk, for example, if the operator or owner were to add another user account to the on board computer.

Other configurations may defeat a cold boot attack; encryption software periodically flushes the encryption key every few minutes when not in use. The user would be required to re-authenticate himself or herself to the on board computer system 5608, after expiration of a selected period of time. A user-friendly transparent proximity solution can exist where the vehicle remote keyless system (the dongle 2008) acts as a type of wireless device to transmit a unique code or signal that can cause the controller 5608 to securely access the encryption key whenever needed or otherwise cause the encryption key to be refreshed periodically.

As will be appreciated, keyless remotes 2008 contain a short-range radio transmitter, and must be within a certain range, usually 5-20 meters, of the vehicle 100 to work. It sends a coded signal by radio waves to a receiver unit in the vehicle 100, which performs a selected function, such as locking or unlocking the door. Alternatively, the secure key can be derived from the coded signal itself by a known key generation algorithm (e.g., in which the seed is the coded signal or the coded signal along with another identifier, for example, a biometric indicator of a user or all or part of the VIN 2436 of the associated vehicle 100.

Figure 44:
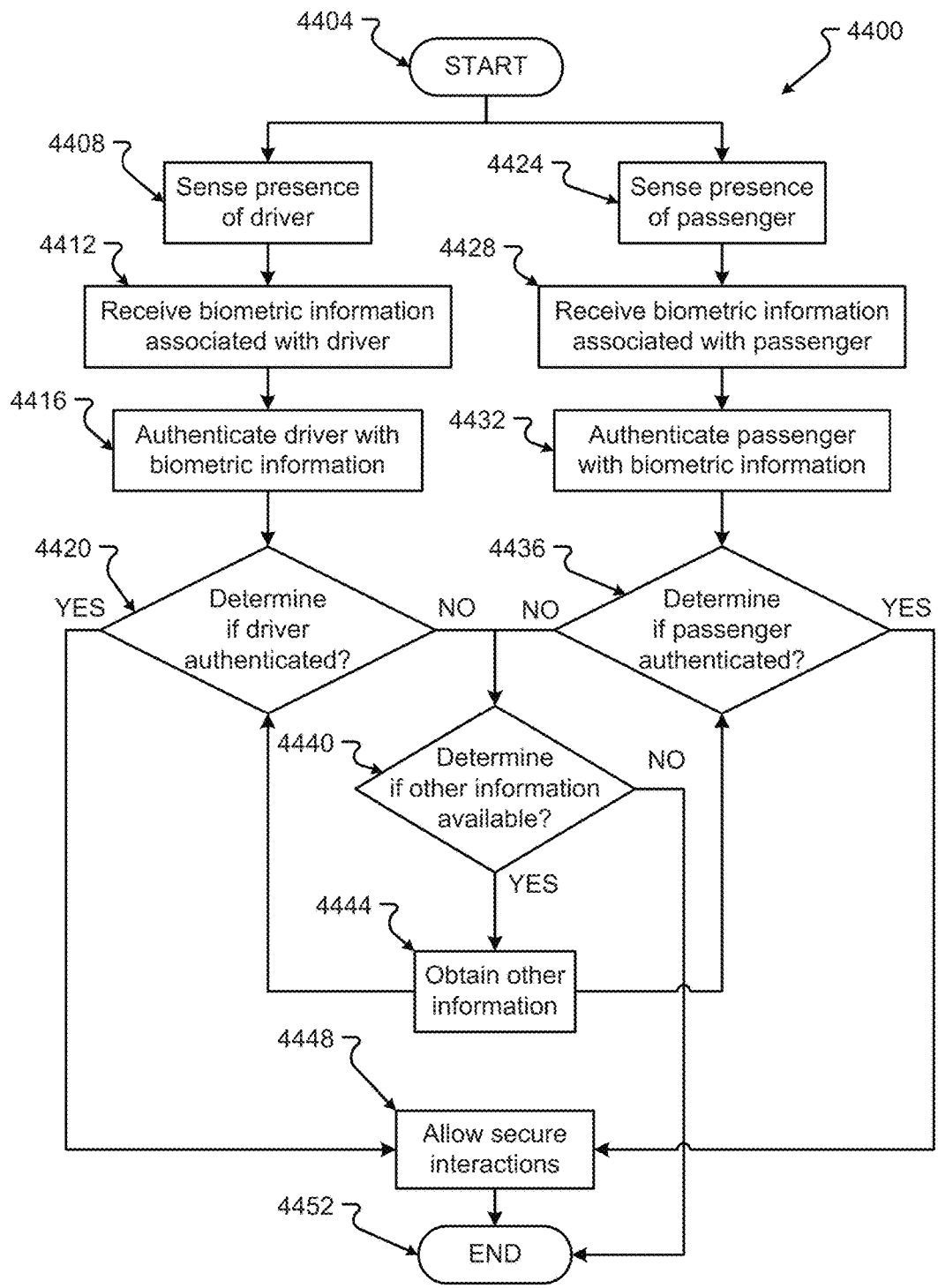
FIG. 44 is another flow diagram of an embodiment of a method for providing secure communications with a vehicle.

An embodiment of a method 4400 for a driver and/or passenger to enter secure information into the vehicle 100 may be as shown in FIG. 44. Generally, the method 4400 starts with a start operation 4404 and ends with operation 4440. The method 4400 can include more or fewer steps or can arrange the order of the steps differently than those shown in FIG. 44. The method 4400 can be executed as a set of computer-executable instructions executed by a computer system or processor and encoded or stored on a computer readable medium. In other configurations, the method 4400 may be executed by a series of components, circuits, gates, etc. created in a hardware device, such as a System of Chip (SOC), Application Specific Integrated Circuit (ASIC), and/r a Field Programmable Gate Array (FPGA). Hereinafter, the method 4400 shall be explained with reference to the systems, components, circuits, modules, software, data structures, signaling processes, models, environments, vehicles, etc. described in conjunction with FIGS. 1-43 and 54A-56.

In steps 4408, 4424, the vehicle 100 can sense the presence of a driver or passenger, respectively. The internal sensors 5437 may sense the presence of a person within the vehicle 100. This person may be a driver or a passenger. The information gleaned from the sensors within the vehicle 100 may then be provided to the CPU 5608. In steps 4412, 4428, the CPU 5608 can receive the biometric information associated with the driver/passenger. This information may then be used to determine whether or not the passenger or driver is previously associated with the vehicle 100. The biometric information may be as stored in data structure 2404 in field 2408.

With the biometric information, the CPU 5608 can compare the received information with the information in field 2408 to determine if the driver or passenger is authenticated, in steps 4416, 4432. If the received biometric information from internal sensors 5437 is the same or similar to stored biometric information 2408, the driver/passenger is authenticated. As such, the CPU 5608 can determine if the driver/passenger is authenticated in steps 4420 or 4436. If the information does compare, then the driver/passenger is authenticated and the method 4400 proceeds "YES" to step 4448. However, if the driver or passenger is not authenticated, the method 4400 proceeds "NO" to step 4440, where the CPU 5608 determines if other information is available.

Other information may include a username 2412, a password 2416, mobile device information 2420, etc. that may be used to authenticate the user. If there is other information, the CPU 5608 can gather or obtain that information, in step 4444. Thus, the CPU 5608 may request the username or password from the user, connect or couple with the mobile device or the dongle, or may conduct other operations to gain that information. If the other information is valid and compares to the information stored in data structure 2404, the user may be authenticated again. However, if no other information is available, the operation may end without the user being authenticated or allowed to do secure communications. If the user finally is authenticated, then in step 4448, the vehicle processor 5608 can allow secure interactions between the vehicle 100 and third parties.

Based on a driver's preferences (e.g., user goes to Starbucks every morning, etc.), the onboard computer automatically pre-authorizes a transaction at a particular time and/or in response to a particular detected location of the vehicle 100. This pre-authorization can be done by observation and based on historic user behavior or spatial proximity of the vehicle 100 to the vendor (e.g., range of a transceiver on the vehicle 100 to a transceiver at the vendor or GPS-based locations of the vehicle 100 and vendor).

In this example, the vehicle 100 can gate release information to avoid unintended purchases. This gate-release of information can be done by an interactive user interface (UI) on the vehicle 100. Presumably, the vehicle 100 may identify a potential purchase by the driver, such as by receiving and pre-filtering purchase options before presenting, to the operator, the option. Otherwise, the operator could be swamped by options while he or she is driving through an area loaded with retail stores. The trigger could be based on prior driver behavior, proximity of the vehicle 100 to a vendor, a state of the vehicle 100 (e.g., stopped, in motion, velocity of vehicle 100, etc.), and the like. There may also be operator authentication prior to the function of pre-purchase being activated. This approval can prevent a thief or family member from using the function without authorization.

In some configurations, the vehicle 100 may anticipate payments to be made, or opportunities to pay, based on a number of factors associated with the vehicle 100 or vehicle state, such as speed, turn signal activation, road or lane change, and the like. In response to detecting one or more of these factors, the vehicle 100 may present the user with a context-sensitive prompt designed to provide an advanced authorization for payment for a good or service. This advanced authorization for payment can save authentication time, processing time, and/or waiting time associated with payment stations, providing a quick transactional exchange.

By way of example, a user may be approaching a gas station and a drive-through coffee shop in a vehicle 100. Upon reducing speed, directing, and/or positioning the vehicle 100 into proximity with the coffee shop, the vehicle 100 may prompt the user for advanced authorization for the coffee shop (e.g., rather than the gas station or any other service). The user may accept the advanced authorization (e.g., for an open-amount, particular amount, etc.). Additionally or alternatively, the vehicle 100 may prompt the user for authorization for a particular drink and/or group of drinks, food, etc. The user may accept a "usual" order (e.g., based on historical data, preferences, and/or voice command), and as the user drives up to the "ordering" window/kiosk, the user may be directed to the "pickup" window where the drink and/or food is waiting for the user and has already been paid for by the vehicle authorization made.

In some configurations, payments made by a vehicle 100 may be conditionally authorized ahead of a transaction time for a limited period of time. This pre-transaction authorization may be restricted and/or only active for a particular time surrounding a determined movement of the vehicle 100. In one example, a user may enter a destination into a driving-navigation program (e.g., GPS navigation system associated with the vehicle 100, etc.). The vehicle 100 may determine a particular path of travel for the vehicle 100 and determine that specific routes require payment (e.g., toll roads, parking garages, congestion tax fees, etc.) or requires charging to be performed. In response to determining that the specific routes require some type of payment, the vehicle 100 may determine to authorize the predicted payments required on the specific routes. This authorization may be valid only for a limited time, while the vehicle 100 is traveling along the route, and/or as long as the vehicle 100 has power, etc. For instance, if the user deviates from the path, the pre-transaction authorization is revoked, preventing any accidental or unintended payments.

A driver may generally associate their payment information with a vehicle 100. Yet, sometimes, the vehicle 100 may transport multiple parties, for example, in a car pool. If a person other than the driver desires to pay for a good or service, the person may not be able to utilize the vehicle's payment system. Thus, the vehicle 100 may be capable of adding multiple buyers/payers to the payment system by associating those other people with the vehicle 100.

A passenger may enter the vehicle 100. The vehicle 100 may sense the presence of the passenger by receiving a phone signal, by receiving sensor data from sensors associated with the passenger (e.g., activation of the airbag, heat, weight, etc.), etc. A user interface presented on the head unit or in a screen of the entertainment system may be prompt the passenger with the option to associate financial information with the vehicle 100. If the passenger participates, the passenger can utilize the payment system. Further, the vehicle 100 may use that person's cell or phone for transactions when the passenger is paying. Any stored data may be erased when the passenger leaves the vehicle 100, which prevents reuse of the payment information. Or, in the alternative, the payment information may be dormant until the user is identified in the vehicle 100 again or their mobile device enters the vehicle 100 again. In some situations, the passenger and driver can use the vehicle payment system to split payments, for example, for battery charging, food, hotel, etc.

Figure 45:
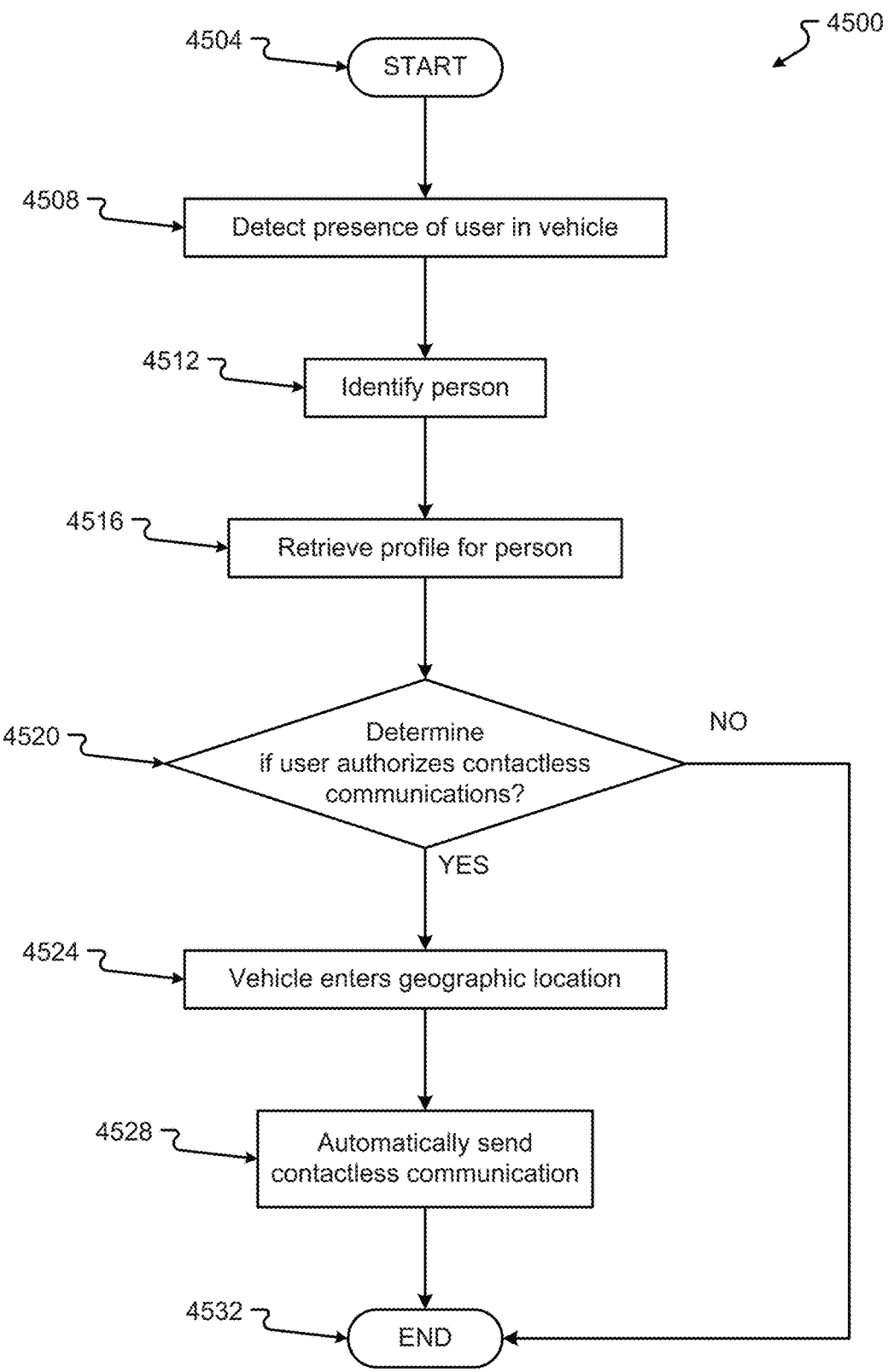
FIG. 45 is another flow diagram of an embodiment of a method for providing secure communications with a vehicle.

An embodiment of a method 4500 for allowing contactless secure communications may be as shown in FIG. 45. Generally, the method 4500 starts with a start operation 4504 and ends with operation 4532. The method 4500 can include more or fewer steps or can arrange the order of the steps differently than those shown in FIG. 45. The method 4500 can be executed as a set of computer-executable instructions executed by a computer system or processor and encoded or stored on a computer readable medium. In other configurations, the method 4500 may be executed by a series of components, circuits, gates, etc. created in a hardware device, such as a System of Chip (SOC), Application Specific Integrated Circuit (ASIC), and/r a Field Programmable Gate Array (FPGA). Hereinafter, the method 4500 shall be explained with reference to the systems, components, circuits, modules, software, data structures, signaling processes, models, environments, vehicles, etc. described in conjunction with FIGS. 1-44 and 54A-56.

The CPU 5608 can receive information from internal sensors 5437 that indicate the presence of a user within the vehicle, in step 4508. As described in conjunction with FIG. 44, the internal sensors 5437 can send information to the CPU 5608 indicating that a person is within the vehicle 100. In step 4512, the CPU 5608 can identify the person by comparing the biometric information received from the internal sensors 5437 with biometric information 2408 in data structure 2404. In other configurations, the user may be identified by the dongle 2008, mobile device, the username 2412 and password 2416, or some other information.

Based on the identity of the person, the CPU 5608 can retrieve a profile for the person, in step 4516. The profile may include data structure 2504 or data structure 2604, as described in conjunction with FIGS. 25 and 26. The profile of the person may include preferences 2528 or rules 2532. The CPU 5608 can determine if a user authorizes contactless communications, in step 4520. Here, the CPU 5608 may check the preferences 2528 or rules 2532 to determine if the user has authorized contactless communications. In other situations, a user interface may be provided to the user to allow for contactless communications, such as window 3004, window 3012, etc. If the user does desire to allow contactless communications with the vehicle 100 and a third party, the method 4500 proceeds "YES" to step 4524. If the user does not desire contactless communication, the method 4500 proceeds "NO" to step 4532.

In step 4524, the vehicle 100 may enter a geographic location. The geographic location can be a route commonly taken by a user of the vehicle 100. This geographical location or route may be as described in conjunction with FIG. 37. Upon entering this location, the CPU 5608 can send contactless communications automatically, in step 4528. For example, the vehicle 100 can use preferences 2528, rules 2532, or other information in data structure 2604 to send automated purchases or other types of secure communications while in the geographic location.

Figure 46:
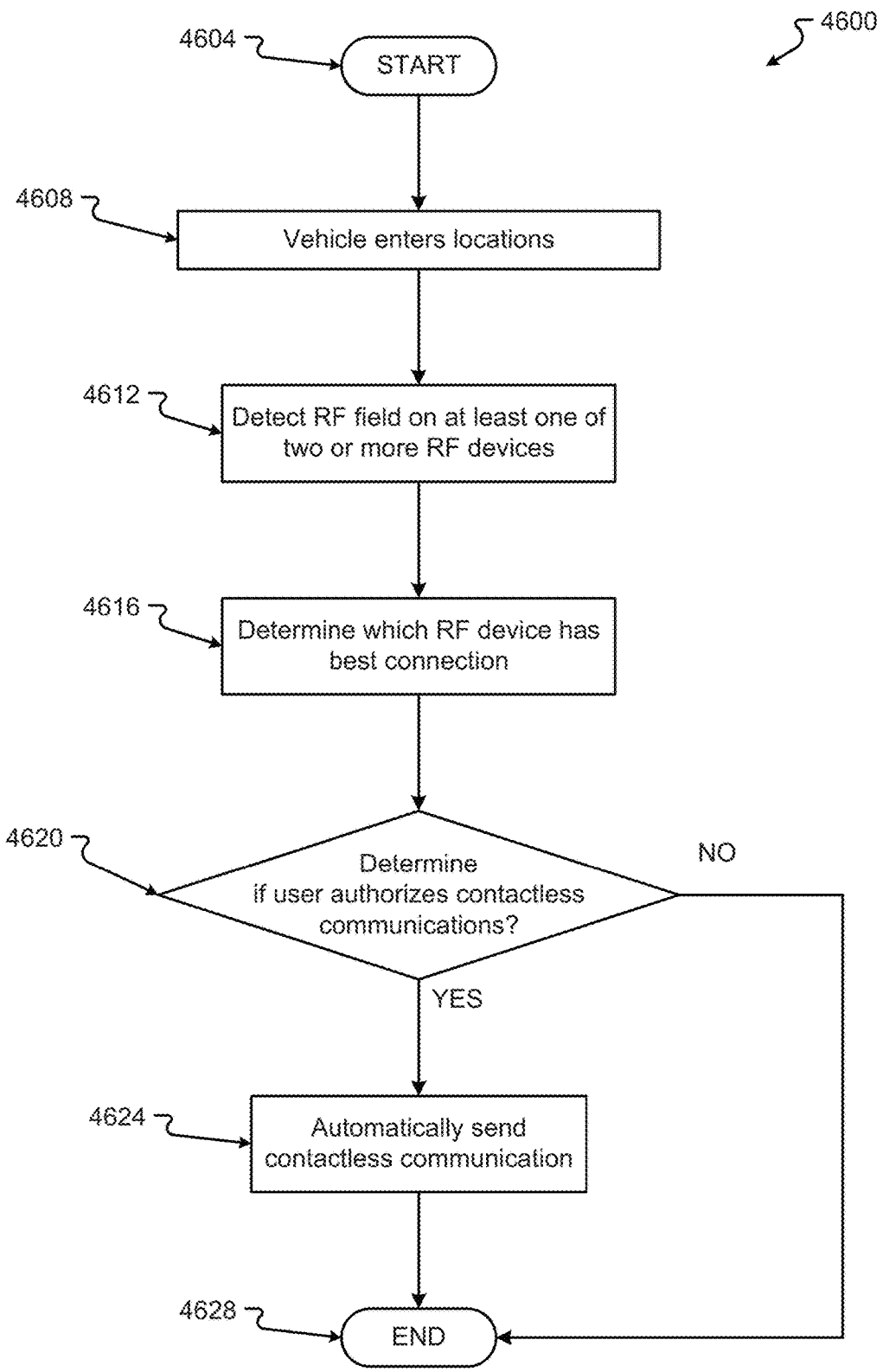
FIG. 46 is another flow diagram of an embodiment of a method for providing secure communications with a vehicle.

An embodiment of a method 4600 for a vehicle to make secure communications may be as shown in FIG. 46. Generally, the method 4600 starts with a start operation 4604 and ends with operation 4628. The method 4600 can include more or fewer steps or can arrange the order of the steps differently than those shown in FIG. 46. The method 4600 can be executed as a set of computer-executable instructions executed by a computer system or processor and encoded or stored on a computer readable medium. In other configurations, the method 4600 may be executed by a series of components, circuits, gates, etc. created in a hardware device, such as a System of Chip (SOC), Application Specific Integrated Circuit (ASIC), and/r a Field Programmable Gate Array (FPGA). Hereinafter, the method 4600 shall be explained with reference to the systems, components, circuits, modules, software, data structures, signaling processes, models, environments, vehicles, etc. described in conjunction with FIGS. 1-45 and 54A-56.

A vehicle 100 may enter a location, in step 4608. For example, the vehicle 100 can enter a drive-through, a toll lane, or some other type of location. The vehicle 100 may then determine if a radio frequency (RF) field is detected at one of the two or more RF devices 2004, as described in conjunction with FIG. 20, in step 4612. The CPU 5608 may be provided signals from the RF devices 2004 to determine if an RF field is detected. In step 4616, the CPU 5608 can determine which of the RF devices 2004 has the best connection or the highest field strength. For example, if the user is at a gas station and device 2004b is nearest, to a gas pump with an RF transceiver, device 2004b may have the best connection, as the field strength there may be higher than at device 2004c or 2004a. If device 2004b has the best connection, then that device 2004b may couple with the RF transceiver at the third party.

The CPU 5608 can then determine if the user authorizes contactless communication, in step 4620. As such, the CPU 5608 can access preferences 2528, rules 2532, or other information in data structure(s) 2504, 2604, etc. to determine if contactless communications are allowed. Further, the user interface 3072 or 3004 may be presented to the user and a determination made if the user provides an authorization of contactless communications. If contactless communications are not authorized, the method 4600 proceeds "NO" to step 4628. However, if contactless communications are authorized, method 4600 proceeds "YES" to step 4624. In step 4624, the CPU 5608 can automatically send contactless communications through the RF device 2004 to the third party. These communications can include financial information or other secure information from the vehicle 100. As such, the vehicle 100 can be an extension of the user in delivering information to a third party.

The method 4600 provides for devices at different location that allow for information exchange using various communication standards (e.g., near field communications (NFC), BLUETOOTH™ Low Energy (BLE), radio frequency identification (RFID). The devices can be mounted or incorporated into the vehicle 100 in various locations, e.g., a wing mirror, a windshield, a roof, etc. A vehicle 100 may have a communication device, e.g., an NFC or RFID device, installed in such a way that the device 2004 may communicate with external devices to conduct transactions including contactless payments.

The devices 2004 may be passive or active. For example, the communication device 2004 may be installed on or near the outer surface of the vehicle 100. The device 2004 may be placed in many areas of the vehicle 100 to communicate with external devices in a number of situations. A driver side device 2004c may be used to communicate and conduct contactless payment transactions in drive-thru situations. An overhead or under-carriage device 2004a may be utilized in situations such as toll-lanes or parking garages to similarly conduct payment transactions while the vehicle 100 may be moving. A communication device 2004c may be placed on or near the gas tank such that the device 2004c may conduct a payment transaction with a gas tank nozzle or gas pump. The device 2004 may be in communication with an onboard computer 5608 placed inside the vehicle 100. The device 2004 may be used to store and share any amount of information.

Figure 47:
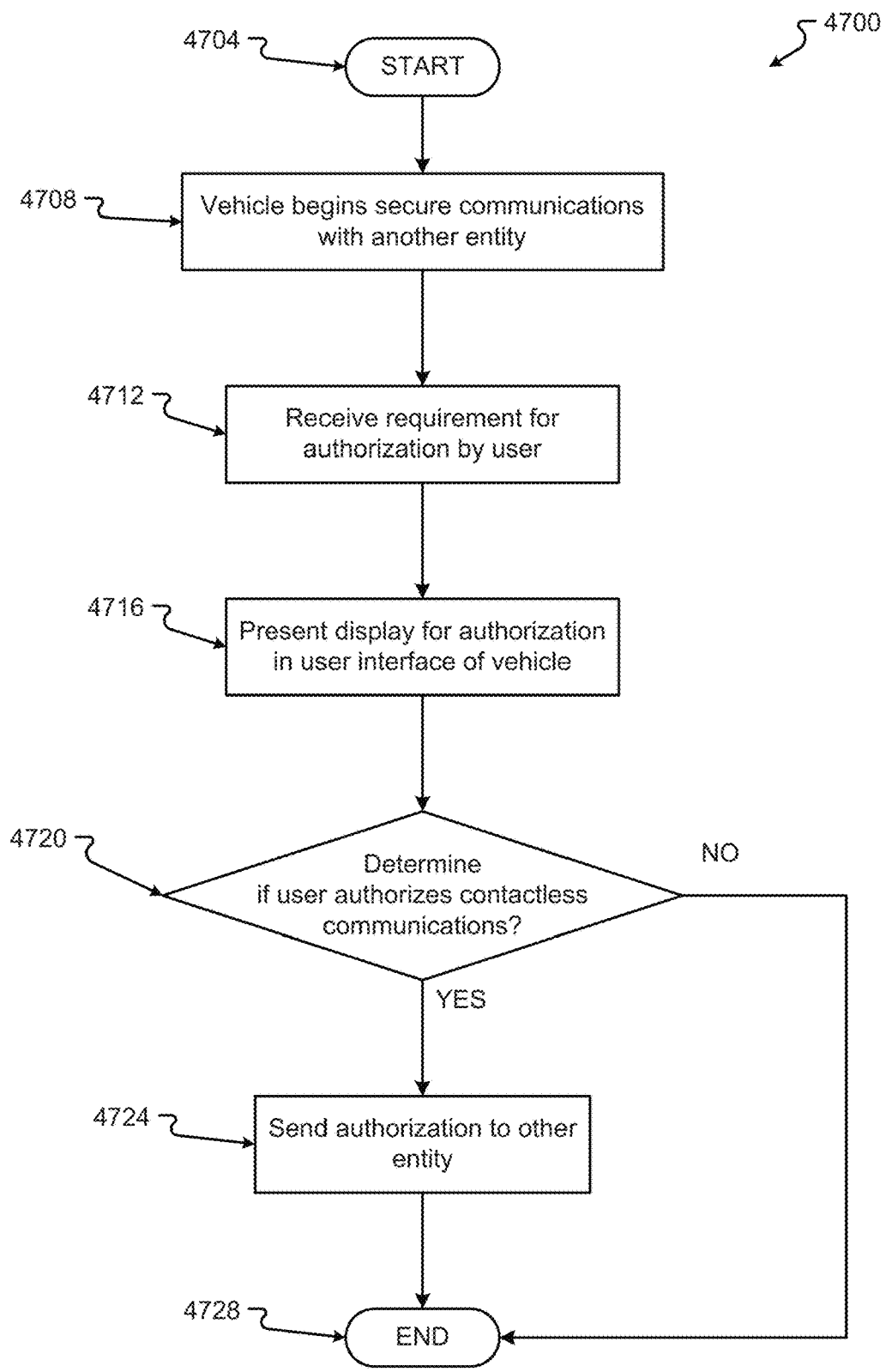
FIG. 47 is another flow diagram of an embodiment of a method for providing secure communications with a vehicle.

An embodiment of a method 4700 for conducting secure communications with the third party may be as shown in FIG. 47. Generally, the method 4700 starts with a start operation 4704 and ends with operation 4728. The method 4700 can include more or fewer steps or can arrange the order of the steps differently than those shown in FIG. 47. The method 4700 can be executed as a set of computer-executable instructions executed by a computer system or processor and encoded or stored on a computer readable medium. In other configurations, the method 4700 may be executed by a series of components, circuits, gates, etc. created in a hardware device, such as a System of Chip (SOC), Application Specific Integrated Circuit (ASIC), and/r a Field Programmable Gate Array (FPGA). Hereinafter, the method 4700 shall be explained with reference to the systems, components, circuits, modules, software, data structures, signaling processes, models, environments, vehicles, etc. described in conjunction with FIGS. 1-46 and 54A-56.

The vehicle 100 begins secure communications with another party, in step 4708. Here, the processor 5608 may communicate through the communications system 1900 to another entity. The communication may be a remote communication used through a wireless or cellular system. In other embodiments, it may be a nearfield communication. The third party may send a request for authorization for some type of communication. In such a case, the vehicle 100 receives a requirement for authorization by the user, in step 4712. In other situations, an internal rule 2532 or some other event may cause the processor 5608 to require authorization by the user.

In step 4716, the processor 5608 may display a user interface (e.g., user interface 2904) to provide authorization to the vehicle 100. This user interface may be user interface 3000 shown in FIG. 30A, window 3072 in FIG. 30B, or some other window as described herein. The processor 5608 can then determine if the user authorizes the contactless communication, in step 4720. For example, if the user provides input into button 3076, then the processor 5608 can determine that contactless communication is authorized. If such authorization is given, the method 4700 proceeds "YES" to step 4724. However, if no authorization is given, method 4700 proceeds "NO" to end operation 4728.

In step 4724, the processor 5608 can create an authorization based on the authorization given by the user and send such authorization through the communications system 1900 to the other entity. As such, the processor 5608 can provide authorizations for secure communications or other events, such as financial transactions, through a display and/or user interfaces on the vehicle 100 rather than through a mobile device or a device (e.g., a credit card terminal) associated with the other party.

User interfaces for authorization of transaction may be provided in a head unit or other display (e.g., dash, heads-up display (HUD), etc.). An in-vehicle display and input device may be provided to conduct contactless payment transactions with external devices. When an external device initiates a payment transaction with a communication device of the vehicle 100, a user inside the vehicle 100 may be presented with a means for authorizing the payment, for example, a user interface that accepts a PIN entry, a signature, fingerprint ID, retina scanner, etc. or another interface that provides a different type of authorization (e.g., voice authorization, gesture authorization, etc.). The means for authorization may be dependent on the amount or type of transaction involved. Authorization may take place prior to, during, or following the transaction. For example, in the case of toll-lanes, the payment may be authorized following the use of the toll-lane. For drive-thru restaurant transactions, the authorization may take place prior to the sale. For the authorization of the sale of gas, the authorization may take place immediately following the pumping of the gas and prior to sale.

In some embodiments, payments made by a vehicle 100 may be authorized ahead of a transaction time and/or for a limited period of time. This pre-transaction authorization may be restricted and/or only active for a particular time surrounding a determined movement of the vehicle 100. In one example, a user may enter a destination into a driving-navigation program 5402 (e.g., GPS navigation system associated with the vehicle, etc.). The vehicle 100 may determine a particular path of travel for the vehicle 100 and determine that specific routes require payment (e.g., toll roads, parking garages, congestion tax fees, etc.). In response to determining that the specific routes require some type of payment, the vehicle 100 may determine to authorize the predicted payments required on the specific routes. This authorization may be valid only for a limited time, while the vehicle 100 is traveling along the route, and/or as long as the vehicle 100 has power, etc. For instance, if the user deviates from the path, the pre-transaction authorization is revoked, preventing any accidental or unintended payments.

Payment may be later authorized based on vehicle identification and later acceptance. When a vehicle 100 conducts a payment transaction, the transaction may be authorized based on a unique identifier associated with the vehicle 100 and/or geolocation information associated with the vehicle 100 and/or the driver. During the initial part of the transaction, the vehicle's contactless payment system may deliver the payment information and information regarding the vehicle 100 and/or driver of the vehicle 100 (e.g., a half token). This information may be collected in other ways by the external payment device to support the authorization. For example, the external device may photograph the vehicle 100, license plate, and/or driver. This information may be used to support the authorization for the transaction.

Such pre-transaction authorization may be useful in situations requiring the driver to manually enter an authorization, such as by PIN code, signature, etc., which may be inconvenient or impossible when driving. For example, the system may be used for payments made while the vehicle 100 is in motion, e.g., for paying while entering/exiting parking garages and/or for paying for toll-lanes.

In some embodiments, the vehicle 100 may anticipate payments to be made, or opportunities to pay, based on a number of factors associated with the vehicle 100. These factors can include location, speed, proximity to a location, preference data, and/or historical information. In response to detecting one or more of these factors, the vehicle 100 may present the user with a context-sensitive prompt designed to provide an advanced authorization for payment for a good or service. This advanced authorization for payment can save authentication time, processing time, and/or waiting time associated with payment stations, providing a quick transactional exchange.

By way of example, a user may be approaching a gas station and a drive-through coffee shop in a vehicle 100, upon reducing speed and/or positioning the vehicle 100 into proximity with the coffee shop, the vehicle 100 may prompt the user for advanced authorization for the coffee shop (e.g., rather than the gas station, or any other service). The user may accept the advanced authorization (e.g., for an open-amount, particular amount, etc.). Additionally or alternatively, the vehicle 100 may prompt the user for authorization for a particular drink and/or group of drinks, food, etc. The user may accept a "usual" order (e.g., based on historical data, preferences, and/or voice command), and as the user drives up to the "ordering" window/kiosk, the user may be directed to the "pickup" window where the drink and/or food is waiting for the user and has already been paid for by the vehicle authorization made in advance.

Multiple communications for authorization, based on geolocation, proximity, etc. may be prompted by a user interface, for example "Are you going to buy a burger?", "Are you filling up for gas?", and so on. The user interface may be set for certain speeds of vehicle, based on preferences, etc. An initial step is the communications could be the "advertisement" (e.g., "Would you like a Starbucks?"). This advertisement could appear in the display of the vehicle 100. If the answer is "Yes", a second step of authenticating the vehicle/driver/passenger(s) to Starbucks could occur to allow the transaction to proceed. Otherwise, the question could time out.

Figure 48:
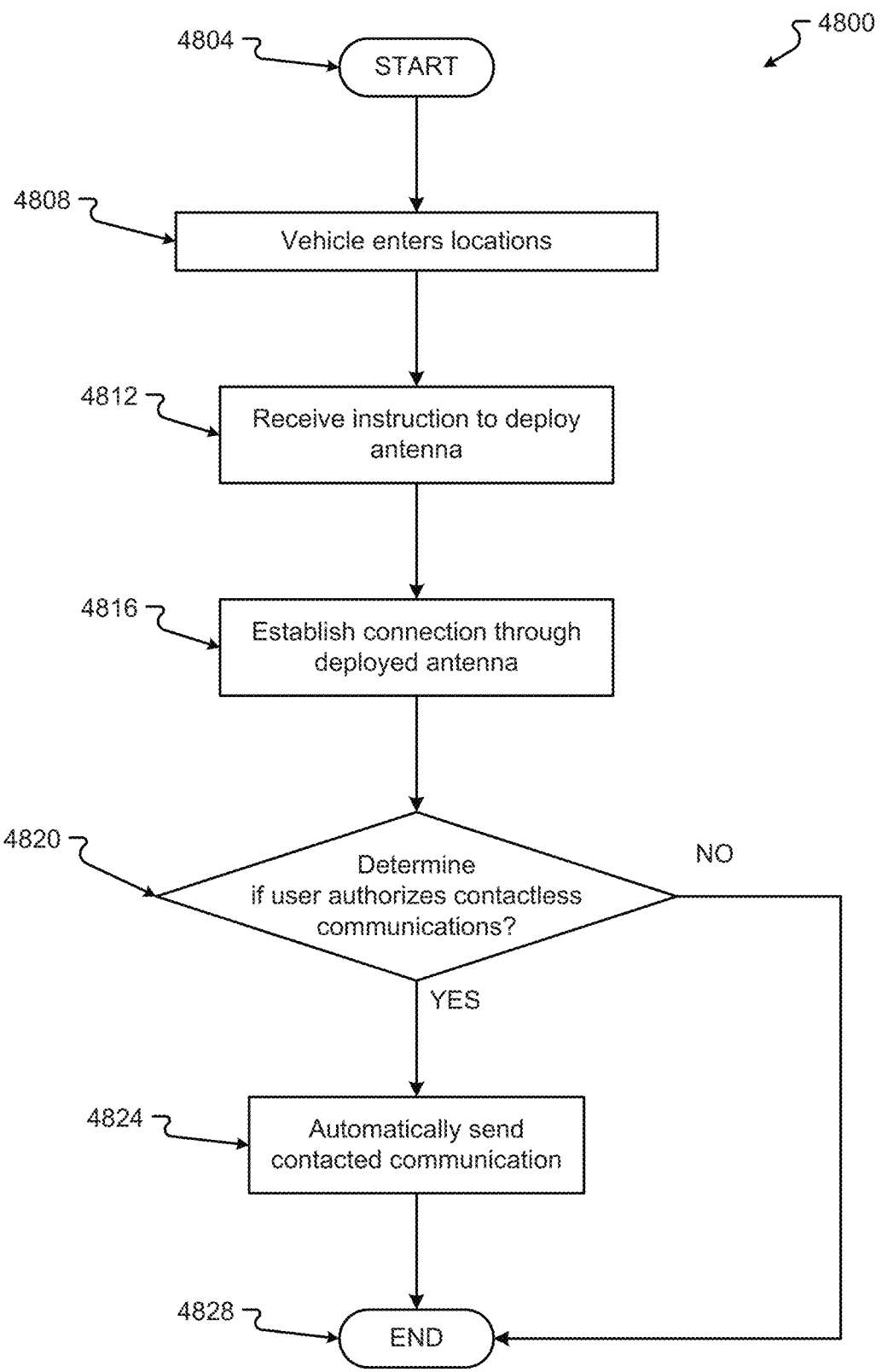
FIG. 48 is another flow diagram of an embodiment of a method for providing secure communications with a vehicle.

An embodiment of a method 4800 for sending secure information or completing a communication through a deployable antenna 2208 may be as shown in FIG. 48. Generally, the method 4800 starts with a start operation 4804 and ends with operation 4828. The method 4800 can include more or fewer steps or can arrange the order of the steps differently than those shown in FIG. 48. The method 4800 can be executed as a set of computer-executable instructions executed by a computer system or processor and encoded or stored on a computer readable medium. In other configurations, the method 4800 may be executed by a series of components, circuits, gates, etc. created in a hardware device, such as a System of Chip (SOC), Application Specific Integrated Circuit (ASIC), and/r a Field Programmable Gate Array (FPGA). Hereinafter, the method 4800 shall be explained with reference to the systems, components, circuits, modules, software, data structures, signaling processes, models, environments, vehicles, etc. described in conjunction with FIGS. 1-47 and 54A-56.

The vehicle 100 may enter a location, in step 4808. Here, the vehicle 100 may maneuver within physical proximity of a third-party location. The third-party location may have a receiving pad 2212. In step 4812, the processor 5608 may receive an instruction to deploy antenna 2208 to touch the pad 2212. In response, the processor 5608 may operate the deploying device 2204 to deploy the antenna 2208 to physically contact the pad 2212.

Upon making an electrical connection through the contact surface(s), the CPU 5608 can establish a communication/ electrical connection through the deployable antenna 2208, in step 4816. For example, authentication or authorization information may be exchanged between the vehicle 100 and the third party through antenna 2208. At this point, the CPU 5608 may provide a user interface, such as user interface 3000 or user interface 3012, to determine if the user authorizes the communication, in step 4820. If the user provides input that communications are authorized, the method 4800 proceeds "YES" to step 4824, where the processor 5608 automatically sends the communication or financial information. If no authorization is given, the method proceeds "NO" to end operation 4828.

The soft contact reader for payment, similar to the close proximity (e.g., NFC, close range, etc.) readers 2004 can be deployed in different locations for different functions (e.g., side of vehicle for coffee or food at drive through; top of vehicle for tolls, parking, etc., or other locations). Most forms of contactless payment utilize NFC protocol antennae. Such communication devices require very near proximity to transfer information. To utilize this technology with the vehicle 100, when conducting contactless payment transactions with external devices, a specially designed scanner device is needed. An NFC antennae device may be installed in a type of "brush" or "arm" wherein the external device 2208 may come in contact with the NFC antennae of the vehicle without damaging the vehicle 100 in any way. For example, when conducting a contactless payment transaction while driving into or out of a parking garage, a vehicle 100 may drive over a brush or arm equipped with an NFC reading device. This reading device may come in contact with an NFC antennae placed on the undercarriage of the vehicle. In other situations, for example a drive-thru restaurant, the vehicle 100 may drive alongside an NFC reader equipped brush or arm, wherein the NFC reader is enabled to accept payment information from an NFC antennae device placed on the driver side of the vehicle 100.

Figure 49:
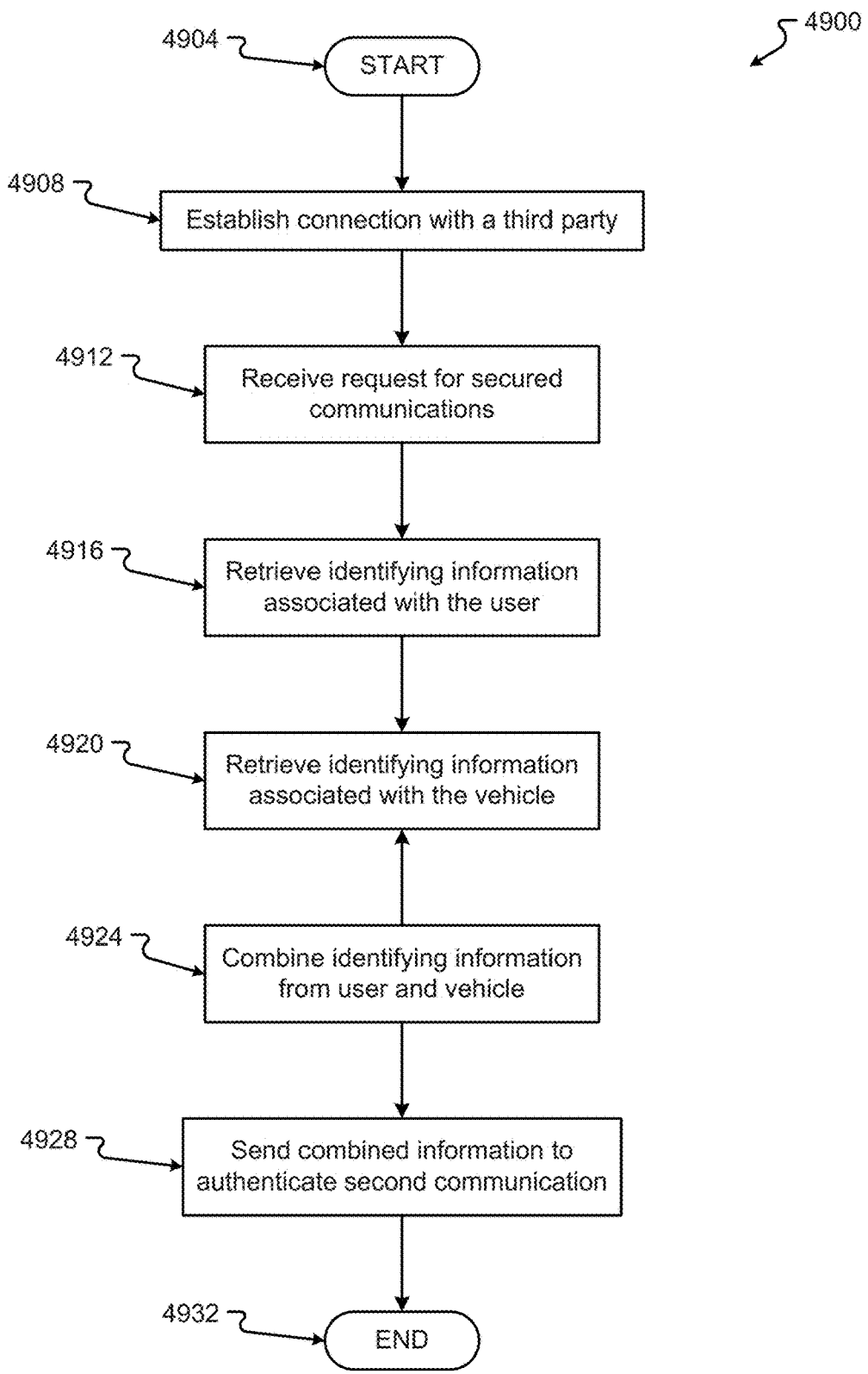
FIG. 49 is another flow diagram of an embodiment of a method for providing secure communications with a vehicle.

An embodiment of sending authentication information in a method 4900 may be as shown in FIG. 49. Generally, the method 4900 starts with a start operation 4904 and ends with operation 4932. The method 4900 can include more or fewer steps or can arrange the order of the steps differently than those shown in FIG. 49. The method 4900 can be executed as a set of computer-executable instructions executed by a computer system or processor and encoded or stored on a computer readable medium. In other configurations, the method 4900 may be executed by a series of components, circuits, gates, etc. created in a hardware device, such as a System of Chip (SOC), Application Specific Integrated Circuit (ASIC), and/r a Field Programmable Gate Array (FPGA). Hereinafter, the method 4900 shall be explained with reference to the systems, components, circuits, modules, software, data structures, signaling processes, models, environments, vehicles, etc. described in conjunction with FIGS. 1-48 and 54A-56.

In step 4908, the communications system 1900 can establish a connection or communication link between the vehicle 100 and a third party. This connection may be a nearfield communication, wireless communication, cellular communication, etc. Any of the preceding or following descriptions of communication connections may be made. In step 4912, the CPU 5608 can then receive a request for a secure communication. This secure communication may be authorized or secured using authenticating information. This authenticating information may be information identifying a user. As such, the CPU 5608 can retrieve identifying information associated with the user, in step 4916. Here, the CPU may extract or create a half-token 2312 or information shown in data structure 2404.

In step 4920, the CPU 5608 may retrieve from memory the information associated with the vehicle 100, for example, a VIN 2436, an ESN 2440, an engine code 2444. The vehicle's information may be combined with the user information into a new grouping of identifying information from both the user and vehicle 100, in step 4924. This combined information may then be sent by the processor 5608 to the communications system 1900 and sent on to another party, in step 4928.

Thus, the vehicle 100 can employ a vehicle VIN 2436, an ESN 2440 for the vehicle 100, an ESN of a mobile device, etc. for communication/purchase authentication. Only if a third party receives both sets of information is there an authentication for a communication/purchase. Another individual cannot purchase anything if the vehicle 100 is carjacked or stolen. Further, in some configurations, a user could provide the VIN 2436 and/or ESN 2440 as an ignition key for vehicle 100. An additional level of authentication may require a PIN 2512, or additional biometrics 2408, for the authorization.

Figure 50:
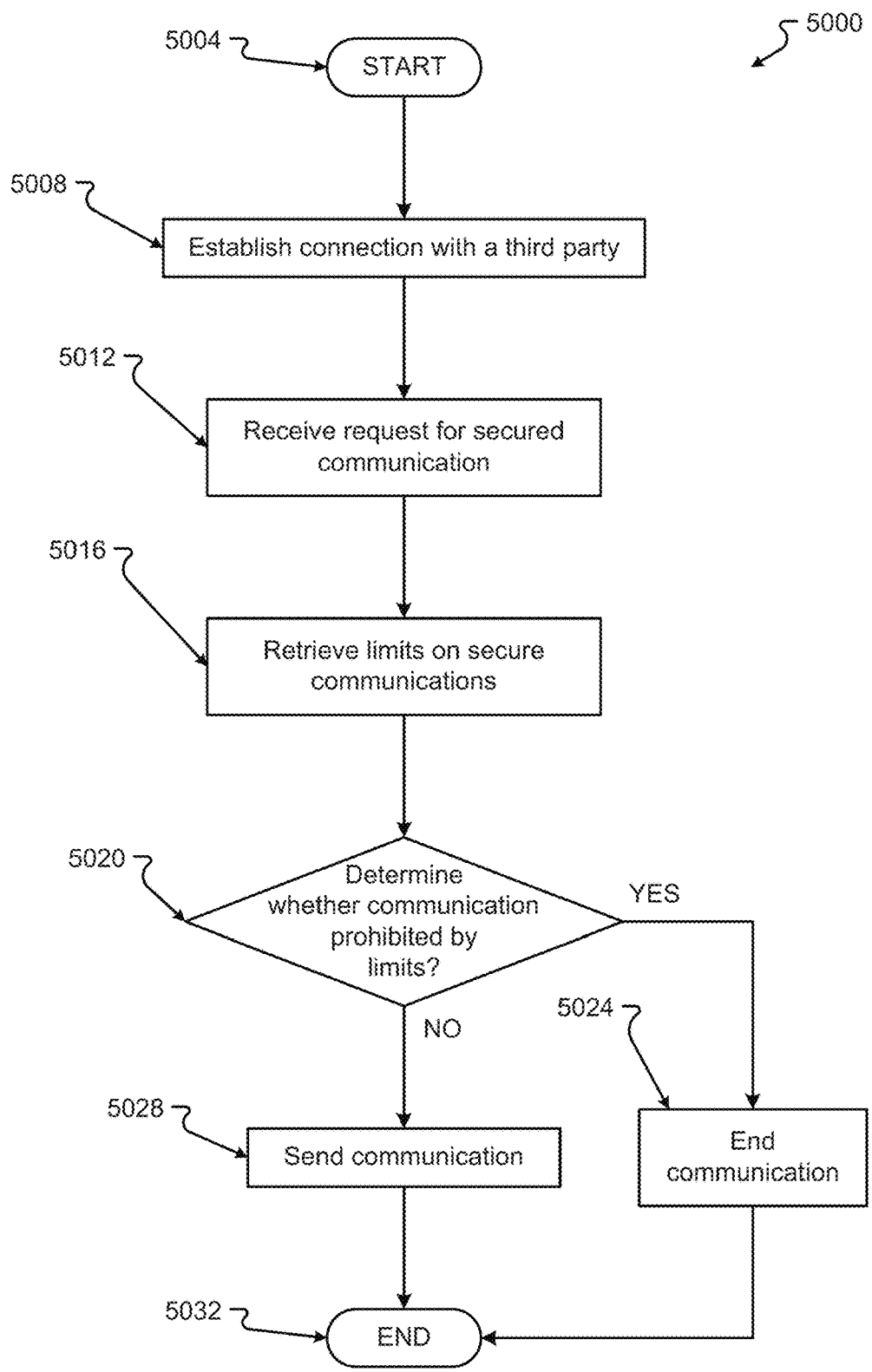
FIG. 50 is another flow diagram of an embodiment of a method for providing secure communications with a vehicle.

An embodiment of a method 5000 for determining whether a communication may be limited by predetermined limits may be as shown in FIG. 50. Generally, the method 5000 starts with a start operation 5004 and ends with operation 5032. The method 5000 can include more or fewer steps or can arrange the order of the steps differently than those shown in FIG. 50. The method 5000 can be executed as a set of computer-executable instructions executed by a computer system or processor and encoded or stored on a computer readable medium. In other configurations, the method 5000 may be executed by a series of components, circuits, gates, etc. created in a hardware device, such as a System of Chip (SOC), Application Specific Integrated Circuit (ASIC), and/r a Field Programmable Gate Array (FPGA). Hereinafter, the method 5000 shall be explained with reference to the systems, components, circuits, modules, software, data structures, signaling processes, models, environments, vehicles, etc. described in conjunction with FIGS. 1-49 and 54A-56.

The communications system 1900 may establish a communications connection with a third party, in step 5008. In step 5012, the processor 5608 may receive a request for secure communication from the third party. Upon receiving and in response to receiving such request, the processor 5608 may access limits field 2524, in data structure 2504, to retrieve limits on such secure communications, in step 5016. The processor 5608 may then determine whether the communications are prohibited by these limits, in step 5020. Here, limits can include limits on the number of communications provided, can include monetary limits on transactions that may be conducted, etc. These limits on financial transactions may be cover two or more vehicles or just for the single vehicle 100. The limits may also be associated with a particular financial account or across family members.

Depending on the limit, the processor 5608 can determine whether a communication is authorized, in step 5020. If the communication is prohibited, the method 5000 proceeds "YES" to step 5024, where the communication is ended. However, if the communication is not prohibited, the method 5000 proceeds "NO" to step 5028, where the communications are sent. For example, without prohibitions, the financial information of the user may be sent to conduct a financial transaction.

The limits placed on transaction amounts can be based on an individual or on a collection of people, on a transaction, or over a specified period of time. The transaction history could be synchronized among multiple vehicles to provide a collective limit for all vehicles or may be based on a limit per-vehicle, per location, etc. Limits on types of transactions or products being purchased could also be imposed on another entity, for example, a parent can set transaction limits on driving teenagers.

Method 5100 may be similar to method 5000. Generally, the method 5100 starts with a start operation 5104 and ends with operation 5132. The method 5100 can include more or fewer steps or can arrange the order of the steps differently than those shown in FIG. 51. The method 5100 can be executed as a set of computer-executable instructions executed by a computer system or processor and encoded or stored on a computer readable medium. In other configurations, the method 5100 may be executed by a series of components, circuits, gates, etc. created in a hardware device, such as a System of Chip (SOC), Application Specific Integrated Circuit (ASIC), and/r a Field Programmable Gate Array (FPGA). Hereinafter, the method 5100 shall be explained with reference to the systems, components, circuits, modules, software, data structures, signaling processes, models, environments, vehicles, etc. described in conjunction with FIGS. 1-50 and 54A-56.

Figure 51:
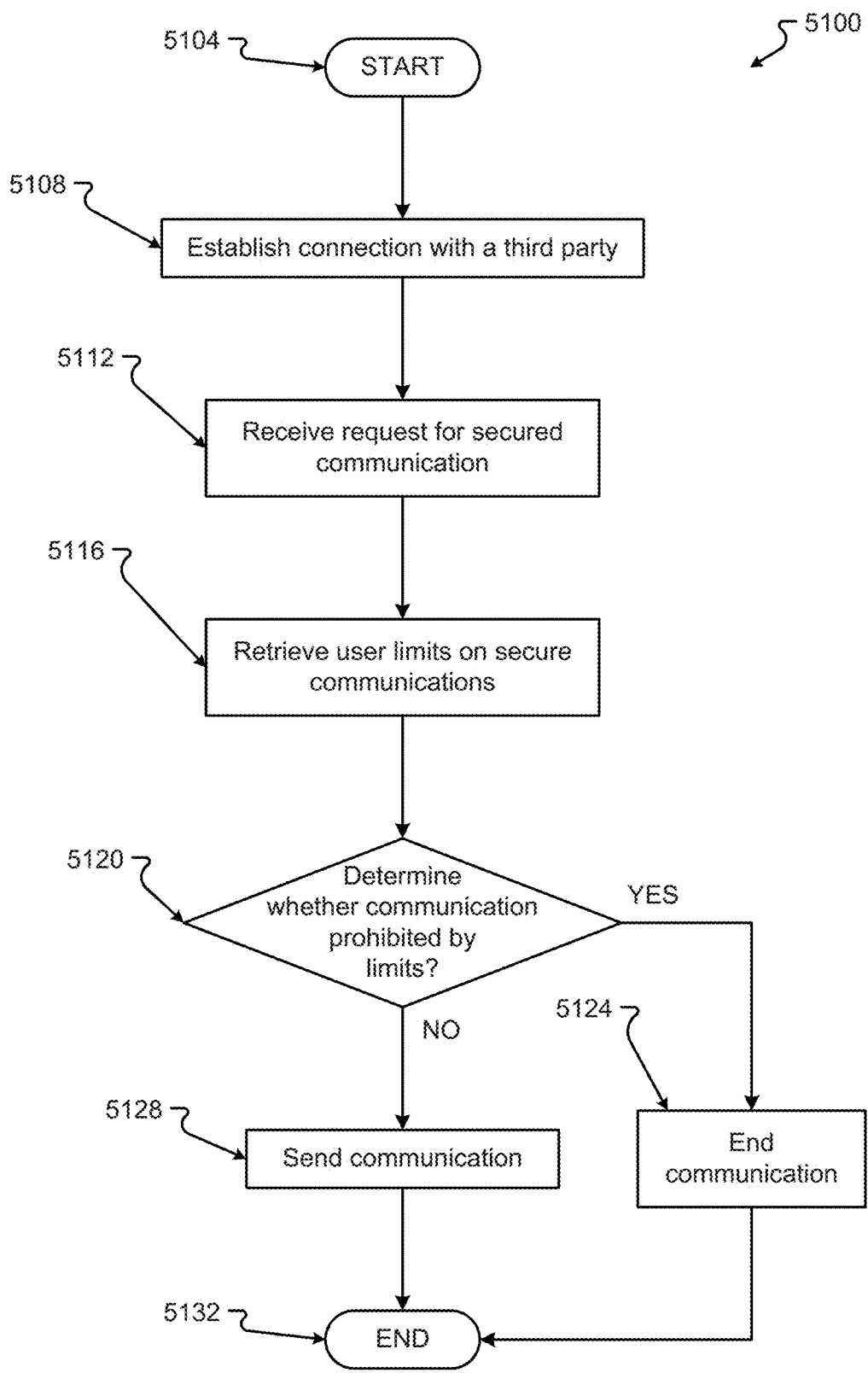
FIG. 51 is another flow diagram of an embodiment of a method for providing secure communications with a vehicle.

The method 5100, shown in FIG. 51, may also set limits on communications, similar to method 5000, but, in this situation, based on third-party limits. Thus, the communication can be established with a third party, in step 5108, and a request for secure communication can be received, in step 5112. Rather than retrieving limits made by a user, the limits may be applied from a third party. As such, the third party may retrieve limits, in step 5116, to determine whether the communication is prohibited by those limits, in step 5120. For example, if the third party is a bank, the bank may limit the amount of a transaction or a communication based on limits set by the bank for the vehicle 100. If the limits prohibit the communication, the method 5100 proceeds "YES" to step 5124, where the communication is ended. However, if the communication is not prohibited, the method 5100 proceeds "NO" to step 5128, where the communication is sent.

Method 5100 is directed to the other side of the transaction in method 5000. A provider/seller can also have business rules that are applied to the supplier side. The supplier sets a different notional set of purchase rules, i.e. business operational minimums or maximums, to facilitate selection or negotiation of battery exchange/repair/charging terms. Such rules are applied when the user seeks such services, as enabled by a searching algorithm querying a database of available service stations. Automated negotiation between user and service provider may occur. The business/user is able to adjust selectable parameters, e.g., the user may be in a particular hurry and increase his/her maximum fee for a certain service, e.g., charging prices. Thus, the business and user may conduct negotiations or bargain within the limits of pre-defined limits or parameters.

Figure 52:
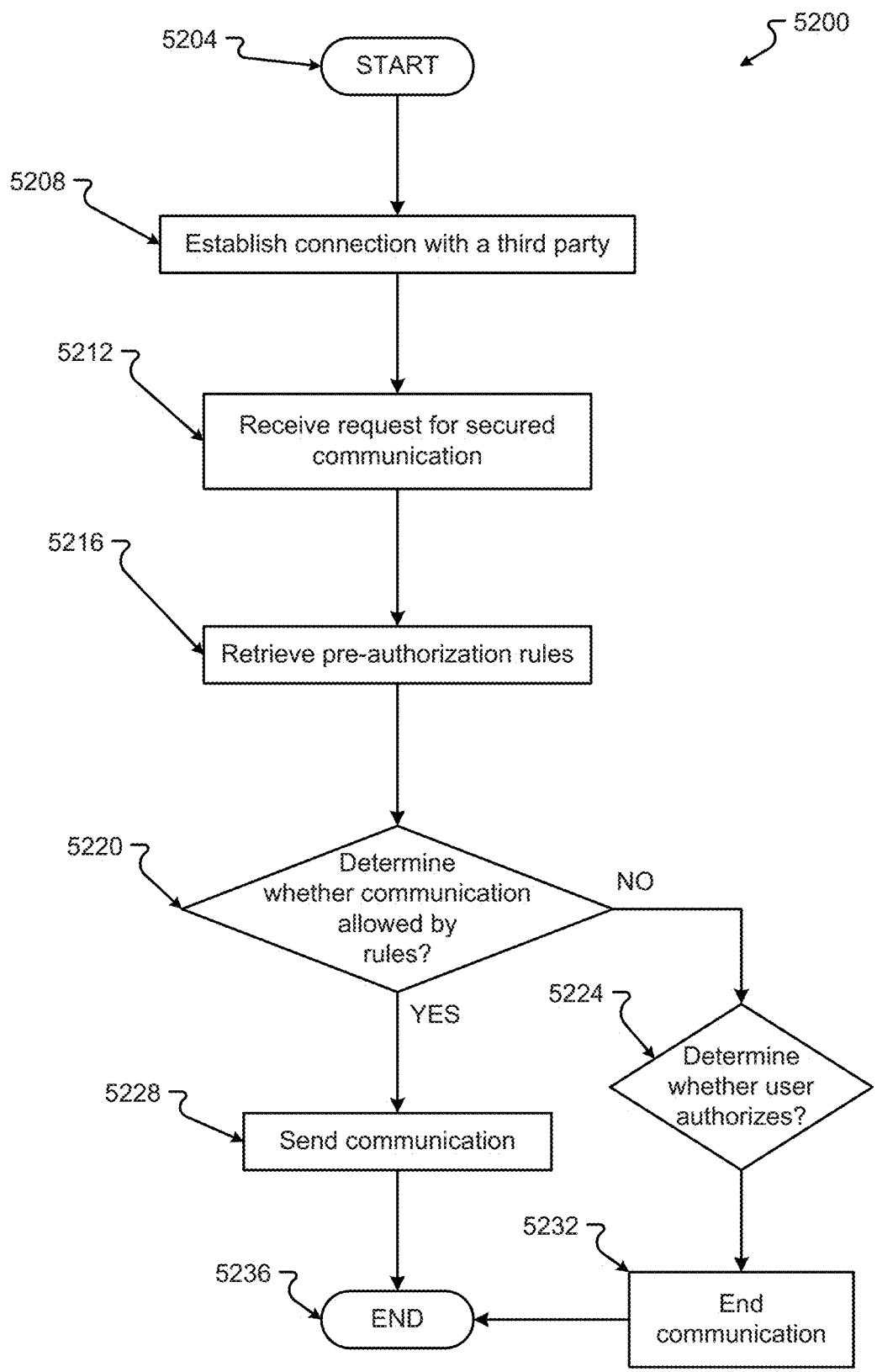
FIG. 52 is another flow diagram of an embodiment of a method for providing secure communications with a vehicle.

Method 5200 provides for conducting secure communications based on a set of preauthorization rules as shown in FIG. 52. Generally, the method 5200 starts with a start operation 5204 and ends with operation 5240. The method 5200 can include more or fewer steps or can arrange the order of the steps differently than those shown in FIG. 52. The method 5200 can be executed as a set of computer-executable instructions executed by a computer system or processor and encoded or stored on a computer readable medium. In other configurations, the method 5200 may be executed by a series of components, circuits, gates, etc. created in a hardware device, such as a System of Chip (SOC), Application Specific Integrated Circuit (ASIC), and/r a Field Programmable Gate Array (FPGA). Hereinafter, the method 5200 shall be explained with reference to the systems, components, circuits, modules, software, data structures, signaling processes, models, environments, vehicles, etc. described in conjunction with FIGS. 1-51 and 54A-56.

In step 5208, the vehicle 100 establishes a connection with a third party through the communications system 1900. Again, the processor 5608 receives a request for a secure communication, in step 5212. Rather than obtaining preferences, the CPU 5608 can retrieve pre-authorization rules from field 2532 of data structure 2504, in step 5216. These pre-authorization rules 2532 may be similar to those that are set in user interface 4000 or 4100. The pre-authorization rules may determine whether a processor 5608 can conduct pre-orders or other communications without user input, at least for a portion of the communications.

If the communication is allowed by the rules 2532, in step 5220, the method 5200 proceeds "YES" to step 5228, where the communication is sent through the communication system 1900. However, if the communication is not allowed by the rules 2532, the method 5200 proceeds "NO" to step 5224, where the CPU 5608 determines whether the user authorizes the communication. If the communication is authorized based on input received in a user interface, such as interface 3000, the method 5200 proceeds "YES" to step 5228, again to send the communication. However, if the communications are not authorized or pre-authorized, the method 5200 proceeds "NO" to step 5232, where the communication is ended.

The user establishes a set of rules triggering automatic authorization for or purchasing of services. For example, the user may establish that when visibility conditions along a route are predicted to drop below certain minimum, a moving map display 3800 with overlaid weather is provided on a vehicle display. Such a display would aid the driver in considering alternative routes or increasing the driver's situational awareness as to the severity, duration, and direction of the cause of the visibility drop (e.g., is it ground fog over a wide area expected to linger or a result of a fast-moving thunderstorm). The real-time moving map overlaid weather display 3800 may require a costly live feed from a weather satellite, and, as such, the feed is not provided unless the triggering event is satisfied. In another example, the user may establish that if his programmed driving route requires in route charging, a purchase of a reserved charging spot at a charging station along the route is automatically made so as to reserve the spot.

Figure 53:
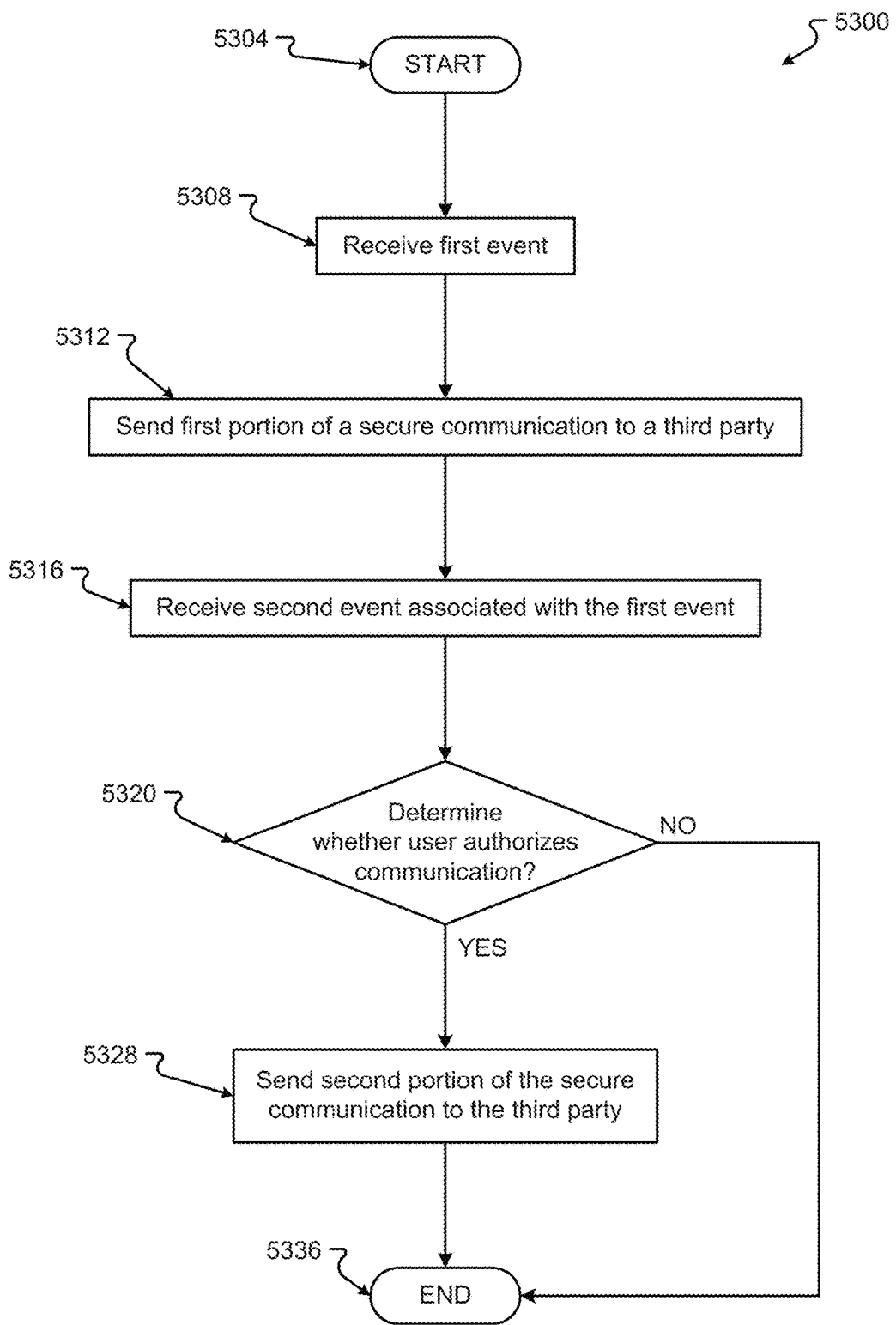
FIG. 53 is another flow diagram of an embodiment of a method for providing secure communications with a vehicle.

An embodiment of a bifurcated communication between the vehicle 100 and a third party may be as shown in FIG. 53. Generally, the method 5300 starts with a start operation 5304 and ends with operation 5340. The method 5300 can include more or fewer steps or can arrange the order of the steps differently than those shown in FIG. 53. The method 5300 can be executed as a set of computer-executable instructions executed by a computer system or processor and encoded or stored on a computer readable medium. In other configurations, the method 5300 may be executed by a series of components, circuits, gates, etc. created in a hardware device, such as a System of Chip (SOC), Application Specific Integrated Circuit (ASIC), and/r a Field Programmable Gate Array (FPGA). Hereinafter, the method 5300 shall be explained with reference to the systems, components, circuits, modules, software, data structures, signaling processes, models, environments, vehicles, etc. described in conjunction with FIGS. 1-52 and 54A-56.

Here, a first event may be received, in step 5308. This event may be the user driving to a certain location, taking a route, or some other type of event that occurs that causes the vehicle 100 to decide to send a first portion of a secure communication to a third party, in step 5312. For example, the processor 5608 may provide a pre-order for some good or service typically purchased by the user at that time of day at that route. This pre-authorization may be sent to the third party to prepare an order. At some point thereinafter, in step 5316, the processor 5608 can receive a second event associated with that first event. The second event may be the vehicle 100 driving to the physical location of the third party. As such, the second event may be the navigation system 302 identifying that the vehicle 100 is at the third party's location.

In step 5320, the processor 5608 can determine whether the user then authorizes the complete communication/transaction. Here, the user may be presented with a user interface 3300, 3500 associated with the preauthorization. If the communication/transaction is authorized, in step 5320, by selecting, for example, button 3512, the method proceeds "YES" to step 5328, where a second portion of the secure communication may be sent to a third party. The second communication can be a second half-token. As such, a half-token 2312 can be sent, in step 5312 while further information—such as financial information 2508, a PIN 2512, or some other type of information to complete the transaction—may be sent as the related second half token, in step 5328. If the user does not authorize the communication, the method 5300 can proceed "NO" to step 5336.

Utilizing the vehicle as a mobile wallet can pose some issues. One issue is the problem with ensuring that the vehicle 100 pays the right merchant, at the right time, in the right location. To ensure accuracy in payment, the vehicle 100 may break the payment procedure into two or more phases. A first phase may order goods or services and may provide some or all of the payment information. A second phase may send the total payment information or confirm the information in the first phase, such as by user input in response to a query (e.g., providing a PIN). Thus, the vehicle 100 can pre-authorize charges.

The vehicle 100 may also use different communication media (e.g., cellular communication, Bluetooth, NFC, etc.) to conduct the two or more phases. Using different communication media can enhance security as merchants or other nefarious individuals may not use the payment information without both phases of the communication and one of the phases may conducted with a communication media that requires physical proximity of the vehicle 100. Moreover, having a second phase requiring operator input can prevent a first vehicle from purchasing goods or services for another second vehicle waiting in line with the first vehicle 100.

As an example, the vehicle 100 may be driving toward a pay-point and pre-order a good. The vehicle 100 may understand that the driver is heading towards Starbucks (through past behavior), and the vehicle 100 can communicate with the Starbucks that payment will be authorized and desires their beverage hot, sweet, etc. (based on driver behavior and location). The pre-authorization may be sent over a cellular network. When the vehicle 100 arrives at the Starbucks, the final authorization may be sent over a local proximity-based payment system, e.g. NFC.

Payment can be authorized based on vehicle identification and later acceptance. When a vehicle 100 conducts a payment transaction, the transaction may be authorized based on a unique identifier associated with the vehicle and/or a geolocation information associated with the vehicle 100 and/or the driver. During the transaction, the vehicle's contactless payment system may deliver the payment information as well as information regarding the vehicle 100 and/or driver of the vehicle. This information may be collected in other ways by the external payment device to support the authorization. For example, the external device may photograph the vehicle 100, license plate, and/or driver. This information may be used to support the authorization for the transaction. Such pre-transaction authorization may be useful in situations where requiring the driver to manually enter an authorization, such as by PIN code, signature, etc., may be inconvenient or impossible because the driver is driving the vehicle 100. For example, the system may be used for payments made while the vehicle 100 is in motion, e.g., for paying while entering/exiting parking garages and/or for paying for toll-lanes.

Figure 54A:
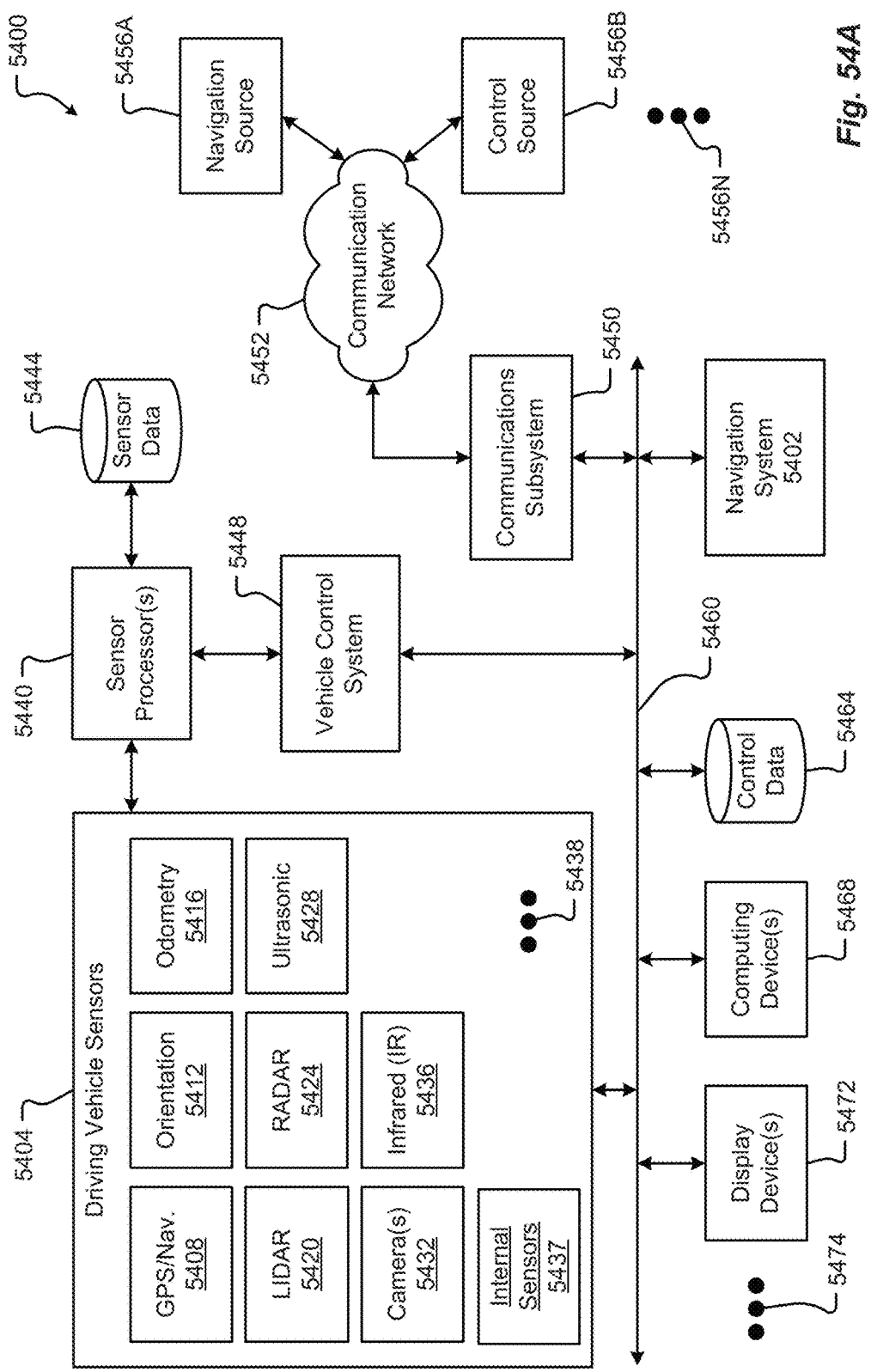
FIG. 54A is a block diagram of vehicle systems.

FIG. 54A is a is a block diagram of an embodiment of a communication environment 5400 of the vehicle 100 in accordance with embodiments of the present disclosure. The communication system 5400 may include one or more vehicle driving vehicle sensors and systems 5404, sensor processors 5440, sensor data memory 5444, vehicle control system 5448, communications subsystem 5450, control data 5464, computing devices 5468, display devices 5472, and other components 5474 that may be associated with a vehicle 100. These associated components may be electrically and/or communicatively coupled to one another via at least one bus 5460. In some embodiments, the one or more associated components may send and/or receive signals across a communication network 5452 to at least one of a navigation source 5455A, a control source 5455B, or some other entity 5455N.

In accordance with at least some embodiments of the present disclosure, the communication network 5452 may comprise any type of known communication medium or collection of communication media and may use any type of protocols, such as SIP, TCP/IP, SNA, IPX, AppleTalk, and the like, to transport messages between endpoints. The communication network 5452 may include wired and/or wireless communication technologies. The Internet is an example of the communication network 5452 that constitutes an Internet Protocol (IP) network consisting of many computers, computing networks, and other communication devices located all over the world, which are connected through many telephone systems and other means. Other examples of the communication network 104 include, without limitation, a standard Plain Old Telephone System (POTS), an Integrated Services Digital Network (ISDN), the Public Switched Telephone Network (PSTN), a Local Area Network (LAN), such as an Ethernet network, a Token-Ring network and/or the like, a Wide Area Network (WAN), a virtual network, including without limitation a virtual private network ("VPN"); the Internet, an intranet, an extranet, a cellular network, an infra-red network; a wireless network (e.g., a network operating under any of the IEEE 802.9 suite of protocols, the Bluetooth® protocol known in the art, and/or any other wireless protocol), and any other type of packet-switched or circuit-switched network known in the art and/or any combination of these and/or other networks. In addition, it can be appreciated that the communication network 5452 need not be limited to any one network type, and instead may be comprised of a number of different networks and/or network types. The communication network 5452 may comprise a number of different communication media such as coaxial cable, copper cable/wire, fiber-optic cable, antennas for transmitting/receiving wireless messages, and combinations thereof.

The driving vehicle sensors and systems 5404 may include at least one navigation 5408 (e.g., global positioning system (GPS), etc.), orientation 5412, odometry 5416, LIDAR 5420, RADAR 5424, ultrasonic 5428, camera 5432, infrared (IR) 5436, and/or other sensor or system 5438. These driving vehicle sensors and systems 5404 may be similar, if not identical, to the sensors and systems 116A-K, 112 described in conjunction with FIGS. 1 and 2.

The navigation sensor 5408 may include one or more sensors having receivers and antennas that are configured to utilize a satellite-based navigation system including a network of navigation satellites capable of providing geolocation and time information to at least one component of the vehicle 100. Examples of the navigation sensor 5408 as described herein may include, but are not limited to, at least one of Garmin® GLO™ family of GPS and GLONASS combination sensors, Garmin® GPS 15x™ family of sensors, Garmin® GPS 16x™ family of sensors with high-sensitivity receiver and antenna, Garmin® GPS 18x OEM family of high-sensitivity GPS sensors, Dewetron DEWE-VGPS series of GPS sensors, GlobalSat 1-Hz series of GPS sensors, other industry-equivalent navigation sensors and/or systems, and may perform navigational and/or geolocation functions using any known or future-developed standard and/or architecture.

The orientation sensor 5412 may include one or more sensors configured to determine an orientation of the vehicle 100 relative to at least one reference point. In some embodiments, the orientation sensor 5412 may include at least one pressure transducer, stress/strain gauge, accelerometer, gyroscope, and/or geomagnetic sensor. Examples of the navigation sensor 5408 as described herein may include, but are not limited to, at least one of Bosch Sensortec BMX 160 series low-power absolute orientation sensors, Bosch Sensortec BMX054 9-axis sensors, Bosch Sensortec BMI054 6-axis inertial sensors, Bosch Sensortec BMI160 6-axis inertial sensors, Bosch Sensortec BMF054 9-axis inertial sensors (accelerometer, gyroscope, and magnetometer) with integrated Cortex M0+ microcontroller, Bosch Sensortec BMP280 absolute barometric pressure sensors, Infineon TLV493D-A1B6 3D magnetic sensors, Infineon TLI493D-W1B6 3D magnetic sensors, Infineon TL family of 3D magnetic sensors, Murata Electronics SCC2000 series combined gyro sensor and accelerometer, Murata Electronics SCC1300 series combined gyro sensor and accelerometer, other industry-equivalent orientation sensors and/or systems, and may perform orientation detection and/or determination functions using any known or future-developed standard and/or architecture.

The odometry sensor and/or system 5416 may include one or more components that is configured to determine a change in position of the vehicle 100 over time. In some embodiments, the odometry system 5416 may utilize data from one or more other sensors and/or systems 5404 in determining a position (e.g., distance, location, etc.) of the vehicle 100 relative to a previously measured position for the vehicle 100. Additionally or alternatively, the odometry sensors 5416 may include one or more encoders, Hall speed sensors, and/or other measurement sensors/devices configured to measure a wheel speed, rotation, and/or number of revolutions made over time. Examples of the odometry sensor/system 5416 as described herein may include, but are not limited to, at least one of Infineon TLE4924/26/27/28C high-performance speed sensors, Infineon TL4941plusC(B) single chip differential Hall wheel-speed sensors, Infineon TL5041plusC Giant Mangnetoresistance (GMR) effect sensors, Infineon TL family of magnetic sensors, EPC Model 25SP Accu-CoderPro™ incremental shaft encoders, EPC Model 30M compact incremental encoders with advanced magnetic sensing and signal processing technology, EPC Model 925 absolute shaft encoders, EPC Model 958 absolute shaft encoders, EPC Model MA36S/MA63S/SA36S absolute shaft encoders, Dynapar™ F18 commutating optical encoder, Dynapar™ HS35R family of phased array encoder sensors, other industry-equivalent odometry sensors and/or systems, and may perform change in position detection and/or determination functions using any known or future-developed standard and/or architecture.

The LIDAR sensor/system 5420 may include one or more components configured to measure distances to targets using laser illumination. In some embodiments, the LIDAR sensor/system 5420 may provide 3D imaging data of an environment around the vehicle 100. The imaging data may be processed to generate a full 360-degree view of the environment around the vehicle 100. The LIDAR sensor/system 5420 may include a laser light generator configured to generate a plurality of target illumination laser beams (e.g., laser light channels). In some embodiments, this plurality of laser beams may be aimed at, or directed to, a rotating reflective surface (e.g., a mirror) and guided outwardly from the LIDAR sensor/system 5420 into a measurement environment. The rotating reflective surface may be configured to continually rotate 360 degrees about an axis, such that the plurality of laser beams is directed in a full 360-degree range around the vehicle 100. A photodiode receiver of the LIDAR sensor/system 5420 may detect when light from the plurality of laser beams emitted into the measurement environment returns (e.g., reflected echo) to the LIDAR sensor/system 5420. The LIDAR sensor/system 5420 may calculate, based on a time associated with the emission of light to the detected return of light, a distance from the vehicle 100 to the illuminated target. In some embodiments, the LIDAR sensor/system 5420 may generate over 2.0 million points per second and have an effective operational range of at least 100 meters. Examples of the LIDAR sensor/system 5420 as described herein may include, but are not limited to, at least one of Velodyne® LiDAR™ HDL-64E 64-channel LIDAR sensors, Velodyne® LiDAR™ HDL-32E 32-channel LIDAR sensors, Velodyne® LiDAR™ PUCK™ VLP-16 16-channel LIDAR sensors, Leica Geosystems Pegasus: Two mobile sensor platform, Garmin® LIDAR-Lite v3 measurement sensor, Quanergy M8 LiDAR sensors, Quanergy S3 solid state LiDAR sensor, LeddarTech® LeddarVU compact solid state fixed-beam LIDAR sensors, other industry-equivalent LIDAR sensors and/or systems, and may perform illuminated target and/or obstacle detection in an environment around the vehicle 100 using any known or future-developed standard and/or architecture.

The RADAR sensors 5424 may include one or more radio components that are configured to detect objects/targets in an environment of the vehicle 100. In some embodiments, the RADAR sensors 5424 may determine a distance, position, and/or movement vector (e.g., angle, speed, etc.) associated with a target over time. The RADAR sensors 5424 may include a transmitter configured to generate and emit electromagnetic waves (e.g., radio, microwaves, etc.) and a receiver configured to detect returned electromagnetic waves. In some embodiments, the RADAR sensors 5424 may include at least one processor configured to interpret the returned electromagnetic waves and determine locational properties of targets. Examples of the RADAR sensors 5424 as described herein may include, but are not limited to, at least one of Infineon RASIC™ RTN7735PL transmitter and RRN7745PL/46PL receiver sensors, Autoliv ASP Vehicle RADAR sensors, Delphi L2C0051TR 77 GHz ESR Electronically Scanning Radar sensors, Fujitsu Ten Ltd. Automotive Compact 77 GHz 3D Electronic Scan Millimeter Wave Radar sensors, other industry-equivalent RADAR sensors and/or systems, and may perform radio target and/or obstacle detection in an environment around the vehicle 100 using any known or future-developed standard and/or architecture.

The ultrasonic sensors 5428 may include one or more components that are configured to detect objects/targets in an environment of the vehicle 100. In some embodiments, the ultrasonic sensors 5428 may determine a distance, position, and/or movement vector (e.g., angle, speed, etc.) associated with a target over time. The ultrasonic sensors 5428 may include an ultrasonic transmitter and receiver, or transceiver, configured to generate and emit ultrasound waves and interpret returned echoes of those waves. In some embodiments, the ultrasonic sensors 5428 may include at least one processor configured to interpret the returned ultrasonic waves and determine locational properties of targets. Examples of the ultrasonic sensors 5428 as described herein may include, but are not limited to, at least one of Texas Instruments TIDA-00151 automotive ultrasonic sensor interface IC sensors, MaxBotix® MB8450 ultrasonic proximity sensor, MaxBotix® ParkSonar™-EZ ultrasonic proximity sensors, Murata Electronics MA40H1S-R open-structure ultrasonic sensors, Murata Electronics MA40S4R/S open-structure ultrasonic sensors, Murata Electronics MA58MF14-7N waterproof ultrasonic sensors, other industry-equivalent ultrasonic sensors and/or systems, and may perform ultrasonic target and/or obstacle detection in an environment around the vehicle 100 using any known or future-developed standard and/or architecture.

The camera sensors 5432 may include one or more components configured to detect image information associated with an environment of the vehicle 100. In some embodiments, the camera sensors 5432 may include a lens, filter, image sensor, and/or a digital image processer. It is an aspect of the present disclosure that multiple camera sensors 5432 may be used together to generate stereo images providing depth measurements. Examples of the camera sensors 5432 as described herein may include, but are not limited to, at least one of ON Semiconductor® MT9V024 Global Shutter VGA GS CMOS image sensors, Teledyne DALSA Falcon2 camera sensors, CMOSIS CMV50000 high-speed CMOS image sensors, other industry-equivalent camera sensors and/or systems, and may perform visual target and/or obstacle detection in an environment around the vehicle 100 using any known or future-developed standard and/or architecture.

The infrared (IR) sensors 5436 may include one or more components configured to detect image information associated with an environment of the vehicle 100. The IR sensors 5436 may be configured to detect targets in low-light, dark, or poorly-lit environments. The IR sensors 5436 may include an IR light emitting element (e.g., IR light emitting diode (LED), etc.) and an IR photodiode. In some embodiments, the IR photodiode may be configured to detect returned IR light at or about the same wavelength to that emitted by the IR light emitting element. In some embodiments, the IR sensors 5436 may include at least one processor configured to interpret the returned IR light and determine locational properties of targets. The IR sensors 5436 may be configured to detect and/or measure a temperature associated with a target (e.g., an object, pedestrian, other vehicle, etc.). Examples of IR sensors 5436 as described herein may include, but are not limited to, at least one of Opto Diode lead-salt IR array sensors, Opto Diode OD-850 Near-IR LED sensors, Opto Diode SA/SHA727 steady state IR emitters and IR detectors, FUR® LS microbolometer sensors, FUR® TacFLIR 380-HD InSb MWIR FPA and HD MWIR thermal sensors, FLIR® VOx 640×480 pixel detector sensors, Delphi IR sensors, other industry-equivalent IR sensors and/or systems, and may perform IR visual target and/or obstacle detection in an environment around the vehicle 100 using any known or future-developed standard and/or architecture.

The vehicle 100 can also include one or more interior sensors 5437. Interior sensors 5437 can measure characteristics of the inside environment of the vehicle 100. The interior sensors 5437 may be as described in conjunction with FIG. 54B.

A navigation system 5402 can include any hardware and/or software used to navigate the vehicle either manually or autonomously. The navigation system 5402 may be as described in conjunction with FIG. 54C.

In some embodiments, the driving vehicle sensors and systems 5404 may include other sensors 5438 and/or combinations of the sensors 5406-5437 described above. Additionally or alternatively, one or more of the sensors 5406-5437 described above may include one or more processors configured to process and/or interpret signals detected by the one or more sensors 5406-5437. In some embodiments, the processing of at least some sensor information provided by the vehicle sensors and systems 5404 may be processed by at least one sensor processor 5440. Raw and/or processed sensor data may be stored in a sensor data memory 5444 storage medium. In some embodiments, the sensor data memory 5444 may store instructions used by the sensor processor 5440 for processing sensor information provided by the sensors and systems 5404. In any event, the sensor data memory 5444 may be a disk drive, optical storage device, solid-state storage device such as a random access memory ("RAM") and/or a read-only memory ("ROM"), which can be programmable, flash-updateable, and/or the like.

The vehicle control system 5448 may receive processed sensor information from the sensor processor 5440 and determine to control an aspect of the vehicle 100. Controlling an aspect of the vehicle 100 may include presenting information via one or more display devices 5472 associated with the vehicle, sending commands to one or more computing devices 5468 associated with the vehicle, and/or controlling a driving operation of the vehicle. In some embodiments, the vehicle control system 5448 may correspond to one or more computing systems that control driving operations of the vehicle 100 in accordance with the Levels of driving autonomy described above. In one embodiment, the vehicle control system 5448 may operate a speed of the vehicle 100 by controlling an output signal to the accelerator and/or braking system of the vehicle. In this example, the vehicle control system 5448 may receive sensor data describing an environment surrounding the vehicle 100 and, based on the sensor data received, determine to adjust the acceleration, power output, and/or braking of the vehicle 100. The vehicle control system 5448 may additionally control steering and/or other driving functions of the vehicle 100.

The vehicle control system 5448 may communicate, in real-time, with the driving sensors and systems 5404 forming a feedback loop. In particular, upon receiving sensor information describing a condition of targets in the environment surrounding the vehicle 100, the vehicle control system 5448 may autonomously make changes to a driving operation of the vehicle 100. The vehicle control system 5448 may then receive subsequent sensor information describing any change to the condition of the targets detected in the environment as a result of the changes made to the driving operation. This continual cycle of observation (e.g., via the sensors, etc.) and action (e.g., selected control or non-control of vehicle operations, etc.) allows the vehicle 100 to operate autonomously in the environment.

In some embodiments, the one or more components of the vehicle 100 (e.g., the driving vehicle sensors 5404, vehicle control system 5448, display devices 5472, etc.) may communicate across the communication network 5452 to one or more entities 5455A-N via a communications subsystem 5450 of the vehicle 100. Embodiments of the communications subsystem 5450 are described in greater detail in conjunction with FIG. 5. For instance, the navigation sensors 5408 may receive global positioning, location, and/or navigational information from a navigation source 5455A. In some embodiments, the navigation source 5455A may be a global navigation satellite system (GNSS) similar, if not identical, to NAVSTAR GPS, GLONASS, EU Galileo, and/or the BeiDou Navigation Satellite System (BDS) to name a few.

In some embodiments, the vehicle control system 5448 may receive control information from one or more control sources 5455B. The control source 5455 may provide vehicle control information including autonomous driving control commands, vehicle operation override control commands, and the like. The control source 5455 may correspond to an autonomous vehicle control system, a traffic control system, an administrative control entity, and/or some other controlling server. It is an aspect of the present disclosure that the vehicle control system 5448 and/or other components of the vehicle 100 may exchange communications with the control source 5455 across the communication network 5452 and via the communications subsystem 5450.

Information associated with controlling driving operations of the vehicle 100 may be stored in a control data memory 5464 storage medium. The control data memory 5464 may store instructions used by the vehicle control system 5448 for controlling driving operations of the vehicle 100, historical control information, autonomous driving control rules, and the like. In some embodiments, the control data memory 5464 may be a disk drive, optical storage device, solid-state storage device such as a random access memory ("RAM") and/or a read-only memory ("ROM"), which can be programmable, flash-updateable, and/or the like.

In addition to the mechanical components described herein, the vehicle 100 may include a number of user interface devices. The user interface devices receive and translate human input into a mechanical movement or electrical signal or stimulus. The human input may be one or more of motion (e.g., body movement, body part movement, in two-dimensional or three-dimensional space, etc.), voice, touch, and/or physical interaction with the components of the vehicle 100. In some embodiments, the human input may be configured to control one or more functions of the vehicle 100 and/or systems of the vehicle 100 described herein. User interfaces may include, but are in no way limited to, at least one graphical user interface of a display device, steering wheel or mechanism, transmission lever or button (e.g., including park, neutral, reverse, and/or drive positions, etc.), throttle control pedal or mechanism, brake control pedal or mechanism, power control switch, communications equipment, etc.

Figure 54B:
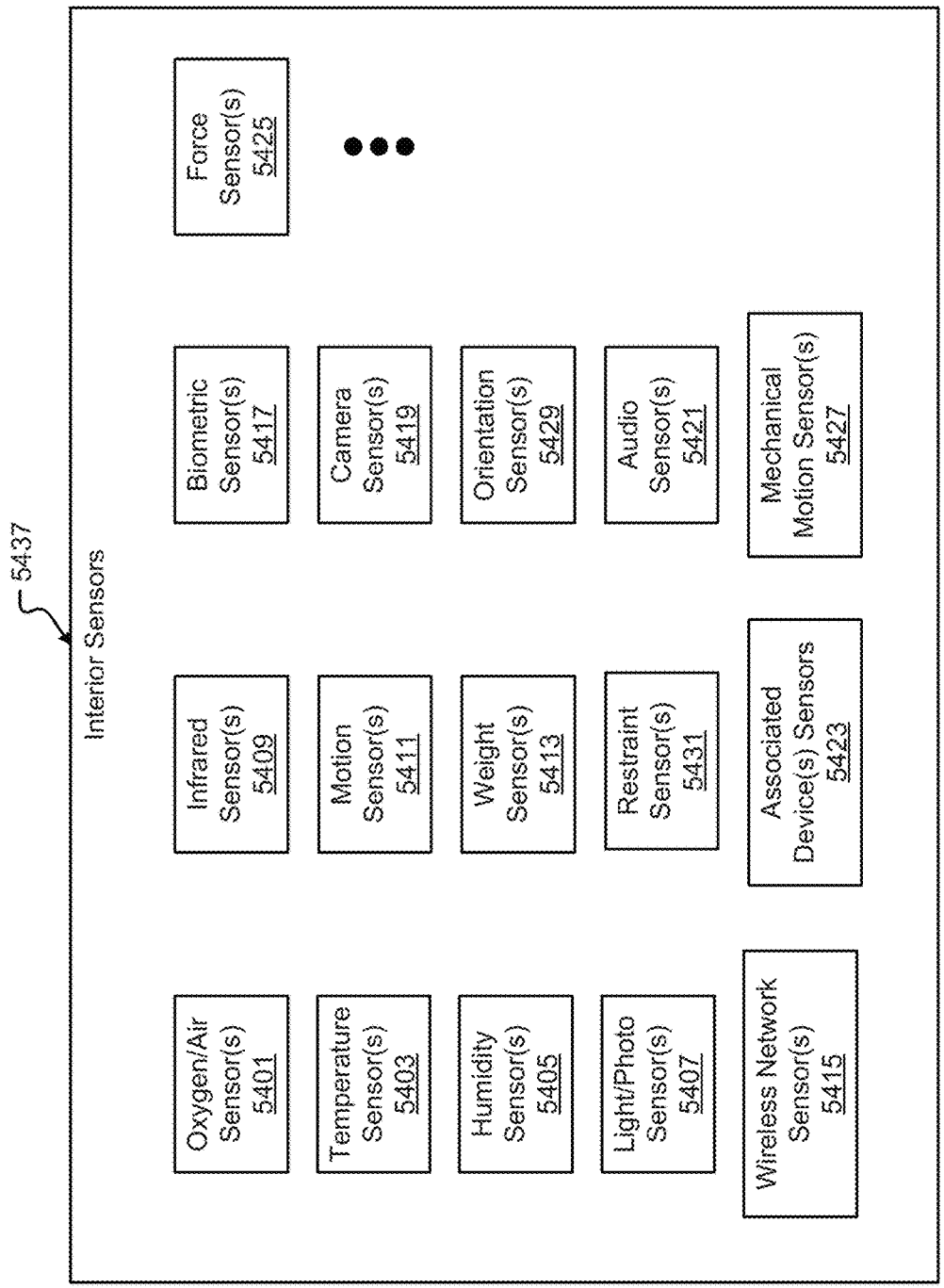
FIG. 54B is a block diagram of a vehicle sensor system.

FIG. 54B shows a block diagram of an embodiment of interior sensors 5437 for a vehicle 100. The interior sensors 5437 may be arranged into one or more groups, based at least partially on the function of the interior sensors 5437. For example, the interior space of a vehicle 100 may include environmental sensors, user interface sensors, and/or safety sensors. Additionally or alternatively, there may be sensors associated with various devices inside the vehicle (e.g., smart phones, tablets, mobile computers, wearables, etc.)

Environmental sensors may comprise sensors configured to collect data relating to the internal environment of a vehicle 100. Examples of environmental sensors may include one or more of, but are not limited to: oxygen/air sensors 5401, temperature sensors 5403, humidity sensors 5405, light/photo sensors 5407, and more. The oxygen/air sensors 5401 may be configured to detect a quality or characteristic of the air in the interior space 108 of the vehicle 100 (e.g., ratios and/or types of gasses comprising the air inside the vehicle 100, dangerous gas levels, safe gas levels, etc.). Temperature sensors 5403 may be configured to detect temperature readings of one or more objects, users 216, and/or areas of a vehicle 100. Humidity sensors 5405 may detect an amount of water vapor present in the air inside the vehicle 100. The light/photo sensors 5407 can detect an amount of light present in the vehicle 100. Further, the light/photo sensors 5407 may be configured to detect various levels of light intensity associated with light in the vehicle 100.

User interface sensors may comprise sensors configured to collect data relating to one or more users (e.g., a driver and/or passenger(s)) in a vehicle 100. As can be appreciated, the user interface sensors may include sensors that are configured to collect data from users 216 in one or more areas of the vehicle 100. Examples of user interface sensors may include one or more of, but are not limited to: infrared sensors 5409, motion sensors 5411, weight sensors 5413, wireless network sensors 5415, biometric sensors 5417, camera (or image) sensors 5419, audio sensors 5421, and more.

Infrared sensors 5409 may be used to measure IR light irradiating from at least one surface, user, or another object in the vehicle 100. Among other things, the Infrared sensors 5409 may be used to measure temperatures, form images (especially in low light conditions), identify users 216, and even detect motion in the vehicle 100.

The motion sensors 5411 may detect motion and/or movement of objects inside the vehicle 104. Optionally, the motion sensors 5411 may be used alone or in combination to detect movement. For example, a user may be operating a vehicle 100 (e.g., while driving, etc.) when a passenger in the rear of the vehicle 100 unbuckles a safety belt and proceeds to move about the vehicle 10. In this example, the movement of the passenger could be detected by the motion sensors 5411. In response to detecting the movement and/or the direction associated with the movement, the passenger may be prevented from interfacing with and/or accessing at least some of the vehicle control features. As can be appreciated, the user may be alerted of the movement/motion such that the user can act to prevent the passenger from interfering with the vehicle controls. Optionally, the number of motion sensors in a vehicle may be increased to increase an accuracy associated with motion detected in the vehicle 100.

Weight sensors 5413 may be employed to collect data relating to objects and/or users in various areas of the vehicle 100. In some cases, the weight sensors 5413 may be included in the seats and/or floor of a vehicle 100. Optionally, the vehicle 100 may include a wireless network sensor 5415. This sensor 5415 may be configured to detect one or more wireless network(s) inside the vehicle 100. Examples of wireless networks may include, but are not limited to, wireless communications utilizing Bluetooth®, Wi-Fi™, ZigBee, IEEE 802.11, and other wireless technology standards. For example, a mobile hotspot may be detected inside the vehicle 100 via the wireless network sensor 5415. In this case, the vehicle 100 may determine to utilize and/or share the mobile hotspot detected via/with one or more other devices associated with the vehicle 100.

Biometric sensors 5417 may be employed to identify and/or record characteristics associated with a user. It is anticipated that biometric sensors 5417 can include at least one of image sensors, IR sensors, fingerprint readers, weight sensors, load cells, force transducers, heart rate monitors, blood pressure monitors, and the like as provided herein.

The camera sensors 5419 may record still images, video, and/or combinations thereof. Camera sensors 5419 may be used alone or in combination to identify objects, users, and/or other features, inside the vehicle 100. Two or more camera sensors 5419 may be used in combination to form, among other things, stereo and/or three-dimensional (3D) images. The stereo images can be recorded and/or used to determine depth associated with objects and/or users in a vehicle 100. Further, the camera sensors 5419 used in combination may determine the complex geometry associated with identifying characteristics of a user. For example, the camera sensors 5419 may be used to determine dimensions between various features of a user's face (e.g., the depth/distance from a user's nose to a user's cheeks, a linear distance between the center of a user's eyes, and more). These dimensions may be used to verify, record, and even modify characteristics that serve to identify a user. The camera sensors 5419 may also be used to determine movement associated with objects and/or users within the vehicle 100. It should be appreciated that the number of image sensors used in a vehicle 100 may be increased to provide greater dimensional accuracy and/or views of a detected image in the vehicle 100.

The audio sensors 5421 may be configured to receive audio input from a user of the vehicle 100. The audio input from a user may correspond to voice commands, conversations detected in the vehicle 100, phone calls made in the vehicle 100, and/or other audible expressions made in the vehicle 100. Audio sensors 5421 may include, but are not limited to, microphones and other types of acoustic-to-electric transducers or sensors. Optionally, the interior audio sensors 5421 may be configured to receive and convert sound waves into an equivalent analog or digital signal. The interior audio sensors 5421 may serve to determine one or more locations associated with various sounds in the vehicle 100. The location of the sounds may be determined based on a comparison of volume levels, intensity, and the like, between sounds detected by two or more interior audio sensors 5421. For instance, a first audio sensor 5421 may be located in a first area of the vehicle 100 and a second audio sensor 5421 may be located in a second area of the vehicle 100. If a sound is detected at a first volume level by the first audio sensors 5421A and a second, higher, volume level by the second audio sensors 5421 in the second area of the vehicle 100, the sound may be determined to be closer to the second area of the vehicle 100. As can be appreciated, the number of sound receivers used in a vehicle 100 may be increased (e.g., more than two, etc.) to increase measurement accuracy surrounding sound detection and location, or source, of the sound (e.g., via triangulation, etc.).

The safety sensors may comprise sensors configured to collect data relating to the safety of a user and/or one or more components of a vehicle 100. Examples of safety sensors may include one or more of, but are not limited to: force sensors 5425, mechanical motion sensors 5427, orientation sensors 5429, restraint sensors 5431, and more.

The force sensors 5425 may include one or more sensors inside the vehicle 100 configured to detect a force observed in the vehicle 100. One example of a force sensor 5425 may include a force transducer that converts measured forces (e.g., force, weight, pressure, etc.) into output signals. Mechanical motion sensors 5427 may correspond to encoders, accelerometers, damped masses, and the like. Optionally, the mechanical motion sensors 5427 may be adapted to measure the force of gravity (i.e., G-force) as observed inside the vehicle 100. Measuring the G-force observed inside a vehicle 100 can provide valuable information related to a vehicle's acceleration, deceleration, collisions, and/or forces that may have been suffered by one or more users in the vehicle 100. Orientation sensors 5429 can include accelerometers, gyroscopes, magnetic sensors, and the like that are configured to detect an orientation associated with the vehicle 100.

The restraint sensors 5431 may correspond to sensors associated with one or more restraint devices and/or systems in a vehicle 100. Seatbelts and airbags are examples of restraint devices and/or systems. As can be appreciated, the restraint devices and/or systems may be associated with one or more sensors that are configured to detect a state of the device/system. The state may include extension, engagement, retraction, disengagement, deployment, and/or other electrical or mechanical conditions associated with the device/system.

The associated device sensors 5423 can include any sensors that are associated with a device in the vehicle 100. As previously stated, typical devices may include smart phones, tablets, laptops, mobile computers, and the like. It is anticipated that the various sensors associated with these devices can be employed by the vehicle control system 5448. For example, a typical smart phone can include, an image sensor, an IR sensor, audio sensor, gyroscope, accelerometer, wireless network sensor, fingerprint reader, and more. It is an aspect of the present disclosure that one or more of these associated device sensors 5423 may be used by one or more subsystems of the vehicle 100.

Figure 54C:
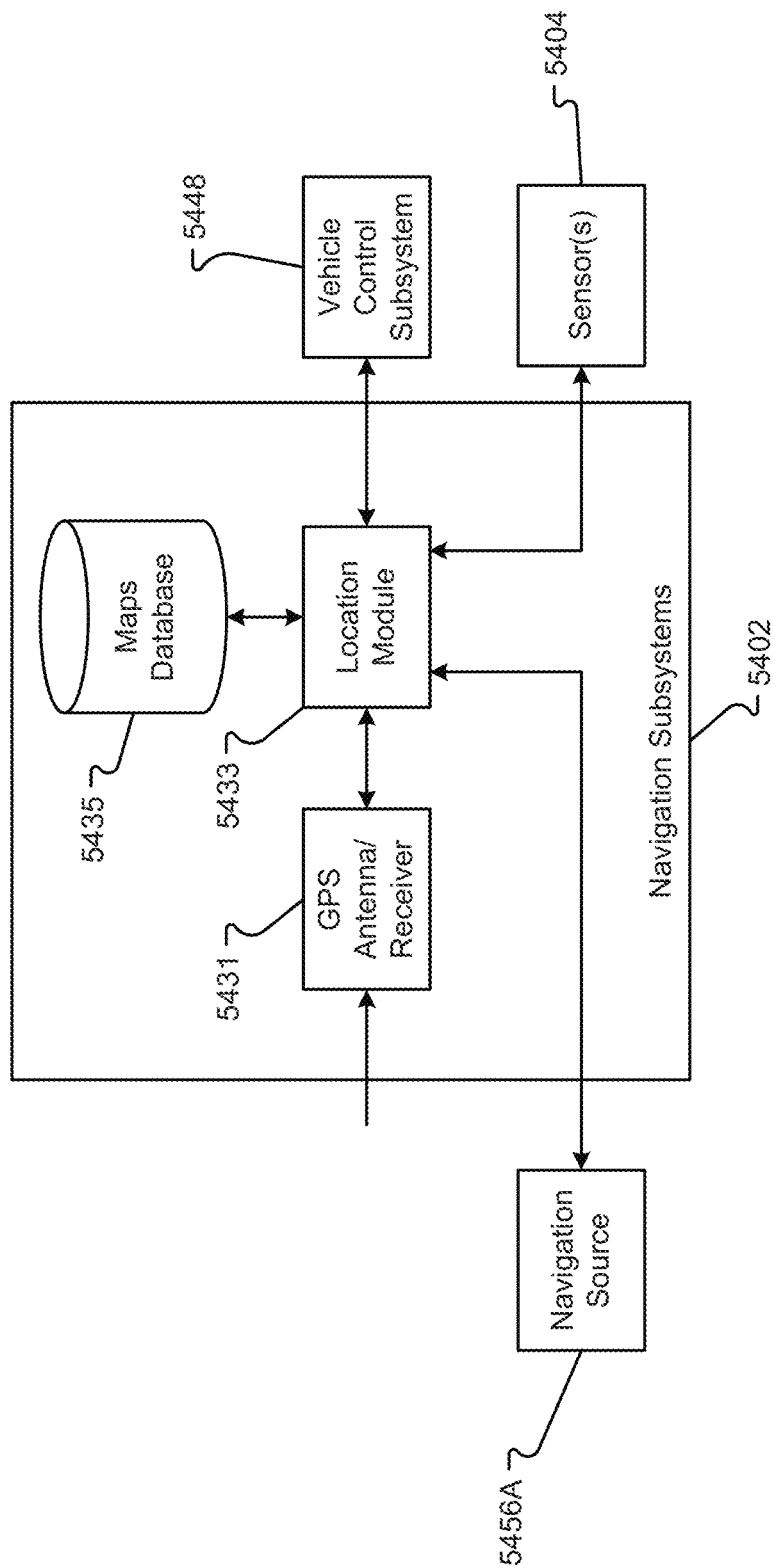
FIG. 54C is a block diagram of a navigation system.

FIG. 54C illustrates a GPS/Navigation subsystem(s) 5402. The navigation subsystem(s) 5402 can be any present or future-built navigation system that may use location data, for example, from the Global Positioning System (GPS), to provide navigation information or control the vehicle 100. The navigation subsystem(s) 5402 can include several components, such as, one or more of, but not limited to: a GPS Antenna/receiver 5431, a location module 5433, a maps database 5435, etc. Generally, the several components or modules 5431-5435 may be hardware, software, firmware, computer readable media, or combinations thereof.

A GPS Antenna/receiver 5431 can be any antenna, GPS puck, and/or receiver capable of receiving signals from a GPS satellite or other navigation system. The signals may be demodulated, converted, interpreted, etc. by the GPS Antenna/receiver 5431 and provided to the location module 5433. Thus, the GPS Antenna/receiver 5431 may convert the time signals from the GPS system and provide a location (e.g., coordinates on a map) to the location module 5433. Alternatively, the location module 5433 can interpret the time signals into coordinates or other location information.

The location module 5433 can be the controller of the satellite navigation system designed for use in the vehicle 100. The location module 5433 can acquire position data, as from the GPS Antenna/receiver 5431, to locate the user or vehicle 100 on a road in the unit's map database 5435. Using the road database 5435, the location module 5433 can give directions to other locations along roads also in the database 5435. When a GPS signal is not available, the location module 5433 may apply dead reckoning to estimate distance data from sensors 5404 including one or more of, but not limited to, a speed sensor attached to the drive train of the vehicle 100, a gyroscope, an accelerometer, etc. Additionally or alternatively, the location module 5433 may use known locations of Wi-Fi hotspots, cell tower data, etc. to determine the position of the vehicle 100, such as by using time difference of arrival (TDOA) and/or frequency difference of arrival (FDOA) techniques.

The maps database 5435 can include any hardware and/or software to store information about maps, geographical information system (GIS) information, location information, etc. The maps database 5435 can include any data definition or other structure to store the information. Generally, the maps database 5435 can include a road database that may include one or more vector maps of areas of interest. Street names, street numbers, house numbers, and other information can be encoded as geographic coordinates so that the user can find some desired destination by street address. Points of interest (waypoints) can also be stored with their geographic coordinates. For example, a point of interest may include speed cameras, fuel stations, public parking, and "parked here" (or "you parked here") information. The maps database 5435 may also include road or street characteristics, for example, speed limits, location of stop lights/stop signs, lane divisions, school locations, etc. The map database contents can be produced or updated by a server connected through a wireless system in communication with the Internet, even as the vehicle 100 is driven along existing streets, yielding an up-to-date map.

Figure 55:
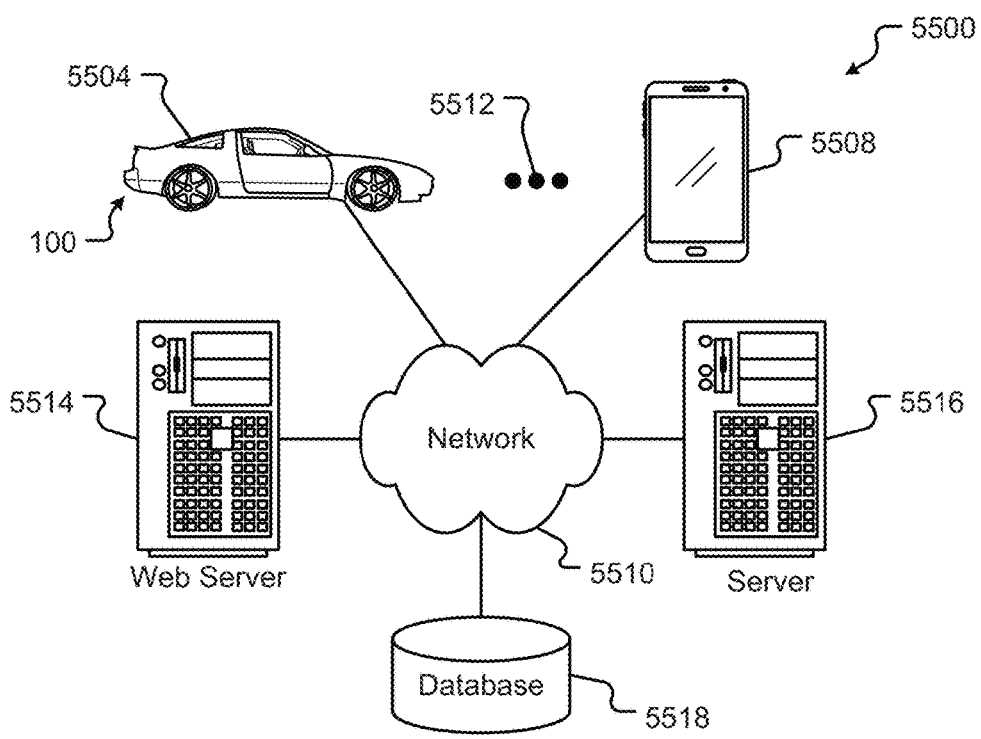
FIG. 55 is a diagram of a computing environment for the vehicle.

FIG. 55 illustrates a block diagram of a computing environment 5500 that may function as the servers, user computers, or other systems provided and described herein. The computing environment 5500 includes one or more user computers, or computing devices, such as a vehicle computing device 5504, a communication device 5508, and/or more 5512. The computing devices 5504, 5508, 5512 may include general purpose personal computers (including, merely by way of example, personal computers, and/or laptop computers running various versions of Microsoft Corp.'s Windows® and/or Apple Corp.'s Macintosh® operating systems) and/or workstation computers running any of a variety of commercially-available UNIX® or UNIX-like operating systems. These computing devices 5504, 5508, 5512 may also have any of a variety of applications, including for example, database client and/or server applications, and web browser applications. Alternatively, the computing devices 5504, 5508, 5512 may be any other electronic device, such as a thin-client computer, Internet-enabled mobile telephone, and/or personal digital assistant, capable of communicating via a network 352 and/or displaying and navigating web pages or other types of electronic documents. Although the exemplary computing environment 5500 is shown with two computing devices, any number of user computers or computing devices may be supported.

The computing environment 5500 may also include one or more servers 5514, 5516. In this example, server 5514 is shown as a web server and server 5516 is shown as an application server. The web server 5514, which may be used to process requests for web pages or other electronic documents from computing devices 5504, 5508, 5512. The web server 5514 can be running an operating system including any of those discussed above, as well as any commercially-available server operating systems. The web server 5514 can also run a variety of server applications, including SIP (Session Initiation Protocol) servers, HTTP(s) servers, FTP servers, CGI servers, database servers, Java servers, and the like. In some instances, the web server 5514 may publish operations available operations as one or more web services.

The computing environment 5500 may also include one or more file and or/application servers 5516, which can, in addition to an operating system, include one or more applications accessible by a client running on one or more of the computing devices 5504, 5508, 5512. The server(s) 5516 and/or 5514 may be one or more general purpose computers capable of executing programs or scripts in response to the computing devices 5504, 5508, 5512. As one example, the server 5516, 5514 may execute one or more web applications. The web application may be implemented as one or more scripts or programs written in any programming language, such as Java™, C, C#®, or C++, and/or any scripting language, such as Perl, Python, or TCL, as well as combinations of any programming/scripting languages. The application server(s) 5516 may also include database servers, including without limitation those commercially available from Oracle®, Microsoft®, Sybase®, IBM® and the like, which can process requests from database clients running on a computing device 5504, 5508, 5512.

The web pages created by the server 5514 and/or 5516 may be forwarded to a computing device 5504, 5508, 5512 via a web (file) server 5514, 5516. Similarly, the web server 5514 may be able to receive web page requests, web services invocations, and/or input data from a computing device 5504, 5508, 5512 (e.g., a user computer, etc.) and can forward the web page requests and/or input data to the web (application) server 5516. In further embodiments, the server 5516 may function as a file server. Although for ease of description, FIG. 55 illustrates a separate web server 5514 and file/application server 5516, those skilled in the art will recognize that the functions described with respect to servers 5514, 5516 may be performed by a single server and/or a plurality of specialized servers, depending on implementation-specific needs and parameters. The computer systems 5504, 5508, 5512, web (file) server 5514 and/or web (application) server 5516 may function as the system, devices, or components described in FIGS. 1-54.

The computing environment 5500 may also include a database 5518. The database 5518 may reside in a variety of locations. By way of example, database 5518 may reside on a storage medium local to (and/or resident in) one or more of the computers 5504, 5508, 5512, 5514, 5516. Alternatively, it may be remote from any or all of the computers 5504, 5508, 5512, 5514, 5516, and in communication (e.g., via the network 5510) with one or more of these. The database 5518 may reside in a storage-area network ("SAN") familiar to those skilled in the art. Similarly, any necessary files for performing the functions attributed to the computers 5504, 5508, 5512, 5514, 5516 may be stored locally on the respective computer and/or remotely, as appropriate. The database 5518 may be a relational database, such as Oracle 20i®, that is adapted to store, update, and retrieve data in response to SQL-formatted commands.

Figure 56:
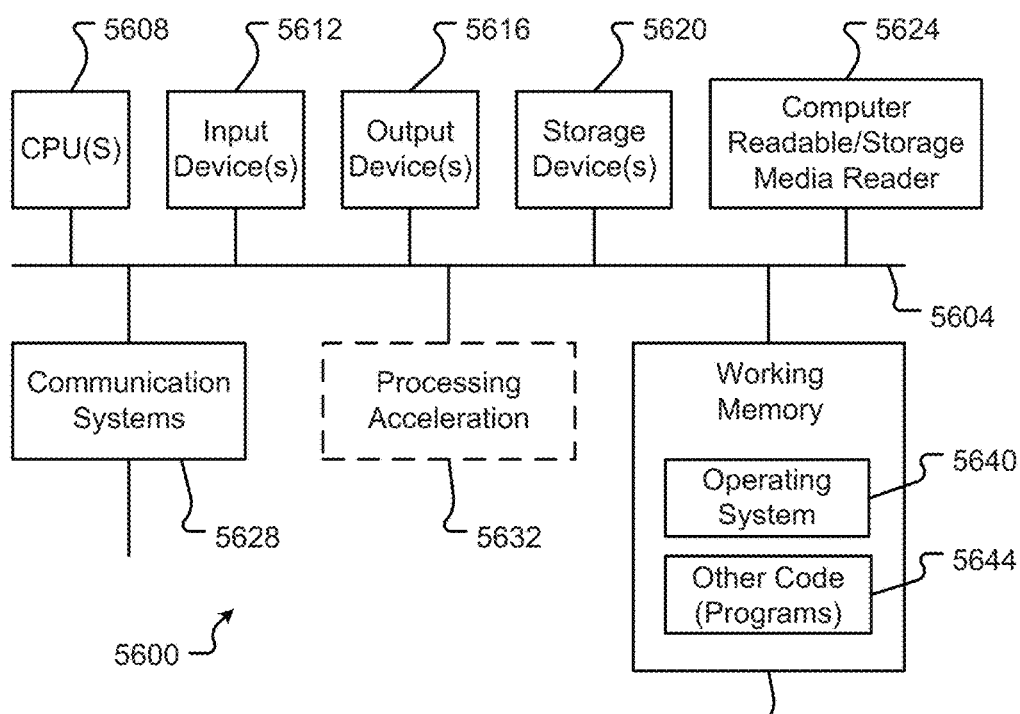
FIG. 56 is a block diagram of a computing system of the vehicle.

FIG. 56 illustrates one embodiment of a computer system 5600 upon which the servers, user computers, computing devices, or other systems or components described above may be deployed or executed. The computer system 5600 is shown comprising hardware elements that may be electrically coupled via a bus 5604. The hardware elements may include one or more central processing units (CPUs) 5608; one or more input devices 5612 (e.g., a mouse, a keyboard, etc.); and one or more output devices 5616 (e.g., a display device, a printer, etc.). The computer system 5600 may also include one or more storage devices 5620. By way of example, storage device(s) 5620 may be disk drives, optical storage devices, solid-state storage devices such as a random access memory ("RANI") and/or a read-only memory ("ROM"), which can be programmable, flash-updateable and/or the like.

The computer system 5600 may additionally include a computer-readable storage media reader 5624; a communications system 5628 (e.g., a modem, a network card (wireless or wired), an infra-red communication device, etc.); and working memory 5636, which may include RANI and ROM devices as described above. The computer system 5600 may also include a processing acceleration unit 5632, which can include a DSP, a special-purpose processor, and/or the like.

The computer-readable storage media reader 5624 can further be connected to a computer-readable storage medium, together (and, optionally, in combination with storage device(s) 5620) comprehensively representing remote, local, fixed, and/or removable storage devices plus storage media for temporarily and/or more permanently containing computer-readable information. The communications system 5628 may permit data to be exchanged with a network and/or any other computer described above with respect to the computer environments described herein. Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information.

The computer system 5600 may also comprise software elements, shown as being currently located within a working memory 5636, including an operating system 5640 and/or other code 5644. It should be appreciated that alternate embodiments of a computer system 5600 may have numerous variations from that described above. For example, customized hardware might also be used and/or particular elements might be implemented in hardware, software (including portable software, such as applets), or both. Further, connection to other computing devices such as network input/output devices may be employed.

Examples of the processors 340, 5608 as described herein may include, but are not limited to, at least one of Qualcomm® Snapdragon® 800 and 801, Qualcomm® Snapdragon® 620 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3560K 22 nm Ivy Bridge, the AMD® FX™ family of processors, AMD® FX-4300, FX-6300, and FX-8350 32 nm Vishera, AMD® Kaveri processors, Texas Instruments® Jacinto C6000™ automotive infotainment processors, Texas Instruments® OMAP™ automotive-grade mobile processors, ARM® Cortex™-M processors, ARM® Cortex-A and ARM926EJ-S™ processors, other industry-equivalent processors, and may perform computational functions using any known or future-developed standard, instruction set, libraries, and/or architecture.

Any of the steps, functions, and operations discussed herein can be performed continuously and automatically.

Aspects of the embodiments can include: A vehicle, comprising: a sensor to: detect a first presence of a driver in a vehicle; detect a second presence of a passenger in the vehicle a memory to: store first sensitive information for the driver of the vehicle; store second sensitive information for a passenger in the vehicle; a processor in communication with the sensor and the memory, the processor to: receive the first presence and second presence; provide a user interface for the passenger to enter the sensitive information; receive the second sensitive information for the passenger; associate the second sensitive information with the vehicle; and send the second sensitive information to the memory for storage.

Any of the one or more above aspects, wherein the sensor receives biometric information associated with the passenger.

Any of the one or more above aspects, wherein the biometric information is also stored with the second sensitive information.

Any of the one or more above aspects, wherein, when the passenger enters the vehicle a second time, the biometric information identifies the passenger.

Any of the one or more above aspects, wherein the second sensitive information is encrypted in the memory.

Any of the one or more above aspects, wherein the second sensitive information comprises one or more of a biometric, a username. a password, mobile device information, payment information, a personal identification number, identifiers, an address, limits, preferences, and/or rules.

Any of the one or more above aspects, wherein the second sensitive information comprises one or more of a desired product, a desired service, and/or a triggering event.

Any of the one or more above aspects, wherein the processor presents a user interface to a head unit display to receive the second sensitive information.

Any of the one or more above aspects, wherein the user interface receives input from the passenger in the user interface.

Any of the one or more above aspects, wherein the input includes financial information.

A method for associated passenger information with a vehicle, comprising: detecting a first presence of a driver in a vehicle; detecting a second presence of a passenger in the vehicle receiving the first presence and second presence; providing a user interface for the passenger to enter the sensitive information; receiving the second sensitive information for the passenger; associating the second sensitive information with the vehicle; and storing second sensitive information for a passenger in the vehicle.

Any of the one or more above aspects, wherein the sensor receives biometric information associated with the passenger, wherein the biometric information is also stored with the second sensitive information, and wherein, when the passenger enters the vehicle a second time, the biometric information identifies the passenger.

Any of the one or more above aspects, wherein the second sensitive information is encrypted in the memory, wherein the second sensitive information comprises one or more of a biometric, a username. a password, mobile device information, payment information, a personal identification number, identifiers, an address, limits, preferences, and/or rules.

Any of the one or more above aspects, wherein the second sensitive information comprises one or more of a desired product, a desired service, and/or a triggering event.

Any of the one or more above aspects, wherein the processor presents a user interface to receive the second sensitive information, wherein the user interface receives input from the passenger, and wherein the input includes financial information.

A non-transitory information storage media having stored thereon one or more instructions, that when executed by one or more processors, cause a vehicle to perform a method, the method comprising: detecting a first presence of a driver in a vehicle; detecting a second presence of a passenger in the vehicle receiving the first presence and second presence; providing a user interface for the passenger to enter the sensitive information; receiving the second sensitive information for the passenger; associating the second sensitive information with the vehicle; and storing second sensitive information for a passenger in the vehicle.

Any of the one or more above aspects, wherein the sensor receives biometric information associated with the passenger, wherein the biometric information is also stored with the second sensitive information, and wherein, when the passenger enters the vehicle a second time, the biometric information identifies the passenger.

Any of the one or more above aspects, wherein the second sensitive information is encrypted in the memory, wherein the second sensitive information comprises one or more of a biometric, a username. a password, mobile device information, payment information, a personal identification number, identifiers, an address, limits, preferences, and/or rules.

Any of the one or more above aspects, wherein the second sensitive information comprises one or more of a desired product, a desired service, and/or a triggering event.

Any of the one or more above aspects, wherein the processor presents a user interface to receive the second sensitive information, wherein the user interface receives input from the passenger, and wherein the input includes financial information.

A vehicle, comprising: two or more radio frequency (RF) antennas to communicate wirelessly sensitive information associated with a user of the vehicle; two or more RF transceivers, each RF transceiver associated with one of the two or more RF antennas, the two or more RF transceivers to communicate wirelessly sensitive information associated with a user of the vehicle; a processor in communication with the two or more RF transceivers, the processor to: determine which one of the two or more RF antennas is receiving a strongest signal; select a first RF transceiver associated with the RF antenna with the strongest signal to send the sensitive information; and send the sensitive information to the first RF transceiver.

Any of the one or more above aspects, wherein the RF transceiver and RF antenna are a radio frequency identification device.

Any of the one or more above aspects, wherein the RFID device is an active RFID device.

Any of the one or more above aspects, wherein the first RF antenna is located near a side mirror of the vehicle.

Any of the one or more above aspects, wherein the first RF antenna communicates with a second RF antenna in physical proximity of a drive through window of a drive through restaurant.

Any of the one or more above aspects, wherein the first RF antenna is located on a roof of the vehicle.

Any of the one or more above aspects, wherein the first RF antenna communicates with a second RF antenna in above the vehicle in a toll lane.

Any of the one or more above aspects, wherein the first RF antenna is located near a charging port or a gas refill door.

Any of the one or more above aspects, wherein the first RF antenna communicates with a second RF antenna on a charging station or gas pump.

Any of the one or more above aspects, wherein the vehicle contemporaneously communicates through two or more RF antennas.

A method for communicating information with a vehicle, comprising: receiving a signal at one of two or more radio frequency (RF) antennas and one of two or more RF transceivers, wherein each RF transceiver is associated with one of the two or more RF antennas, to communicate wirelessly sensitive information associated with a user of the vehicle; determining which one of the two or more RF antennas is receiving a strongest signal; selecting a first RF transceiver associated with the RF antenna with the strongest signal to send the sensitive information; and sending the sensitive information through the first RF transceiver.

Any of the one or more above aspects, wherein the RF transceiver and RF antenna are a radio frequency identification device, and wherein the RFID device is an active RFID device.

Any of the one or more above aspects, wherein the first RF antenna is located near a side mirror of the vehicle, wherein the first RF antenna communicates with a second RF antenna in physical proximity of a drive through window of a drive through restaurant.

Any of the one or more above aspects, wherein the first RF antenna is located on a roof of the vehicle, and wherein the first RF antenna communicates with a second RF antenna in above the vehicle in a toll lane.

Any of the one or more above aspects, wherein the first RF antenna is located near a charging port or a gas refill door, and wherein the first RF antenna communicates with a second RF antenna on a charging station or gas pump.

A non-transitory information storage media having stored thereon one or more instructions, that when executed by one or more processors, cause a vehicle to perform a method, the method comprising: receiving a signal at one of two or more radio frequency (RF) antennas and one of two or more RF transceivers, wherein each RF transceiver is associated with one of the two or more RF antennas, to communicate wirelessly sensitive information associated with a user of the vehicle; determining which one of the two or more RF antennas is receiving a strongest signal; selecting a first RF transceiver associated with the RF antenna with the strongest signal to send the sensitive information; and sending the sensitive information through the first RF transceiver.

Any of the one or more above aspects, wherein the RF transceiver and RF antenna are a radio frequency identification device, and wherein the RFID device is an active RFID device.

Any of the one or more above aspects, wherein the first RF antenna is located near a side mirror of the vehicle, wherein the first RF antenna communicates with a second RF antenna in physical proximity of a drive through window of a drive through restaurant.

Any of the one or more above aspects, wherein the first RF antenna is located on a roof of the vehicle, and wherein the first RF antenna communicates with a second RF antenna in above the vehicle in a toll lane.

Any of the one or more above aspects, wherein the first RF antenna is located near a charging port or a gas refill door, and wherein the first RF antenna communicates with a second RF antenna on a charging station or gas pump.

A vehicle, comprising: a sensor to: detect a presence of a driver in a vehicle; a memory to: store sensitive information for the driver of the vehicle; a processor in communication with the sensor and the memory, the processor to: receive the presence; based upon receiving the presence, provide a user interface for the passenger to enter user information; receive vehicle information associated with the vehicle; combine the user information and the vehicle information to generate sensitive information; and send the sensitive information to the memory for storage.

Any of the one or more above aspects, wherein the sensor receives biometric information associated with the passenger.

Any of the one or more above aspects, wherein the biometric information is also stored with the sensitive information.

Any of the one or more above aspects, wherein the sensitive information is sent to a third party to authenticate the user.

Any of the one or more above aspects, wherein the sensitive information is encrypted in the memory.

Any of the one or more above aspects, wherein the user information comprises one or more of a biometric, a username. a password, mobile device information, payment information, a personal identification number, identifiers, an address, limits, preferences, and/or rules.

Any of the one or more above aspects, wherein the user information comprises one or more of a desired product, a desired service, and/or a triggering event.

Any of the one or more above aspects, wherein the processor presents a user interface to a head unit display to receive the second sensitive information.

Any of the one or more above aspects, wherein the user interface receives input from the passenger in the user interface, wherein the input includes financial information.

Any of the one or more above aspects, wherein the vehicle information comprises a vehicle identification number (VIN), an electronic serial number (ESN), and/or an engine code.

A method for communicating information with a vehicle, comprising: detecting a presence of a driver in a vehicle; based upon receiving the presence, providing a user interface for the passenger to enter user information; receiving vehicle information associated with the vehicle; combining the user information and the vehicle information to generate sensitive information; and sending the sensitive information to the memory for storage.

Any of the one or more above aspects, wherein a sensor associated with the vehicle receives biometric information associated with the passenger, and wherein the biometric information is also stored with the sensitive information.

Any of the one or more above aspects, wherein the sensitive information is sent to a third party to authenticate the user.

Any of the one or more above aspects, wherein the user information comprises one or more of a biometric, a username. a password, mobile device information, payment information, a personal identification number, identifiers, an address, limits, preferences, rules, a desired product, a desired service, and/or a triggering event.

Any of the one or more above aspects, wherein the vehicle information comprises a vehicle identification number (VIN), an electronic serial number (ESN), and/or an engine code.

A non-transitory information storage media having stored thereon one or more instructions, that when executed by one or more processors, cause a vehicle to perform a method, the method comprising: detecting a presence of a driver in a vehicle; based upon receiving the presence, providing a user interface for the passenger to enter user information; receiving vehicle information associated with the vehicle; combining the user information and the vehicle information to generate sensitive information; and sending the sensitive information to the memory for storage.

Any of the one or more above aspects, wherein a sensor associated with the vehicle receives biometric information associated with the passenger, and wherein the biometric information is also stored with the sensitive information.

Any of the one or more above aspects, wherein the sensitive information is sent to a third party to authenticate the user.

Any of the one or more above aspects, wherein the user information comprises one or more of a biometric, a username. a password, mobile device information, payment information, a personal identification number, identifiers, an address, limits, preferences, rules, a desired product, a desired service, and/or a triggering event.

Any of the one or more above aspects, wherein the vehicle information comprises a vehicle identification number (VIN), an electronic serial number (ESN), and/or an engine code.

A vehicle, comprising: a navigation system to provide a location and/or a route of the vehicle; a memory to: store user preferences associated with a user in the vehicle; a processor in communication with the navigation system and the memory, the processor to: determine a third party resident in the location and/or on the route of the vehicle; retrieve user preferences from the memory; determine, based on the user preferences, whether the user would desire to communicate with the third party; and automatically send a first communication to the third party for the user.

Any of the one or more above aspects, wherein a sensor associated with the vehicle receives biometric information associated with the passenger.

Any of the one or more above aspects, wherein, when the passenger enters the vehicle a second time, the biometric information identifies the passenger.

Any of the one or more above aspects, wherein the first communication is an order for a good or service.

Any of the one or more above aspects, wherein user preference is a usual order based on historical information from a user's past behavior.

Any of the one or more above aspects, wherein the user is prompted to approve the first communication with a user interface displayed in a display in the vehicle.

Any of the one or more above aspects, wherein the vehicle sends a second communication to complete an interaction with the third party.

Any of the one or more above aspects, wherein the second communication is sent when the vehicle is in physical proximity to the third party.

Any of the one or more above aspects, wherein the second communication is a final authorization for a transaction.

Any of the one or more above aspects, wherein the final authorization includes a PIN entered by the user in a display of the vehicle.

A method for communicating information with a vehicle, comprising: determining a location and/or a route of the vehicle; determining a third party resident in the location and/or on the route of the vehicle; retrieving user preferences associated with a user in the vehicle from a memory; determining, based on the user preferences, whether the user would desire to communicate with the third party; and automatically sending a first communication to the third party for the user.

Any of the one or more above aspects, wherein a sensor associated with the vehicle receives biometric information associated with the passenger, and wherein, when the passenger enters the vehicle a second time, the biometric information identifies the passenger.

Any of the one or more above aspects, wherein the first communication is an order for a good or service, wherein user preference is a usual order based on historical information from a user's past behavior, and wherein the user is prompted to approve the first communication with a user interface displayed in a display in the vehicle.

Any of the one or more above aspects, wherein the vehicle sends a second communication to complete an interaction with the third party, and wherein the second communication is sent when the vehicle is in physical proximity to the third party.

Any of the one or more above aspects, wherein the second communication is a final authorization for a transaction, and wherein the final authorization includes a PIN entered by the user in a display of the vehicle.

A non-transitory information storage media having stored thereon one or more instructions, that when executed by one or more processors, cause a vehicle to perform a method, the method comprising: determining a location and/or a route of the vehicle; determining a third party resident in the location and/or on the route of the vehicle; retrieving user preferences associated with a user in the vehicle from a memory; determining, based on the user preferences, whether the user would desire to communicate with the third party; and automatically sending a first communication to the third party for the user.

Any of the one or more above aspects, wherein a sensor associated with the vehicle receives biometric information associated with the passenger, and wherein, when the passenger enters the vehicle a second time, the biometric information identifies the passenger.

Any of the one or more above aspects, wherein the first communication is an order for a good or service, wherein user preference is a usual order based on historical information from a user's past behavior, and wherein the user is prompted to approve the first communication with a user interface displayed in a display in the vehicle.

Any of the one or more above aspects, wherein the vehicle sends a second communication to complete an interaction with the third party, and wherein the second communication is sent when the vehicle is in physical proximity to the third party.

Any of the one or more above aspects, wherein the second communication is a final authorization for a transaction, and wherein the final authorization includes a PIN entered by the user in a display of the vehicle.

A vehicle, comprising: a display in the vehicle to display a user interface; a processor in communication with the display, the processor to: determine a user in the vehicle desires to interact with a third party; render the user interface for the display to request authorization from the user to allow a communication to the third party; receive user input associated with the request for authorization; and based on the user input, automatically send a first communication to the third party for the user.

Any of the one or more above aspects, wherein a sensor associated with the vehicle receives biometric information associated with the passenger.

Any of the one or more above aspects, wherein, when the passenger enters the vehicle a second time, the biometric information identifies the passenger.

Any of the one or more above aspects, wherein the first communication is an order for a good or service.

Any of the one or more above aspects, wherein the user interface is an authorization for the vehicle to pre-order the good or service.

Any of the one or more above aspects, wherein the vehicle sends a second communication to complete an interaction with the third party.

Any of the one or more above aspects, wherein the second communication is sent when the vehicle is in physical proximity to the third party.

Any of the one or more above aspects, wherein the second communication is a final authorization for a transaction.

Any of the one or more above aspects, wherein the user interface is presented to authorize finally the second communication.

Any of the one or more above aspects, wherein the final authorization includes a PIN entered by the user in the user interface.

A method for communicating information with a vehicle, comprising: determining a user in the vehicle desires to interact with a third party; displaying a user interface to request authorization from the user to allow a communication to the third party; receiving user input associated with the request for authorization; and based on the user input, automatically sending a first communication to the third party for the user.

Any of the one or more above aspects, wherein a sensor associated with the vehicle receives biometric information associated with the passenger, and wherein, when the passenger enters the vehicle a second time, the biometric information identifies the passenger.

Any of the one or more above aspects, wherein the first communication is an order for a good or service, and wherein the user interface is an authorization for the vehicle to pre-order the good or service.

Any of the one or more above aspects, wherein the vehicle sends a second communication to complete an interaction with the third party, and wherein the second communication is sent when the vehicle is in physical proximity to the third party.

Any of the one or more above aspects, wherein the second communication is a final authorization for a transaction, wherein the user interface is presented to authorize finally the second communication, and wherein the final authorization includes a PIN entered by the user in the user interface.

A non-transitory information storage media having stored thereon one or more instructions, that when executed by one or more processors, cause a vehicle to perform a method, the method comprising: determining a user in the vehicle desires to interact with a third party; displaying a user interface to request authorization from the user to allow a communication to the third party; receiving user input associated with the request for authorization; and based on the user input, automatically sending a first communication to the third party for the user.

Any of the one or more above aspects, wherein a sensor associated with the vehicle receives biometric information associated with the passenger, and wherein, when the passenger enters the vehicle a second time, the biometric information identifies the passenger.

Any of the one or more above aspects, wherein the first communication is an order for a good or service, and wherein the user interface is an authorization for the vehicle to pre-order the good or service.

Any of the one or more above aspects, wherein the vehicle sends a second communication to complete an interaction with the third party, and wherein the second communication is sent when the vehicle is in physical proximity to the third party.

Any of the one or more above aspects, wherein the second communication is a final authorization for a transaction, wherein the user interface is presented to authorize finally the second communication, and wherein the final authorization includes a PIN entered by the user in the user interface.

A vehicle, comprising: a memory to: store user information associated with a user in the vehicle; store vehicle information associated with the vehicle; a processor in communication with the memory, the processor to: determine the user desires to interact with a third party; retrieve user information from the memory; retrieve vehicle information from the memory; combine the user information and the vehicle information into a first communication for the third party; and automatically send the first communication to the third party for the user.

Any of the one or more above aspects, wherein a sensor associated with the vehicle receives biometric information associated with the passenger.

Any of the one or more above aspects, wherein, when the passenger enters the vehicle a second time, the biometric information identifies the passenger.

Any of the one or more above aspects, wherein the first communication is an order for a good or service and the user information and vehicle information authenticate the user for the order.

Any of the one or more above aspects, wherein the user information comprises financial information, biometric information, and/or a PIN.

Any of the one or more above aspects, wherein the vehicle information comprises a vehicle identification number, an electronic serial number, and/or an engine code.

Any of the one or more above aspects, wherein the vehicle sends a second communication to complete an interaction with the third party, and wherein the second communication is sent when the vehicle is in physical proximity to the third party.

Any of the one or more above aspects, wherein the second communication is a final authorization for a transaction.

Any of the one or more above aspects, wherein the second communication includes user information or vehicle information not in the first communication.

Any of the one or more above aspects, wherein the final authorization includes a PIN entered by the user in a user interface in the vehicle.

A method for communicating information with a vehicle, comprising: storing user information associated with a user in the vehicle; storing vehicle information associated with the vehicle determining the user desires to interact with a third party; combining the user information and the vehicle information into a first communication for the third party; and automatically send the first communication to the third party for the user.

Any of the one or more above aspects, wherein a sensor associated with the vehicle receives biometric information associated with the passenger, and wherein, when the passenger enters the vehicle a second time, the biometric information identifies the passenger.

Any of the one or more above aspects, wherein the first communication is an order for a good or service and the user information and vehicle information authenticate the user for the order.

Any of the one or more above aspects, wherein the user information comprises financial information, biometric information, and/or a PIN, and wherein the vehicle information comprises a vehicle identification number, an electronic serial number, and/or an engine code.

Any of the one or more above aspects, wherein the vehicle sends a second communication to complete an interaction with the third party, and wherein the second communication is sent when the vehicle is in physical proximity to the third party, wherein the second communication is a final authorization for a transaction, wherein the second communication includes user information or vehicle information not in the first communication, and wherein the final authorization includes a PIN entered by the user in a user interface in the vehicle.

A non-transitory information storage media having stored thereon one or more instructions, that when executed by one or more processors, cause a vehicle to perform a method, the method comprising: storing user information associated with a user in the vehicle; storing vehicle information associated with the vehicle determining the user desires to interact with a third party; combining the user information and the vehicle information into a first communication for the third party; and automatically send the first communication to the third party for the user.

Any of the one or more above aspects, wherein a sensor associated with the vehicle receives biometric information associated with the passenger, and wherein, when the passenger enters the vehicle a second time, the biometric information identifies the passenger.

Any of the one or more above aspects, wherein the first communication is an order for a good or service and the user information and vehicle information authenticate the user for the order.

Any of the one or more above aspects, wherein the user information comprises financial information, biometric information, and/or a PIN, and wherein the vehicle information comprises a vehicle identification number, an electronic serial number, and/or an engine code.

Any of the one or more above aspects, wherein the vehicle sends a second communication to complete an interaction with the third party, and wherein the second communication is sent when the vehicle is in physical proximity to the third party, wherein the second communication is a final authorization for a transaction, wherein the second communication includes user information or vehicle information not in the first communication, and wherein the final authorization includes a PIN entered by the user in a user interface in the vehicle.

A vehicle, comprising: a memory to store limits on communications associated with a user in the vehicle; a processor in communication with the memory, the processor to: determine the user desires to interact with a third party; retrieve the limits from the memory; based on the limits, determine if the vehicle can send a first communication for the third party; and when allowed by the limits, automatically send the first communication to the third party for the user.

Any of the one or more above aspects, wherein a sensor associated with the vehicle receives biometric information associated with the passenger.

Any of the one or more above aspects, wherein, when the passenger enters the vehicle a second time, the biometric information identifies the passenger.

Any of the one or more above aspects, wherein the first communication is an order for a good or service and the limits are a monetary limit applied to the order.

Any of the one or more above aspects, wherein the limit applies only to the user and the vehicle.

Any of the one or more above aspects, wherein the limit applies only to the user and to two or more vehicles.

Any of the one or more above aspects, wherein the limit applies only to two or more users and the vehicle.

Any of the one or more above aspects, wherein the limit is set on the user by a second user.

Any of the one or more above aspects, wherein the limit is on a number of communications that may be completed between the vehicle and third party.

Any of the one or more above aspects, wherein the limit only applies for a predetermined time period or route.

A method for communicating information with a vehicle, comprising: a memory storing limits on communications associated with a user in the vehicle; a processor determining the user desires to interact with a third party; retrieving the limits from the memory; based on the limits, determining if the vehicle can send a first communication for the third party; and when allowed by the limits, automatically sending the first communication to the third party for the user.

Any of the one or more above aspects, wherein a sensor associated with the vehicle receives, and wherein, when the passenger enters the vehicle a second time, the biometric information identifies the passenger.

Any of the one or more above aspects, wherein the first communication is an order for a good or service and the limits are a monetary limit applied to the order.

Any of the one or more above aspects, wherein one or more of: the limit applies only to the user and the vehicle, the limit applies only to the user and to two or more vehicles, the limit applies only to two or more users and the vehicle, and/or the limit is set on the user by a second user.

Any of the one or more above aspects, wherein the limit only applies for a predetermined time period or route.

A non-transitory information storage media having stored thereon one or more instructions, that when executed by one or more processors, cause a vehicle to perform a method, the method comprising: storing limits on communications associated with a user in the vehicle; determining the user desires to interact with a third party; retrieving the limits from the memory; based on the limits, determining if the vehicle can send a first communication for the third party; and when allowed by the limits, automatically sending the first communication to the third party for the user.

Any of the one or more above aspects, wherein a sensor associated with the vehicle receives, and wherein, when the passenger enters the vehicle a second time, the biometric information identifies the passenger.

Any of the one or more above aspects, wherein the first communication is an order for a good or service and the limits are a monetary limit applied to the order.

Any of the one or more above aspects, wherein one or more of: the limit applies only to the user and the vehicle, the limit applies only to the user and to two or more vehicles, the limit applies only to two or more users and the vehicle, and/or the limit is set on the user by a second user.

Any of the one or more above aspects, wherein the limit only applies for a predetermined time period or route.

A vehicle, comprising: a memory to store a user rule applicable to communications associated with a user in the vehicle; a processor in communication with the memory, the processor to: determine a need for communication with a third party; retrieve the user rule from the memory; based on the user rule, determine to which third party the vehicle can send a first communication to address the need; select the third party; and when determined by the user rule, automatically send the first communication to the selected third party to address the need.

Any of the one or more above aspects, wherein a sensor associated with the vehicle receives biometric information associated with the passenger.

Any of the one or more above aspects, wherein, when the passenger enters the vehicle a second time, the biometric information identifies the passenger.

Any of the one or more above aspects, wherein the first communication is an order for a good or service.

Any of the one or more above aspects, wherein the user rule determines a distance the vehicle can travel to the third party.

Any of the one or more above aspects, wherein the user rule determines a monetary amount the vehicle can pay to the third party.

Any of the one or more above aspects, wherein the user rule allows the processor to bargain with the third party.

Any of the one or more above aspects, wherein the third party also has a vendor rule to govern an interaction with the vehicle.

Any of the one or more above aspects, wherein the use rule allows a search of two or more third parties that can address the need.

Any of the one or more above aspects, wherein the user rule is a time limit to address the need.

A method for communicating information with a vehicle, comprising: a memory storing a user rule applicable to communications associated with a user in the vehicle; a processor determining a need for communication with a third party; retrieving the user rule from the memory; based on the user rule, determining to which third party the vehicle can send a first communication to address the need; selecting the third party; and when determined by the user rule, automatically sending the first communication to the selected third party to address the need.

Any of the one or more above aspects, wherein a sensor associated with the vehicle receives biometric information associated with the passenger, and wherein, when the passenger enters the vehicle a second time, the biometric information identifies the passenger.

Any of the one or more above aspects, wherein the first communication is an order for a good or service.

Any of the one or more above aspects, wherein one or more of: wherein the user rule determines a distance the vehicle can travel to the third party, wherein the user rule determines a monetary amount the vehicle can pay to the third party, wherein the user rule allows the processor to bargain with the third, and/or wherein the user rule is a time limit to address the need.

Any of the one or more above aspects, wherein the use rule allows a search of two or more third parties that can address the need.

A non-transitory information storage media having stored thereon one or more instructions, that when executed by one or more processors, cause a vehicle to perform a method, the method comprising: storing a user rule applicable to communications associated with a user in the vehicle; determining a need for communication with a third party; retrieving the user rule from the memory; based on the user rule, determining to which third party the vehicle can send a first communication to address the need; selecting the third party; and when determined by the user rule, automatically sending the first communication to the selected third party to address the need.

Any of the one or more above aspects, wherein a sensor associated with the vehicle receives biometric information associated with the passenger, and wherein, when the passenger enters the vehicle a second time, the biometric information identifies the passenger.

Any of the one or more above aspects, wherein the first communication is an order for a good or service.

Any of the one or more above aspects, wherein one or more of: wherein the user rule determines a distance the vehicle can travel to the third party, wherein the user rule determines a monetary amount the vehicle can pay to the third party, wherein the user rule allows the processor to bargain with the third, and/or wherein the user rule is a time limit to address the need.

Any of the one or more above aspects, wherein the use rule allows a search of two or more third parties that can address the need.

A vehicle, comprising: a memory to store triggering event information applicable to communications associated with a user in the vehicle; a processor in communication with the memory, the processor to: determine a triggering event has occurred; retrieve the triggering event information from the memory; based on the triggering event information, determine a third party to which the vehicle send a first communication; and when determined by the trigger event information, automatically send the first communication to the selected third party to address the need.

Any of the one or more above aspects, wherein a sensor associated with the vehicle receives biometric information associated with the passenger.

Any of the one or more above aspects, wherein, when the passenger enters the vehicle a second time, the biometric information identifies the passenger.

Any of the one or more above aspects, wherein the first communication is an order for a good or service.

Any of the one or more above aspects, wherein the triggering event information causes a change to a user interface in the vehicle.

Any of the one or more above aspects, wherein the triggering event is a weather related event.

Any of the one or more above aspects, wherein the first communication purchases weather information to be overlaid on the user interface.

Any of the one or more above aspects, wherein the triggering event is a police action.

Any of the one or more above aspects, wherein the first communication purchases real time traffic information to be overlaid on the user interface to avoid the police action.

Any of the one or more above aspects, wherein the triggering event is a malfunction of the vehicle, and wherein the first communication purchases a tow service or a part to address the malfunction.

A method for communicating information with a vehicle, comprising: a memory storing triggering event information applicable to communications associated with a user in the vehicle; a processor determining a triggering event has occurred; retrieving the triggering event information from the memory; based on the triggering event information, determining a third party to which the vehicle send a first communication; and when determined by the trigger event information, automatically sending the first communication to the selected third party to address the need.

Any of the one or more above aspects, wherein a sensor associated with the vehicle receives biometric information associated with the passenger, and wherein, when the passenger enters the vehicle a second time, the biometric information identifies the passenger.

Any of the one or more above aspects, wherein the first communication is an order for a good or service.

Any of the one or more above aspects, wherein the triggering event information causes a change to a user interface in the vehicle, wherein the triggering event is a weather related event, and wherein the first communication purchases weather information to be overlaid on the user interface.

Any of the one or more above aspects, wherein the triggering event information causes a change to a user interface in the vehicle, wherein the triggering event is a police action, and wherein the first communication purchases real time traffic information to be overlaid on the user interface to avoid the police action.

A non-transitory information storage media having stored thereon one or more instructions, that when executed by one or more processors, cause a vehicle to perform a method, the method comprising: storing triggering event information applicable to communications associated with a user in the vehicle; determining a triggering event has occurred; retrieving the triggering event information from the memory; based on the triggering event information, determining a third party to which the vehicle send a first communication; and when determined by the trigger event information, automatically sending the first communication to the selected third party to address the need.

Any of the one or more above aspects, wherein a sensor associated with the vehicle receives biometric information associated with the passenger, and wherein, when the passenger enters the vehicle a second time, the biometric information identifies the passenger.

Any of the one or more above aspects, wherein the first communication is an order for a good or service.

Any of the one or more above aspects, wherein the triggering event information causes a change to a user interface in the vehicle, wherein the triggering event is a weather related event, and wherein the first communication purchases weather information to be overlaid on the user interface.

Any of the one or more above aspects, wherein the triggering event information causes a change to a user interface in the vehicle, wherein the triggering event is a police action, and wherein the first communication purchases real time traffic information to be overlaid on the user interface to avoid the police action.

A vehicle, comprising: two or more soft touch radio frequency (RF) antennas to communicate sensitive information associated with a user of the vehicle; two or more RF transceivers, each RF transceiver associated with one of the two or more soft touch RF antennas, the two or more RF transceivers to communicate sensitive information associated with a user of the vehicle; a processor in communication with the two or more RF transceivers, the processor to: receive an input to deploy one of the two or more RF antennas; select a first RF transceiver associated with the deployed RF antenna to send the sensitive information; and send the sensitive information to the first RF transceiver.

Any of the one or more above aspects, wherein the RF transceiver and RF antenna are a radio frequency identification device.

Any of the one or more above aspects, wherein the RFID device is an active RFID device.

Any of the one or more above aspects, wherein the deployed RF antenna is located near a side mirror of the vehicle.

Any of the one or more above aspects, wherein the deployed RF antenna contacts a pad physically attached to a structure, associated with a second RF antenna, in physical proximity with a drive through window of a drive through restaurant.

Any of the one or more above aspects, wherein the deployed RF antenna is located on a roof of the vehicle.

Any of the one or more above aspects, wherein the deployed RF antenna contacts a pad physically attached to a structure, associated with a second RF antenna, above the vehicle in a toll lane.

Any of the one or more above aspects, wherein the deployed RF antenna is located near a charging port or a gas refill door.

Any of the one or more above aspects, wherein the deployed RF antenna contacts a pad physically attached to a structure on a charging station or gas pump.

Any of the one or more above aspects, wherein the vehicle contemporaneously communicates through two or more soft touch RF antennas.

A method for communicating information with a vehicle, comprising: receiving an input to deploy one of two or more soft touch radio frequency (RF) antennas to communicate sensitive information associated with a user of the vehicle; selecting a first RF transceiver associated with the deployed RF antenna to send the sensitive information; and sending the sensitive information through the first RF transceiver.

Any of the one or more above aspects, wherein the RF transceiver and RF antenna are a radio frequency identification device, and wherein the RFID device is an active RFID device.

Any of the one or more above aspects, wherein the deployed RF antenna is located near a side mirror of the vehicle, and wherein the deployed RF antenna contacts a pad physically attached to a structure, associated with a second RF antenna, in physical proximity with a drive through window of a drive through restaurant.

Any of the one or more above aspects, wherein the deployed RF antenna is located on a roof of the vehicle, and wherein the deployed RF antenna contacts a pad physically attached to a structure, associated with a second RF antenna, above the vehicle in a toll lane.

Any of the one or more above aspects, wherein the deployed RF antenna is located near a charging port or a gas refill door, and wherein the deployed RF antenna contacts a pad physically attached to a structure on a charging station or gas pump.

A non-transitory information storage media having stored thereon one or more instructions, that when executed by one or more processors, cause a vehicle to perform a method, the method comprising: receiving an input to deploy one of two or more soft touch radio frequency (RF) antennas to communicate sensitive information associated with a user of the vehicle; selecting a first RF transceiver associated with the deployed RF antenna to send the sensitive information; and sending the sensitive information through the first RF transceiver.

Any of the one or more above aspects, wherein the RF transceiver and RF antenna are a radio frequency identification device, and wherein the RFID device is an active RFID device.

Any of the one or more above aspects, wherein the deployed RF antenna is located near a side mirror of the vehicle, and wherein the deployed RF antenna contacts a pad physically attached to a structure, associated with a second RF antenna, in physical proximity with a drive through window of a drive through restaurant.

Any of the one or more above aspects, wherein the deployed RF antenna is located on a roof of the vehicle, and wherein the deployed RF antenna contacts a pad physically attached to a structure, associated with a second RF antenna, above the vehicle in a toll lane.

Any of the one or more above aspects, wherein the deployed RF antenna is located near a charging port or a gas refill door, and wherein the deployed RF antenna contacts a pad physically attached to a structure on a charging station or gas pump.

A vehicle, comprising: a memory to: store sensitive information associated with a user in the vehicle; store user preferences associated with a user in the vehicle a processor in communication with the memory, the processor to: based on the user preferences, determine the user desires to communicate with a third party in an interaction; automatically send a first communication to the third party; and send a second communication to the third party for the user to complete the interaction.

Any of the one or more above aspects, wherein a sensor associated with the vehicle receives biometric information associated with the passenger.

Any of the one or more above aspects, wherein, when the passenger enters the vehicle a second time, the biometric information identifies the passenger.

Any of the one or more above aspects, wherein the first communication is a pre-order for a good or service.

Any of the one or more above aspects, wherein user preference is a usual order based on historical information from a user's past behavior.

Any of the one or more above aspects, wherein the user is prompted to approve the first communication with a user interface displayed in a display in the vehicle.

Any of the one or more above aspects, wherein the second communication is an authorization to complete the order with the third party.

Any of the one or more above aspects, wherein the second communication is sent when the vehicle is in physical proximity to the third party.

Any of the one or more above aspects, wherein the first communication is sent over a first communication network, wherein the second communication is sent over a second communication network, and wherein the first and second communication networks are different.

Any of the one or more above aspects, wherein the first communication is sent when the vehicle is distant from the third party.

A method for communicating information with a vehicle, comprising: storing sensitive information associated with a user in the vehicle; storing user preferences associated with a user in the vehicle based on the user preferences, determining the user desires to communicate with a third party in an interaction; automatically sending a first communication to the third party; and sending a second communication to the third party for the user to complete the interaction.

Any of the one or more above aspects, wherein a sensor associated with the vehicle receives biometric information associated with the passenger, and wherein, when the passenger enters the vehicle a second time, the biometric information identifies the passenger.

Any of the one or more above aspects, wherein the first communication is a pre-order for a good or service.

Any of the one or more above aspects, wherein user preference is a usual order based on historical information from a user's past behavior, and wherein the user is prompted to approve the first communication with a user interface displayed in a display in the vehicle.

Any of the one or more above aspects, wherein the second communication is sent when the vehicle is in physical proximity to the third party, wherein the first communication is sent over a first communication network, wherein the second communication is sent over a second communication network, and wherein the first and second communication networks are different, and wherein the first communication is sent when the vehicle is distant from the third party.

A non-transitory information storage media having stored thereon one or more instructions, that when executed by one or more processors, cause a vehicle to perform a method, the method comprising: storing sensitive information associated with a user in the vehicle; storing user preferences associated with a user in the vehicle based on the user preferences, determining the user desires to communicate with a third party in an interaction; automatically sending a first communication to the third party; and sending a second communication to the third party for the user to complete the interaction.

Any of the one or more above aspects, wherein a sensor associated with the vehicle receives biometric information associated with the passenger, and wherein, when the passenger enters the vehicle a second time, the biometric information identifies the passenger.

Any of the one or more above aspects, wherein the first communication is a pre-order for a good or service.

Any of the one or more above aspects, wherein user preference is a usual order based on historical information from a user's past behavior, and wherein the user is prompted to approve the first communication with a user interface displayed in a display in the vehicle.

Any of the one or more above aspects, wherein the second communication is sent when the vehicle is in physical proximity to the third party, wherein the first communication is sent over a first communication network, wherein the second communication is sent over a second communication network, and wherein the first and second communication networks are different, and wherein the first communication is sent when the vehicle is distant from the third party.

A means, system, SOC, ASIC, FPGA, device, circuit, component, software component, or other module for conducting any of the methods and/or any of the one or more aspects above.

The exemplary systems and methods of this disclosure have been described in relation to vehicle systems and electric vehicles. However, to avoid unnecessarily obscuring the present disclosure, the preceding description omits a number of known structures and devices. This omission is not to be construed as a limitation of the scope of the claimed disclosure. Specific details are set forth to provide an understanding of the present disclosure. It should, however, be appreciated that the present disclosure may be practiced in a variety of ways beyond the specific detail set forth herein.

Furthermore, while the exemplary embodiments illustrated herein show the various components of the system collocated, certain components of the system can be located remotely, at distant portions of a distributed network, such as a LAN and/or the Internet, or within a dedicated system. Thus, it should be appreciated, that the components of the system can be combined into one or more devices, such as a server, communication device, or collocated on a particular node of a distributed network, such as an analog and/or digital telecommunications network, a packet-switched network, or a circuit-switched network. It will be appreciated from the preceding description, and for reasons of computational efficiency, that the components of the system can be arranged at any location within a distributed network of components without affecting the operation of the system. For example, the various components can be located in a switch such as a PBX and media server, gateway, in one or more communications devices, at one or more users' premises, or some combination thereof. Similarly, one or more functional portions of the system could be distributed between a telecommunications device(s) and an associated computing device.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire, and fiber optics, and may take the form of acoustic or light waves, such as those generated during radio-wave and infra-red data communications.

While the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others.

In yet another embodiment, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the present disclosure includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as a program embedded on a personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the embodiments with reference to particular standards and protocols, the disclosure is not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various embodiments, configurations, and aspects, includes components, methods, processes, systems and/or apparatus substantially as depicted and described herein, including various embodiments, subcombinations, and subsets thereof. Those of skill in the art will understand how to make and use the systems and methods disclosed herein after understanding the present disclosure. The present disclosure, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease, and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments, configurations, or aspects for the purpose of streamlining the disclosure. The features of the embodiments, configurations, or aspects of the disclosure may be combined in alternate embodiments, configurations, or aspects other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the disclosure.

Moreover, though the description of the disclosure has included description of one or more embodiments, configurations, or aspects and certain variations and modifications, other variations, combinations, and modifications are within the scope of the disclosure, e.g., as may be within the skill and knowledge of those in the art, after understanding the present disclosure. It is intended to obtain rights, which include alternative embodiments, configurations, or aspects to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Aspects of the present disclosure may take the form of an embodiment that is entirely hardware, an embodiment that is entirely software (including firmware, resident software, micro-code, etc.) or an embodiment combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device. Program code embodied on a computer-readable medium may be transmitted using any appropriate medium, including, but not limited to, wireless, wireline, optical fiber cable, RF, etc., or any suitable combination of the foregoing.

The terms "determine," "calculate," "compute," and variations thereof, as used herein, are used interchangeably and include any type of methodology, process, mathematical operation or technique.

Examples of the processors as described herein may include, but are not limited to, at least one of Qualcomm® Snapdragon® 800 and 801, Qualcomm® Snapdragon® 610 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMD® FX™ family of processors, AMD® FX-4300, FX-6300, and FX-8350 32 nm Vishera, AMD® Kaveri processors, Texas Instruments® Jacinto C6000™ automotive infotainment processors, Texas Instruments® OMAP™ automotive-grade mobile processors, ARM® Cortex™-M processors, ARM® Cortex-A and ARM926EJ-S™ processors, other industry-equivalent processors, and may perform computational functions using any known or future-developed standard, instruction set, libraries, and/or architecture.

The term "means" as used herein shall be given its broadest possible interpretation in accordance with 35 U.S.C., Section 112(f) and/or Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

What is claimed is:

1. A vehicle, comprising:
  a memory to store a user rule applicable to third party vendor communications associated with a user in the vehicle;
  a processor in communication with the memory, the processor is programmed to:
    determine a need for communication with a third party vendor;
    retrieve the user rule from the memory, wherein the user rule defines to which third party vendor the vehicle can send a first communication to address the need, the need relating to a product or service of the third party vendor and wherein the user rule defines one or more of a geographic location of the third party vendor relative to a current location of the vehicle, a monetary amount the vehicle can pay to a third party vendor for a product or service to address the need, and a time limit for the third party vendor to provide the product or service to address the need;
    based on the user rule, select a third party vendor from among multiple possible third party vendors, wherein each of the multiple possible third party vendors is capable of providing the product or service to meet the need; and
    when determined by the user rule, automatically send the first communication to the selected third party vendor to address the need, wherein the first communication is associated with an order for the product or service, wherein the processor provides an authorization to the selected third party vendor to complete the order, wherein the authorization comprises the financial information of the user, and wherein the vehicle uses different antennas positioned at different physical locations on an exterior of the vehicle to provide the first communication and authorization to the selected third party vendor.

2. The vehicle of claim 1, wherein the memory stores one or more limits on third party vendor communications associated with a user in the vehicle, wherein the one or more limits restrict financial transactions of the user with third party vendors, the one or more limits comprising one or more of a financial transaction amount limit and a limit on a number of financial transactions, and wherein the processor, based on the one or more limits, determines whether the vehicle can send the first communication to one of the multiple possible third party vendors, the first communication being related to initiating or completing a financial transaction with the third party vendor regarding the order for the product or service; when allowed by the one or more limits, automatically sends the first communication to the selected third party vendor for the user; and when not allowed by the one or more limits, does not send the first communication to the selected third party vendor for the user.

3. The vehicle of claim 1, wherein the different antennas transmit the first communication and authorization using different communication protocols, wherein a first of the different communication protocols is one or more of a near field communications (NFC), BLUETOOTH™, Low Energy (BLE), and radio frequency identification (RFID) protocol and a second of the different communication protocols is a cellular network communication protocol, wherein one or more of the first communication and authorization comprises vehicle information and user information, wherein the vehicle information comprises a vehicle identification number of the vehicle, an electronic serial number associated with the vehicle, and/or an engine code of the vehicle, wherein the first communication enables the selected third party vendor to authenticate the user, wherein the user information comprises biometric information of the user, the biometric information being received by a sensor associated with the vehicle, wherein the biometric information comprises one or more of facial structure, facial recognition information, voiceprint, voice recognition information, eye color, DNA information, and fingerprint information, wherein the selected third party vendor authenticates the user to enable the financial transaction between the selected third party vendor and user using the user information while the vehicle is in motion, and wherein the processor is programmed to initiate automatically, on behalf of the user and subject to the one or more limits, the financial transaction with the selected third party vendor in response to a sensed state or location of the vehicle.

4. The vehicle of claim 1, wherein the different antennas transmit the first communication and authorization using different communication protocols, wherein a first of the different communication protocols is one or more of a near field communications (NFC), BLUETOOTH™, Low Energy (BLE), and radio frequency identification (RFID) protocol and a second of the different communication protocols is a cellular network communication protocol, wherein one or more of the first communication and authorization comprises vehicle information and user information, wherein the vehicle information comprises a vehicle identification number of the vehicle, an electronic serial number associated with the vehicle, and/or an engine code of the vehicle, wherein the first communication enables the selected third party vendor to authenticate the user, wherein the user is a passenger of the vehicle, wherein the sensor detects a second presence of the passenger in the vehicle, wherein the processor receives the second presence, provides a user interface for the passenger to enter the user information; wherein the user information comprises financial information of the passenger, wherein the financial transaction is initiated by a request from the selected third party vendor, wherein the processor, as part of the request, communicates the user and vehicle information to the selected third party vendor to authenticate the passenger to enable the selected third party vendor to perform the financial transaction with the passenger using the user information, and wherein the processor is programmed to: while the vehicle is in motion, receive a plurality of transaction options from a plurality of vendors, each transaction option comprising an offer for the user to purchase a product or service; retrieve user preferences from the memory; in response to the transaction options and based on the user preferences, pre-filter the plurality of transaction options to identify which of the plurality of transaction options to present to the user by a user interface; in response to identifying a transaction option to present to the user, render the user interface for the display to request authorization from the user to allow a communication to the selected third party vendor associated with the identified transaction option; receive user input associated with the identified transaction option regarding authorization of the associated transaction, the associated transaction being the financial transaction, the user input indicating that the user authorizes the communication; and based on the user input and while the vehicle is in motion, automatically send, by a secure session, the first communication to the selected third party vendor on behalf of the user, the first communication enabling the selected third party vendor to complete the associated transaction.

5. The vehicle of claim 1, wherein the different antennas transmit the first communication and authorization using different communication protocols, wherein a first of the different communication protocols is one or more of a near field communications (NFC), BLUETOOTH™, Low Energy (BLE), and radio frequency identification (RFID) protocol and a second of the different communication protocols is a cellular network communication protocol, wherein the user rule determines a distance the vehicle can travel to the third party, wherein one or more of the first communication and authorization comprises vehicle information and user information, wherein the vehicle information comprises a vehicle identification number of the vehicle, an electronic serial number associated with the vehicle, and/or an engine code of the vehicle, wherein the first communication enables the selected third party vendor to authenticate the user, wherein user information and vehicle information authenticate the user for the order, wherein the user information comprises mobile device information of a device associated with the user, and wherein the mobile device information comprises one or more of the mobile device number, the media access control (MAC) address, and a uniform resource locator (URL).

6. The vehicle of claim 5, wherein the user rule allows the processor to bargain automatically with the third party, wherein the one or more limits applies only to the user and to two or more vehicles, wherein the user information comprises a triggering event, the triggering event being a weather condition, and wherein the processor provides to the selected third party vendor, by the first communication protocol, the order of a product or service and by the different second protocol, financial information of the user.

7. The vehicle of claim 1, wherein the different antennas transmit the first communication and authorization using different communication protocols, wherein the user rule determines a monetary amount the vehicle can pay to the selected third party vendor, wherein the first communication comprises vehicle information and user information, wherein the vehicle information comprises a vehicle identification number of the vehicle, an electronic serial number associated with the vehicle, and/or an engine code of the vehicle, wherein the first communication enables the selected third party vendor to authenticate the user, wherein the user information comprises financial information, biometric information, and/or a PIN, wherein the authorization comprises the financial information of the user, wherein the vehicle uses different communication protocols to provide the vehicle information and financial information, and wherein a first of the different communication protocols is one or more of a near field communications (NFC), BLUETOOTH™, Low Energy (BLE), and radio frequency identification (RFID) protocol and a second of the different communication protocols is a cellular network communication protocol, wherein the user information is encrypted in the memory, wherein the processor authorizes the financial transaction in response to a plurality of a vehicle location, speed, proximity to a location, preference data and historical information associated with the user, wherein the user information comprises one or more of a biometric, a username, a password, mobile device information, payment information, a personal identification number, identifiers, an address, limits, preferences, and/or rules, wherein the processor, in response to a first event, the first event being a vehicle route, automatically forwards a first portion of a secure communication to the selected third party vendor to preorder a product or service of the selected third party vendor in connection with a transaction with the user, wherein the processor, in response to a later second event, the second event being a vehicle location, automatically completes the transaction by providing financial information to the selected third party vendor, and wherein the one or more limits applies only to the user and the vehicle.

8. The vehicle of claim 1, wherein the third party also has a vendor rule to govern an interaction with the vehicle, wherein the one or more limits applies only to two or more users and the vehicle, wherein the processor is authorized and programmed to initiate automatically on behalf of the user and without further input from the user the financial transaction with the selected third party vendor, wherein the authorization is restricted temporally or limited to a selected route or spatial location of the vehicle, wherein the user interface receives input from the user in the user interface and further comprising an active or passive payment device positioned on or near an outer surface of the vehicle, the payment device using one or more of near field communications (NFC), BLUETOOTH™, Low Energy (BLE), and radio frequency identification (RFID) protocol to provide wirelessly financial information of the user to the selected third party vendor, and wherein the payment device comprises one of the antennas, wherein the processor:
- determines, at a first time, which one of the different antennas is receiving a strongest signal from a common signal source associated with the third party vendor;
- selects a first transceiver associated with the first antenna receiving the strongest signal to send the first communication or authorization to the common signal source;
- sends the first communication or authorization to the first transceiver for transmission to the common signal source;
- determines, at a second time, which one of the different antennas is receiving a strongest signal from the common signal source;
- selects a second transceiver associated with the second antenna receiving the strongest signal to send the other of the first communication or authorization to the common signal source; and
- sends the other of the first communication or authorization to the second transceiver for transmission to the common signal source.

9. The vehicle of claim 1, wherein the one or more limits is set on the user by a second user and further comprising a deployable antenna that one or more of physically contacts a receiving pad of the selected third party vendor as the vehicle is in proximity to the selected third party vendor and communicates with a receiver of the selected third party vendor by a near field communication protocol to provide the financial information to the selected third party vendor, the deployable antenna being one of the antennas.

10. The vehicle of claim 1, wherein the user rule is a time limit to address the need and wherein the one or more limits is on a number of communications that may be completed between the vehicle and third party.

11. A method for communicating information with a vehicle, comprising:
- providing a vehicle comprising a memory storing a user rule applicable to communications associated with a user in the vehicle and a processor determining a need for communication with a third party;
- determining, by the processor, a need for communication with a third party vendor;
- retrieving, by the processor, the user rule from the memory, wherein the user rule defines to which third party vendor the vehicle can send a first communication to address the need, the need relating to a product or service of the third party vendor and wherein the user rule defines one or more of a geographic location of the third party vendor relative to a current location of the vehicle, a monetary amount the vehicle can pay to a third party vendor for a product or service to address the need, and a time limit for the third party vendor to provide the product or service to address the need;
- based on the user rule, selecting, by the processor, a third party vendor from among multiple possible third party vendors, wherein each of the multiple possible third party vendors is capable of providing the product or service to meet the need; and
- when determined by the user rule, automatically sending, by the processor, the first communication to the selected third party vendor to address the need, wherein the first communication is associated with an order for the product or service, wherein the processor provides an authorization to the selected third party vendor to complete the order, wherein the authorization comprises the financial information of the user, and wherein the vehicle uses different antennas positioned at different physical locations on an exterior of the vehicle to provide the first communication and authorization to the selected third party vendor.

12. The method of claim 10, wherein the memory stores one or more limits on third party vendor communications associated with a user in the vehicle, wherein the one or more limits restrict financial transactions of the user with third party vendors, the one or more limits comprising one or more of a financial transaction amount limit and a limit on a number of financial transactions, and wherein the processor, based on the one or more limits, determines whether the vehicle can send the first communication to one of the multiple possible third party vendors, the first communication being related to initiating or completing a financial transaction with the third party vendor regarding the order for the product or service; when allowed by the one or more limits, automatically sends the first communication to the selected third party vendor for the user; and when not allowed by the one or more limits, does not send the first communication to the selected third party vendor for the user.

13. The method of claim 11, wherein the different antennas transmit the first communication and authorization using different communication protocols, wherein a first of the different communication protocols is one or more of a near field communications (NFC), BLUETOOTH™, Low Energy (BLE), and radio frequency identification (RFID) protocol and a second of the different communication protocols is a cellular network communication protocol, wherein one or more of the first communication and authorization comprises vehicle information and user information, wherein the vehicle information comprises a vehicle identification number of the vehicle, an electronic serial number associated with the vehicle, and/or an engine code of the vehicle, wherein the first communication enables the selected third party vendor to authenticate the user, wherein the user information comprises biometric information of the user, the biometric information being received by a sensor associated with the vehicle, wherein the biometric information comprises one or more of facial structure, facial recognition information, voiceprint, voice recognition information, eye color, DNA information, and fingerprint information, wherein the selected third party vendor authenticates the user to enable the financial transaction between the selected third party vendor and user using the user information while the vehicle is in motion, and wherein the processor is programmed to initiate automatically, on behalf of the user and subject to the one or more limits, the financial transaction with the selected third party vendor in response to a sensed state or location of the vehicle.

14. The method of claim 11, wherein the different antennas transmit the first communication and authorization using different communication protocols, wherein a first of the different communication protocols is one or more of a near field communications (NFC), BLUETOOTH™, Low Energy (BLE), and radio frequency identification (RFID) protocol and a second of the different communication protocols is a cellular network communication protocol, wherein one or more of the first communication and authorization comprises vehicle information and user information, wherein the vehicle information comprises a vehicle identification number of the vehicle, an electronic serial number associated with the vehicle, and/or an engine code of the vehicle, wherein the first communication enables the selected third party vendor to authenticate the user, wherein the user is a passenger of the vehicle, wherein the sensor detects a second presence of the passenger in the vehicle, wherein the processor receives the second presence, provides a user interface for the passenger to enter the user information; wherein the user information comprises financial information of the passenger, wherein the financial transaction is initiated by a request from the selected third party vendor, wherein the processor, as part of the request, communicates the user and vehicle information to the selected third party vendor to authenticate the passenger to enable the selected third party vendor to perform the financial transaction with the passenger using the user information, and wherein the processor is programmed to: while the vehicle is in motion, receive a plurality of transaction options from a plurality of vendors, each transaction option comprising an offer for the user to purchase a product or service; retrieve user preferences from the memory; in response to the transaction options and based on the user preferences, pre-filter the plurality of transaction options to identify which of the plurality of transaction options to present to the user by a user interface; in response to identifying a transaction option to present to the user, render the user interface for the display to request authorization from the user to allow a communication to the selected third party vendor associated with the identified transaction option; receive user input associated with the identified transaction option regarding authorization of the associated transaction, the associated transaction being the financial transaction, the user input indicating that the user authorizes the communication; and based on the user input and while the vehicle is in motion, automatically send, by a secure session, the first communication to the selected third party vendor on behalf of the user, the first communication enabling the selected third party vendor to complete the associated transaction.

15. The method of claim 11, wherein the different antennas transmit the first communication and authorization using different communication protocols, wherein a first of the different communication protocols is one or more of a near field communications (NFC), BLUETOOTH™, Low Energy (BLE), and radio frequency identification (RFID) protocol and a second of the different communication protocols is a cellular network communication protocol, wherein the user rule determines a distance the vehicle can travel to the third party, wherein one or more of the first communication and authorization comprises vehicle information and user information, wherein the vehicle information comprises a vehicle identification number of the vehicle, an electronic serial number associated with the vehicle, and/or an engine code of the vehicle, wherein the first communication enables the selected third party vendor to authenticate the user, wherein user information and vehicle information authenticate the user for the order, wherein the user information comprises mobile device information of a device associated with the user, and wherein the mobile device information comprises one or more of the mobile device number, the media access control (MAC) address, and a uniform resource locator (URL).

16. The method of claim 11, wherein the different antennas transmit the first communication and authorization using different communication protocols, wherein the user rule determines a monetary amount the vehicle can pay to the selected third party vendor, wherein the first communication comprises vehicle information and user information, wherein the vehicle information comprises a vehicle identification number of the vehicle, an electronic serial number associated with the vehicle, and/or an engine code of the vehicle, wherein the first communication enables the selected third party vendor to authenticate the user, wherein the user information comprises financial information, biometric information, and/or a PIN, wherein the authorization comprises the financial information of the user, wherein the vehicle uses different communication protocols to provide the vehicle information and financial information, and wherein a first of the different communication protocols is one or more of a near field communications (NFC), BLUETOOTH™, Low Energy (BLE), and radio frequency identification (RFID) protocol and a second of the different communication protocols is a cellular network communication protocol, wherein the user information is encrypted in the memory, wherein the processor authorizes the financial transaction in response to a plurality of a vehicle location, speed, proximity to a location, preference data and historical information associated with the user, wherein the user information comprises one or more of a biometric, a username, a password, mobile device information, payment information, a personal identification number, identifiers, an address, limits, preferences, and/or rules, wherein the processor, in response to a first event, the first event being a vehicle route, automatically forwards a first portion of a secure communication to the selected third party vendor to preorder a product or service of the selected third party vendor in connection with a transaction with the user, wherein the processor, in response to a later second event, the second event being a vehicle location, automatically completes the transaction by providing financial information to the selected third party vendor, and wherein the one or more limits applies only to the user and the vehicle.

17. The method of claim 15, wherein the user rule allows the processor to bargain automatically with the third party, wherein the one or more limits applies only to the user and to two or more vehicles, wherein the user information comprises a triggering event, the triggering event being a weather condition, and wherein the processor provides to the selected third party vendor, by the first communication protocol, the order of a product or service and by the different second protocol, financial information of the user.

18. The method of claim 11, wherein the third party also has a vendor rule to govern an interaction with the vehicle, wherein the one or more limits applies only to two or more users and the vehicle, wherein the processor is authorized and programmed to initiate automatically on behalf of the user and without further input from the user the financial transaction with the selected third party vendor, wherein the authorization is restricted temporally or limited to a selected route or spatial location of the vehicle, wherein the user interface receives input from the user in the user interface and further comprising an active or passive payment device positioned on or near an outer surface of the vehicle, the payment device using one or more of near field communications (NFC), BLUETOOTH™, Low Energy (BLE), and radio frequency identification (RFID) protocol to provide wirelessly financial information of the user to the selected third party vendor, and wherein the payment device comprises one of the antennas and further comprising:

determining, by the processor and at a first time, which one of the different antennas is receiving a strongest signal from a common signal source associated with the third party vendor;

selecting, by the processor, a first transceiver associated with the first antenna receiving the strongest signal to send the first communication or authorization to the common signal source;

sending, by the processor, the first communication or authorization to the first transceiver for transmission to the common signal source;

determining, by the processor and at a second time, which one of the different antennas is receiving a strongest signal from the common signal source;

selecting, by the processor, a second transceiver associated with the second antenna receiving the strongest signal to send the other of the first communication or authorization to the common signal source; and sending, by the processor, the other of the first communication or authorization to the second transceiver for transmission to the common signal source.

19. The method of claim 11, wherein the one or more limits is set on the user by a second user and further comprising a deployable antenna that one or more of physically contacts a receiving pad of the selected third party vendor as the vehicle is in proximity to the selected third party vendor and communicates with a receiver of the selected third party vendor by a near field communication protocol to provide the financial information to the selected third party vendor, the deployable antenna being one of the antennas.

20. The method of claim 11, wherein the user rule is a time limit to address the need and wherein the one or more limits is on a number of communications that may be completed between the vehicle and third party.

21. A vehicle, comprising:
- a non-transitory memory to store a user rule applicable to third party vendor communications associated with a user in the vehicle;
- a processor in communication with the memory, the processor to:
  - determine a need for communication with a third party vendor;
  - retrieve the user rule from the memory, wherein the user rule defines to which third party vendor the vehicle can send a first communication to address the need, the need relating to a product or service of the third party vendor and wherein the user rule defines one or more of a geographic location of the third party vendor relative to a current location of the vehicle, a monetary amount the vehicle can pay to a third party vendor for a product or service to address the need, and a time limit for the third party vendor to provide the product or service to address the need;
  - based on the user rule, select a third party vendor from among multiple possible third party vendors, wherein each of the multiple possible third party vendors is capable of providing the product or service to meet the need; and
  - when determined by the user rule, automatically send the first communication to the selected third party vendor to address the need, wherein the first communication is associated with an order for the product or service, wherein the processor provides an authorization to the selected third party vendor to complete the order, wherein the authorization comprises the financial information of the user, wherein the vehicle uses different antennas, positioned at different physical locations on the vehicle, and different communication protocols to provide the first communication and authorization to the selected third party vendor, and wherein a first of the different communication protocols is one or more of a near field communications (NFC), BLUETOOTH™, Low Energy (BLE), and radio frequency identification (RFID) protocol and a second of the different communication protocols is a cellular network communication protocol.

* * * * *

UNITED STATES PATENT AND TRADEMARK OFFICE
CERTIFICATE OF CORRECTION

| | | |
|---|---|---|
| PATENT NO. | : 10,032,319 B2 | Page 1 of 1 |
| APPLICATION NO. | : 15/396620 | |
| DATED | : July 24, 2018 | |
| INVENTOR(S) | : Christopher P. Ricci | |

It is certified that error appears in the above-identified patent and that said Letters Patent is hereby corrected as shown below:

In the Claims

At Column 89, Line 16, after "is on a" insert --non-transitory--.

Signed and Sealed this
Twenty-eighth Day of April, 2020

Andrei Iancu
*Director of the United States Patent and Trademark Office*